(12) United States Patent
Dutartre et al.

(10) Patent No.: US 9,885,017 B2
(45) Date of Patent: Feb. 6, 2018

(54) COMPOSITIONS AND METHODS TO IMMUNIZE AGAINST HEPATITIS C VIRUS

(71) Applicants: Baylor Research Institute, Dallas, TX (US); Institut National de la Sante et de la Recherche Medicale (INSERM), Paris (FR)

(72) Inventors: Helene Dutartre, Dallas, TX (US); Yves Levy, Paris (FR); Jacques Banchereau, Montclair, NJ (US); Gerard Zurawski, Midlothian, TX (US)

(73) Assignees: BAYLOR RESEARCH INSTITUTE, Dallas, TX (US); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 2 days.

(21) Appl. No.: 14/152,448

(22) Filed: Jan. 10, 2014

(65) Prior Publication Data
US 2014/0199763 A1 Jul. 17, 2014

Related U.S. Application Data

(62) Division of application No. 13/430,206, filed on Mar. 26, 2012, now abandoned.

(60) Provisional application No. 61/467,840, filed on Mar. 25, 2011, provisional application No. 61/529,700, filed on Aug. 31, 2011.

(51) Int. Cl.
| | |
|---|---|
| *A61K 39/395* | (2006.01) |
| *A61K 39/00* | (2006.01) |
| *C07K 16/28* | (2006.01) |
| *A61P 37/04* | (2006.01) |
| *C12N 5/0784* | (2010.01) |
| *A61K 39/29* | (2006.01) |
| *A61K 39/12* | (2006.01) |
| *C07K 14/005* | (2006.01) |

(52) U.S. Cl.
CPC ............ *C12N 5/0639* (2013.01); *A61K 39/12* (2013.01); *A61K 39/29* (2013.01); *C07K 14/005* (2013.01); *C07K 16/2851* (2013.01); *C07K 16/2878* (2013.01); *A61K 2039/6056* (2013.01); *C07K 2319/00* (2013.01); *C07K 2319/33* (2013.01); *C12N 2770/24222* (2013.01); *C12N 2770/24234* (2013.01)

(58) Field of Classification Search
CPC .......... A61K 2039/505; A61K 2039/57; C07K 2319/00; C07K 2319/30
See application file for complete search history.

(56) References Cited

U.S. PATENT DOCUMENTS

| | | | |
|---|---|---|---|
| 4,235,871 A | 11/1980 | Papahadjopoulos et al. | 424/450 |
| 4,501,728 A | 2/1985 | Geho et al. | 424/450 |
| 4,578,770 A | 3/1986 | Mitani | 250/559.2 |
| 4,599,230 A | 7/1986 | Milich et al. | 424/189.1 |
| 4,599,231 A | 7/1986 | Milich et al. | 424/189.1 |
| 4,601,903 A | 7/1986 | Frasch | 424/250.1 |
| 4,608,251 A | 8/1986 | Mia | 424/185.1 |
| 4,837,028 A | 6/1989 | Allen | 424/1.21 |
| 4,902,505 A | 2/1990 | Pardrige et al. | 424/85.7 |
| 4,957,735 A | 9/1990 | Huang | 424/178.1 |
| 5,004,697 A | 4/1991 | Pardridge | 424/1.49 |
| 5,019,369 A | 5/1991 | Present et al. | 424/1.21 |
| 5,055,303 A | 10/1991 | Riley, Jr. | 424/436 |
| 5,188,837 A | 2/1993 | Domb | 424/450 |
| 5,254,342 A | 10/1993 | Shen et al. | 424/401 |
| 5,268,164 A | 12/1993 | Kozarich et al. | 424/1.11 |
| 5,271,961 A | 12/1993 | Mathiowitz et al. | 427/213.31 |
| 5,413,797 A | 5/1995 | Khan et al. | 424/489 |
| 5,506,206 A | 4/1996 | Kozarich et al. | 514/1.2 |
| 5,514,670 A | 5/1996 | Friedman et al. | 514/185.1 |
| 5,534,496 A | 7/1996 | Lee et al. | 514/5.9 |
| 5,545,806 A | 8/1996 | Lonberg et al. | 800/6 |
| 5,569,825 A | 10/1996 | Lonberg et al. | 800/18 |

(Continued)

FOREIGN PATENT DOCUMENTS

| | | |
|---|---|---|
| EP | 0491628 | 6/1992 |
| EP | 0438474 | 5/1996 |
| EP | 0463151 | 6/1996 |
| EP | 0546073 | 9/1997 |
| EP | 1391464 | 2/2004 |
| WO | 88/01649 | 3/1988 |
| WO | 90/07861 | 7/1990 |
| WO | 01/83755 | 11/2001 |
| WO | 02/28905 | 4/2002 |
| WO | 03/029296 | 4/2003 |

(Continued)

OTHER PUBLICATIONS

Li, "Synergistic antibody induction by antigen-CD40 ligand fusion protein as improved immunogen", 2005, Immunology, 115:215-222.*

(Continued)

*Primary Examiner* — Barry A Chestnut
(74) *Attorney, Agent, or Firm* — Norton Rose Fulbright US LLP

(57) ABSTRACT

Compositions comprising viral antigens and antigenic peptides corresponding to or derived from Hepatitis C virus (HCV) proteins or fragments thereof, fused to heavy and/or light chain of antibodies, or fragments thereof specific for dendritic cells (DCs) are described herein. Included herein are immunostimulatory compositions (HCV vaccines, HCV antigen presenting dendritic cells, etc.) and methods for increasing effectiveness of HCV antigen presentation by an antigen presenting cell, for a treatment, a prophylaxis or a combination thereof against hepatitis C in a human subject, and methods of providing immunostimulation by activation of one or more dendritic cells, methods to treat or prevent hepatitis C.

14 Claims, 41 Drawing Sheets

(56) References Cited

U.S. PATENT DOCUMENTS

Figure 1:
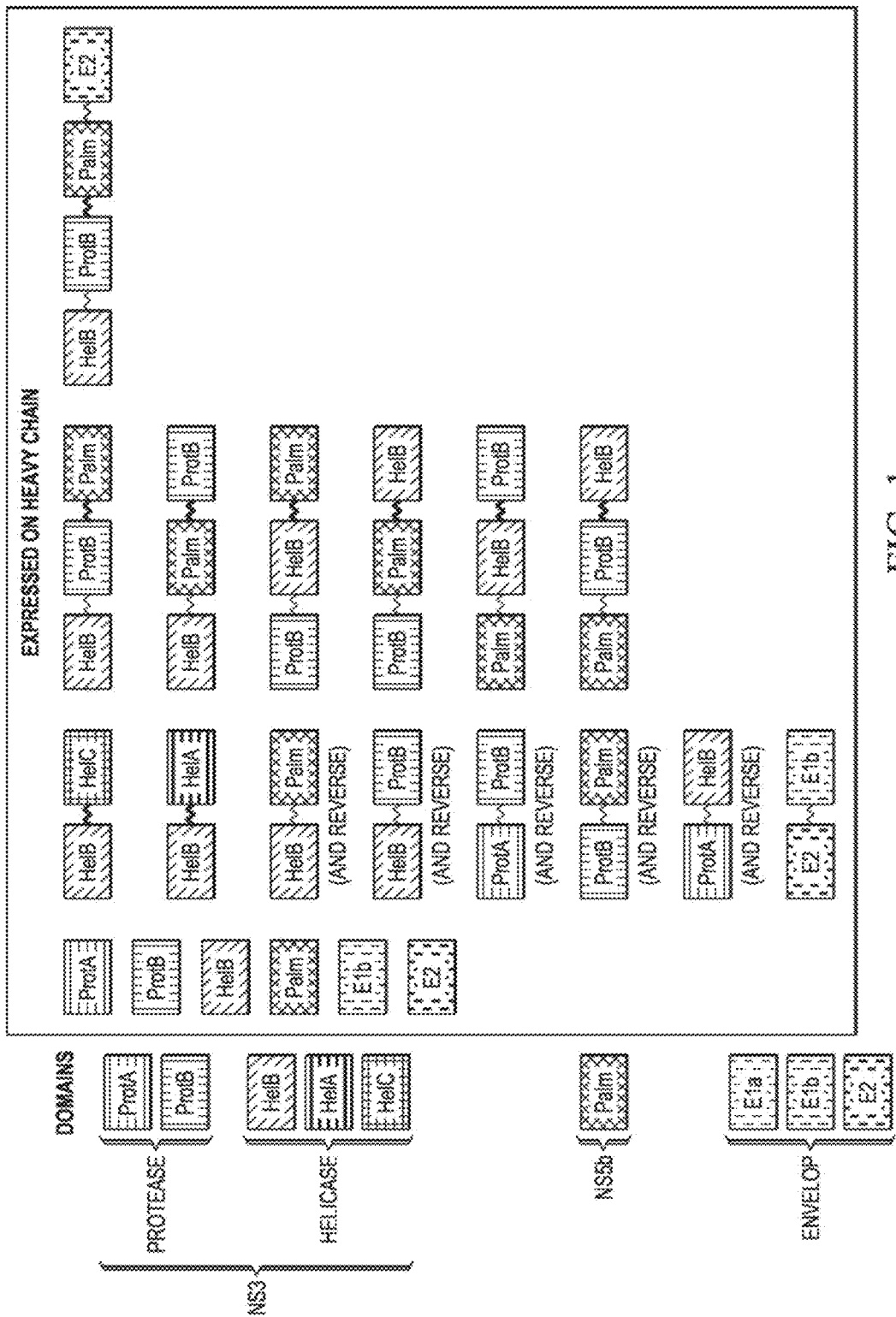

| | | | |
|---|---|---|---|
| 5,625,126 | A | 4/1997 | Lonberg et al. ............... 800/18 |
| 5,633,425 | A | 5/1997 | Lonberg et al. ............... 800/18 |
| 5,661,016 | A | 8/1997 | Lonberg et al. ............. 435/452 |
| 5,770,429 | A | 6/1998 | Lonberg et al. ............. 435/328 |
| 5,871,746 | A | 2/1999 | Boutillon et al. ......... 424/208.1 |
| 6,140,059 | A | 10/2000 | Shawaller ..................... 435/7.1 |
| 6,469,143 | B2 | 10/2002 | Sallberg ........................ 530/350 |
| 6,541,011 | B2 | 4/2003 | Punnonen et al. ......... 424/204.1 |
| 6,573,245 | B1 | 6/2003 | Marciani ......................... 514/25 |
| 7,060,495 | B2 | 6/2006 | Gehrmann et al. ........ 424/94.61 |
| 7,118,751 | B1 | 10/2006 | Ledbetter et al. ......... 424/192.1 |
| 7,261,897 | B2 | 8/2007 | Skeiky et al. ............. 424/192.1 |
| 7,456,260 | B2 | 11/2008 | Rybak et al. ............. 530/387.3 |
| 7,560,534 | B2 | 7/2009 | Deo et al. ................ 530/388.73 |
| 2004/0146948 | A1 | 7/2004 | Britton et al. ................. 435/7.2 |
| 2005/0013828 | A1 | 1/2005 | George et al. ............. 424/189.1 |
| 2005/0074465 | A1* | 4/2005 | Houghton ............ C07K 14/005 424/189.1 |
| 2006/0246089 | A1 | 11/2006 | Wu et al. .................... 424/189.1 |
| 2008/0181915 | A1 | 7/2008 | Tripp ........................ 424/211.1 |
| 2008/0199471 | A1 | 8/2008 | Bernett et al. ............. 424/138.1 |
| 2008/0233083 | A1 | 9/2008 | Ansari et al. ................ 424/85.2 |
| 2008/0241139 | A1 | 10/2008 | DeLucia .................... 424/135.1 |
| 2008/0241170 | A1 | 10/2008 | Zurawski et al. ......... 424/178.1 |
| 2008/0254026 | A1 | 10/2008 | Long et al. ................. 424/133.1 |
| 2009/0023822 | A1 | 1/2009 | Tijm ............................. 518/715 |
| 2010/0239575 | A1 | 9/2010 | Banchereau et al. ...... 424/133.1 |

FOREIGN PATENT DOCUMENTS

| | | | |
|---|---|---|---|
| WO | 06/128103 | | 11/2006 |
| WO | 2007041861 | | 4/2007 |
| WO | WO2007041861 | * | 4/2007 |
| WO | WO2010009346 | * | 1/2010 |
| WO | 2011032161 | | 3/2011 |
| WO | 2011140255 | | 11/2011 |

OTHER PUBLICATIONS

Zhang et al., Characterization of a Monoclonal Antibody and its single-chain antibody fragment recognizing the nucleoside triphosphatase/helicase domain of the hepatitis C virus nonstructural 3 protein, 2000, Clinical and Diagnostic laboratory immunology, 7(1):58-63.*

Austyn, Jonathan M., et al., "Migration Patterns of Dendritic Cells in the Mouse," J. Exp. Med., Feb. 1988, vol. 167, pp. 646-651.

Banchereau, Jacques, et al., "Immunobiology of Dendritic Cells," Annu. Rev. Immunol., (2000), 18:767-811.

Bates, et al., "APCs Express DCIR, a Novel C-Type Lectin Surface Receptor Containing an Immunoreceptor Tyrosine-Based Inhibitory Motif," J. Immunol. (1999) 163:1973-1983.

Beauchamp, Charles O., et al., "A New Procedure for the Synthesis of Polyethylene Glycol-Protein Adducts; Effects on Function, Receptor Recognition, and Clearance of Superoxide Dismutase, Lactoferrin, and a2-Macroglobulin," Analytical Biochemistry 131 (1983), pp. 25-33.

Benton, Trish, et al., "The Use of UCOE Vectors in Combination with a Preadapted Serum Free, Suspension Cell Line Allows for Rapid Production of Large Quantities of Protein," Cytotechnology, (2002), 38:43-46.

Dakappagari, et al., "Internalizing antibodies to the C-Type lectins, L-SIGN and DC-SIGN, inhibit viral glycoprotein binding and deliver antigen to human dendritic cells for the induction of T Cell responses," The Journal of Immunology (2006) 176:426-440.

Dye, Christopher, et al., "Global Burden of Tuberculosis-Estimated Incidence, Prevalence, and Mortality by Country," JAMA, (1999), 282:677-686.

Finn, O., "Cancer Vaccines: Between the Idea and the Reality," Nature Reviews Immunology, (Aug. 2003), 3:630-641.

Hougardy, Jean-Michel, et al., "Heparin-Binding-Hemagglutinin-Induced IFN-y Release as a Diagnostic Tool for Latent Tuberculosis," PLOS ONE, Oct. 2007, Issue 10, 8 pages.

International Search Report and Written Opinion for PCT/US2010/026375 prepared by Korean Intellectual Property Office, dated Nov. 19, 2010, 12 pages.

International Search Report and Written Opinion for PCT/US2010/026268 prepared by Korean Intellectual Property Office, dated Dec. 31, 2010, 13 pages.

International Search Report and Written Opinion for PCT/US2010/026273 prepared by Korean Intellectual Property Office, dated Jan. 9, 2011, 12 pages.

International Search Report and Written Opinion for PCT/US2010/026275 prepared by Korean Intellectual Property Office, dated Jan. 7, 2011, 13 pages.

Klinguer, et al., "Characterization of a multi-lipopeptides mixture used as an HIV-1 vaccine candidate," Vaccine (2000) 18:259-267.

Langer, R., "Polymer-Controlled Drug Delivery Systems," Acc. Chem. Res., (1993), 26:537-542.

Li, Wei, "Synergistic Antibody Induction by Antigen-CD40 Ligand Fusion Protein as Improved Immunogen," Immunology, 115, (Jun. 2005), pp. 215-222.

Lo-Man, et al., "Anti-tumor immunity provided by a synthetic multiple antigenic glycopeptide displaying a Tri-Tn glycotope," The Journal of Immunology (2001) 166:2849-2854.

Reddy, Manjula P., et al., "Elimination of Fc Receptor-Dependent Effector Functions of a Modified IgG4 Monoclonal Antibody to Human CD4," The Journal of Immunology, (2000), 164; pp. 1925-1933.

Rescigno, Maria, et al., "Bacteria-Induced Neo-Biosynthesis, Stabilization, and Surface Expression of Functional Class I Molecules in Mouse Dendritic Cells," Proc. Natl. Acad. Sci., Apr. 1998, vol. 95, pp. 5229-5234.

Soares, et al., "Three different vaccines based on the 140-amino acid MUC1 peptide with seven tandemly repeated tumor-specific epitopes elicit distinct immune effector mechanisms in wild-type versus MUC1-Transgenic mice with different potential for tumor rejection," The Journal of Immunology (2001) 166:6555-6563.

Steinman, Ralph M., "The Dendritic Cell System and its Role in Immunogenicity," Annual Review Immunology, (1991), 9:271-296.

Van Vliet, Sandra J., et al., "Dendritic Cells and C-Type Lectin Receptors: Coupling Innate to Adaptive Immune Responses," Immunology and Cell Biology, (2008), 86:580-587.

Xiang, Rong, et al., "A Dual-Function DNA Vaccine Encoding Carcinoembryonic Antigen and CD40 Ligand Trimer Induces T Cell-Mediated Protective Immunity Against Colon Cancer and Carcinoembryonic Antigenin-Transgenic Mice," The Journal of Immunology, (2001), 167;pp. 4560-4565.

Zhang, Lixin, et al., "An Adenoviral Vector Cancer Vaccine that Delivers a Tumor-Associated Antigen/CD40-Ligand Fusion Protein to Dendritic Cells," PNAS, Dec. 9, 2003, vol. 100, No. 25, pp. 15101-15106.

Yin, X. et al. Chinese Journal of Virology. Jan. 2011, vol. 27, No. 1, pp. 45-49.

International Preliminary Report on Patentability in International Application No. PCT/US2012/030593 dated Oct. 10, 2013.

Rollier C, et al., "Control of heterologous hepatitis C virus infection in chimpanzees is associated with the quality of vaccine-induced peripheral T-helper immune response," J. Virol., vol. 75, p. 187-196.

Heile JM, et al., "Evaluation of hepatitis C virus glycoprotein E2 for vaccine design: an endoplasmic reticulum-retained recombinant protein is superior to secreted recombinant protein and DNA-based vaccine candidates," J. Virol., vol. 74, pp. 6885-6892.

Zhang, et al., "Characterization of a Monoclonal Antibody and its Single-chain Antibody Fragment Recognizing the Nucleoside Triphosphatase/Helicase Domain of the Hepatitis C Virus Nonstructural 3 Protein," Clinical and Diagnostic Laboratory Immunology, 7(1), pp. 58-63, 2000.

\* cited by examiner

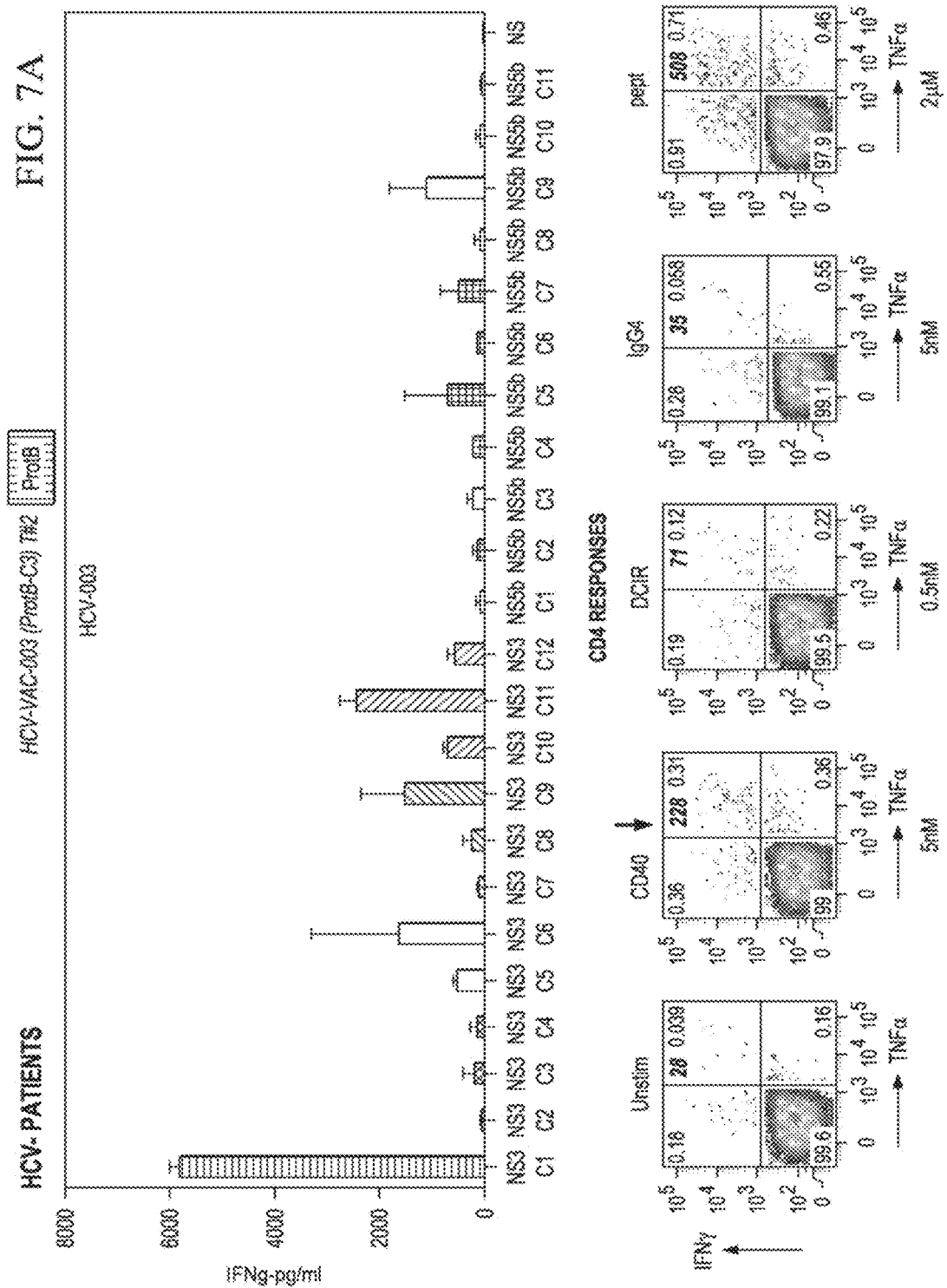

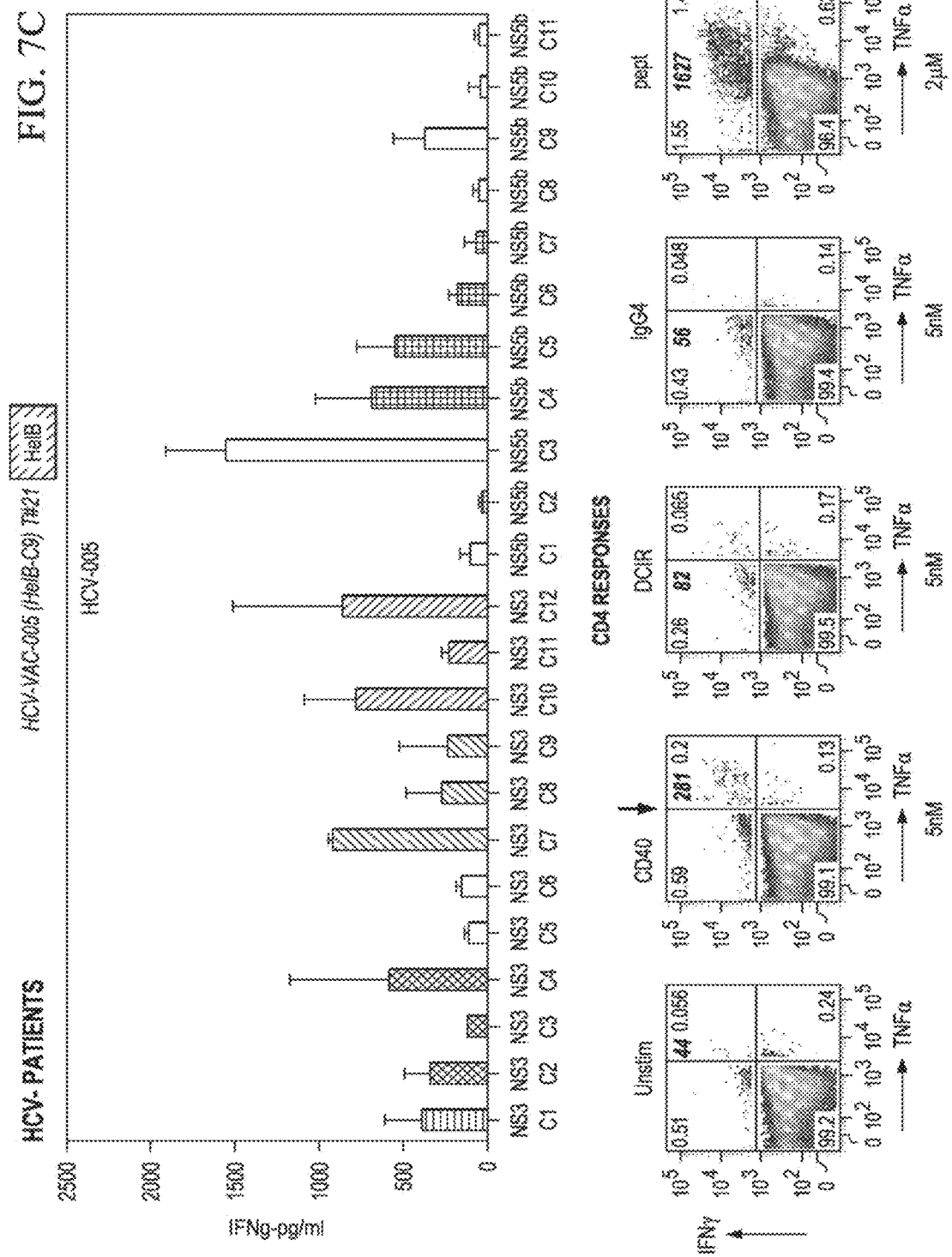

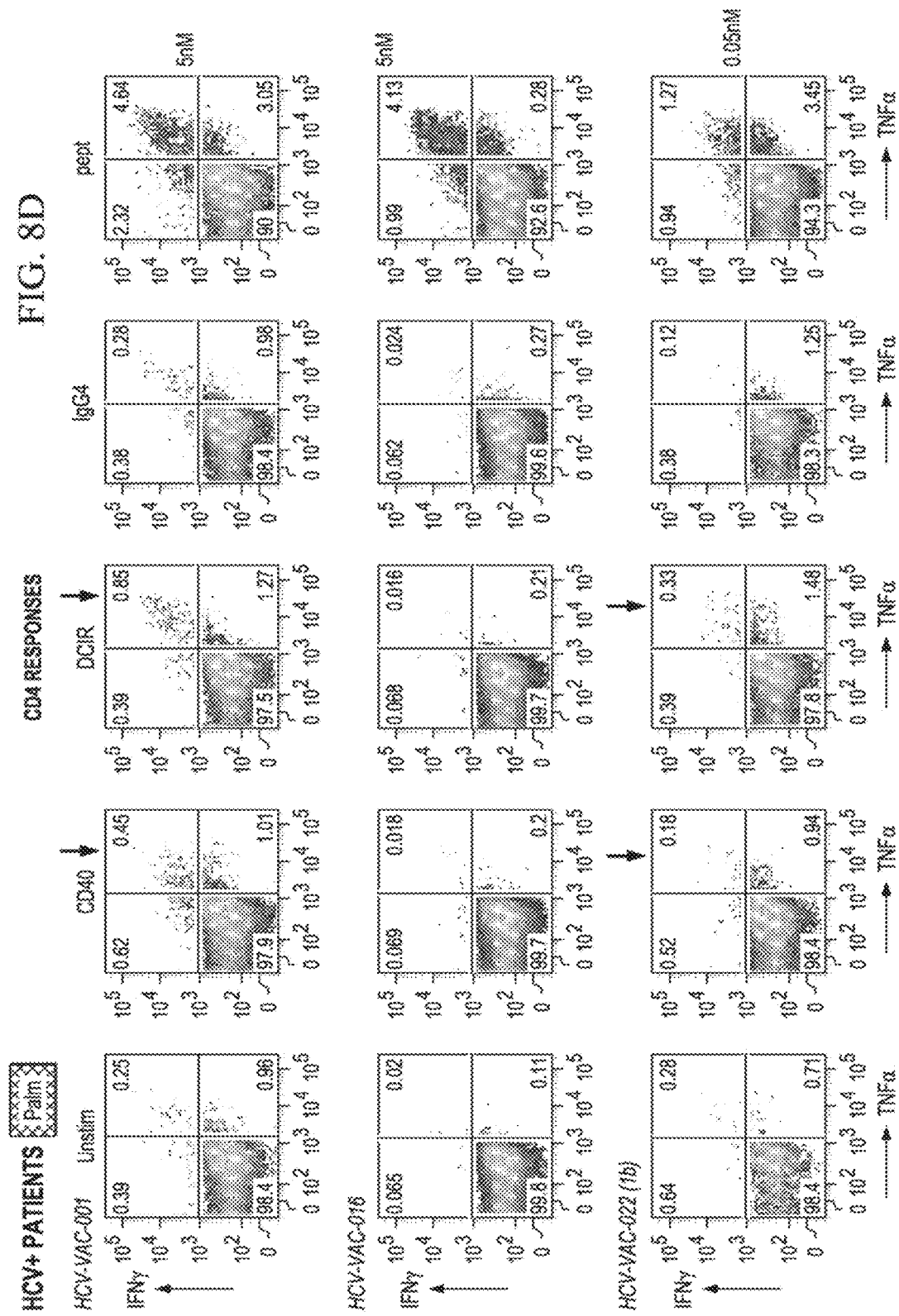

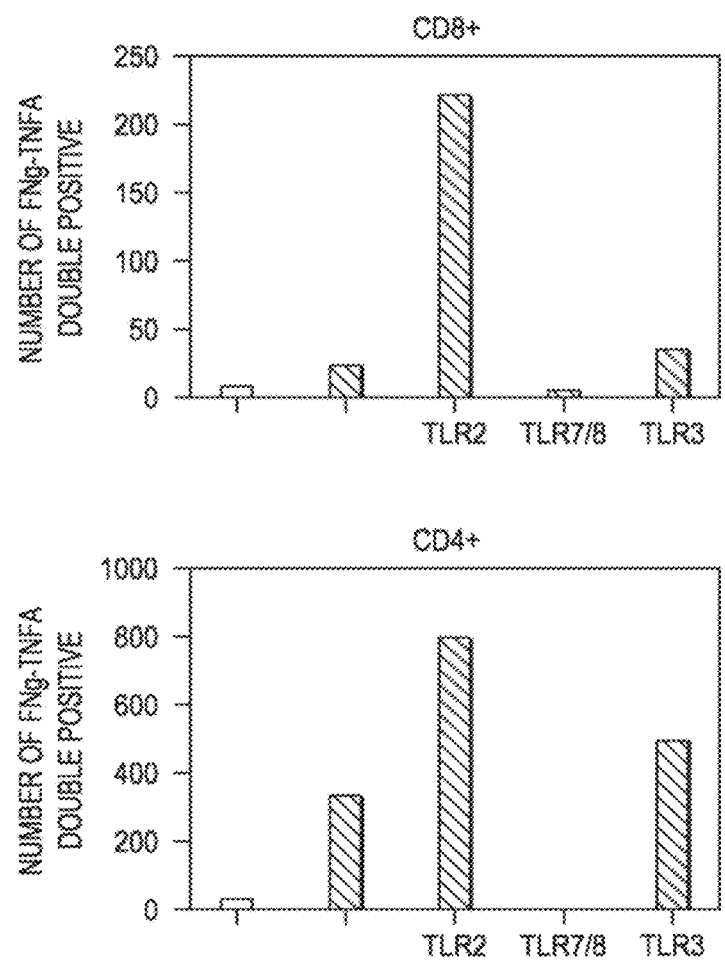

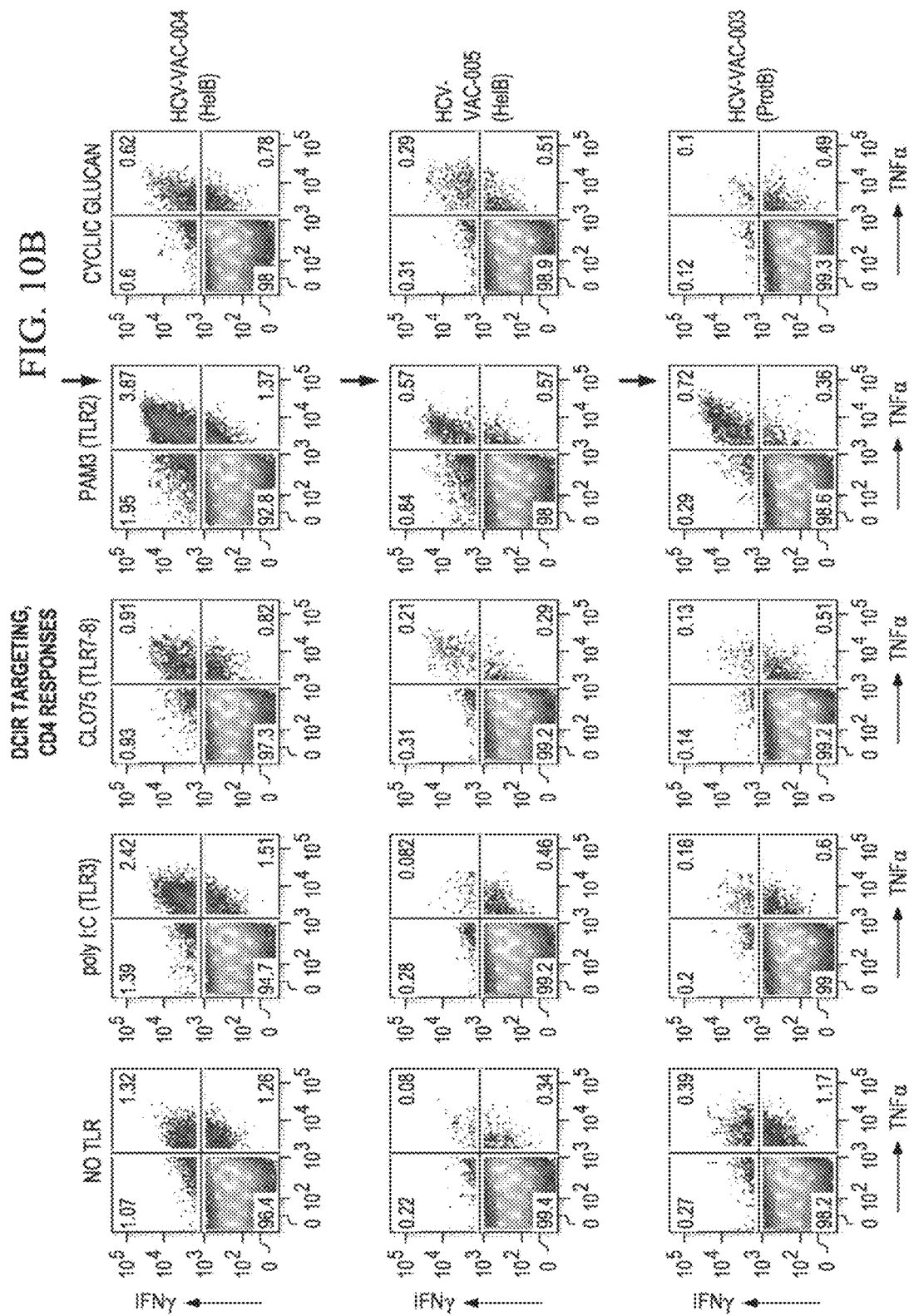

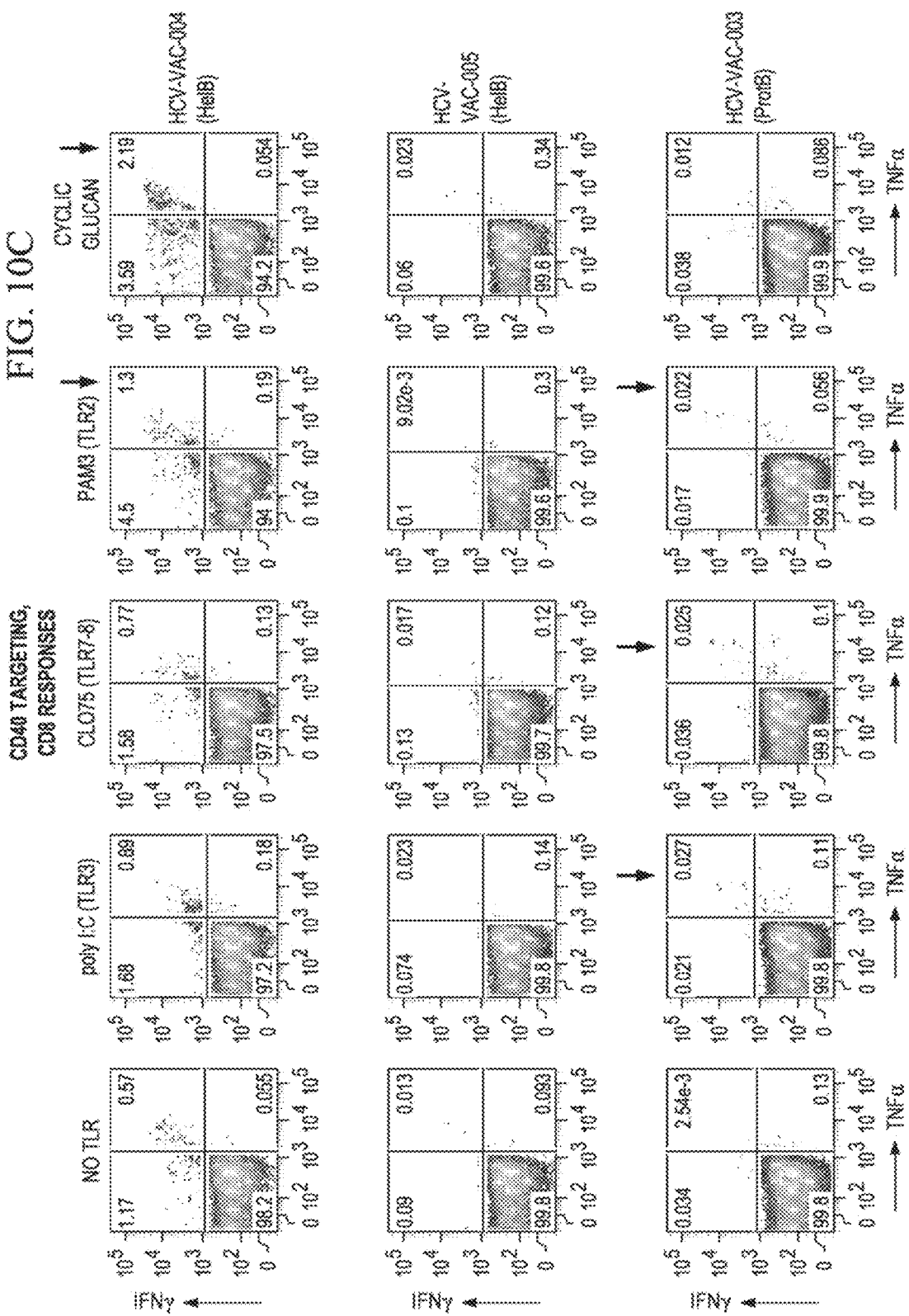

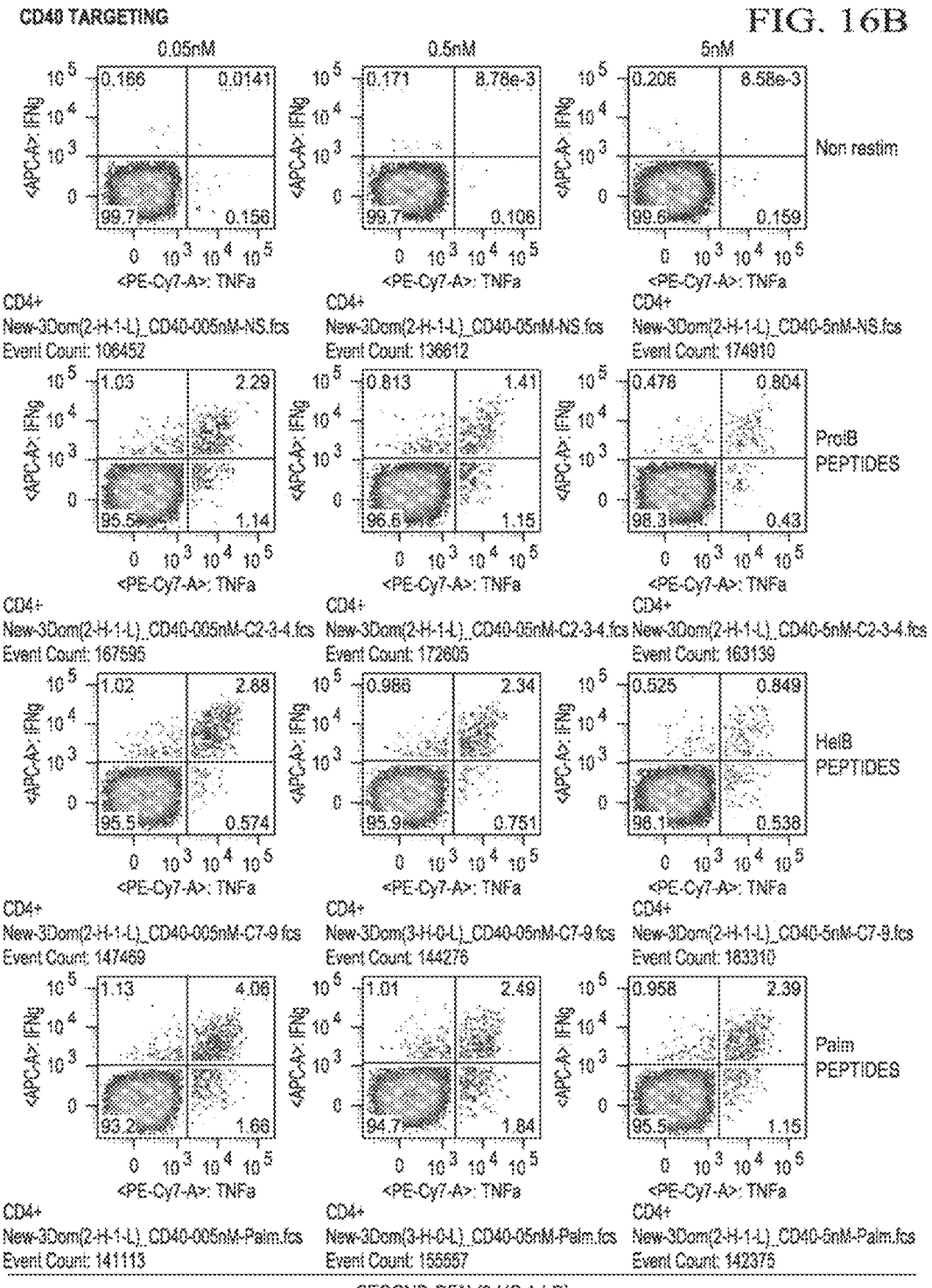

COMPOSITIONS AND METHODS TO IMMUNIZE AGAINST HEPATITIS C VIRUS

CROSS-REFERENCE TO RELATED APPLICATIONS

This application is a divisional of co-pending U.S. patent application Ser. No. 13/430,206 filed Mar. 26, 2012, which claims priority to U.S. Provisional Application Ser. No. 61/467,840, filed Mar. 25, 2011, and U.S. Provisional Application Ser. No. 61/529,700, filed Aug. 31, 2011, the entire contents of each of which are incorporated herein by reference.

TECHNICAL FIELD OF THE INVENTION

The present invention relates in general to the field of immunology, and more particularly, to hepatitis C virus (HCV) immunization, vaccines, and targeting of the HCV peptides to human dendritic cells. The application also describes a bi-functional antibody fused to a HCV target antigen(s) that is directed against a dendritic cell (DC)-specific receptor.

STATEMENT OF FEDERALLY FUNDED RESEARCH

None.

REFERENCE TO A SEQUENCE LISTING

The instant application contains a Sequence Listing which has been submitted in ASCII format via EFS-Web and is hereby incorporated by reference in its entirety. Said ASCII copy, created on Mar. 15, 2012, is named BHCS1118.txt and is 388,419 bytes in size.

BACKGROUND OF THE INVENTION

Without limiting the scope of the application, its background is described in connection with immunostimulatory methods and compositions, including vaccines, and increased effectiveness in antigen presentation of HCV peptides in relation to HCV immunization and vaccines.

U.S. Patent Application Publication No. 2009/0238822 (Rajan et al. 2009) relates to chimeric antigens for targeting and activating antigen presenting cells to elicit cellular and humoral immune responses. The Rajan invention describes compositions and methods that contain or use one or more chimeric antigens that contain one or more pre-selected HCV antigen(s), and an immunoglobulin fragment. The invention further discloses chimeric antigens, comprising an HCV antigen and a Fc fragment of an immunoglobulin for eliciting an immune response against said antigen. The immune response is said to be enhanced upon presenting the host immune system with an immune response domain (HCV antigen from HCV core, envelope, or non-structural protein fragments) and a target-binding domain (an Fc fragment).

U.S. Patent Application Publication No. 2008/0241170 (Zurawski et al. 2008) discloses compositions and methods for making and using vaccine that specifically target (deliver) antigens to antigen-presenting cells for the purpose of eliciting potent and broad immune responses directed against the antigen. The purpose is primarily to evoke protective or therapeutic immune responses against the agent (pathogen or cancer) from which the antigen was derived.

U.S. Patent Application Publication 2010/0239575 (Banchereau et al. 2010) refers to compositions and methods for the expression, secretion, and use of novel compositions for use as, e.g., vaccines and antigen delivery vectors, to delivery antigens to antigen presenting cells. In one embodiment, the vector is an anti-CD40 antibody, or fragments thereof, and one or more antigenic peptides linked to the anti-CD40 antibody or fragments thereof, including humanized antibodies.

SUMMARY OF THE INVENTION

The present invention describes immunostimulatory compositions, vaccines, HCV vaccines, HCV antigen presenting dendritic cells, methods for increasing effectiveness of HCV antigen presentation by an antigen presenting cell, methods for increasing effectiveness of HCV antigen presentation by an antigen presenting cell, methods for increasing effectiveness of antigen presentation by an antigen presenting cell, methods for a treatment, a prophylaxis or a combination thereof against hepatitis C in a human subject, methods of providing immunostimulation by activation of one or more dendritic cells, methods to treat or prevent hepatitis C in a subject, and methods for generating a HCV presenting dendritic cell. The present invention further describes virus antigens, e.g., proteins and peptides corresponding to HCV proteins or fragments thereof, fused to heavy and/or light chain of antibodies, or fragments thereof specific for dendritic cells (DCs). The vaccine composition as described herein delivers HCV antigen specifically to DCs for the purpose of invoking an immune response. The vaccine composition may also promote efficient recall memory in hepatitis C patients.

In one embodiment the instant invention discloses an immunostimulatory composition for generating an immune response for a prophylaxis, a therapy, or any combination thereof against a Hepatitis C infection in a human or animal subject comprising: one or more antibodies or fragments thereof specific for a dendritic cell (DC) and one or more HCV antigens attached to the one or more antibodies or fragments thereof. In one aspect the composition disclosed hereinabove further comprises at least one Toll-Like Receptor (TLR) agonist selected from the group consisting of TLR1, TLR2, TLR3, TLR4, TLR5, TLR6, TLR7, and TLR8 agonists. In another aspect the composition further comprises an optional pharmaceutically acceptable carrier that is effective, in combination, to produce the immune response for prophylaxis, for therapy, or any combination thereof in the human or animal subject in need of immunostimulation. In yet another aspect the DC-specific antibody or fragment is specific for a DC specific receptor, wherein the DC-specific antibody or fragment is selected from an antibody that specifically binds to MHC class I, MHC class II, CD1, CD2, CD3, CD4, CD8, CD11b, CD14, CD15, CD16, CD19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fcγ receptor, LOX-1, and ASPGR.

In the composition of the instant invention the HCV antigens comprises a peptide sequence derived from a HCV 1a genotype protein or a fragment thereof and the HCV antigens are selected from the group consisting of protein E1, envelope protein E2, non-structural protein NS3, non-structural protein NS4b, non-structural protein NS5b, and a fragment thereof. The one or more HCV antigens are selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and a fragment thereof and from the group consisting of SEQ ID NO: 8, SEQ ID NO: 9, SEQ ID NO: 10, SEQ ID NO: 12, SEQ ID NO: 14, E1b, and a fragment thereof. In one aspect of the composition of the instant invention the composition comprises a recombinant antibody that comprises a fusion protein and the one or more HCV antigen are at a C-terminal position relative to the one or more antibody or fragment thereof within a fusion protein. In another aspect the composition comprises a recombinant antibody, and the one or more HCV antigens are fused to a C-terminus of a heavy chain of the antibody. In yet another aspect the composition comprises a recombinant antibody, and the one or more HCV antigens are fused to a C-terminus of a light chain of the one or more antibody or fragment thereof specific for a DC.

The one or more HCV antigens are selected from the group consisting of SEQ ID NO: 12-linker A-SEQ ID NO: 13, SEQ ID NO: 12-linker A-SEQ ID NO: 11, SEQ ID NO: 12-linker B-SEQ ID NO: 14, SEQ ID NO: 14-linker B-SEQ ID NO: 12, SEQ ID NO: 12-linker B-SEQ ID NO: 10, SEQ ID NO: 10-linker B-SEQ ID NO: 12, SEQ ID NO: 9-linker B-SEQ ID NO: 10, SEQ ID NO: 10-linker B-SEQ ID NO: 9, SEQ ID NO: 10-linker B-SEQ ID NO: 14, SEQ ID NO: 14-linker B-SEQ ID NO: 10, SEQ ID NO: 9-linker B-SEQ ID NO: 12, SEQ ID NO: 12-linker B-SEQ ID NO: 9, SEQ ID NO: 8-linker B-E1b. SEQ ID NO: 12-linker B-SEQ ID NO: 10-linker C-SEQ ID NO: 14, SEQ ID NO: 12-linker B-SEQ ID NO: 14-linker C-SEQ ID NO: 10, SEQ ID NO: 10-linker B-SEQ ID NO: 12-linker C-SEQ ID NO: 14, SEQ ID NO: 10-linker B-SEQ ID NO: 14-linker C-SEQ ID NO: 12, SEQ ID NO: 14-linker B-SEQ ID NO: 12-linker C-SEQ ID NO: 10, SEQ ID NO: 14-linker B-SEQ ID NO: 10-linker C-SEQ ID NO: 12, and SEQ ID NO: 12-linker B-SEQ ID NO: 10-linker C-SEQ ID NO: 14-linker D-SEQ ID NO: 8. In another aspect the one or more HCV antigens are attached to a C-terminus of a light chain of the recombinant antibody and selected from a group consisting of: SEQ ID NO: 9; SEQ ID NO: 11, and E1b. In yet another aspect the one or more HCV antigens are selected from the group consisting of SEQ ID NO: 9 fused to the C-terminus of a light chain and SEQ ID NO: 10-linker B-SEQ ID NO: 12-linker C-SEQ ID NO: 14 fused to the C-terminus of the heavy chain of the antibody. In a related aspect the one or more HCV antigen are chemically coupled to the one or more antibodies or fragments thereof or are attached to the one or more antibodies or fragments thereof via an affinity association. In a specific aspect the DC-specific antibody is humanized. In another aspect the composition is optimized to be administered to the human or animal subject by an oral route, a nasal route, topically, or as an injection.

Another embodiment of the present invention discloses a vaccine comprising: one or more antibodies or fragments thereof specific for a dendritic cell (DC); and one or more HCV antigens attached to the one or more antibodies or fragments thereof. The vaccine described herein further comprises at least one Toll-Like Receptor (TLR) agonist selected from the group consisting of TLR1, TLR2, TLR3, TLR4, TLR5, TLR6, TLR7, and TLR8 agonists and an optional pharmaceutically acceptable carrier or an adjuvant that is effective, in combination, to produce an immune response for prophylaxis, for therapy, or any combination thereof in the human or animal subject in need of immunostimulation. In one aspect of the vaccine the DC-specific antibody or fragment is specific for a dendritic cell specific receptor. In another aspect the HCV antigen comprises a peptide sequence derived from a HCV 1a genotype protein or a fragment thereof, wherein the HCV antigen is selected from the group consisting of protein E1, envelope protein E2, non-structural protein NS3, non-structural protein NS4b, non-structural protein NS5b, and a fragment thereof. In other related aspects the DC-specific antibody is humanized and the composition is optimized to be administered to the human or animal subject by an oral route, a nasal route, topically, or as an injection.

In yet another embodiment the instant invention discloses a Hepatitis C vaccine (HCV) comprising a fusion protein comprising: (i) one or more antibodies or fragments thereof specific for a dendritic cell (DC), (ii) one or more HCV antigens located C-terminal of the antibodies or fragments thereof, (iii) at least one Toll-Like Receptor (TLR) agonist which is selected from the group consisting of TLR1, TLR2, TLR3, TLR4, TLR5, TLR6, TLR7, and TLR8 agonists, and (iv) one or more optional pharmaceutically acceptable carriers and adjuvants, wherein the vaccine is effective to produce an immune response, for a prophylaxis, a therapy, or any combination thereof against hepatitis C in a human or an animal subject in need thereof. In one aspect the vaccine comprises one or more optional agents selected from the group consisting of an agonistic anti-CD40 antibody, an agonistic anti-CD40 antibody fragment, a CD40 ligand (CD40L) polypeptide, a CD40L polypeptide fragment, anti-4-1BB antibody, an anti-4-1BB antibody fragment, 4-1BB ligand polypeptide, a 4-1BB ligand polypeptide fragment, IFN-γ, TNF-α, type 1 cytokines, type 2 cytokines or combinations and modifications thereof.

The instant invention in one embodiment discloses a method for increasing effectiveness of Hepatitis C virus (HCV) antigen presentation by an antigen presenting cell (APC) comprising the steps of: (i) providing an antibody conjugate comprising a dendritic cell (DC) specific antibody or a fragment thereof and one or more native or engineered HCV antigenic peptides, (ii) providing one or more APCs; and (iii) contacting the APC with the conjugate, wherein the antibody-antigen complex is processed and presented for T cell recognition. In a specific aspect of the method the antigen presenting cell comprises a dendritic cell (DC).

In another embodiment the instant invention provides a method for increasing effectiveness of antigen presentation by an antigen presenting cell (APC) comprising the steps of: i) isolating and purifying one or more dendritic cell (DC)-specific antibody or a fragment thereof, ii) providing one or more HCV antigens or antigenic peptides, iii) loading or chemically coupling the one or more HCV antigens or antigenic peptides to the DC-specific antibody to form an antibody-antigen conjugate, and iv) contacting the antigen presenting cell with the conjugate, wherein the antibody-antigen complex is processed and presented for T cell recognition.

The method as described hereinabove further comprises adding at least one Toll-Like Receptor (TLR) agonist which is selected from the group consisting of TLR1, TLR2, TLR3, TLR4, TLR5, TLR6, TLR7, and TLR8 agonists and one or more optional steps comprising i) adding one or more optional agents selected from the group consisting of an agonistic anti-CD40 antibody, an agonistic anti-CD40 antibody fragment, a CD40 ligand (CD40L) polypeptide, a CD40L polypeptide fragment, anti-4-1BB antibody, an anti-4-1BB antibody fragment, 4-1BB ligand polypeptide, a 4-1BB ligand polypeptide fragment, IFN-γ, TNF-α, type 1 cytokines, type 2 cytokines or combinations and modifications thereof to the antibody-antigen conjugate and the TLR agonist prior to contacting the antigen presenting cells, ii) measuring a level of one or more agents selected from the group consisting of IFN-γ, TNF-α, IL-12p40, IL-4, IL-5, and IL-13, wherein a change in the level of the one or more agents is indicative of the increase in the effectiveness antigen presentation by the antigen presenting cell, and iii) adding one or more optional agents selected from the group consisting of an agonistic anti-CD40 antibody, an agonistic anti-CD40 antibody fragment, a CD40 ligand (CD40L) polypeptide, a CD40L polypeptide fragment, anti-4-1BB antibody, an anti-4-1BB antibody fragment, 4-1BB ligand polypeptide, a 4-1BB ligand polypeptide fragment, IFN-γ, TNF-α, type 1 cytokines, type 2 cytokines or combinations and modifications thereof.

In yet another embodiment the instant invention provides method for a treatment, a prophylaxis or a combination thereof against hepatitis C in a human subject comprising the steps of: identifying the human subject in need of the treatment, the prophylaxis, or a combination thereof against the hepatisti and administering a vaccine composition comprising one or more antibodies or fragments thereof specific for a dendritic cell (DC) and one or more HCV antigens attached to the one or more antibodies or fragments thereof. In one aspect of the method the vaccine composition further comprises at least one Toll-Like Receptor (TLR) agonist which is selected from the group consisting of TLR1, TLR2, TLR3, TLR4, TLR5, TLR6, TLR7, and TLR8 agonists, and one or more optional pharmaceutically acceptable carriers and adjuvants, wherein the conjugate and agonist are each comprised in an amount such that, in combination with the other, are effective to produce an immune response, for the prophylaxis, the therapy or any combination thereof against the influenza in the human subject. In another aspect the vaccine composition further comprises one or more optional agents selected from the group consisting of an agonistic anti-CD40 antibody, an agonistic anti-CD40 antibody fragment, a CD40 ligand (CD40L) polypeptide, a CD40L polypeptide fragment, anti-4-1BB antibody, an anti-4-1BB antibody fragment, 4-1BB ligand polypeptide, a 4-1BB ligand polypeptide fragment, IFN-γ, TNF-α, type 1 cytokines, type 2 cytokines or combinations and modifications thereof. In yet another aspect the vaccine is administered to the human subject by an oral route, a nasal route, topically or as an injection.

In another aspect the one or more antibodies or fragments thereof specific for a dendritic cell comprises antibodies specifically binds to MHC class I, MHC class II, CD1, CD2, CD3, CD4, CD8, CD11b, CD14, CD15, CD16, CD19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fey receptor, LOX-1, or ASPGR. In yet another aspect the HCV antigen is selected from the group consisting of protein E1, envelope protein E2, non-structural protein NS3, non-structural protein NS4b, non-structural protein NS5b, and a fragment thereof, from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and a fragment thereof, or from the group consisting of SEQ ID NO: 8, SEQ ID NO: 9, SEQ ID NO: 10, SEQ ID NO: 12, SEQ ID NO: 14, E1b, and a fragment thereof.

A method of providing immunostimulation by activation of one or more dendritic cells (DCs) to a human subject for a prophylaxis, a therapy or a combination thereof against HCV is described in one embodiment of the present invention. The method comprises the steps of: a) identifying the human subject in need of immunostimulation for the prophylaxis, the therapy or a combination thereof against HCV, b) isolating one or more DCs from the human subject, c) exposing the isolated DCs to activating amounts of a composition or a vaccine comprising an anti-dendritic cell immunoreceptor (DCIR) monoclonal antibody or fragments thereof attached to one or more HCV antigens, and d) reintroducing the activated DC complex into the human subject.

The method described above further comprises the steps of contacting the one or more DCs with at least one Toll-Like Receptor (TLR) agonist which is selected from the group consisting of TLR1, TLR2, TLR3, TLR4, TLR5, TLR6, TLR7, and TLR8 agonists and a pharmaceutically acceptable carrier to form an activated DC complex and the step of adding one or more optional agents selected from the group consisting of an agonistic anti-CD40 antibody, an agonistic anti-CD40 antibody fragment, a CD40 ligand (CD40L) polypeptide, a CD40L polypeptide fragment, anti-4-1BB antibody, an anti-4-1BB antibody fragment, 4-1BB ligand polypeptide, a 4-1BB ligand polypeptide fragment, IFN-γ, TNF-α, type 1 cytokines, type 2 cytokines or combinations and modifications thereof to the conjugate and the TLR agonist prior to exposing the DCs. The method disclosed hereinabove further comprises the optional step of measuring a level of one or more agents selected from the group consisting of IFN-γ, TNF-α, IL-12p40, IL-4, IL-5, and IL-13, wherein a change in the level of the one or more agents is indicative of the immunostimulation.

The present invention also discloses a method to treat or prevent Hepatitis C in a subject comprising the step of administering to the subject a fusion protein comprising an antibody or fragment thereof specific for a dendritic cell (DC) and a Hepatitis C virus antigen or antigenic peptide fused to the antibody or fragment thereof. A Hepatitis C virus antigen presenting dendritic cell (DC) is also disclosed in one embodiment of the present invention. The HCV antigen presenting DC further comprises one or more isolated dendritic cells (DCs) in contact with a fusion protein comprising an antibody or fragment thereof specific for the DC, the fusion protein further comprising a HCV peptide.

The present invention describes one or more vaccines against HCV comprising one or more antibodies or fragments thereof specific for a dendritic cell (DC) and one or more HCV antigens or antigenic domains attached to the one or more antibodies or fragments thereof. The vaccine has a general structure given by: H-w, H-w-x, H-w-x-y, or H-w-x-y-z, wherein H represents a heavy chain of an antibody or a fragment thereof specific for a DC, w, x, y, and z represent one or more HCV antigens or domains selected from the group consisting of protein E1, envelope protein E2, non-structural protein NS3, non-structural protein NS4b, non-structural protein NS5b, or any combinations thereof. In one aspect w comprises the HCV antigenic domains selected from the group consisting of ProtA, ProtB, HelB, Palm, E1b, and E2. In another aspect x comprises the HCV antigenic domains selected from the group consisting of Hel C, Hel A, Palm, ProtA, ProtB, and E1b. In yet another aspect comprises the HCV antigenic domains selected from the group consisting of Palm, ProtB, and Protb. In another aspect z comprises HCV antigenic domains selected from E2, ProtA, and HelB. In a related aspect the one or more HCV antigens or antigenic domains are linked or attached to one another by one or more flexible linkers.

Another embodiment disclosed herein relates to a vaccine comprising one or more antibodies or fragments thereof specific for a dendritic cell (DC) and one or more HCV antigens or antigenic domains attached to the one or more antibodies or fragments thereof, wherein the vaccine has a general structure given by L-w-x-y-z, wherein L represents a light chain of an antibody or a fragment thereof specific for a DC, w, x, y, and z represent one or more HCV antigens or domains selected from the group consisting of protein E1, envelope protein E2, non-structural protein NS3, non-structural protein NS4b, non-structural protein NS5b, or any combinations thereof.

In yet another embodiment the present invention discloses a vaccine comprising one or more antibodies or fragments thereof specific for a dendritic cell (DC) and one or more HCV antigens or antigenic domains attached to the one or more antibodies or fragments thereof, wherein the vaccine has a general structure given by:

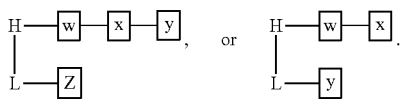

Wherein H represents a heavy chain of an antibody or a fragment thereof specific for a DC, L represents a light chain of an antibody or a fragment thereof specific for the DC, w, x, y, and z represent one or more HCV antigens or domains selected from the group consisting of protein E1, envelope protein E2, non-structural protein NS3, non-structural protein NS4b, non-structural protein NS5b, or any combinations thereof.

Figure 9A:
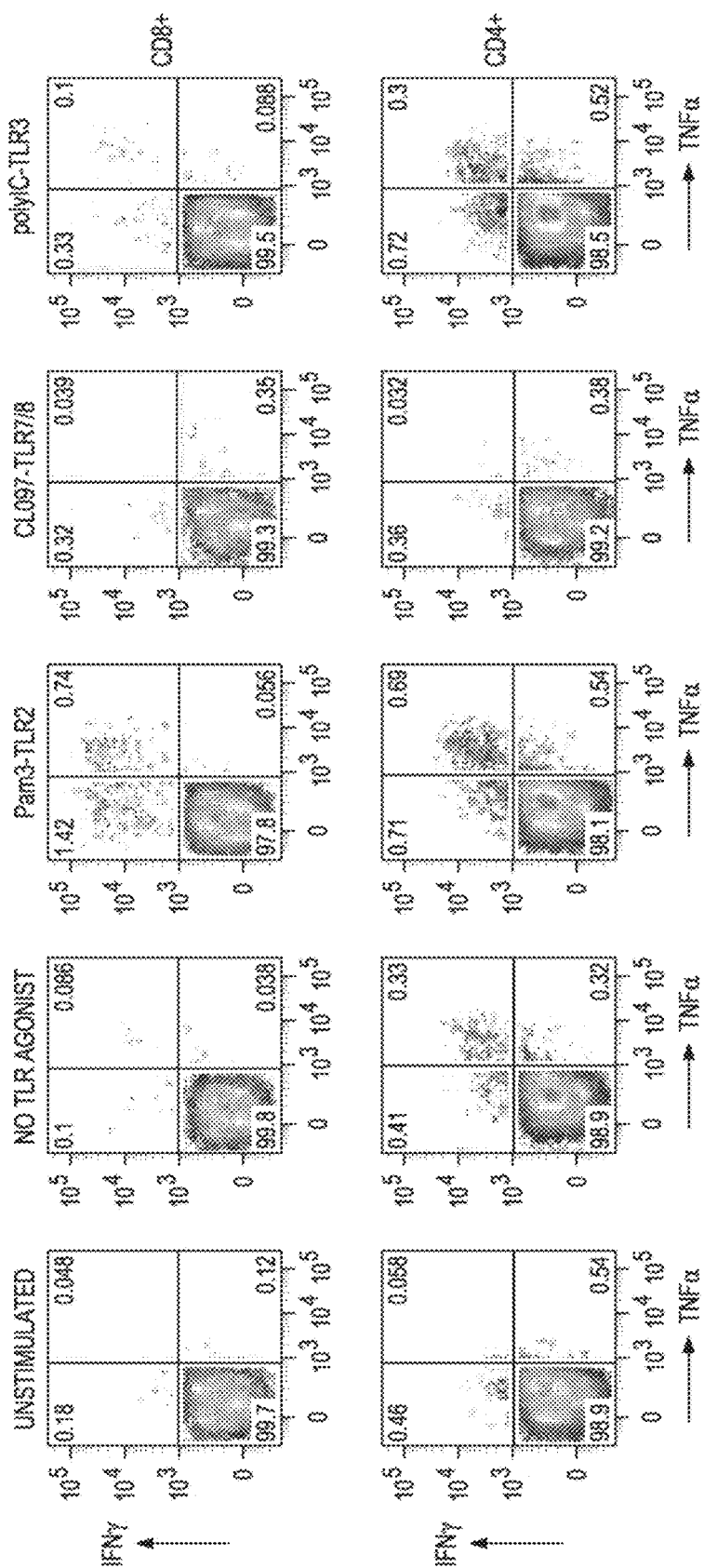
Figure 10A:
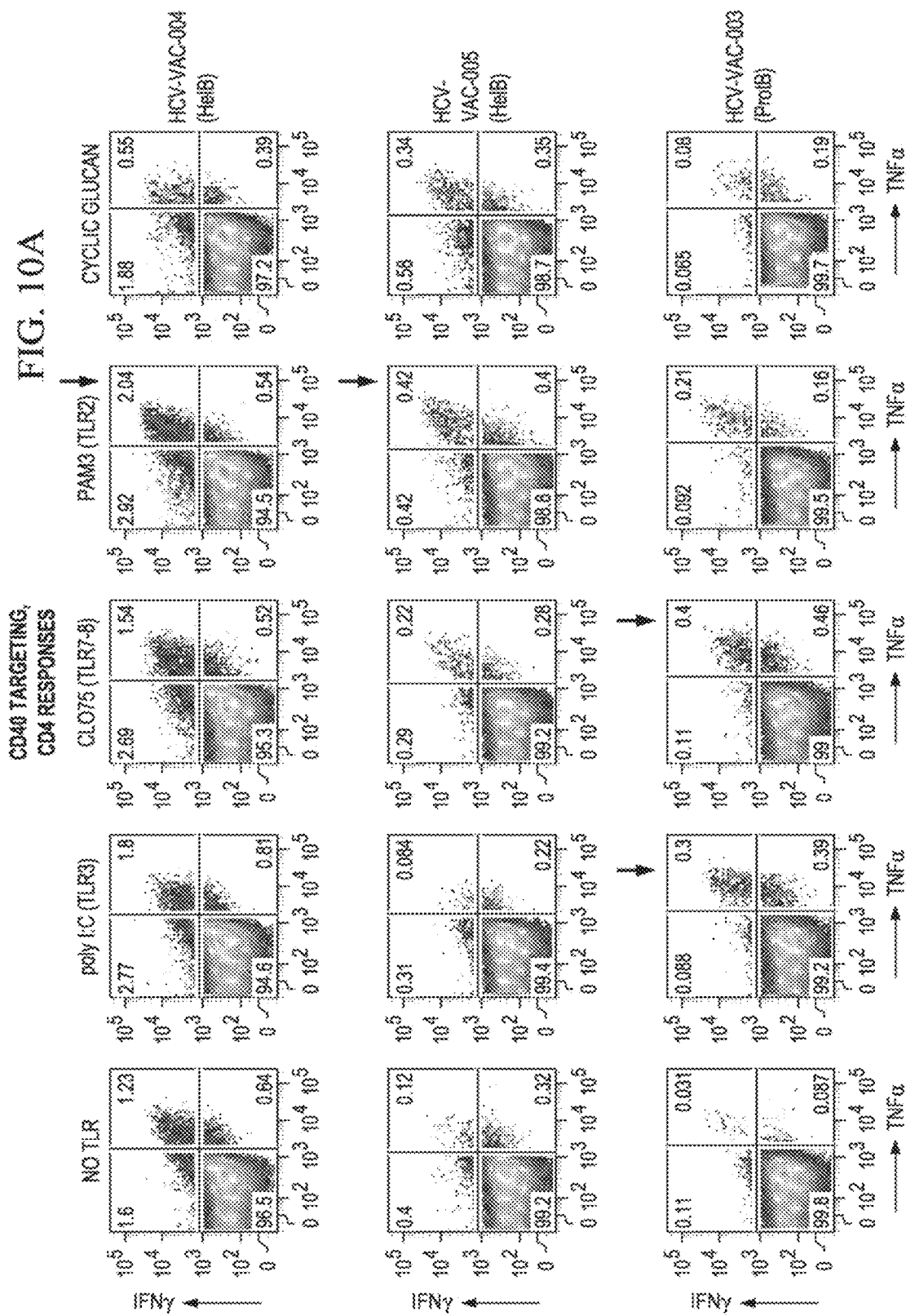
Figure 10D:
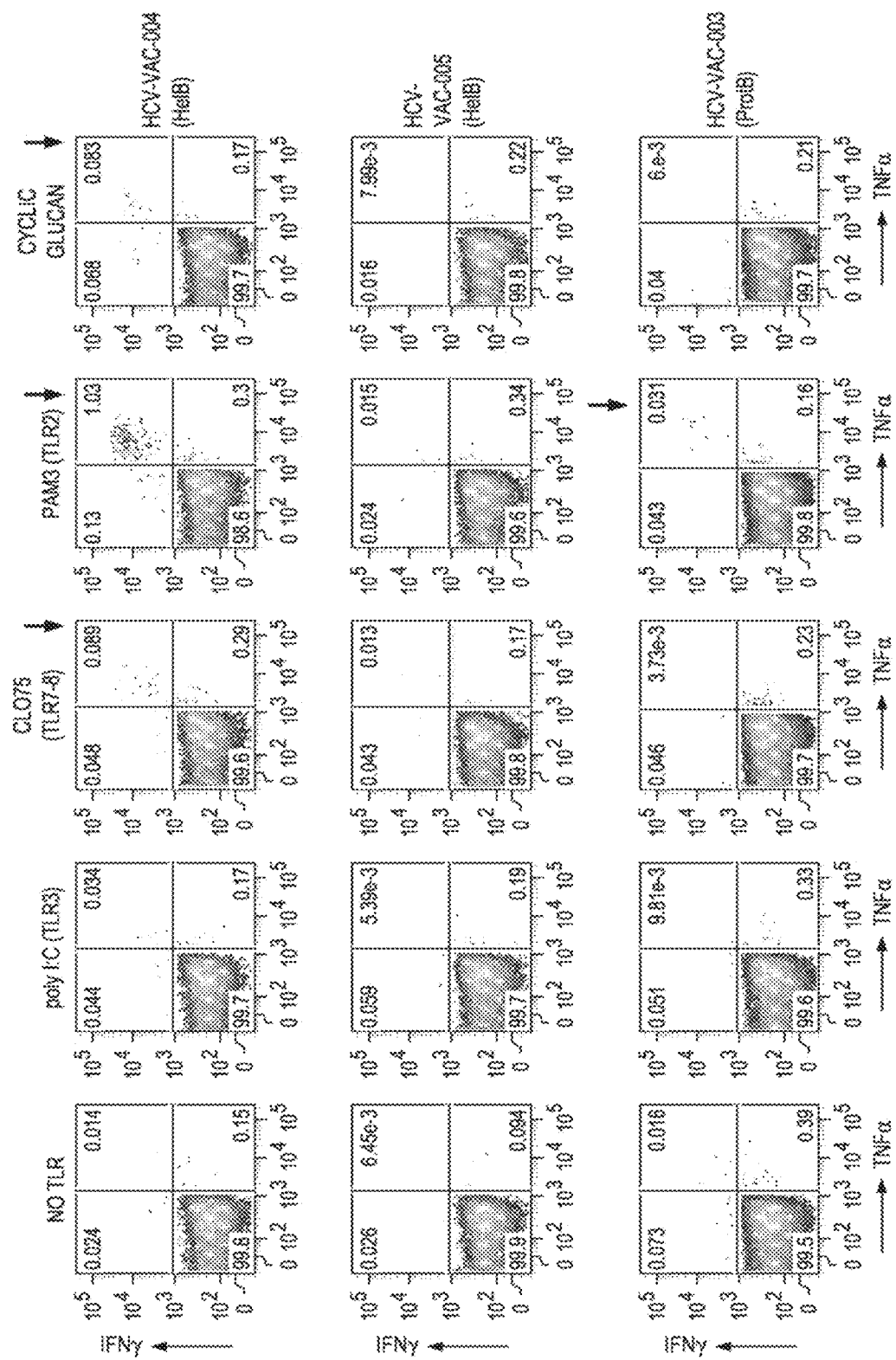
Figure 11:
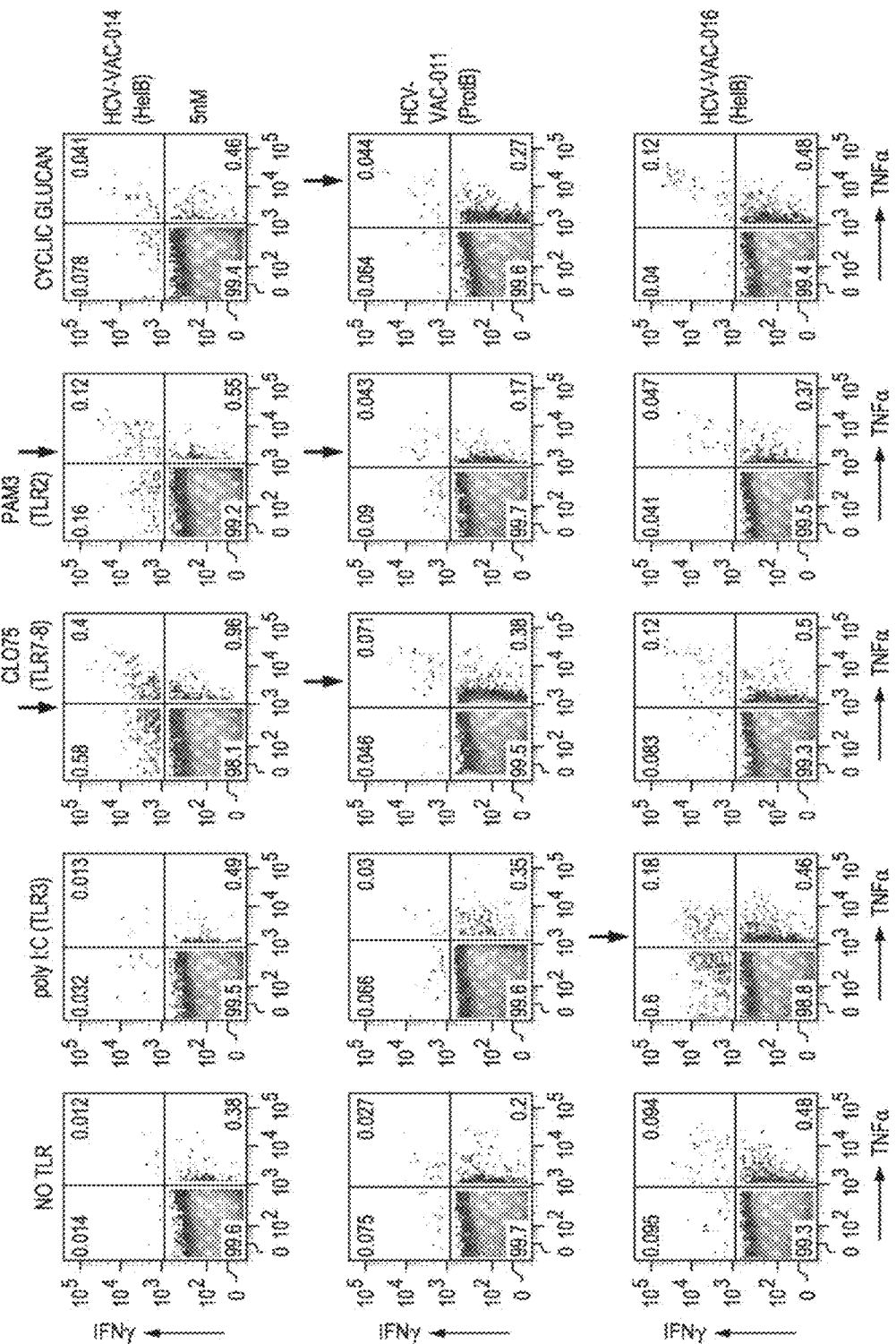
Figure 12A:
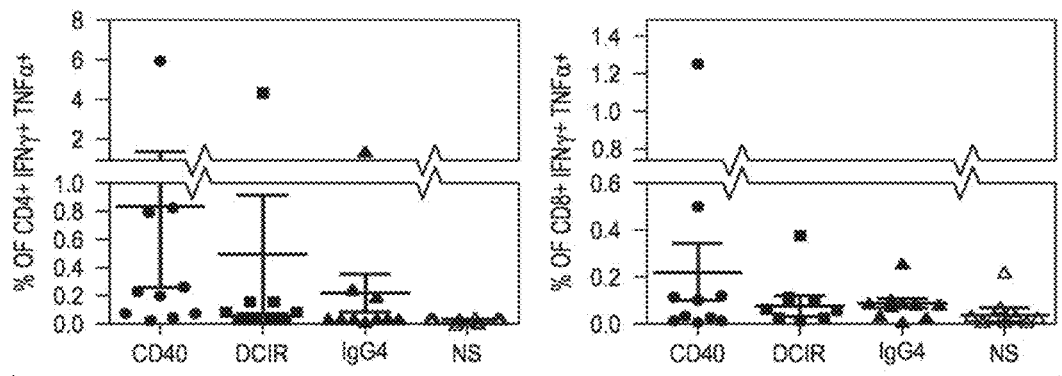
Figure 12B:
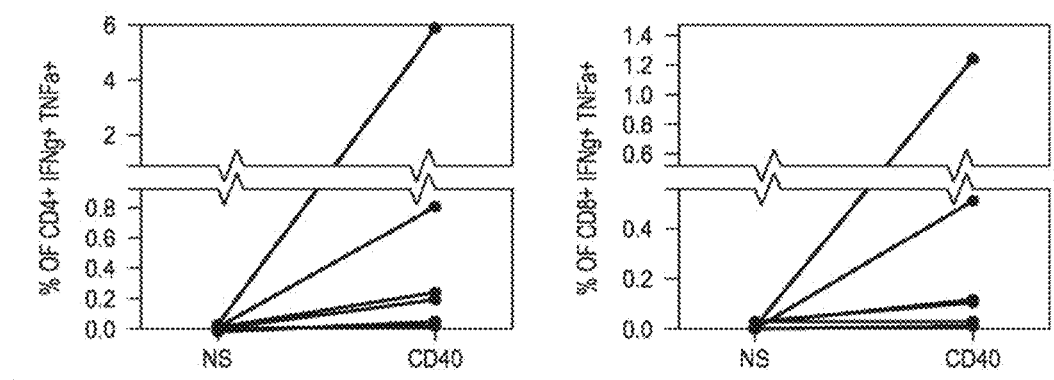
Figure 12C:
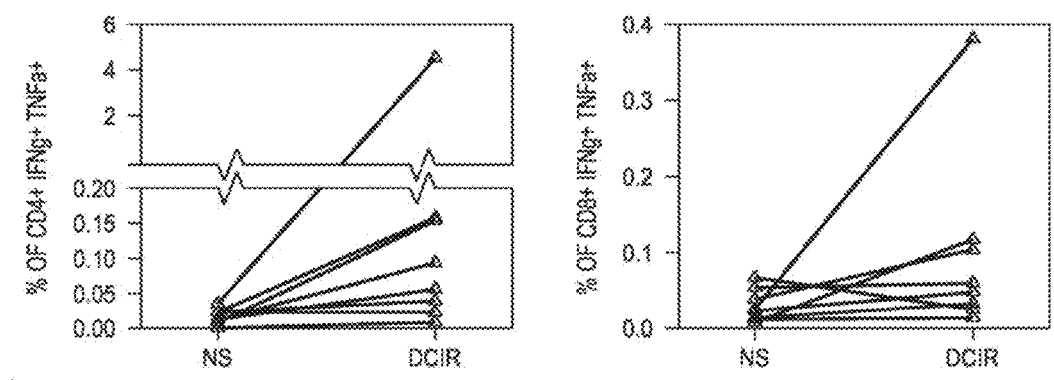
Figure 13A:
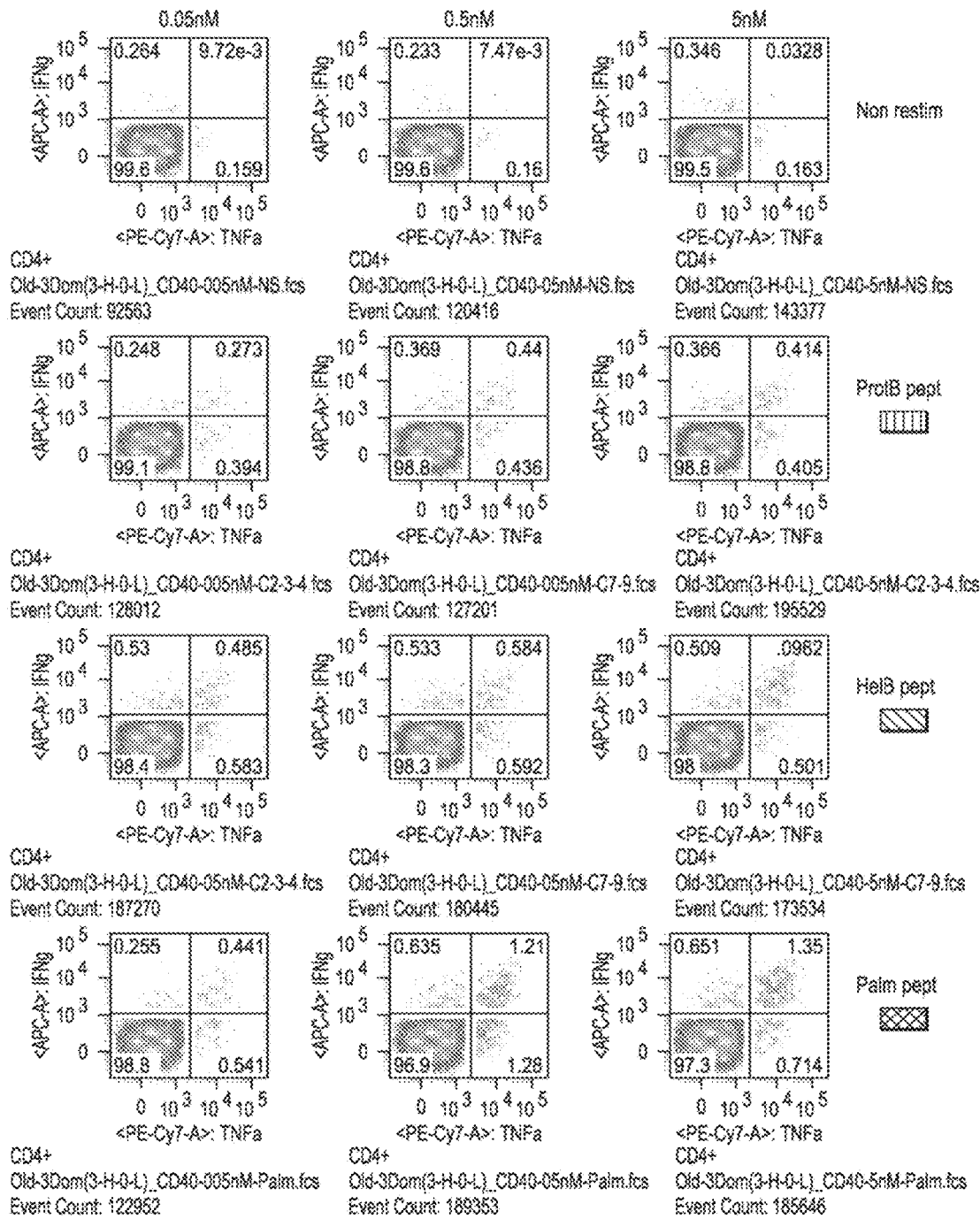
Figure 13B:
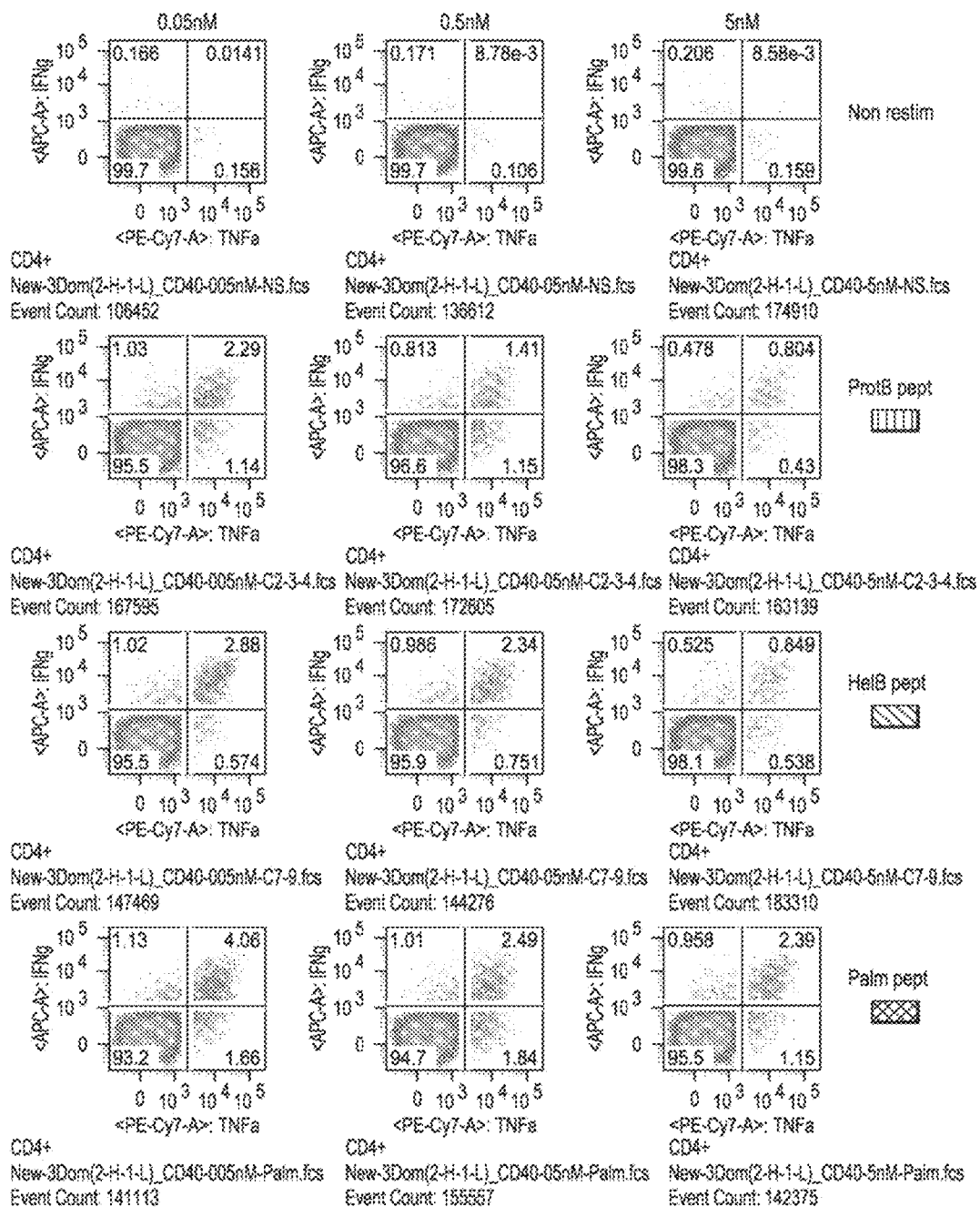
Figure 13C:
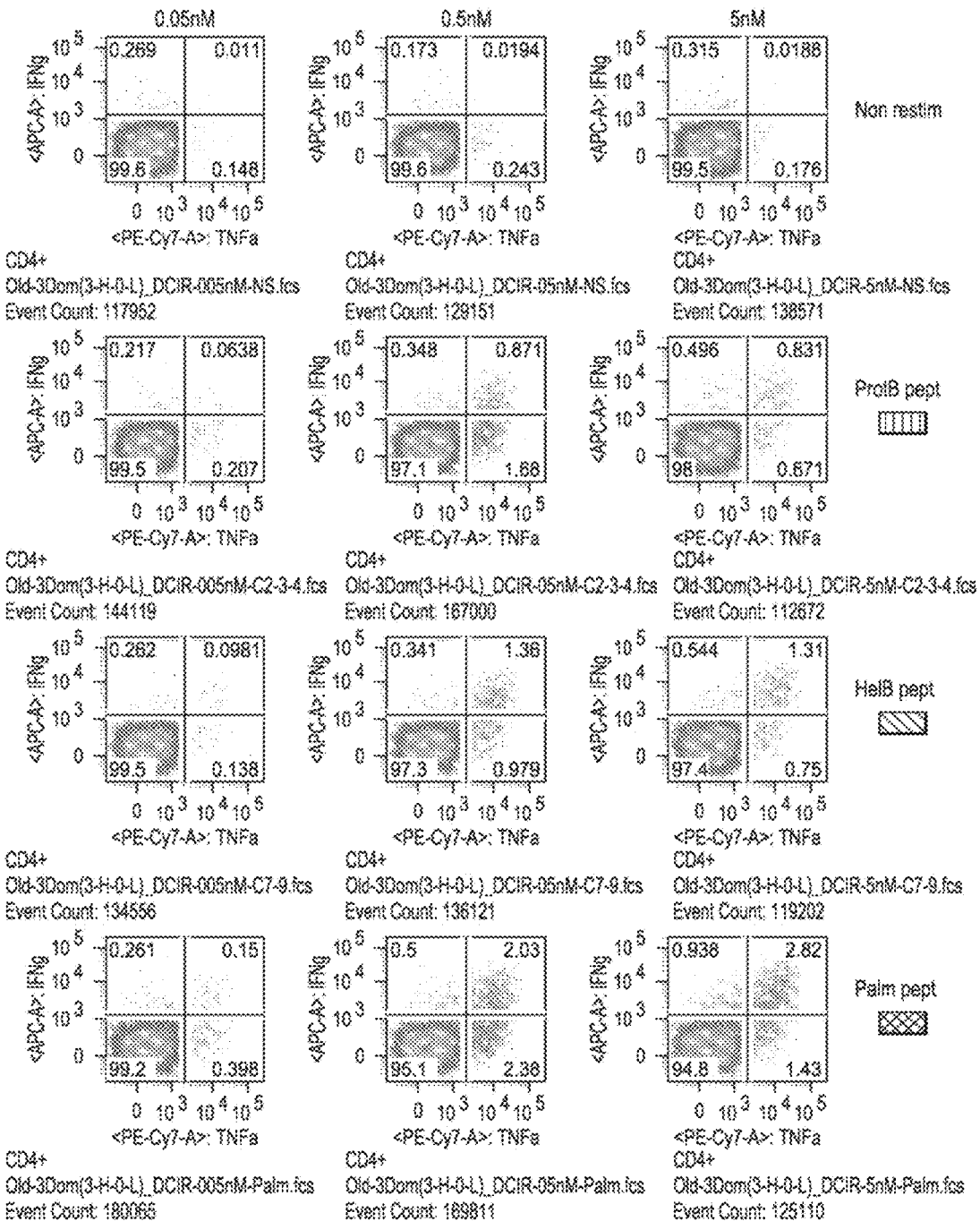
Figure 13D:
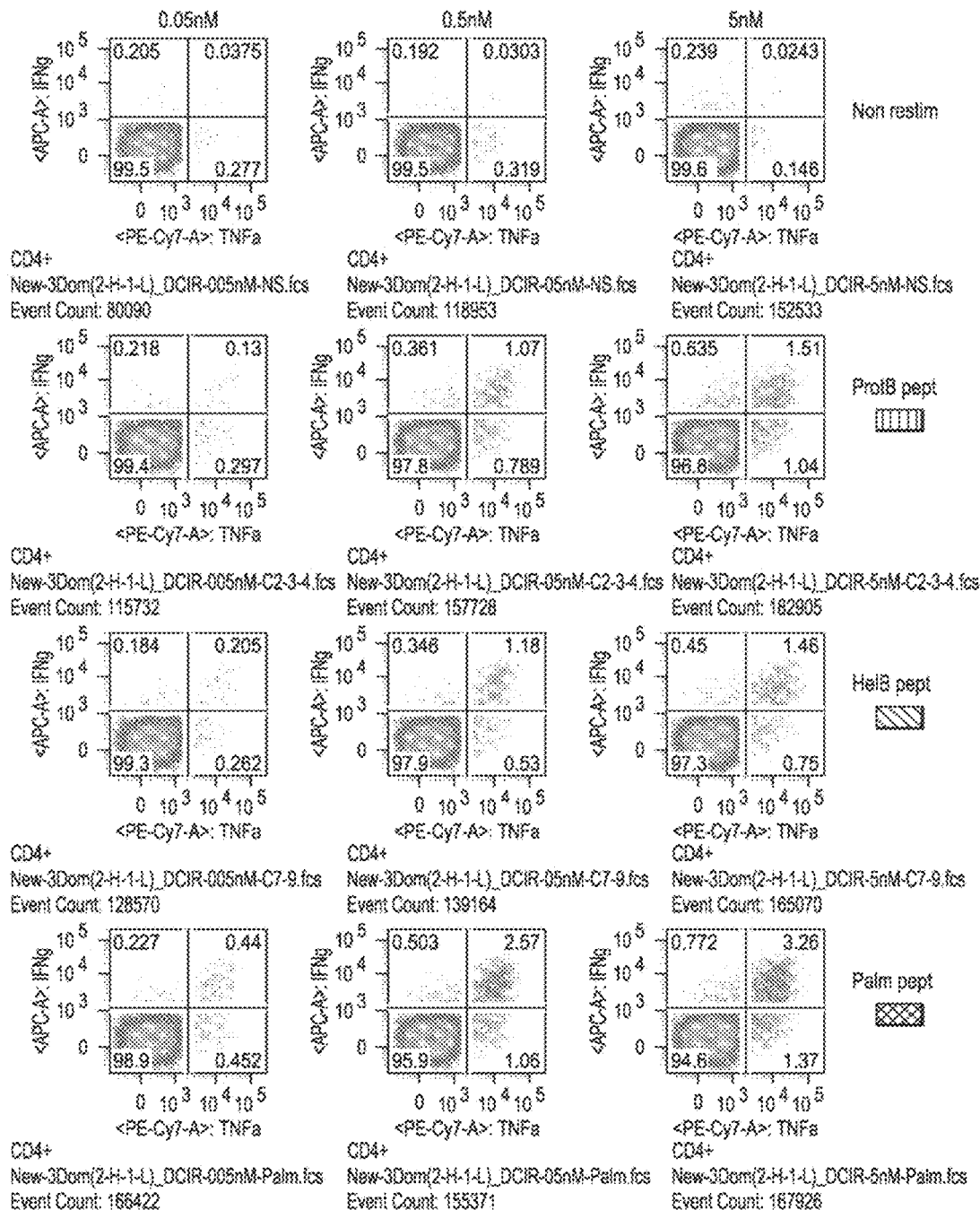
Figure 13E:
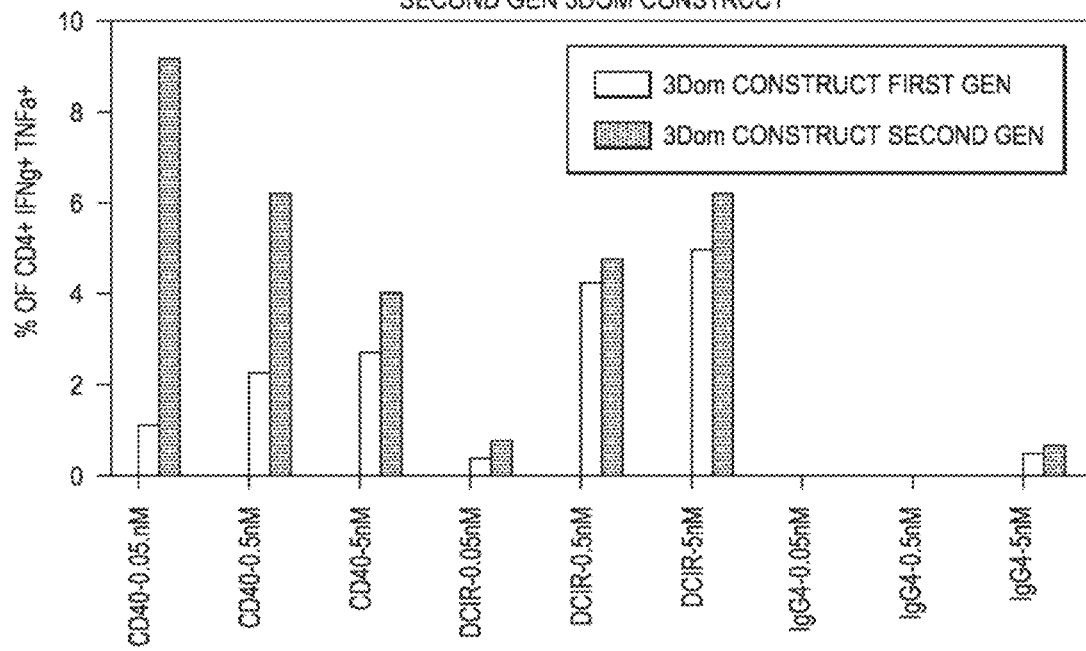
Figure 14A:
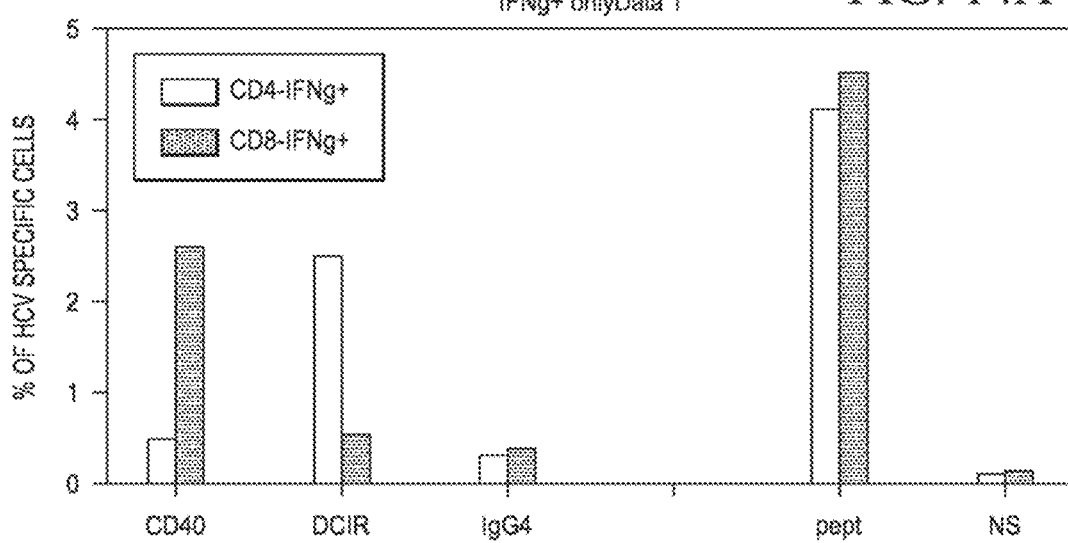
Figure 14B:
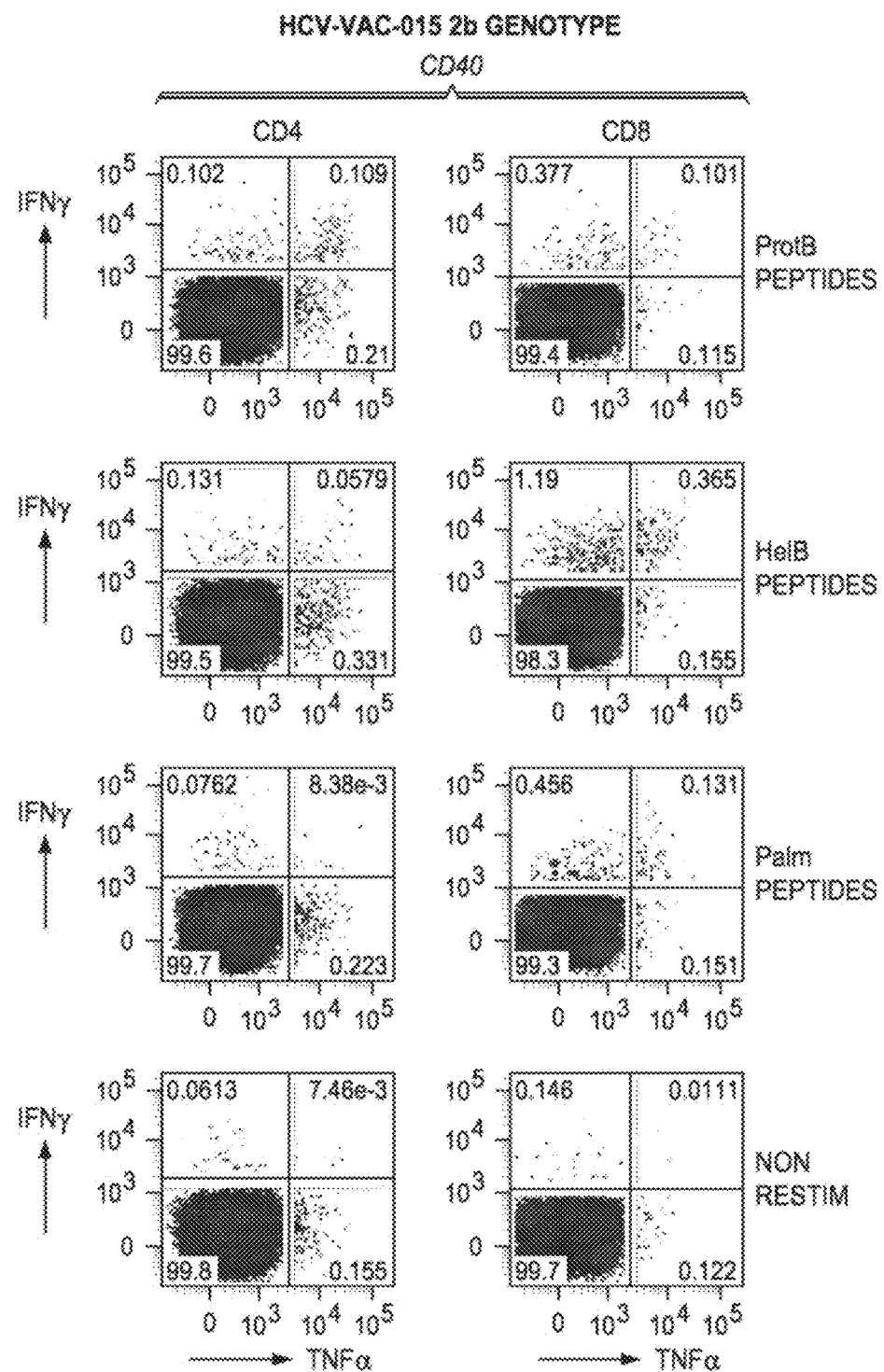
Figure 14C:
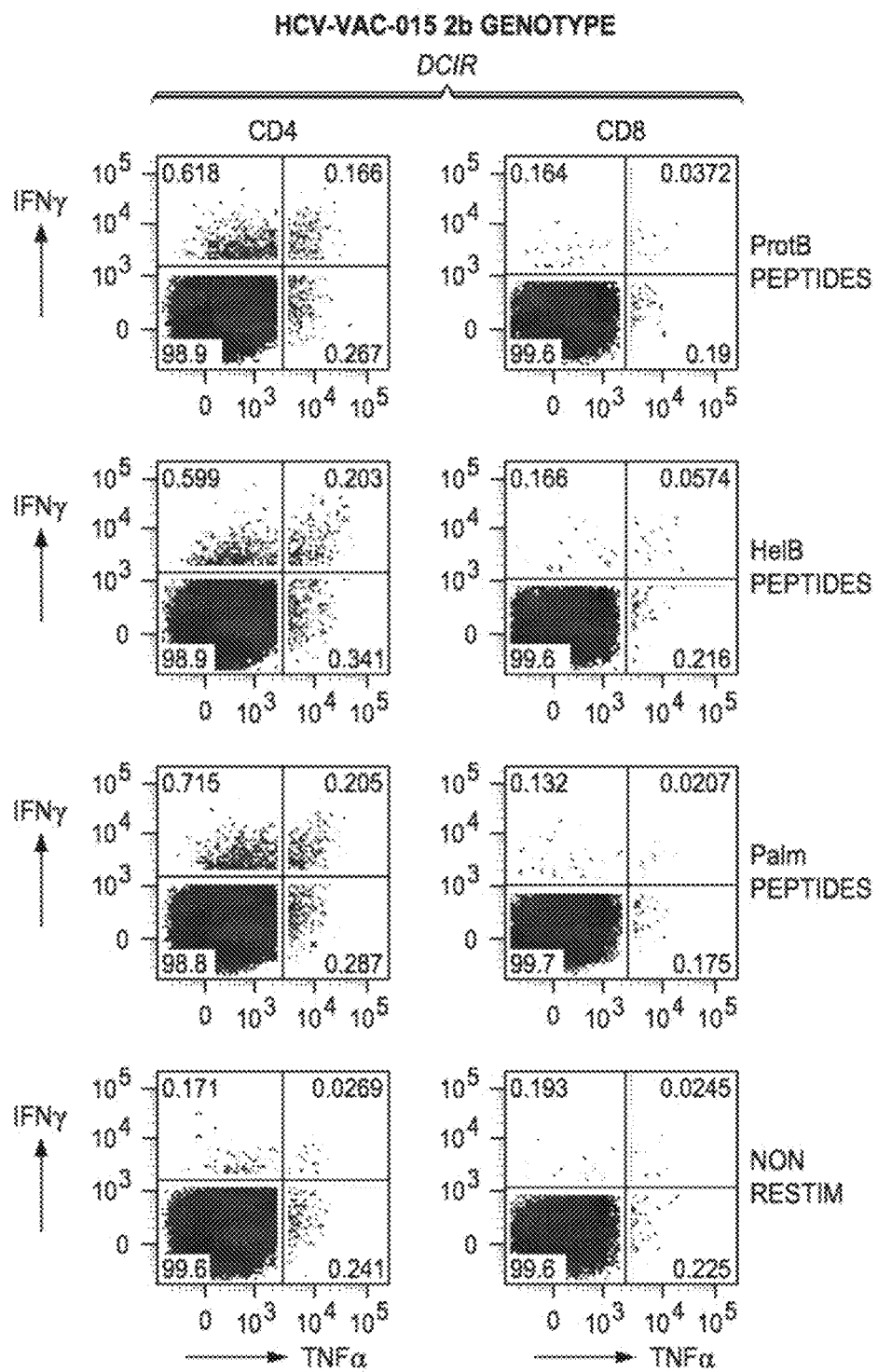
Figure 14D:
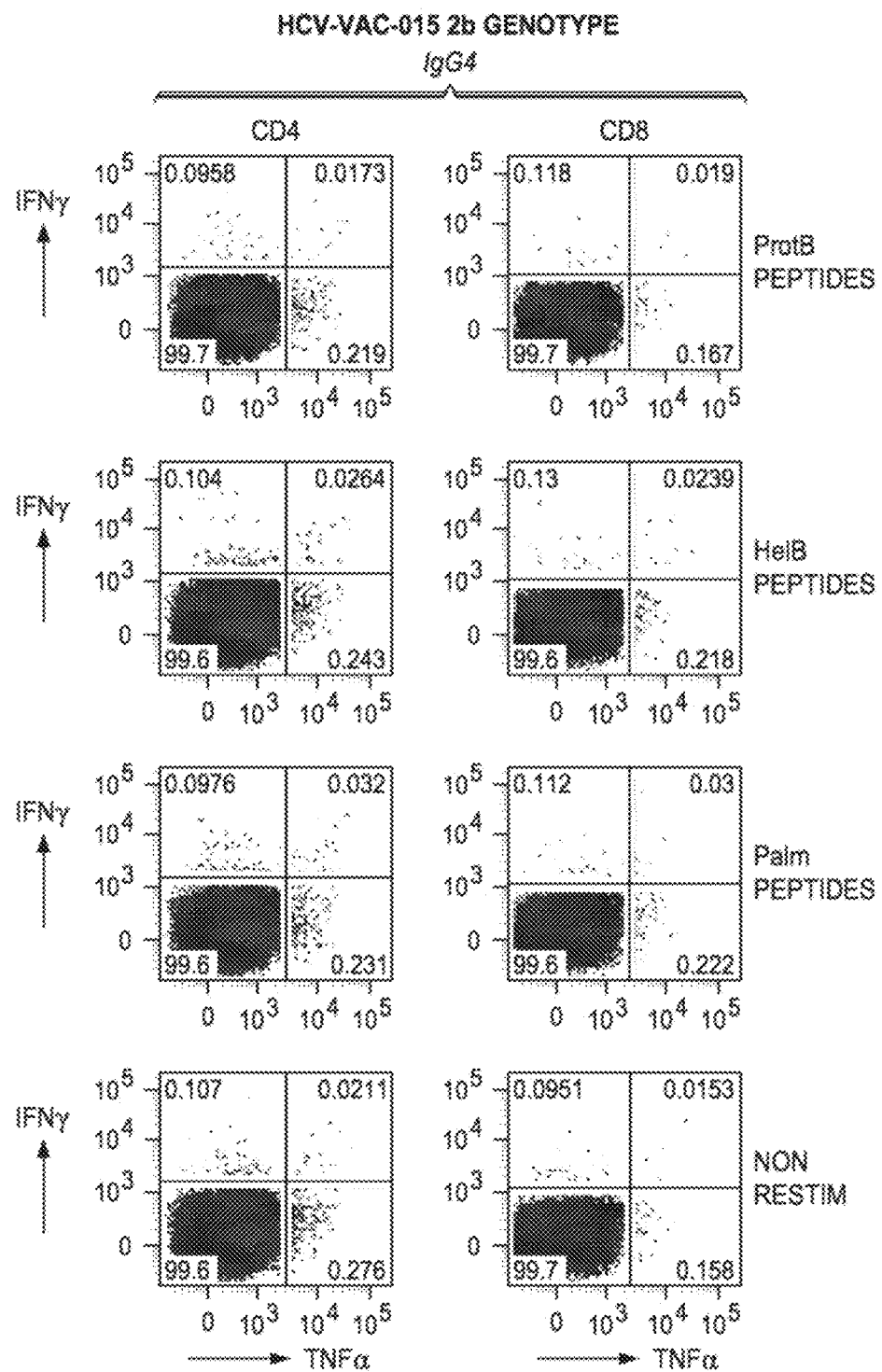
Figure 14E:
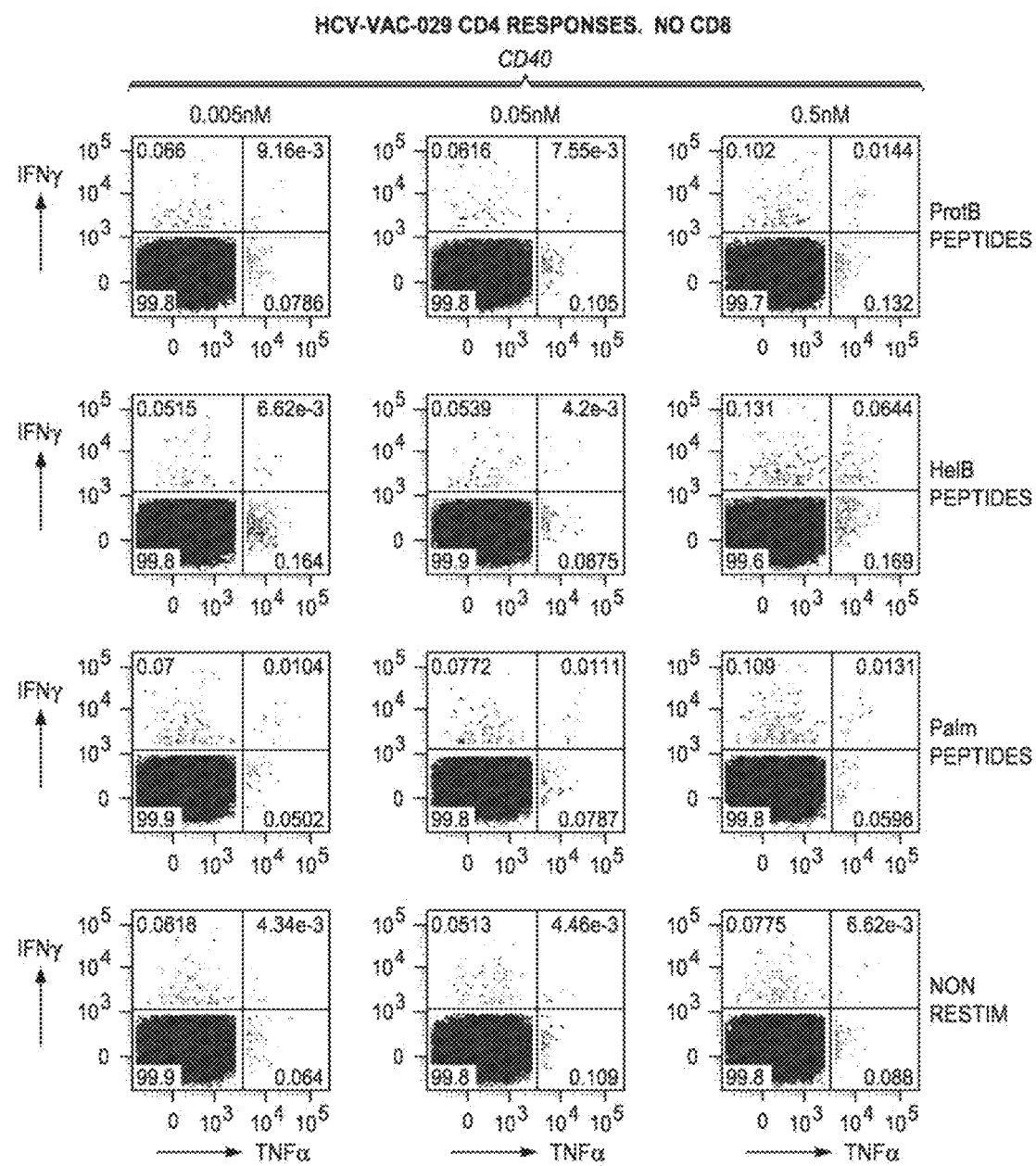
Figure 14F:
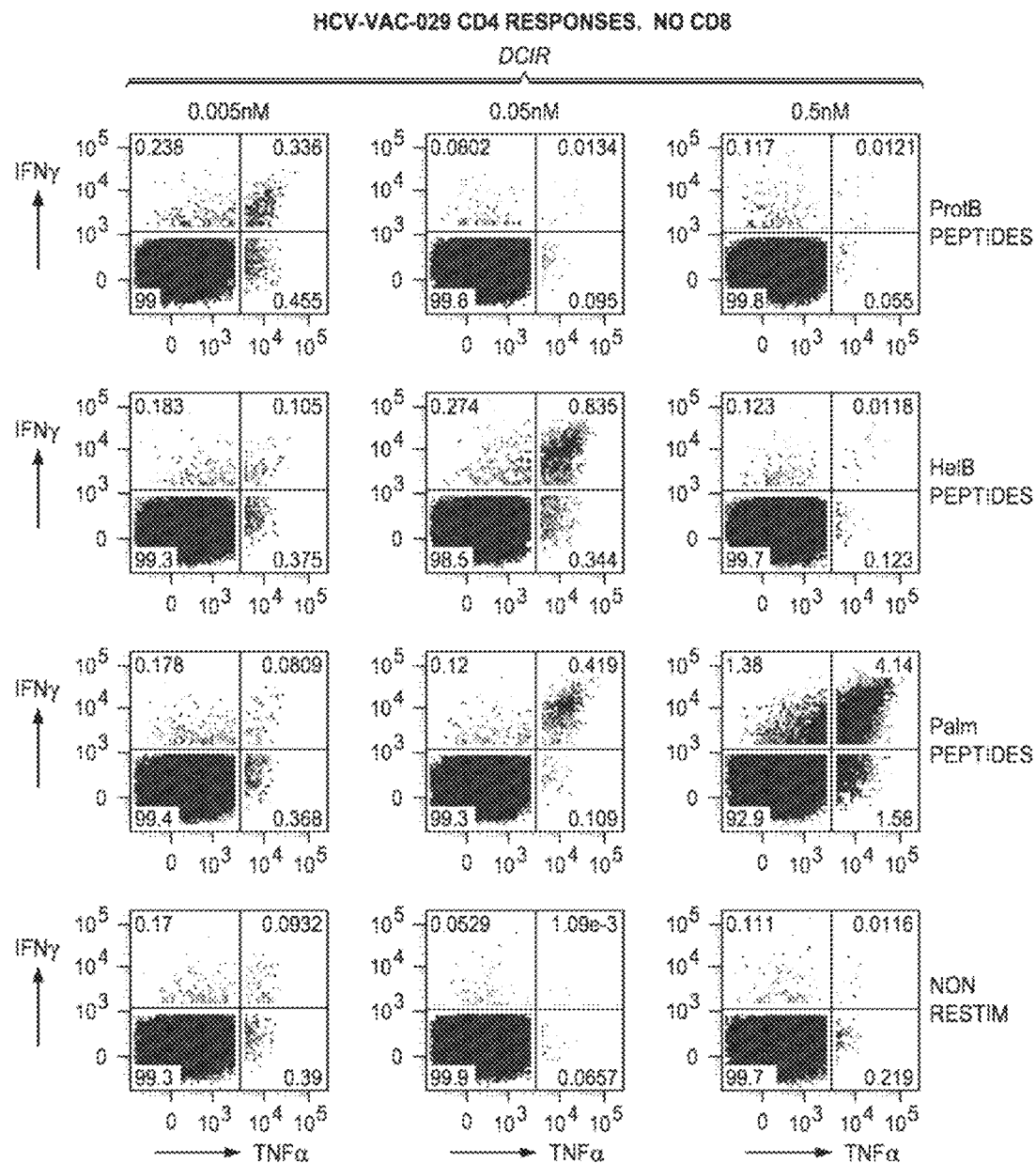
Figure 14G:
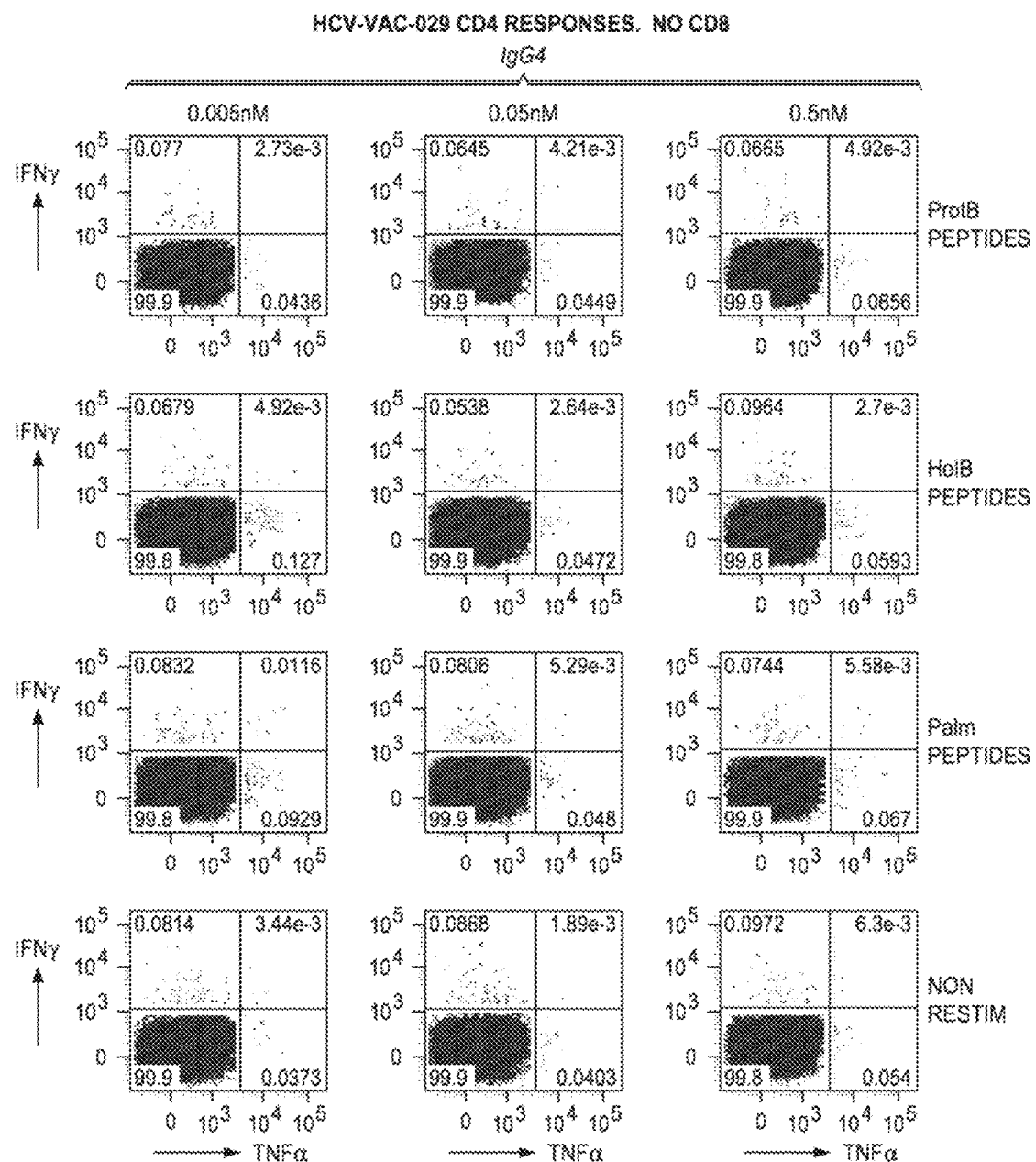
Figure 14H:
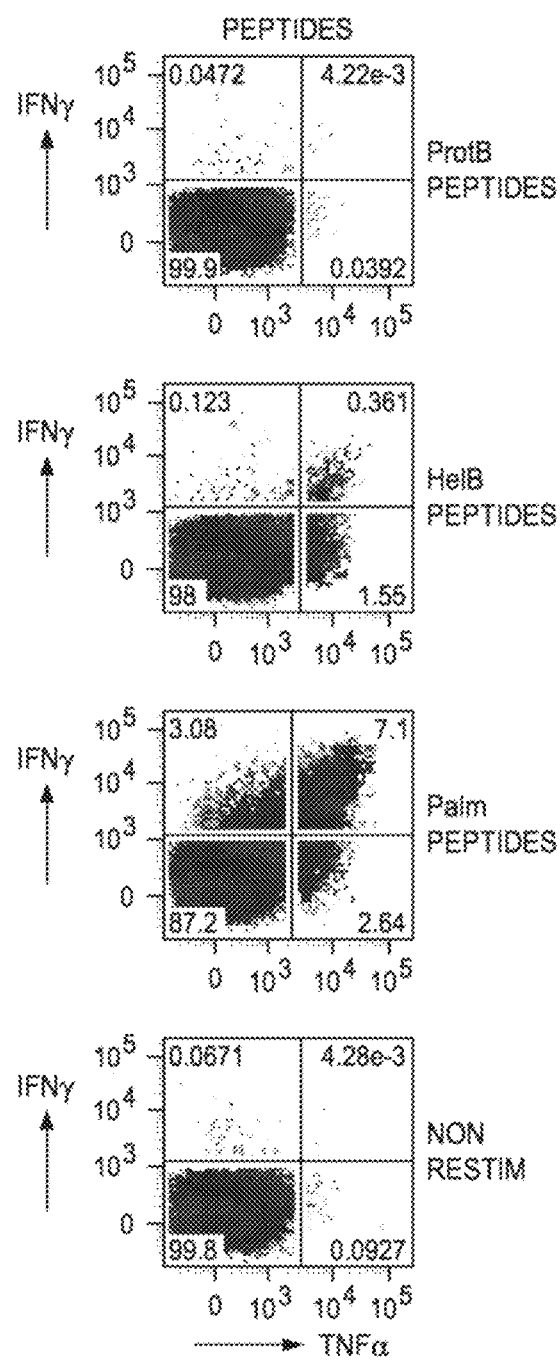

Finally, the present invention discloses a method for generating a Hepatitis C virus (HCV) presenting dendritic cells (DCs) in a human subject comprising the steps of: providing one or more DCs and incubating the dendritic cells with a fusion protein, wherein the fusion protein comprises an antibody or fragment thereof specific for a dendritic cell and a HCV antigen fused to the antibody or fragment thereof. The method disclosed herein further comprises the step of administering to the subject an effective amount of IFNA, Ribavirin, or a combination thereof.

BRIEF DESCRIPTION OF THE DRAWINGS

For a more complete understanding of the features and advantages of the present invention, reference is now made to the detailed description of the invention along with the accompanying figures and in which:

FIG. 1 provides a summary of HCV antigen combined constructs expressed at the C-terminus end of antibody heavy chain. Each HCV domains, as defined in FIG. 2, is represented as color rectangle. Flexible linkers are shown as curved lines. Each color represents a different linker. Domains are fused to the carboxyl terminus end of antibody heavy chain. “Expressed” means that domains fused to the carboxyl terminus end of antibody heavy chain are expressed as fusion antibody after co-transfection with antibody light chain in 293F cells. All possible combination of HCV domains have been constructed, and FIG. 3 shows only those that were expressed as soluble fusion proteins in 293F cells and in CHO cells and purified as recombinant antibodies;

FIG. 2 provides a summary of HCV antigen combined constructs expressed at the C-terminus end of antibody light chain. All possible combinations of HCV domains have been constructed, and the figure shows only those that are expressed as soluble fusion proteins in 293F cells and in CHO cells and purified as recombinant antibodies. The same color code as in FIG. 1 is used;

FIGS. 3A-3B demonstrate the ability of recombinant anti-DCIR and anti-CD40 antibodies fused to HCV NS3HelB specific antigen to elicit the expansion of antigen-specific CD4+ T cells from a chronic HCV infected patient cured after IFNa-Ribavirin therapy. Delivering NS3HelB to DCs through CD40 and DCIR induces IFNγ-TNFa-producing HCV NS3HelB-specific CD4+ T cells. PBMC cells from chronic HCV infected patients; either cured after therapy or in treatment failure, were co-cultured with IFNDCs targeted with anti-CD40-NS3HelB or anti-DCIR-NS3HelB for 10 days. Cells were stimulated with peptides clusters (10 peptides of 15-mers in each clusters) covering HCV NS3 HelB (10 μM): FIG. 3A after 2 days, culture supernatants were analyzed for measuring IFNγ and FIG. 3B PBMC cells were stained for measuring the frequency of peptide-specific CD4+ T cells intracellular IFNγ+TNFα+ cells;

FIG. 4 demonstrates the ability of long HCV antigen bearing vaccine constructs to induce multi epitope CD4+ T cells. HCV antigens from NS3 Helicase HelBC construct were delivered to DCs through CD40 or DCIR. PBMC cells from chronic HCV infected patients; either cured after therapy or in treatment failure, were co-cultured with IFNDCs targeted with anti-CD40-NS3HelB, anti-CD40-NS3HelBC or anti-DCIR-NS3HelB, anti-DCIR-NS3HelBC for 10 days. Cells were stimulated for 6 h with peptides clusters (10 μM; 10 peptides of 15-mers in each clusters) covering HCV NS3 HelB or HelBC constructs. PBMC cells were stained for measuring the frequency of peptide-specific CD4+ T cells intracellular IFNγ+TNFα+ cells, an analyzed by FACS. Number of double positive CD4+ T cells induced after each peptide cluster stimulation were plotted for each vaccine targeting agent;

FIGS. 5A to 5C demonstrate the ability of recombinant anti-DCIR and anti-CD40 antibodies fused to HCV NS3HelB, HCV NS3ProtB and HCV NS5BPalm specific antigens to elicit the expansion of antigen-specific CD4+ T cells from a chronic HCV infected patient cured after IFNa-Ribavirin therapy. Delivering HCV antigen to DCs through CD40 and DCIR induces IFNγ-TNFa-producing HCV-specific CD4+ T cells, with multi epitopes, specific CD4 T cells. PBMC cells from chronic HCV infected patients cured after therapy were co-cultured with autologous IFNαDCs targeted with anti-CD40-NS3HelB-NS3ProtB-NS5BPalm or anti-DCIR-NS3HelB-NS3ProtB-NS5BPalm for 10 days. Cells were stimulated with peptides clusters (10 peptides of 15-mers in each clusters) covering HCV NS3HelB, NS3ProtB or NS5BPalm (2 μM). PBMC cells were stained for measuring the frequency of peptide-specific CD4+ T cells intracellular IFNγ+TNFα+ cells;

FIGS. 6A to 6C demonstrate the ability of recombinant anti-DCIR and anti-CD40 antibodies fused to HCV NS3HelB, HCV NS3ProtB and HCV NS5BPalm specific antigens to elicit the expansion of antigen-specific CD8+ T cells from a chronic HCV infected patient cured after IFNa-Ribavirin therapy. Delivering HCV antigen to DCs through CD40 and DCIR induces IFNγ-TNFa-producing HCV-specific CD4+ T cells, with multi epitopes, specific CD4 T cells. PBMC cells from chronic HCV infected patients cured after therapy were co-cultured with autologous IFNαDCs targeted with anti-CD40-NS3HelB-NS3ProtB-NS5BPalm or anti-DCIR-NS3HelB-NS3ProtB-NS5BPalm for 10 days. Cells were stimulated with peptides clusters (10 peptides of 15-mers in each clusters) covering HCV NS3HelB, NS3ProtB or NS5BPalm (2 µM). PBMC cells were stained for measuring the frequency of peptide-specific CD8+T cells intracellular IFNγ+TNFα+ cells;

FIGS. 7A to 7D demonstrate the ability of recombinant anti-DCIR and anti-CD40 antibodies fused to HCV NS3HelB, HCV NS3ProtB or HCV NS5BPalm specific antigens to elicit the expansion of antigen-specific CD4+ T cells from chronic HCV infected patients cured after IFNa-Ribavirin therapy. HCV antigens from were delivered to DCs through CD40 or DCIR. IFNαDCs were targeted with anti-CD40-NS3HelB; anti-CD40-NS3ProtB; anti-CD40NS5bPalm or anti-DCIR-NS3HelB; anti-DCIR-NS3ProtB; anti-DCIRNS5bPalm and co-cultured for 10 days with PBMC cells from 3 chronic HCV infected patients cured after therapy. Cells were stimulated for 6 h with peptide clusters C7 and C9 (10 µM; 10 peptides of 15-mers) covering HCV NS3 HelB constructs; with peptide clusters C2 and C3 covering HCV NS3 ProtB constructs or peptide cluster C2 C4 C5 C6 C7 covering NS5bPalm construct. PBMC cells were stained for measuring the frequency of peptide-specific CD4+ intracellular IFNγ+TNFα+ cells, an analyzed by FACS. The left panel represent IFNγ amount secreted after 10 days culture of PBMCs with peptide cluster covering HCVNS3 and HCVNS5b entire proteins;

FIGS. 8A to 8D demonstrates the ability of recombinant anti-DCIR and anti-CD40 antibodies fused to HCV NS3HelB, HCV NS3ProtB or HCV NS5BPalm specific antigens to elicit the expansion of antigen-specific CD4+ T cells from chronic HCV infected patients in treatment failure. HCV antigens from were delivered to DCs through CD40 or DCIR. IFNαDCs were targeted with anti-CD40-NS3HelB; anti-CD40-NS3ProtB or anti-DCIR-NS3HelB; anti-CD40NS5bPalm or anti-DCIR-NS3HelB; anti-DCIR-NS3ProtB; anti-DCIRNS5bPalm and co-cultured for 10 days with PBMC cells from 3 chronic HCV infected patients in treatment failure (HCV+). Cells were stimulated for 6 h with peptide clusters C7 and C9 (10 µM; 10 peptides of 15-mers) covering HCV NS3 HelB constructs; with peptide clusters C2 and C3 covering HCV NS3 ProtB constructs or peptide cluster C2 C4 C5 C6 C7 covering NS5bPalm construct. PBMC cells were stained for measuring the frequency of peptide-specific CD4+ intracellular IFNγ+TNFα+ cells, an analyzed by FACS. The left panel represent IFNγ amount secreted after 10 days culture of PBMCs with peptide cluster covering HCVNS3 and HCVNS5b entire proteins;

FIGS. 9A and 9B demonstrate the ability of combination of TLR agonist and anti-DCIR HCV-NS3HelB can induced multi epitopes CD8+ T cells. HCV antigens from NS3 Helicase HelB construct were delivered to DCs through CD40 or DCIR. IFNDCs were targeted with anti-CD40-NS3HelB, or anti-DCIR-NS3HelB in presence of PAM3 (TLR2 agonist; 200 ng/ml), CL097 (TLR7/8 agonist; 5 µg/ml) or polyIC (TLR3 agonist; 25 µg/ml) before co-culture for 10 days with PBMC cells from chronic HCV infected patients; either cured after therapy or in treatment failure. Cells were stimulated for 6 h with peptide clusters C7 (10 µM; 10 peptides of 15-mers) covering HCV NS3 HelB constructs: (FIG. 9A) PBMC cells were stained for measuring the frequency of peptide-specific CD4+ and CD8+ intracellular IFNγ+TNFα+ cells, an analyzed by FACS, (FIG. 9B) Number of double positive CD4+ and CD8+ intracellular IFNγ+TNFα+ T cells induced after each TLR agonist stimulation were plotted;

FIGS. 10A-10D demonstrate the ability of combination of TLR agonist and anti-DCIR HCV-construct to increase CD4+ and induce CD8+ T cells responses in chronic HCV infected patients cured after therapy. HCV antigens from NS3 Helicase HelB or from NS3 Protease ProtB constructs were delivered to DCs through CD40 or DCIR. IFNαDCs were targeted with anti-CD40-NS3HelB, anti-DCIR-NS3HelB, anti-CD40-NS3ProtB, anti-DCIR-NS3ProtB, in presence of PAM3 (TLR2 agonist; 200 ng/ml), CL095 (TLR7/8 agonist; 5 µg/ml) or polyIC (TLR3 agonist; 25 µg/ml) or cyclic glucan (TLR4 agonist, 10 m/ml) before co-culture for 10 days with PBMC cells from chronic HCV infected patients cured after therapy. Cells were stimulated for 6 h with peptide clusters C7 (10 µM; 10 peptides of 15-mers) covering HCV NS3 HelB constructs or with peptide clusters C3 (10 µM; 10 peptides of 15-mers) covering HCV NS3 ProtB constructs: FIGS. 10A and 10B PBMC cells were stained for measuring the frequency of peptide-specific CD4+ intracellular IFNγ+TNFα+ cells, and analyzed by FACS and FIGS. 10C and 10D PBMC cells were stained for measuring the frequency of peptide-specific CD8+ intracellular IFNγ+TNFα+ cells, an analyzed by FACS;

FIG. 11 demonstrates the ability of combination of TLR agonists and anti-CD40 HCV-constructs to increase CD4+ T cells responses in chronic HCV infected patients in treatment failure. HCV antigens from NS3 Helicase HelB or from NS3 Protease ProtB constructs were delivered to DCs through CD40 or DCIR. IFNαDCs were targeted with anti-CD40-NS3HelB, anti-DCIR-NS3HelB, anti-CD40-NS3ProtB, anti-DCIR-NS3ProtB, in presence of PAM3 (TLR2 agonist; 200 ng/ml), CL095 (TLR7/8 agonist; 5 µg/ml) or polyIC (TLR3 agonist; 25 µg/ml) or cyclic glucan (TLR4 agonist, 10 µg/ml) before co-culture for 10 days with PBMC cells from chronic HCV infected patients cured after therapy. Cells were stimulated for 6 h with peptide clusters C7 (10 µM; 10 peptides of 15-mers) covering HCV NS3 HelB constructs or with peptide clusters C3 (10 µM; 10 peptides of 15-mers) covering HCV NS3 ProtB constructs. PBMC cells were stained for measuring the frequency of peptide-specific CD4+ intracellular IFNγ+TNFα+ cells, an analyzed by FACS;

FIGS. 12A-12C demonstrate the ability of HCV vaccine candidates to recall CD4+ T cells responses in all chronic HCV infected patients (cured or in treatment failure). HCV antigens from NS3 Helicase HelB, NS5b polymerase Palm or from NS3 Protease ProtB constructs were delivered to DCs through CD40 or DCIR. IFNγDCs were targeted with anti-CD40-[NS3HelB~NS3ProtB~NS5bPalm on heavy chain], anti-DCIR-[NS3HelB~NS3ProtB~NS5bPalm on heavy chain] before co-culture for 10 days with PBMC cells from chronic HCV infected patients cured after therapy. Cells were stimulated for 6 h with peptide clusters C7, C9 (10 µM; 10 peptides of 15-mers) covering HCV NS3 HelB domain, with peptide clusters C2-C3-C4 (10 µM; 10 peptides of 15-mers) covering HCV NS3 ProtB domain or with peptide clusters C2-C4-C5-C6-C7 (10 µM; 10 peptides of 15-mers) covering HCV NS5b Palm domain. PBMC cells were stained for measuring the frequency of peptide-specific CD4+ and CD8+ intracellular IFNγ+TNFα+ cells, and analyzed by FACS. The number of CD4+IFNγ+TNFα+ cells induced vaccine candidate is shown;

FIGS. 13A-13E demonstrate of the ability of different HCV antigen combination on vaccine candidate for recall CD4+ T cells responses in chronic HCV infected cured patients. HCV antigens from NS3 Helicase HelB, NS5b polymerase Palm or from NS3 Protease ProtB combination constructs were delivered to DCs through CD40 or DCIR. IFNaDCs were targeted with second-generation vaccines anti-CD40-[NS3HelB on light chain and NS3ProtB~NS5bPalm on heavy chain], anti-DCIR-[NS3HelB on light chain and NS3ProtB~ NS5bPalm on heavy chain], or first-generation vaccines anti-CD40-[NS3HelB~NS3ProtB~NS5bPalm on heavy chain], anti-DCIR—[NS3HelB~NS3ProtB~NS5bPalm on heavy chain] before co-culture for 10 days with PBMC cells from chronic HCV infected patients cured after therapy. Cells were stimulated for 6 h with peptide clusters C7 and C9 (10 µM; 10 peptides of 15-mers) covering HCV NS3 HelB domain (shown in green on the figure), with peptide clusters C2-C3-C4 (10 µM; 10 peptides of 15-mers) covering HCV NS3 ProtB domain (shown in pink on the figure) or with peptide clusters C2-C4-C5-C6-C7 (10 µM; 10 peptides of 15-mers) covering HCV NS5b Palm domain (shown in orange in the figure). PBMC cells were stained for measuring the frequency of peptide-specific CD4+ intracellular IFNγ+TNFa+ cells, an analyzed by FACS. The number of CD4+IFNγ+TNFα+ cells induced by first-generation vaccine or second-generation vaccine is compared in the last panel; and FIGS. 14A to 14H demonstrate the ability of vaccine candidate to recall CD4+ T cells responses in HCV patients infected with non 1 genotype and HCV-exposed but non-infected individual. HCV antigens from NS3 Helicase HelB, NS5b polymerase Palm or from NS3 Protease ProtB combination constructs were delivered to DCs through CD40 or DCIR and DC loaded were co-culture for 10 days with PBMC cells from HCV patients infected with non 1 genotype HCV-infected patients (HCV-015, 2b) and HCV-exposed but non infected individual (HCV-029). Cells were stimulated for 6 h with peptide clusters C7 and C9 (10 µM; 10 peptides of 15-mers) covering HCV NS3 HelB domain, with peptide clusters C2-C3-C4 (10 µM; 10 peptides of 15-mers) covering HCV NS3 ProtB domain or with peptide clusters C2-C4-C5-C6-C7 (10 µM; 10 peptides of 15-mers) covering HCV NS5b Palm domain. PBMC cells were stained for measuring the frequency of peptide-specific CD4+ intracellular IFNγ+TNFα+ cells, an analyzed by FACS.

Figure 15A:
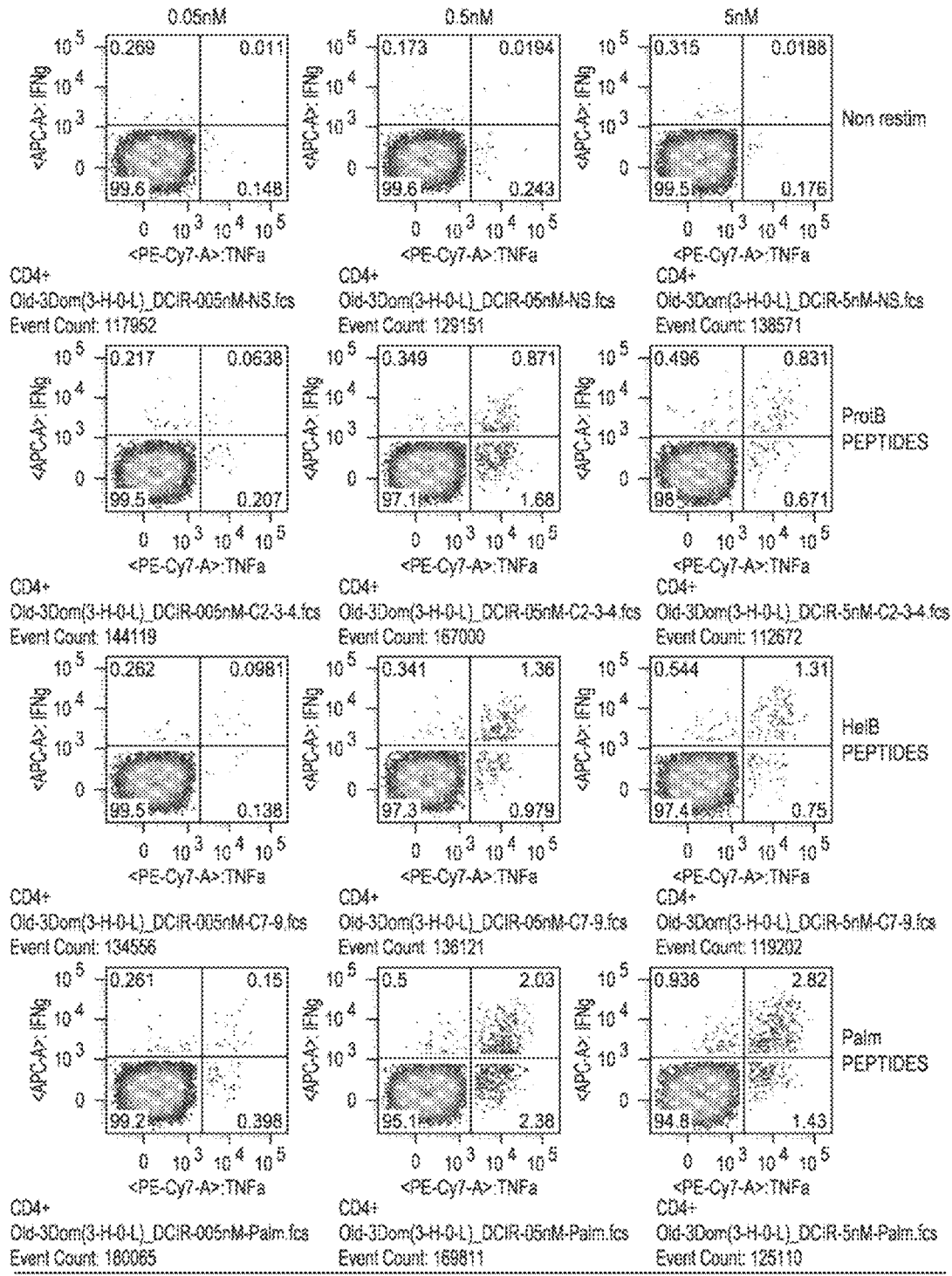
Figure 15B:
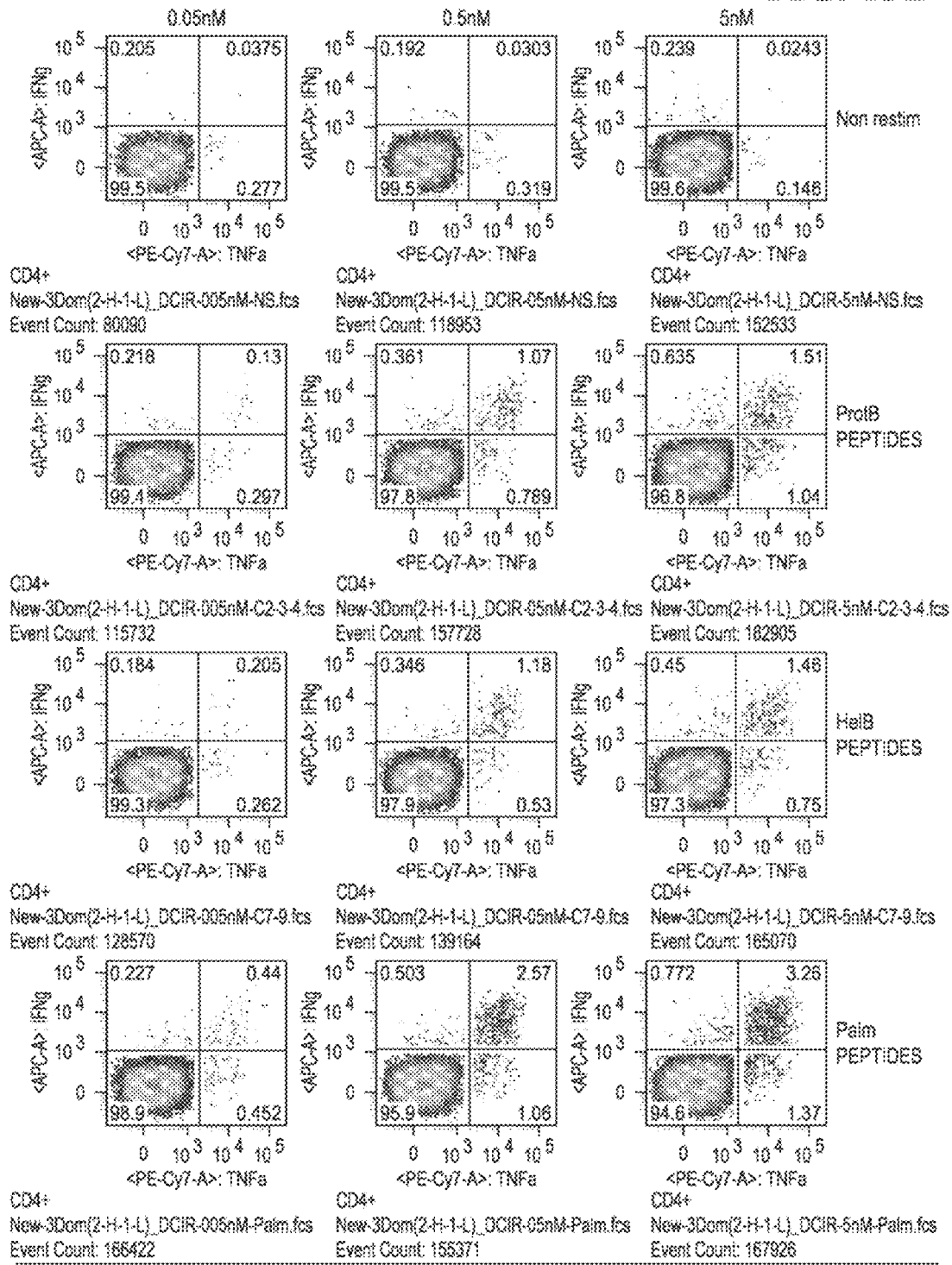

FIGS. 15A to 15B shows the results from a 10 day expansion culture whereby a dose range of 1st generation anti-DCIR-HCV vaccine (left panels) is compared to second generation anti-DCIR-HCV vaccine (right panels). Doses were 0.05 nM, 0.5 nM, and 5 nM and antigen-specific responses were ascertained by stimulation with no peptide (control) or ProtA, HelB, or Palm peptide pools in the presence of Brefeldin, followed by staining for CD3+, CD4+ and intracellular IFNg and TNFa. Samples were analyzed by FACS. Shown are comparable CD4+ HCV antigen-specific responses to the two generations of vaccines.

Figure 16A:
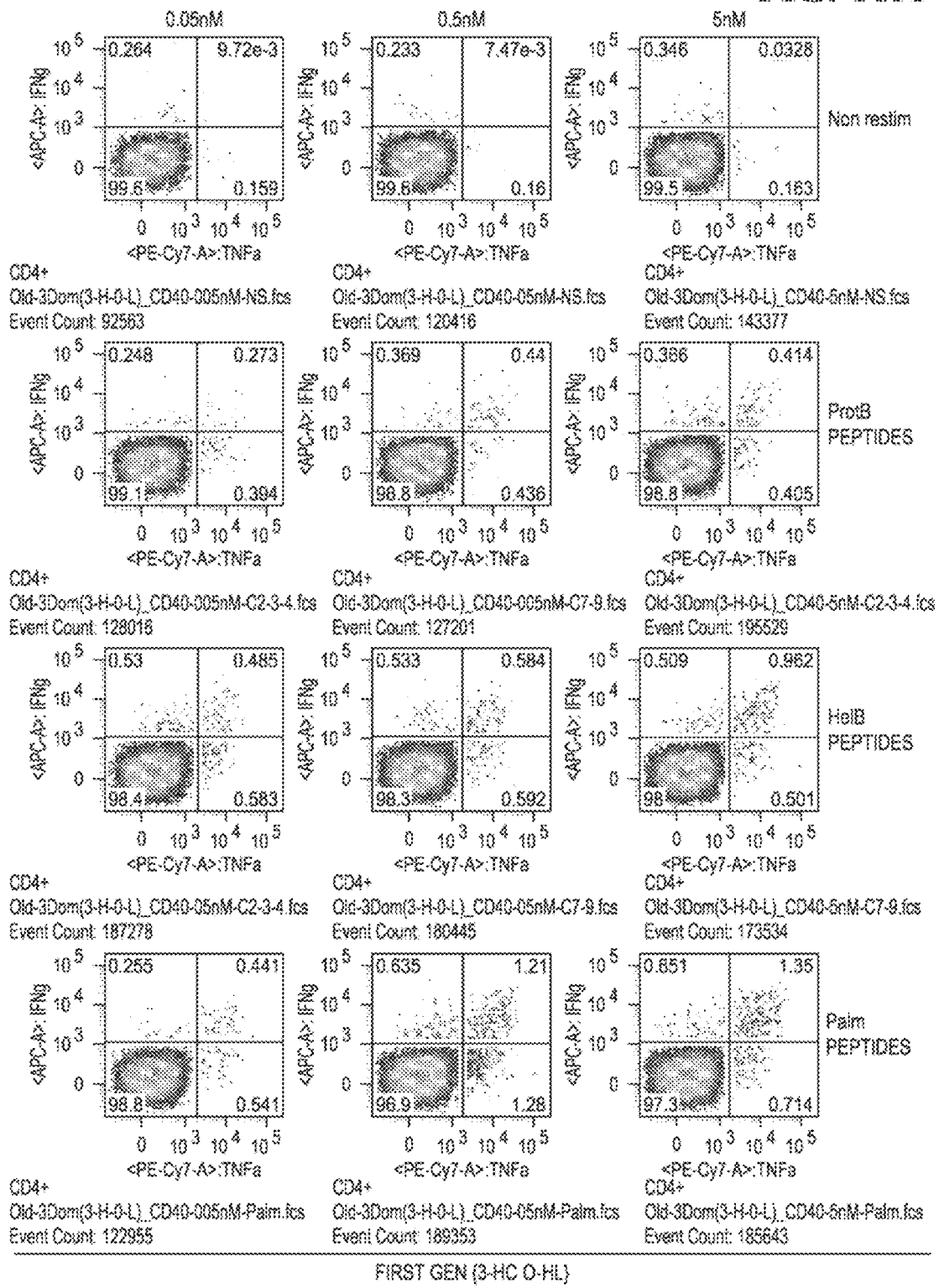

FIGS. 16A to 16B shows the results from a 10 day expansion culture whereby a dose range of 1st generation anti-CD40-HCV vaccine (left panels) is compared to second generation anti-CD40-HCV vaccine (right panels). Doses were 0.05 nM, 0.5 nM, and 5 nM and antigen-specific responses were ascertained by stimulation with no peptide (control) or ProtA, HelB, or Palm peptide pools in the presence of Brefeldin, followed by staining for CD3+, CD4+ and intracellular IFNg and TNFa. Samples were analyzed by FACS. Shown are comparable CD4+ HCV antigen-specific responses to the two generations of vaccines.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The invention includes also variants and other modification of an antibody (or "Ab") of fragments thereof, e.g., anti-CD40 fusion protein (antibody is used interchangeably with the term "immunoglobulin"). As used herein, the term "antibodies or fragments thereof," includes whole antibodies or fragments of an antibody, e.g., Fv, Fab, Fab', F(ab')2, Fc, and single chain Fv fragments (ScFv) or any biologically effective fragments of an immunoglobulins that binds specifically to, e.g., CD40. Antibodies from human origin or humanized antibodies have lowered or no immunogenicity in humans and have a lower number or no immunogenic epitopes compared to non-human antibodies. Antibodies and their fragments will generally be selected to have a reduced level or no antigenicity in humans.

As used herein, the terms "Ag" or "antigen" refer to a substance capable of either binding to an antigen binding region of an immunoglobulin molecule or of eliciting an immune response, e.g., a T cell-mediated immune response by the presentation of the antigen on Major Histocompatibility Antigen (MHC) cellular proteins. As used herein, "antigen" includes, but is not limited to, antigenic determinants, haptens, and immunogens, which may be peptides, small molecules, carbohydrates, lipids, nucleic acids or combinations thereof. The skilled immunologist will recognize that when discussing antigens that are processed for presentation to T cells, the term "antigen" refers to those portions of the antigen (e.g., a peptide fragment) that is a T cell epitope presented by MHC to the T cell receptor. When used in the context of a B cell mediated immune response in the form of an antibody that is specific for an "antigen", the portion of the antigen that binds to the complementarity determining regions of the variable domains of the antibody (light and heavy) the bound portion may be a linear or three-dimensional epitope. In the context of the present invention, the term antigen is used on both contexts, that is, the antibody is specific for a protein antigen (CD40), but also carries one or more peptide epitopes for presentation by MHC to T cells. In certain cases, the antigens delivered by the vaccine or fusion protein of the present invention are internalized and processed by antigen presenting cells prior to presentation, e.g., by cleavage of one or more portions of the antibody or fusion protein.

As used herein, the term "conjugate" refers to a protein having one or more targeting domains, e.g., an antibody, and at least one antigen, e.g., a small peptide or a protein. These conjugates include those produced by chemical methods, such as by chemical coupling, for example, coupling to sulfhydryl groups, and those produced by any other method whereby one or more antibody targeting domains and at least one antigen, are linked, directly or indirectly via linker(s) to a targeting agent. An example of a linker is a cohesin-dockerin (coh-doc) pair, a biotin-avidin pair, histidine tags bound by Zn, and the like.

As used herein, the term "Antigen Presenting Cells" (APC) refers to cells that are capable of activating T cells, and include, but are not limited to, certain macrophages, B cells and dendritic cells. "Dendritic cells" (DCs) refers to any member of a diverse population of morphologically similar cell types found in lymphoid or non-lymphoid tissues. These cells are characterized by their distinctive morphology, high levels of surface MHC-class II expression (Steinman, et al., Ann. Rev. Immunol. 9:271 (1991); incorporated herein by reference for its description of such cells). These cells can be isolated from a number of tissue sources, and conveniently, from peripheral blood, as described herein. Dendritic cell binding proteins refers to any protein for which receptors are expressed on a dendritic cell. Examples include GMCSF, IL-1, TNF, IL-4, CD40L, CTLA4, CD28, and FLT-3 ligand.

For the purpose of the present invention, the term "vaccine composition" is intended to mean a composition that can be administered to humans or to animals in order to induce an immune system response; this immune system response can result in a production of antibodies or simply in the activation of certain cells, in particular antigen-presenting cells, T lymphocytes and B lymphocytes. The vaccine composition can be a composition for prophylactic purposes or for therapeutic purposes, or both. As used herein, the term "antigen" refers to any antigen which can be used in a vaccine, whether it involves a whole microorganism or a subunit, and whatever its nature: peptide, protein, glycoprotein, polysaccharide, glycolipid, lipopeptide, etc. They may be viral antigens, bacterial antigens, or the like; the term "antigen" also comprises the polynucleotides, the sequences of which are chosen so as to encode the antigens whose expression by the individuals to which the polynucleotides are administered is desired, in the case of the immunization technique referred to as DNA immunization. They may also be a set of antigens, in particular in the case of a multivalent vaccine composition which comprises antigens capable of protecting against several diseases, and which is then generally referred to as a vaccine combination, or in the case of a composition which comprises several different antigens in order to protect against a single disease, as is the case for certain vaccines against whooping cough or the flu, for example. The term "antibodies" refers to immunoglobulins, whether natural or partially or wholly produced artificially, e.g. recombinant. An antibody may be monoclonal or polyclonal. The antibody may, in some cases, be a member of one, or a combination immunoglobulin classes, including: IgG, IgM, IgA, IgD, and IgE.

The term "adjuvant" refers to a substance that enhances, augments or potentiates the host's immune response to a vaccine antigen.

The term "gene" is used to refer to a functional protein, polypeptide or peptide-encoding unit. As will be understood by those in the art, this functional term includes both genomic sequences, cDNA sequences, and fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated.

As used herein, the term "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

As used herein, "polynucleotide" or "nucleic acid" refers to a strand of deoxyribonucleotides or ribonucleotides in either a single- or a double-stranded form (including known analogs of natural nucleotides). A double-stranded nucleic acid sequence will include the complementary sequence. The polynucleotide sequence may encode variable and/or constant region domains of immunoglobulin that are formed into a fusion protein with one or more linkers. For use with the present invention, multiple cloning sites (MCS) may be engineered into the locations at the carboxy-terminal end of the heavy and/or light chains of the antibodies to allow for in-frame insertion of peptide for expression between the linkers. As used herein, the term "isolated polynucleotide" refers to a polynucleotide of genomic, cDNA, or synthetic origin or some combination thereof. By virtue of its origin the "isolated polynucleotide" (1) is not associated with all or a portion of a polynucleotide in which the "isolated polynucleotides" are found in nature, (2) is operably linked to a polynucleotide which it is not linked to in nature, or (3) does not occur in nature as part of a larger sequence. The skilled artisan will recognize that to design and implement a vector can be manipulated at the nucleic acid level by using techniques known in the art, such as those taught in Current Protocols in Molecular Biology, 2007 by John Wiley and Sons, relevant portions incorporated herein by reference. Briefly, the encoding nucleic acid sequences can be inserted using polymerase chain reaction, enzymatic insertion of oligonucleotides or polymerase chain reaction fragments in a vector, which may be an expression vector. To facilitate the insertion of inserts at the carboxy terminus of the antibody light chain, the heavy chain, or both, a multiple cloning site (MCS) may be engineered in sequence with the antibody sequences.

As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring. The term "domain," or "polypeptide domain" refers to that sequence of a polypeptide that folds into a single globular region in its native conformation, and that may exhibit discrete binding or functional properties.

As used in this application, the term "amino acid" means one of the naturally occurring amino carboxylic acids of which proteins are comprised. The term "polypeptide" as described herein refers to a polymer of amino acid residues joined by peptide bonds, whether produced naturally or synthetically. Polypeptides of less than about 10 amino acid residues are commonly referred to as "peptides." A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3-5 amino acids, preferably at least 4-7 amino acids, more preferably at least 8-10 amino acids, and even more preferably at least 11-15 amino acids, or which is immunologically identifiable with a polypeptide encoded in the sequence. This terminology also includes a polypeptide expressed from a designated nucleic acid sequence.

As used herein, the terms "stable," "soluble," or "unstable" when referring to proteins is used to describe a peptide or protein that maintains its three-dimensional structure and/or activity (stable) or that loses immediately or over time its three-dimensional structure and/or activity (unstable). As used herein, the term "insoluble" refers to those proteins that when produced in a cell (e.g., a recombinant protein expressed in a eukaryotic or prokaryotic cell or in vitro) are not soluble in solution absent the use of denaturing conditions or agents (e.g., heat or chemical denaturants, respectively). The antibody or fragment thereof and the linkers taught herein have been found to convert antibody fusion proteins with the peptides from insoluble and/or unstable into proteins that are stable and/or soluble. Another example of stability versus instability is when the domain of the protein with a stable conformation has a higher melting temperature (Tm) than the unstable domain of the protein when measured in the same solution. A domain is stable compared to another domain when the difference in the Tm is at least about 2° C., more preferably about 4° C., still more preferably about 7° C., yet more preferably about 10° C., even more preferably about 15° C., still more preferably about 20° C., even still more preferably about 25° C., and most preferably about 30° C., when measured in the same solution.

As used herein, the term "in vivo" refers to being inside the body. The term "in vitro" used as used in the present application is to be understood as indicating an operation carried out in a non-living system.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

As used herein, "pharmaceutically acceptable carrier" refers to any material that when combined with an immunoglobulin (Ig) fusion protein of the present invention allows the Ig to retain biological activity and is generally non-reactive with the subject's immune system. Examples include, but are not limited to, standard pharmaceutical carriers such as a phosphate buffered saline solution, water, emulsions such as an oil/water emulsion, and various types of wetting agents. Certain diluents may be used with the present invention, e.g., for aerosol or parenteral administration, that may be phosphate buffered saline or normal (0.85%) saline.

Substantial similarity of a peptide refers to similarity of a peptide as reflected in the amino acid sequence of the peptide. Identity of a continuous stretch of at least 8 amino acids in an antigenic epitope of the peptide may be sufficient to establish substantial identity that enables cross reactivity. A first peptide and a second peptide are substantially similar in this regard if they have substantial similar antigenic epitopes so that immunization with the first peptide causes an immune response against the second peptide.

A fragment of an antibody, as used in the present application, refers to a portion of an antibody, created by protein engineering including proteolysis, or genetic engineering including recombination of nucleic acids; the fragment of an antibody retains specificity for the antigen.

A fragment of a peptide used as antigen refers to a portion of the peptide that retains its immunogenicity. A person of ordinary skill in the art will recognize that a continuous stretch of at least 8 amino acids in an antigenic epitope of the peptide may be sufficient I order for a peptide to retain its immunogenicity.

Recombinant protein or antibody is generated by genetic engineering of nucleic acid encoding the protein or antibody and subsequent translation of the coding sequence by a cell or in a cell-free translation system.

The present invention describes a vaccine composition for delivering a HCV antigen specifically to DCs for the purpose of invoking an immune response In one embodiment, due to the high polymorphism of HCV, a sequence that is representative of most of circulating HCV sequence was selected. Based on sequence variation HCV can be classified into 6 genotypes that differs one to the other on the basis of sequence identity. World wide, 1 genotype is the most represented and also the most difficult to treat with the current IFNa-Ribavirin double therapy. More precisely, 1a genotype is the most represented subsequence in industrial country, and especially in US.

In one embodiment, 1a genotype was used as target sequence to derive a vaccine. It was observed that sequence alignment with all available 1a sequences found in data bases (euHCVdb and Los Alamos National Laboratory) showed less than 70% of sequence identity and the sequence of the HCV antigen would have to be adjusted accordingly.

A mosaic sequence was derived using the mosaic vaccine tools at www.hiv.lanl.gov/content/sequence/MOSAIC/ interface choosing mosaic sequence cocktail, 1 as cocktail size and 9 as epitope size. We used 249 sequences for E1 mosaic, 656 sequences for E2 mosaic, 213 sequences for NS3 mosaic and 310 sequences for NS5b mosaic. All sequences correspond to complete genes of 576, 1089, 1893, 1773 nucleotides respectively and found in euHCVdb (eu-hcvdb.ibcp.fr/euHCVdb/).

HCV antigen choice: HCV is an RNA enveloped virus. Virions are consisted by 4 structural proteins Core, E1, E2 and p7. As an RNA virus replication is based on viral proteins that need to be expressed after infection. Six non-structural proteins (NS2, NS3, NS4a, NS4b, NS5a, NS5b) are necessary to establish and maintain replication and virus production. HCV targets the liver and can infect barely all the liver with 90% of hepatocytes infected. However, the virus is able to replicate only in 30% of hepatocytes. Infected cells presented at their surface epitopes coming from structural proteins, while infected virus-producing cells presented all HCV antigens, structural and non structural.

Because HCV targets a vital organ such as the liver, therapeutic vaccine need to be very specific in order to avoid complete liver destruction and death of the patients. Indeed, we choose for our therapeutic vaccine antigens that are only found in infected virus producing hepatocytes, and then target antigen will be non-structural proteins. Moreover, NS3 and NS4b are highly immunogenic in chronic infected patients, as efficient as structural core or E1 E2 structural proteins. Therefore the present inventors included NS5b as an antigen too.

In one embodiment, NS3 and NS5b were chosen because of their possible expression as recombinant protein and the availability of their 3D structure.

Description of an embodiment of a vaccine: A particular embodiment of a vaccine consisted of bifunctional antibodies, which were directed against Dendritic Cells specific receptors and have target antigens fused at C terminus part of heavy chain. This allows unique targeting of DC and more precisely different DC subset that expressed different receptors, DC activation through the targeted receptor, and direct delivery of antigen to DC. In turn antigens are presented more efficiently and APC function is associated to cytokine secretion that orient T cells activation towards different functions.

Design of domains: It is not readily predictable whether any particular non-structural viral protein will be efficiently expressed as a direct antibody-antigen fusion protein. Commonly, fusion proteins may not be soluble and not be secreted. The present application describes that by using flexible linker modules, fragmenting the antigen coding sequence, and varying the fragment order, efficient secretion of recombinant antibody-antigen vaccines bearing extensive stretches of non-structural proteins can be achieved. The current application describes a first testing of constructs by expression of antibody fused to individual HCV non-structural proteins, then linking those that are expressible as soluble protein to each other to maximize the antigen load. Domains were first designed based on the 3D structure of the corresponding full-length proteins. Domains were design as the minimal structured regions in between unfolded loops. Length of the loops was varied in order to increase expression of corresponding domains. Pymol software was used to visualize 3d structures. The domains that expressed at the C-terminal of the antibody heavy chain are represented by SEQ ID NOs: 7-14.

Multiple combinations of individual domains have been made in order to provide as much HCV antigen as possible. In some embodiments, each single domain is separated from the next by flexible linkers, which can be as small as two amino acids (e.g., AS) but can also be longer, e.g., 3, 4, 5, 6, 7 8, 9, 10, 12, 15, 18, 20, 25 or 30 amino acids long. FIG. 1 shows the summary of all combine constructs. The linkers are found in the assembled sequences, can also be SSVSPTTSVHPTPTSVPPTPTKSSP (SEQ ID NO.: 166); PTSTPADSSTITPTATPTATPTIKG (SEQ ID NO.: 167); TVTPTATATPSAIVTTITPTATTKP (SEQ ID NO.: 168); TNGSITVAATAPTVTPTVNATPSAA (SEQ ID NO.: 169).

Figure 2:
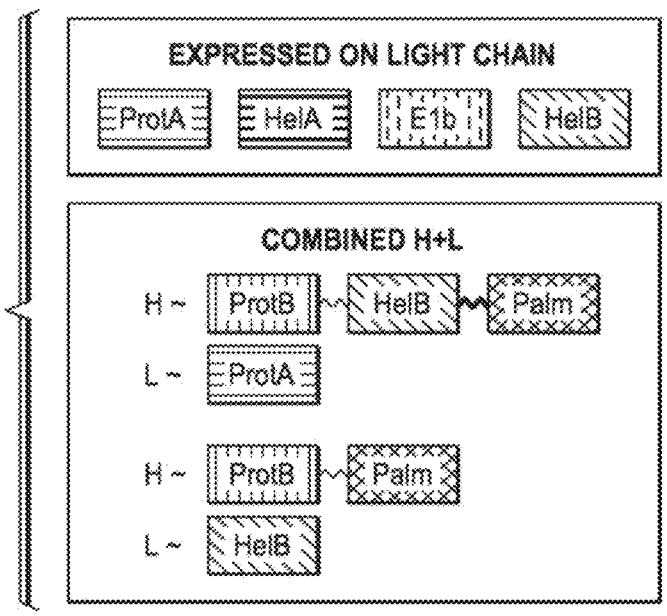

In another embodiment, domains were also expressed at the C-terminus part of the light chain, and used in combination with heavy chain fused to multiple HCV domains. This allows the formation of a combine antibody with 3HCV domains fused to the heavy chain and one fused to the light chain. FIG. 2 summarizes the construct obtain after fusion of HCV domains at the C-terminus end of light chain.

Preparation of targeting constructs: Anti human DCIR and CD40 V region form H and L chain were cloned in a IgG4 backbone. Spe I cloning site was introduced at the end of the carboxy terminus to clone in frame antigen sequences. HCV antigens from NS3 and NS5b viral proteins represented as subdomains of these proteins were subcloned as a Spe-Not fragment in Nhe-Not linearized pIRES vector.

HCV-domains were designed based on the 3D-structure of the corresponding full-length proteins (PDB code IJXP for NS3protease, 1HEI for NS3Helicase and 1GX5 for NS5b). 3D-structures were visualized using PyMol software. Domains were designed as the minimal structured regions in between unfolded loops. Length of the loops was varied in order to increase expression of corresponding domains fused to the recombinant antibody. For multiple domains cloning, linkers were introduced between domains using Spe-Not/Nhe-Not strategy. Mosaic sequences, used in this study, corresponding to the maximum HCV-domains expressed as antibody-antigen recombinant fusion proteins are shown below. They included amino acids 95 to 180 from NS3Protease, amino acids 132 to 254 from NS3Helicase and a recombinant fusion of amino acids 55 to 80; 172 to 261 and 276 to 362 from NS5bPolymerase. Spe, Nhe and Not introduced cloning sites are underlined.

SEQ ID NOS: 1-6 show the amino acid sequence of the HCV proteins E1, E2, NS3, and NS5b mosaic sequences. Membrane domains are underlined. The full-length protein NS3 contains 631 amino acids and is also presented as being cut in its two enzymatic activities proteins: NS3Protease and NS3Helicase. These may also be produced as recombinant proteins N-terminal fused to either histidine tag or Cohesin tag.

```
Envelop protein E1 (192 amino acids)
(SEQ ID NO: 1):
YQVRNSSGLYHVTNDCPNSSIVYEAADAILHTPGCVPCVREGNASRCWVA
VTPTVATRDGKLPTTQLRRHIDLLVGSATLCSALYVGDLCGSVFLVGQLF
TFSPRRHWTTQDCNCSIYPGHITGHRMAWDMMMNWSPTTAVVAQLLRIPQ
AILDMIAGAHWGVLAGIAYFSMVGNWAKVLVVLLLFAGVDA Envelop protein E2 (363 amino acids)
(SEQ ID NO: 2):
ETHVTGGSAARTTAGLAGLFTPGAKQNIQLINTNGSWHINRTALNCNDSL
NTGWVAGLFYYHKFNSSGCPERLASCRPLTDFDQGWGPISYANGSGPDQR
PYCWHYPPKPCGIVPAKSVCGPVYCFTPSPVVVGTTDRSGAPTYNWGEND
TDVFVLNNTRPPLGNWFGCTWMNSTGFTKVCGAPPCVIGGVGNNTLHCPT
DCFRKHPEATYSRCGSGPWITPRCLVDYPYRLWHYPCTINYTIFKIRMYV
GGVEHRLEAACNWTRGERCDLEDRDRSELSPLLLSTTQWQVLPCSFTTLP
ALSTGLIHLHQNIVDVQYLYGVGSSIASWAIKWEYVVLLFLLLADARVC
SCLWMMLLISQAEA
```

-continued

Non structural protein 3 NS3 (FL 631 amino acids)
(SEQ ID NO: 3):
APITAYAQQTRGLLGCIITSLTGRDKNQVEGEVQIVSTAAQTFLATCING
VCWTVYHGAGTRTIASPKGPVIQMYTNVDQDLVGWPAPQGARSLTPCTCG
SSDLYLVTRHADVIPVRRRGDSRGSLLSPRPISYLKGSSGGPLLCPAGHA
VGIFRAAVCTRGVAKAVDFIPVENLETTMRSPVFTDNSSPPAVPQSFQVA
HLHAPTGSGKSTKVPAAYAAQGYKVLVLNPSVAATLGFGAYMSKAHGIDP
NIRTGVRTITTGSPITYSTYGKFLADGGCSGGAYDIIICDECHSTDATSI
LGIGTVLDQAETAGARLVVLATATPPGSVTVPHPNIEEVALSTTGEIPFY
GKAIPLEVIKGGRHLIFCHSKKKCDELAAKLVALGINAVAYYRGLDVSVI
PTSGVVVVVATDALMTGFTGDFDSVIDCNTCVTQTVDFSLDPTFTIETTT
LPQDAVSRTQRRGRTGRGKPGIYRFVAPGERPSGMFDSSVLCECYDAGCA
WYELTPAETTVRLRAYMNTPGLPVCQDHLEFWEGVFTGLTHIDAHFLSQT
KQSGENLPYLVAYQATVCARAQAPPPSWDQMWKCLIRLKPTLHGPTPLLY
RLGAVQNEVTLTHPITKYIMTCMSADLEVVT NS3 (prot 189 amino acids) (SEQ ID NO: 4):
APITAYAQQTRGLLGCIITSLTGRDKNQVEGEVQIVSTAAQTFLATCING
VCWTVYHGAGTRTIASPKGPVIQMYTNVDQDLVGWPAPQGARSLTPCTCG
SSDLYLVTRHADVIPVRRRGDSRGSLLSPRPISYLKGSSGGPLLCPAGHA
VGIFRAAVCTRGVAKAVDFIPVENLETTMRSPVFTDNSSPPAVPQS NS3 (hel 442 amino acids) (SEQ ID NO: 5):
FQVAHLHAPTGSGKSTKVPAAYAAQGYKVLVLNPSVAATLGFGAYMSKAH
GIDPNIRTGVRTITTGSPITYSTYGKFLADGCSGGAYDIIICDECHSTD
ATSILGIGTVLDQAETAGARLVVLATATPPGSVTVPHPNIEEVALSTTGE
IPFYGKAIPLEVIKGGRHLIFCHSKKKCDELAAKLVALGINAVAYYRGLD
VSVIPTSGVVVVVATDALMTGFTGDFDSVIDCNTCVTQTVDFSLDPTFTI
ETTTLPQDAVSRTQRRGRTGRGKPGIYRFVAPGERPSGMFDSSVLCECYD
AGCAWYELTPAETTVRLRAYMNTPGLPVCQDHLEFWEGVFTGLTHIDAHF
LSQTKQSGENLPYLVAYQATVCARAQAPPPSWDQMWKCLIRLKPTLHGPT
PLLYRLGAVQNEVTLTHPITKYIMTCMSADLEVVT Non structural NS5b (591 Amino acids)
(SEQ ID NO: 6):
SMSYSWTGALVTPCAAEEQKLPINALSNSLLRHHNLVYSTTSRSACQRQK
KVTFDRLQVLDSHYQDVLKEVKAAASKVKANLLSVEEACSLTPPHSAKSK
FGYGAKDVRCHARKAVNHINSVWKDLLEDSVTPIDTTIMAKNEVFCVQPE
KGGRKPARLIVFPDLGVRVCEKMALYDVVSKLPLAVMGSSYGFQYSPGQR
VEFLVQAWKSKKTPMGFSYDTRCFDSTVTESDIRTEEAIYQCCDLDPQAR
VAIKSLTERLYVGGPLTNSRGENCGYRRCRASGVLTTSCGNTLTCYIKAR
AACRAAGLQDCTMLVCGDDLVVICESAGVQEDAASLRAFTEAMTRYSAPP
GDPPQPEYDLELITSCSSNVSVAHDGAGKRVYYLTRDPTTPLARAAWETA
RHTPVNSWLGNIIMFAPTLWARMILMTHFFSVLIARDQLEQALDCEIYGA
CYSIEPLDLPPIIQRLHGLSAFSLHSYSPGEINRVAACLRKLGVPPLRAW
RHRARSVRARLLSRGGRAAICGKYLFNWAVRTKLKLTPIAAAGQLDLSGW
FTAGYSGGDIYHSVSHARPRWFWFCLLLLAAGVGIYLLPNR The nucleotide sequences are presented herein below.

NS3Protease domain B (SEQ ID NO: 145)
ACTAGTACTCCTTGTACCTGCGGCTCATCCGACCTGTACCTGGTCACCCG
GCACGCAGACGTCATTCCTGTACGCCGACGCGGGGATAGTAGGGGGAGCC
TGCTCTCTCCAAGACCCATATCCTACCTCAAGGGCAGCAGCGGTGGACCA
CTGCTGTGTCCCGCTGGTCATGCTGTGGGAATATTTAGGGCGCAGTGTG
TACCAGAGGCGTGGCCAAAGCTGTTGATTTATTCCCGTCGAAAATCTTG
AAACAACCATGAGAAGCCCAGTGTTCACAGACAACTCATCTCCCCCAGCA
GTGCCGCAGAGTGCTAGCTGAGAATTCGCGGCCGC

NS3Helicase domain B (SEQ ID NO: 146):
ACTAGTGTGACTGTGCCCCACCCCAATATCGAAGAGGTGGCCCTTAGTAC
TACCGGGGAAATTCCTTTCTACGGGAAGGCCATCCCTCTCGAGGTTATTA
AAGGAGGGCGACATCTGATTTTTTGCCACTCCAAGAAGAAGTGTGACGAG
CTGGCCGCGAAACTGGTTGCCTTGGGCATCAACGCTGTCGCATACTATCG
GGGACTGGATGTATCAGTGATACCCACCAGCGGAGTGGTAGTTGTCGTCG
CTACAGACGCATTGATGACCGGCTTTACAGGAGATTTCGACTCCGTCATC
GACTGTAACACATGCGTGACTCAGACAGTGGATTTCAGCCTTGACCCGAC
GTTTACGATTGAGACCACCACTCTCCCTCAGGATGCTGTGTCTAGGACCC
AAAGACGCGGTCGCACAGGCCGGGCAAACCAGGCATCTATAGGTTCGTG
GCACCAGGGGAAAGAGCTAGCTGAgaattcGCGGCCGC

NS5bPalm (SEQ ID NO: 147):
ACTAGTGTGCTGGACTCTCACTACCAGGATGTCCTGAAGGAAGTAAAAGC
AGCCGCTTCTAAAGTCAAAGCGAACCTCTGTACGATGTCGTTTCCAAAC
TGCCGCTGGCTGTCATGGGCTCTTCCTACGGCTTTCAGTATTCCCCGGGT
CAGCGCGTTGAGTTCCTGGTCCAGGCGTGGAAATCCAAAAAGACTCCGAT
GGGTTTTTCCTATGACACTCGCTGCTTCGACAGCACCGTTACCGAAAGCG
ACATTCGCACCGAGGAAGCAATCTACCAGTGCTGCGACCTGGACCCACAG
GCCCGCGTGGCGATCAAATCTCTGACCGAACGCCTGTACGTTGGCCGCTG -continued
TCGCGCTTCCGGTGTTCTGACGACCTCCTGCGGTAATACGCTGACCTGCT
ACATCAAAGCACGCGCTGCCTGTCGCGCAGCCGGTCTGCAGGACTGCACC
ATGCTGGTGTGTGGCGATGACCTGGTGGTGATCTGCGAAAGCGCTGGCGT
GCAGGAAGACGCAGCAAGCCTGCGCGCTTTCACCGAAGCTATGACTCGCT
ACTCTGCGCCGCCGGGTGACCCGCCGCAGCCAGAATACGATCTGGAGCTG
ATCACCGCTAGCTAAGAATTCGCGGCCGC

SEQ ID NOS: 7-14 show the HCV antigen domains E1a, E2, ProtA, Prot B, Hel A, Hel B, Hel C, and NS5 bpalm. These were expressed as antibody fusion proteins. For all constructs, amino acids TS and AS (shown in red) have been added for cloning purpose to the mosaic HCV sequence. NS5b palm has been constructed based on NS5b 3D structure (1C2P). It is based on structural domain corresponding of the palm domain of NS5b polymerase and do not correspond to the linear amino acid sequence;

Envelop protein E1a construct (63 amino acids)
(SEQ ID NO: 7):
TSVGQLFTFSPRRHWTTQDCNCSIYPGHITGHRMAWDMMMMNWSPTTAVVA

QLLRIPQAILDMIAGAS

In SEQ ID NO: 7 membrane domain and predicted unfolded regions have been removed from E1 mosaic 192 aa sequence to increase expression of the Ab fusion protein.

Envelop protein E2 mosaic sequence (342 amino
acids) (SEQ ID NO: 8):
TSETHVTGGSAARTTAGLAGLFTPGAKQNIQLINTNGSWHINRTALNCND

SLNTGWVAGLFYYHKFNSSGCPERLASCRPLTDFDQGWGPISYANGSGP

DQRPYCWHYPPKPCGIVPAKSVCGPVYCFTPSPVVVGTTDRSGAPTYN

WGENDTDVFVLNNTRPPLGNWFGCTWMNSTGFTKVCGAPPCVIGGVGNNT

LHCPTDCFRKHPEATYSRCGSGPWITPRCLVDYPYRLWHYPCTINYTIFK

IRMYVGGVEHRLEAACNWTRGERCDLEDRDRSELSPLLLSTTQWQVLPCS

FTTLPALSTGLIHLHQNIVDVQYLYGVGSSIASWAIKWEYVVLLFLLAS

In SEQ ID NO: 8 the membrane domain has been removed for E2 mosaic sequence.

NS3Protease has been cut in 2 structural domains based on its 3D structure (IJXP).

ProtA
(SEQ ID NO: 9)
TSAPITAYAQQTRGLLGCIITSLTGRDKNQVEGEVQIVSTAAQTFLATCI
NGVCWTVYHGAGTRTIAS Prot B
(SEQ ID NO: 10)
TSTPCTCGSSDLYLVTRHADVIPVRRRGDSRGSLLSPRPISYLKGSSGGP
LLCPAGHAVGIFRAAVCTRGVAKAVDFIPVENLETTMRSPVFTDNSSPPA
VPQSAS

NS3 Helicase enzymatic protein has been cut in 3 structural domains based on NS3 Helicase 3D structure. (1HEI)
Hel A
(SEQ ID NO: 11)
*TS*FQVAHLHAPTGSGKSTKVPAAYAAQGYKVLVLNPSVAATLGFGAYMSK
AHGIDPNIRTGVRTITTGSPITYSTYGKFLADGGCSGGAYDIIICDECHS
TDATSILGIGTVLDQAETAGARLVVLATATPPGSAS

-continued

Hel B (SEQ ID NO: 12)
TSVTVPHPNIEEVALSTTGEIPFYGKAIPLEVIKGGRHLIFCHSKKKCDE
LAAKLVALGINAVAYYRGLDVSVIPTSGVVVVVATDALMTGFTGDFDSVI
DCNTCVTQTVDFSLDPTFTIETTTLPQDAVSRTQRRGRTGRGKPGIYRFV
APGERAS

Hel C (SEQ ID NO: 13)
TSPSGMFDSSVLCECYDAGCAWYELTPAETTVRLRAYMNTPGLPVCQDHL
EFWEGVFTGLTHIDAHFLSQTKQSGENLPYLVAYQATVCARAQAPPPSWD
QMWKCLIRLKPTLHGPTPLLYRLGAVQNEVTLTHPITKYIMTCMSA*DLEV*
*VTAS*

NS5bpalm (SEQ ID NO: 14)
TSVLDSHYQDVLKEVKAAASKVKANALYDVVSKLPLAVMGSSYGFQYSPG
QRVEFLVQAWKSKKTPMGFSYDTRCFDSTVTESDIRTEEAIYQCCDLDPQ
ARVAIKSLTERLYVGRCRASGVLTTSCGNTLTCYIKARAACRAAGLQDCT
MLVCGDDLVVICESAGVQEDAASLRAFTEAMTRYSAPPGDPPQPEYDLEL
ITAS

HCV sequence and HCV domains constructions: Due to the high polymorphism of HCV, a sequence that is representative of most of circulating HCV sequence was selected.

A mosaic sequence was derived using the mosaic vaccine tools at http://www.hiv.lanl.gov/content/sequence/MOSAIC/ interface choosing mosaic sequence cocktail, 1 as cocktail size and 9 as epitope size. We used 213 sequences for NS3 mosaic and 310 sequences for NS5b mosaic. All sequences correspond to complete genes of 1893, 1773 nucleotides respectively and found in euHCVdb (available on the internet at: euhcvdb.ibcp.fr/euHCVdb/).

Synthetic corresponding genes were purchased from Bio Basic Inc. (Ontario Canada). For cloning purposes, Spe cloning site was introduced at 5' end and Nhe, EcoRI and Not I at the 3' end. HCV domains were then constructed by PCR. NS3Protease domain B was construct using the synthetic gene cloned in pUC57 as template and the following primers: NS3Protease domain B forward: 5'-GAGCTCGGATCCACTAGTACTCCTTGTACCTGCGGCTCATCC-3' (SEQ ID NO: 148) NS3Protease domain B reverse: 5'-GCCCGCGGCCGCGAATTCTCAGCTAGCACTCTGCGGCACTCTGGGGG-3' (SEQ ID NO: 149). NS3Helicase domain B was ordered directly as a synthetic gene. For NS5bPolymerase Palm domain construction, regions coding for amino acids 172 to 261 and 276 to 362 were amplified using NS5b synthetic gene and the respective following primers: Ns5b Palm (aa 172-261) forward: 5'-TCTAAAGTCAAAGCGAACGCTCTGTACGATGTCGTTTCC-3' (SEQ ID NO: 150), Ns5b Palm (aa 172-261) reverse: 5'-ACCGGAAGCGCGACAGCGGCCAACGTACAGGCGTTCGGT-3' (SEQ ID NO: 151), NS5b Palm (aa 276-362) forward: 5'-ACCGAACGCCTGTACGTTGGCCGCTGTCGCGCTTCCGGT-3' (SEQ ID NO: 152), NS5b Palm (aa 276-362) reverse: 5'-GCGGCCGCGAATTCttAGCTAGCGGTGATCAGCTCCAG-3' (SEQ ID NO: 153). Amplified products were then used as templates together with annealed primers 5'-CAAGCCCAACCCCACTAGTGTGCTGGACTCTCACTACCAGGATGTCCTGAAGGAAGTAAAAG CAGCCGCTTCTAAAGTCAAAGCGAACGCTCTGTACGAT-3' (SEQ ID NO: 154) and 5'-ATCGTACAGAGCGTTCGCTTTGACTTTAGAAGCGGCTGCTTTTACTTCCTTCAGGACATCCTG GTAGTGAGAGTCCAGCACACTAGTGGGGTTGGGCTTG-3' (SEQ ID NO: 155) in a final PCR using primers 5'-CAAGCCCAACCCC-3' (SEQ ID NO: 156) and 5'-GCGGCCGCGAATTCTTAGCTAGCGGTGATCAGCTCCAG-3' (SEQ ID NO: 157). The amplified NS5bPolymerase Palm domain was then cloned in TA vector and sub-cloned in XX vector using Nhe/Not strategy.

Chimeric Recombinant Antibodies Purification: For construct selection, chimeric DC-specific antibodies were transiently expressed in HEK293 cells and purified from the supernatant using Protein A sepharose chromatography. DNA from chimeric constructs expressed in HEK293 was then sub-cloned in cetHSpuro vector as AgeI/NotI fragment for expression in CHO cells after stable transfection. Antibodies were purified from supernatants using ProteinA sepharose.

Patients were recruited at the Baylor Hospital Liver Transplant Clinic (BHLTC, Dallas, Tex.) after obtaining informed consent. The study was approved by the Institutional Review Board of the Baylor Health Care System (Dallas, Tex.). Peripheral blood (100 ml) was collected at the BHLTC from 29 chronic HCV-infected adult patients and one healthy donor in contact with chronic HCV-infected patient. Leukapheresis were collected at Baylor University Medical Center Apharesis Collection Center (Dallas, Tex.) from all the enrolled individuals within 30 days after the first visit. Patient information is summarized in Table I.

Preparation of dendritic cells and PBMCs: PBMCs were isolated from heparinized blood on Ficoll density gradients. Monocytes were enriched from the leukapheresis according to cellular density and size by elutriation (Elutra™, CaridianBCT, Lakewood, Colo.) as per the manufacturer's recommendations. Elutriation Fraction 5 consisted mainly on monocytes (85% on average). Cells were cryopreserved in 10% DMSO 50% FCS 10% culture medium before use. For dendritic cell generation, monocytes were resuspended in serum-free CellGro DC culture medium (CellGenix Technologie Transfer Gmbh, Germany) at a concentration of 1 $10^6$ cells/ml. Media were supplemented with 100 ng/ml granulocyte-macrophage colony-stimulated factor (GMCSF, Leukine, Berlex, Wayne, N.J.) and 500 UI/ml alpha-interferon (IFN-α, Intro A, IFN-α-2b, Merck/Schering-Plough, Kenilworth, N.J.). After 24 h of culture at 37 degree Celsius, 5% $CO_2$, fresh cytokines were added. On day 3, recombinant antibody vaccines were added at various concentration (5 nM, 0.5 nM or 0.05 nM) or peptide cluster controls (2 µM each peptide) as indicated. Alternatively, TLR agonists (polyIC, 25 µg/ml; CL075 1 µg/ml; or PAM3, 200 ng/ml; all from Invivogen) were added in the culture at the same time as vaccine candidates or peptide controls. DC were pulsed for 16 h before harvest and used in PBMCs co-culture.

TABLE I

Demographics of patients used in the study.

| Patient ID | Genotype | Sex | Ethnicity | Race | HCV status | Age | Viral Load | HLA A* | HLA B* | HLA Cw* | HLA DRB1 | HLA DQB1 |
|---|---|---|---|---|---|---|---|---|---|---|---|---|
| HCV-VAC-001 | 1a | M | Hispanic | White | non responder | 39 | 5 877033 (H) | 0201; 0205 | 1302; 5101 | 0202; 0602 | 0701; 1301 | 0202; 0603 |
| HCV-VAC-002 | 1a | F | Non Hispanic | White | cured after therapy | 57 | UnDectable (UD) | 0101; 0301 | 0818; 5108 | 0701G; 1502 | 1101; 1301 | 0301; 0603 |

TABLE I-continued

Demographics of patients used in the study.

| Patient ID | Geno-type | Sex | Ethnicity | Race | HCV status | Age | Viral Load | HLA A* | HLA B* | HLA Cw* | HLA DRB1 | HLA DQB1 |
|---|---|---|---|---|---|---|---|---|---|---|---|---|
| HCV-VAC-003 | 1a | M | Non Hispanic | White | cured after therapy | 59 | UD | 0301; 3004 | 0702; 3501 | 0401; 0702 | 0101; 0402 | 0501; 0302 |
| HCV-VAC-004 | 1a | M | Non Hispanic | White | cured after therapy | 55 | UD | 0201; 3201 | 0702; 1002 | 0202; 0702 | 0401; 0901 | 0302; 0303 |
| HCV-VAC-005 | 1a | M | Non Hispanic | White | cured after therapy | 58 | UD | 0101; 1101 | 1801; 5101 | 0501; 1402 | 0301; 1407 | 0503; 0201 |
| HCV-VAC-006 | 3a | M | Non Hispanic | White | cured after therapy | 57 | UD | 0101; 2902 | 0702; 5701 | 0602; 0702 | 0701; | 0303; |
| HCV-VAC-007 | 3a | M | Non Hispanic | White | cured after therapy | 48 | UD | no apheresis | no apheresis | no apheresis | no apheresis | no apheresis |
| HCV-VAC-008 | 1b | M | Non Hispanic | White | non responder | 63 | | 0101; 6901 | 0801; 3508 | 0701; 1203 | 0301; | 0201; |
| HCV-VAC-009 | 1a | M | Non Hispanic | White | non responder | 51 | | 0101; 3004 | 0801; | 0701G; 0701 | 0301; 0701 | 0201; 0303 |
| HCV-VAC-010 | 1a | M | Non Hispanic | White | cured after therapy | 48 | UD | 0201; 2402 | 0801; 4002 | 0202; 0701G | 0301; 0701 | 0201; 0202 |
| HCV-VAC-011 | 1a | F | Non Hispanic | White | non responder | 52 | ? | 0205; 3101 | 1530; 4901 | 0102; 0707G | 0301; 0802 | 0201; 0402 |
| HCV-VAC-012 | 1a | M | Non Hispanic | White | cured after therapy | 43 | UD | 0101; 1101 | 4101; 5101 | 1502; 1710G | 0301; 1305 | 0201; 0301 |
| HCV-VAC-013 | 1a | M | Non Hispanic | White | non responder | 55 | | 0101; 0201 | 0801; 3502 | 0401; 0701G | 0301; 1601 | 0502; 0201 |
| HCV-VAC-014 | 1b | F | Non Hispanic | White | non responder | 56 | | 3101; 6801 | 0702; 3503 | 0401; 0702 | 0403; 1501 | 0302; 0602 |
| HCV-VAC-015 | 2b | M | Non Hispanic | White | positive untreated | 50 | | 0101; 0301 | 0801; 3501 | 0401; 0701G | 0301; 0701 | 0201; 0303 |
| HCV-VAC-016 | 1a | M | Non Hispanic | White | non responder | 55 | | 0101; 5501 | 5001; | 0303; 0602 | 0701; 1401 | 0503; 0202 |
| HCV-VAC-017 | 1a | M | Non Hispanic | White | positive untreated | 52 | | 2402; 2501 | 3901; 5701 | 0602; 1203 | 0701; | 0202; 0303 |
| HCV-VAC-018 | 1a | M | Non Hispanic | White | non responder | 53 | | no apheresis | no apheresis | no apheresis | no apheresis | no apheresis |
| HCV-VAC-019 | 1a | M | Non Hispanic | White | cured after therapy | 62 | UD | 2402; 2501 | 3901; 4402 | 0102; 1203 | 0701; 1501 | 0202; 0602 |
| HCV-VAC-020 | 1a | F | Non Hispanic | White | cured after therapy | 46 | UD | 0201; 0301 | 1501; 2705 | 0202; 0304 | 0401; 1101 | 0301; 0302 |
| HCV-VAC-021 | 1a | M | Non Hispanic | White | non responder | 64 | | 0101; 3002 | 0801; 4001 | 0304; 0701G | 0101; 0301 | 0501; 0201 |
| HCV-VAC-022 | 1b | F | Non Hispanic | White | non responder | 58 | | 0301; 6801 | 1801; 4001 | 0304; 0501 | 0301; 1302 | 0201; 0604 |
| HCV-VAC-023 | 2 | F | Non Hispanic | White | positive untreated | 45 | | no apheresis | no apheresis | no apheresis | no apheresis | no apheresis |
| HCV-VAC-024 | 2b | M | Non Hispanic | White | positive untreated | 43 | | 0301; | 1402; 4701 | | | 0202; 0602 |
| HCV-VAC-025 | 3a | F | Non Hispanic | White | positive untreated | 31 | ? | no apheresis | no apheresis | no apheresis | no apheresis | no apheresis |
| HCV-VAC-026 | 3a | M | Non Hispanic | White | positive untreated | 29 | ? | no apheresis | no apheresis | no apheresis | no apheresis | no apheresis |
| HCV-VAC-027 | 1a | F | Non Hispanic | White | positive untreated | 26 | | 02; 26 | 15(62); 51 | | | 03(7); 05 |
| HCV-VAC-028 | 1a | F | Hispanic | other | positive untreated | 47 | | 03; 25 | 07; 18 | | | 06; |
| HCV-VAC-029 | Non infected | F | Non Hispanic | White | uninfected | 63 | | 01; 11 | 44; 55 | | | 02; 05 |
| HCV-VAC-030 | 1 | M | Non Hispanic | White | positive untreated | 57 | ? | 03; 24 | 07; 27 | | | 03(7); 06 |

Expansion of Antigen-specific T cells in DC/PBMCs coculture. Frozen PBMCs from leukapharesis were thawed, washed by centrifugation and resuspended at $2\times10^6$ cells/ml in cRPMI medium. Autologous DC loaded with vaccine candidates or peptides cluster controls were co-cultured with PBMCs in a 24 well tissue plate at a ratio of 1/20 and incubated for a total of 10 days. IL2 (20 IU/ml, Aldesleukine, ProleukineR; Bayer Healthcare and Novartis, Emeryville, Calif.) was added every two days. At day 9, PBMCs from a 24-well plate were washed, distributed in 2 wells in a 96-well plates and rested for 24 h. The specificity of the T-cell response elicited by vaccine candidate loaded-DC was assessed by restimulation of PBMCs with peptide clusters (2 µM each peptide). For each condition, a negative background control was included as a restimulation without peptides.

Flow cytometry: After 1 hour of peptide clusters restimulation, BFA (Sigma) was added for the last 5-6 h to block cytokine secretion. The cells were stained for surface markers with a combination of fluorochrome antibodies (perCP-CD3, PE-CD8, APCH7-CD4), fixed, permeabilized and intracellular-stained with a mixture of APC-IFNγ, FITC-IL2 and PEcy7-TNFα antibodies. For CTL marker function analysis, FITC-CD107a antibody was added with BFA in the culture medium and the following antibodies combination was used for the surface staining: PerCP-CD3, pacific blue-CD8, APCH7-CD4 and for the intracellular staining: PE-IFNγ, APC-GranzB, APCcy7-TNFα. All antibodies were purchased from BD sciences except APC-GranzB (Invitrogen). Cells were analyzed on a FACS-Canto collecting 500,000 events, and results analyzed using FlowJo software. Most of the data were displayed as two colors plot to measure IFN-γ and TNF-α production in $CD3^+CD8^+$ or $CD3^+CD4^+$ cells.

Luminex: Supernatants of DC-PBMCs co-culture were harvested 48 h after PBMCs restimulation with peptide clusters. Cytokine multiplex assays were employed to analyzed IFN-γ, IL-10, and IL-13.

Evaluation of embodiments of vaccines: Vaccine candidate were tested in targeting experiment by co-culture of vaccine with PBMCs from chronic HCV infected patients or chronic HCV infected patients cured after IFNa-Ribavirin therapy. The data show that anti-CD40 or anti-DCIR vaccines bearing a HCV NS3HelB antigen can recall a potent memory antigen-specific anti-CD4+ T cell response in vitro using immune cells from HCV infected patients. In this in vitro culture system anti-CD40 and anti-DCIR are equally potent vaccines—these DCs express both receptors. Anti-DCIR vaccine construct bearing longer HCV antigen coverage induced multifunctional CD4+ antigen specific T cells against multiple HCV epitopes.

The data further show that anti-DCIR vaccines bearing a HCV NS3HelBC antigen can recall a potent memory antigen-specific anti-CD4+ T cell response in vitro using immune cells from HCV infected patients. This response is directed against multiples HCV epitopes. In this in vitro culture system, both concentration used for anti-DCIR HCV-NS3HelBC targeting are equally potent in contrast to anti-DCIR HCV-NS3HelB vaccine.

Figure 3A:
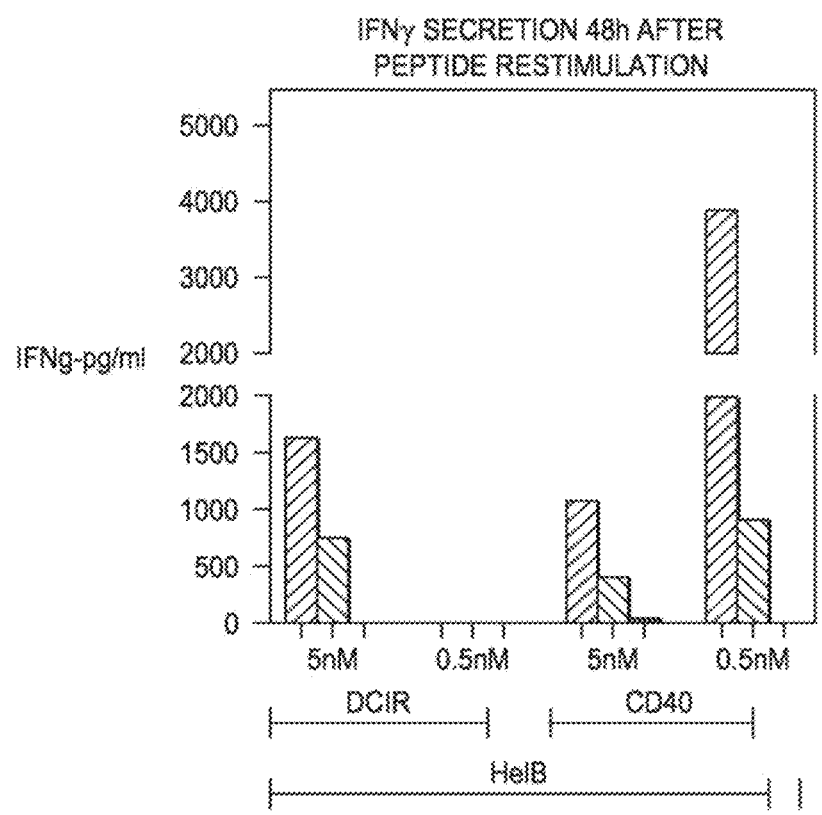
Figure 3B:
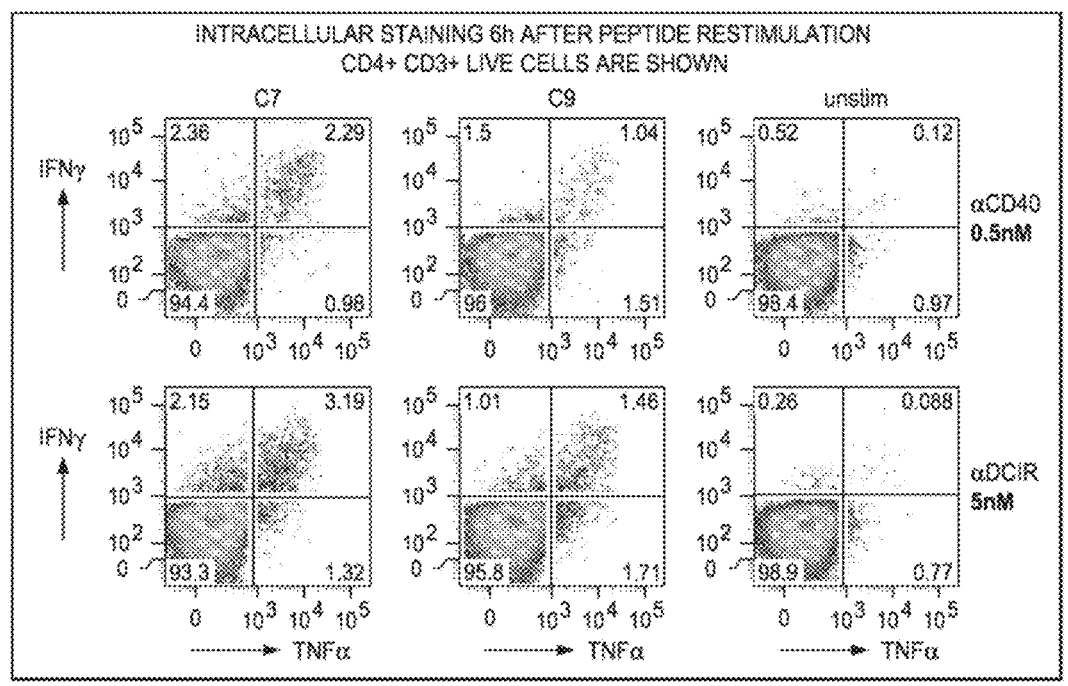

FIGS. 3A-3B demonstrate the ability of recombinant anti-DCIR and anti-CD40 antibodies fused to HCV NS3HelB specific antigen to elicit the expansion of antigen-specific CD4+ T cells from a chronic HCV infected patient cured after IFNa-Ribavirin therapy. Delivering NS3HelB to DCs through CD40 and DCIR induces IFNγ-TNFa-producing HCV NS3HelB-specific CD4+ T cells. PBMC cells from chronic HCV infected patients; either cured after therapy or in treatment failure, were co-cultured with IFNDCs targeted with anti-CD40-NS3HelB or anti-DCIR-NS3HelB for 10 days. Cells were stimulated with peptides clusters (10 peptides of 15-mers in each clusters) covering HCV NS3 HelB (10 µM): FIG. 3A after 2 days, culture supernatants were analyzed for measuring IFNγ and FIG. 3B PBMC cells were stained for measuring the frequency of peptide-specific CD4+ T cells intracellular IFNγ+TNFα+ cells.

Figure 4:
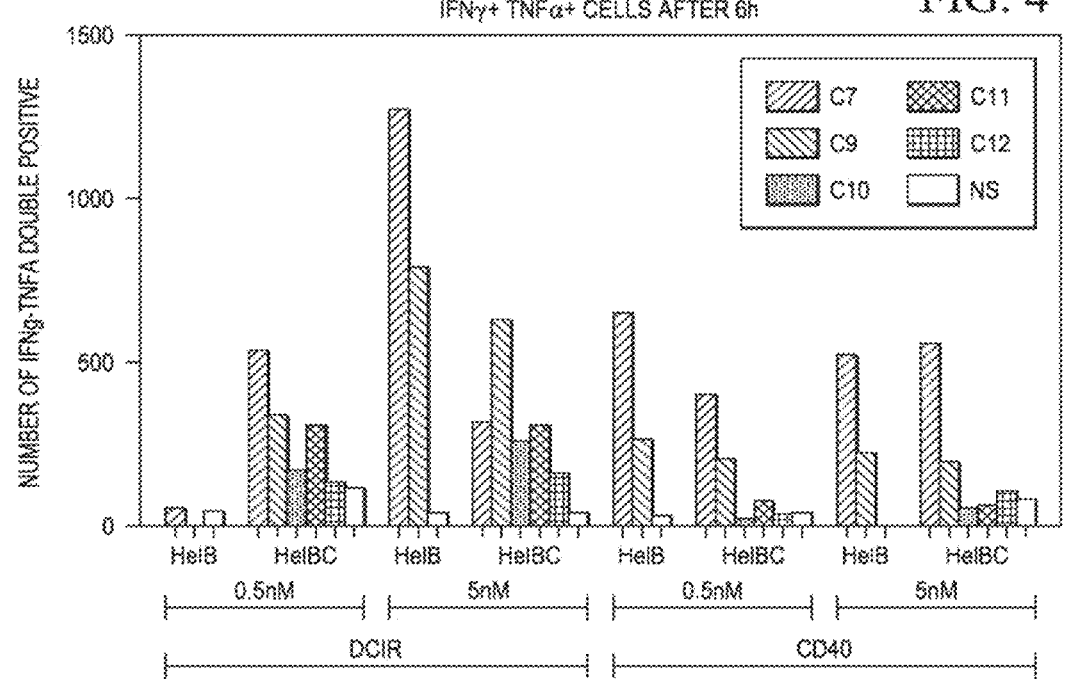

Longer construct are equally potent to recall multi epitopes HCV specific T cells. The data in e.g., FIG. 4, show that both anti-CD40 and anti-DCIR vaccines bearing HCV NS3HelB NS3ProtB and NS5BPalm antigens can recall a potent memory antigen-specific anti-CD4+ T cell response in vitro using immune cells from HCV infected patients cured after IFN-Ribavirin therapy. This response is directed against multiples HCV epitopes. In this in vitro culture system, dose effect is observed consistent with clear targeting, with an optimum concentration being at 5 nM for anti-CD40 construct and 0.5 nM for anti-DCIR construct. At these concentrations IgG4 controls induce significantly lower CD4+ T cells responses, consistent with antibody targeting of DC.

Figure 5A:
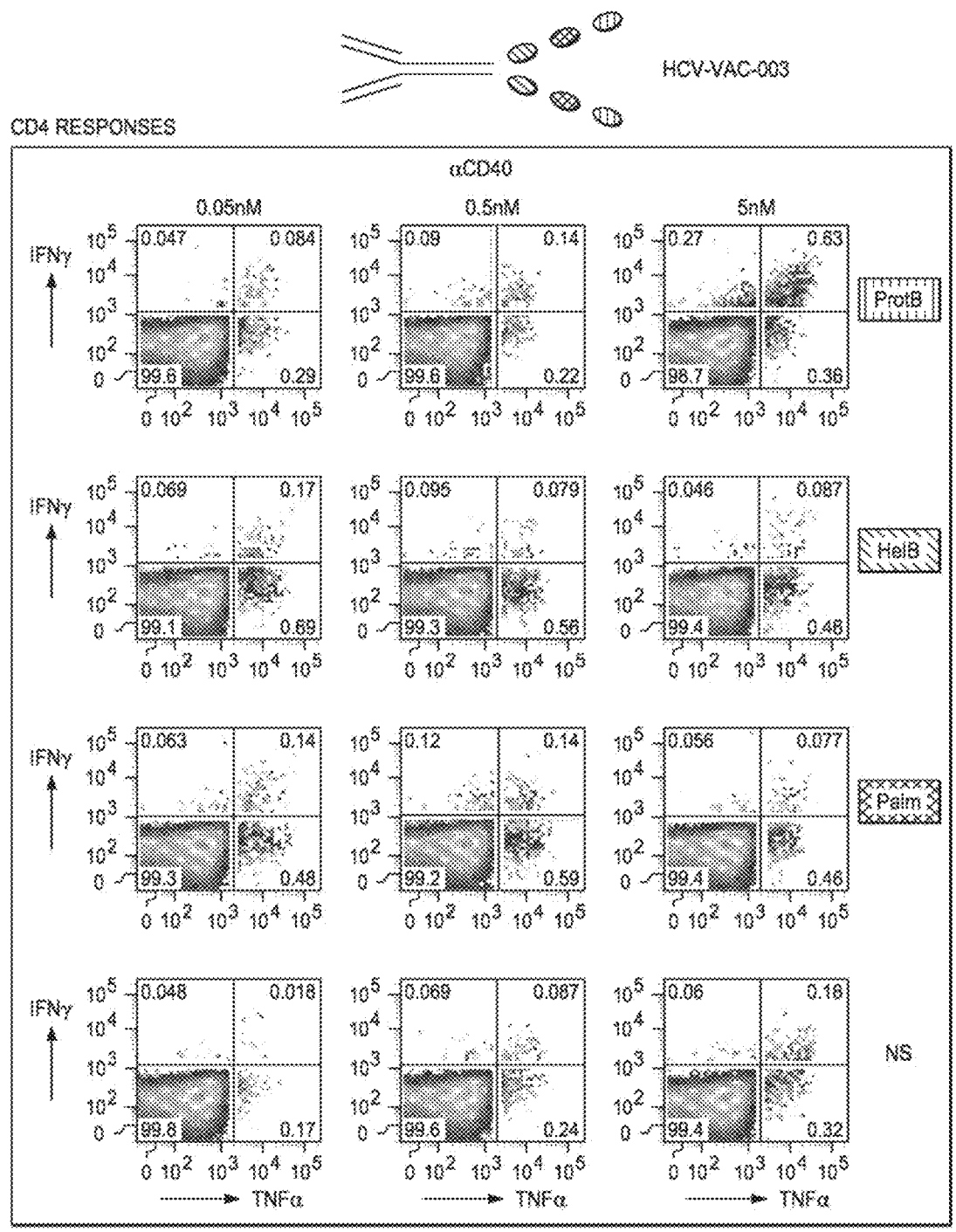
Figure 5B:
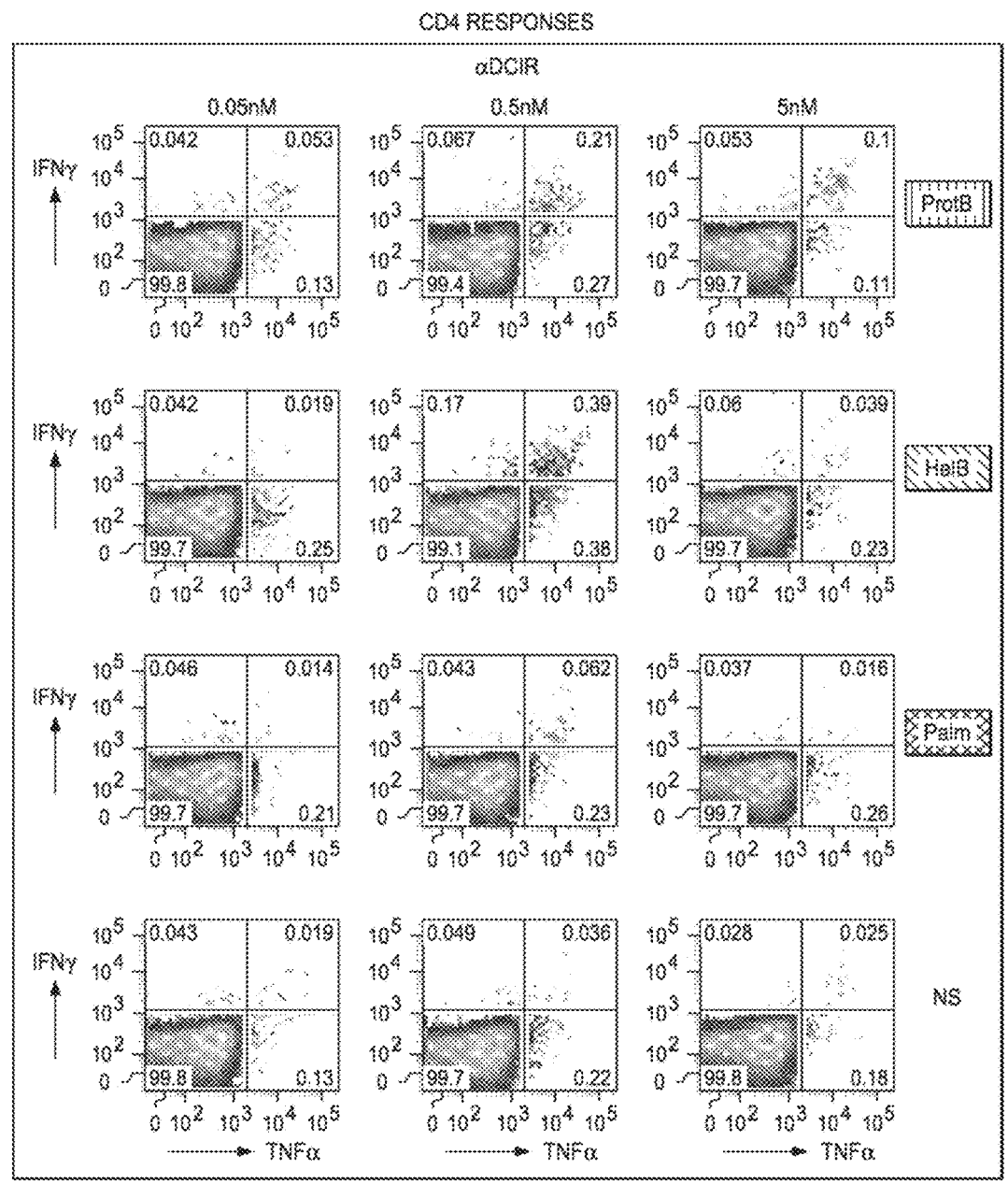
Figure 5C:
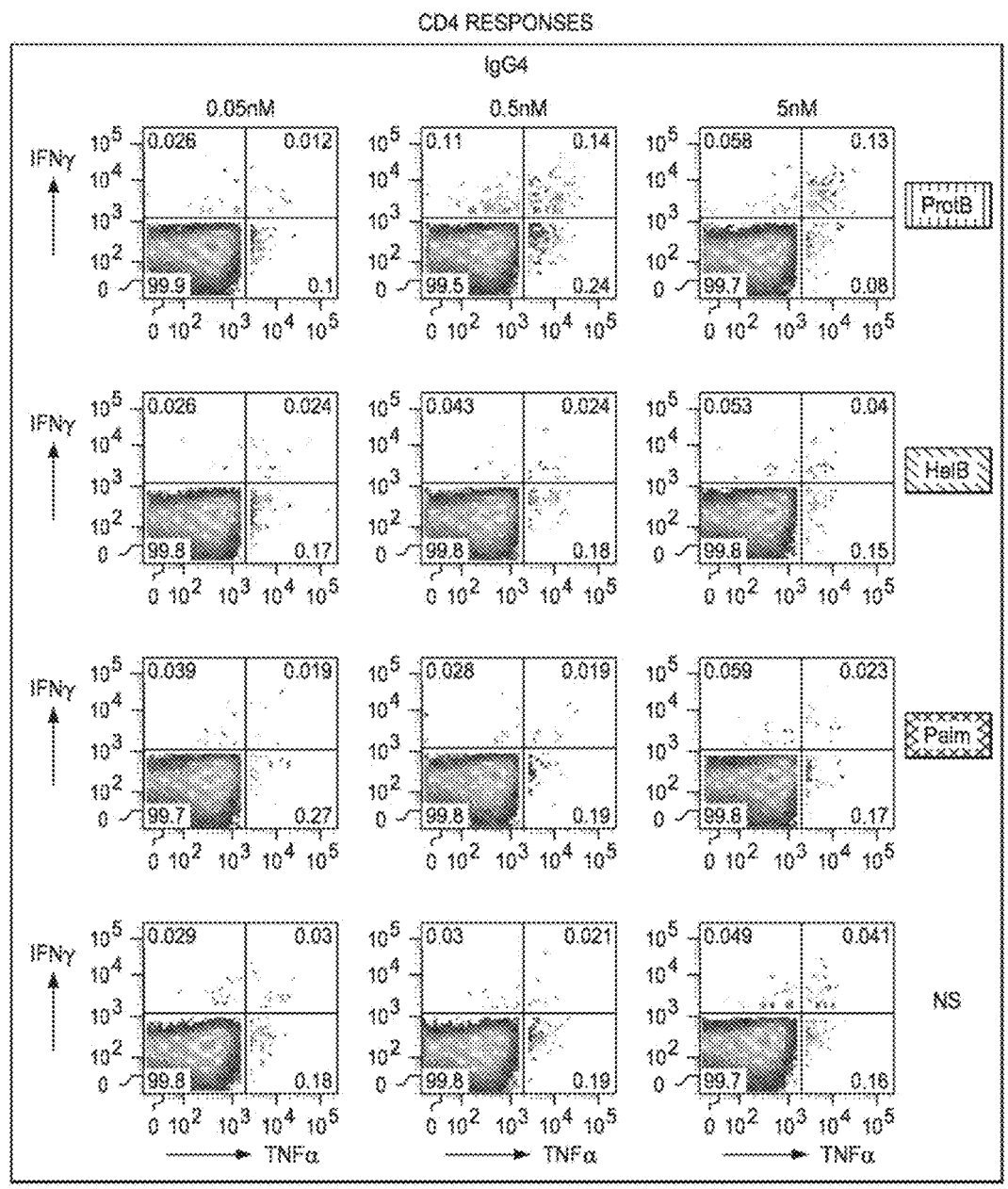

FIGS. 5A to 5C demonstrate the ability of recombinant anti-DCIR and anti-CD40 antibodies fused to HCV NS3HelB, HCV NS3ProtB and HCV NS5BPalm specific antigens to elicit the expansion of antigen-specific CD4+ T cells from a chronic HCV infected patient cured after IFNa-Ribavirin therapy. Delivering HCV antigen to DCs through CD40 and DCIR induces IFNγ-TNFa-producing HCV-specific CD4+ T cells, with multi epitopes, specific CD4 T cells. PBMC cells from chronic HCV infected patients cured after therapy were co-cultured with autologous IFNαDCs targeted with anti-CD40-NS3HelB-NS3ProtB-NS5BPalm or anti-DCIR-NS3HelB-NS3ProtB-NS5BPalm for 10 days. Cells were stimulated with peptides clusters (10 peptides of 15-mers in each clusters) covering HCV NS3HelB, NS3ProtB or NS5BPalm (2 µM). PBMC cells were stained for measuring the frequency of peptide-specific CD4+ T cells intracellular IFNγ+TNFα+ cells.

Figure 6A:
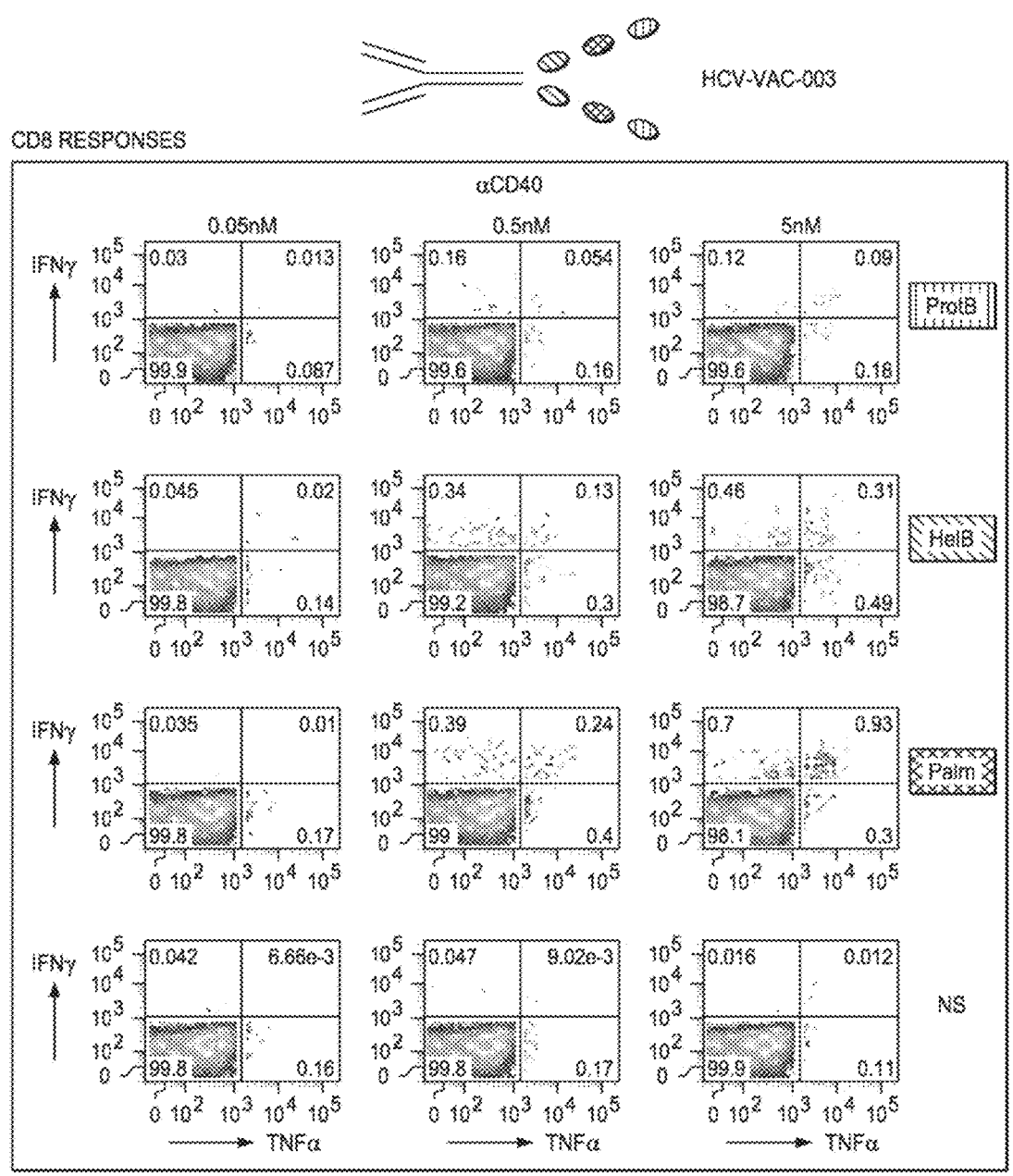
Figure 6B:
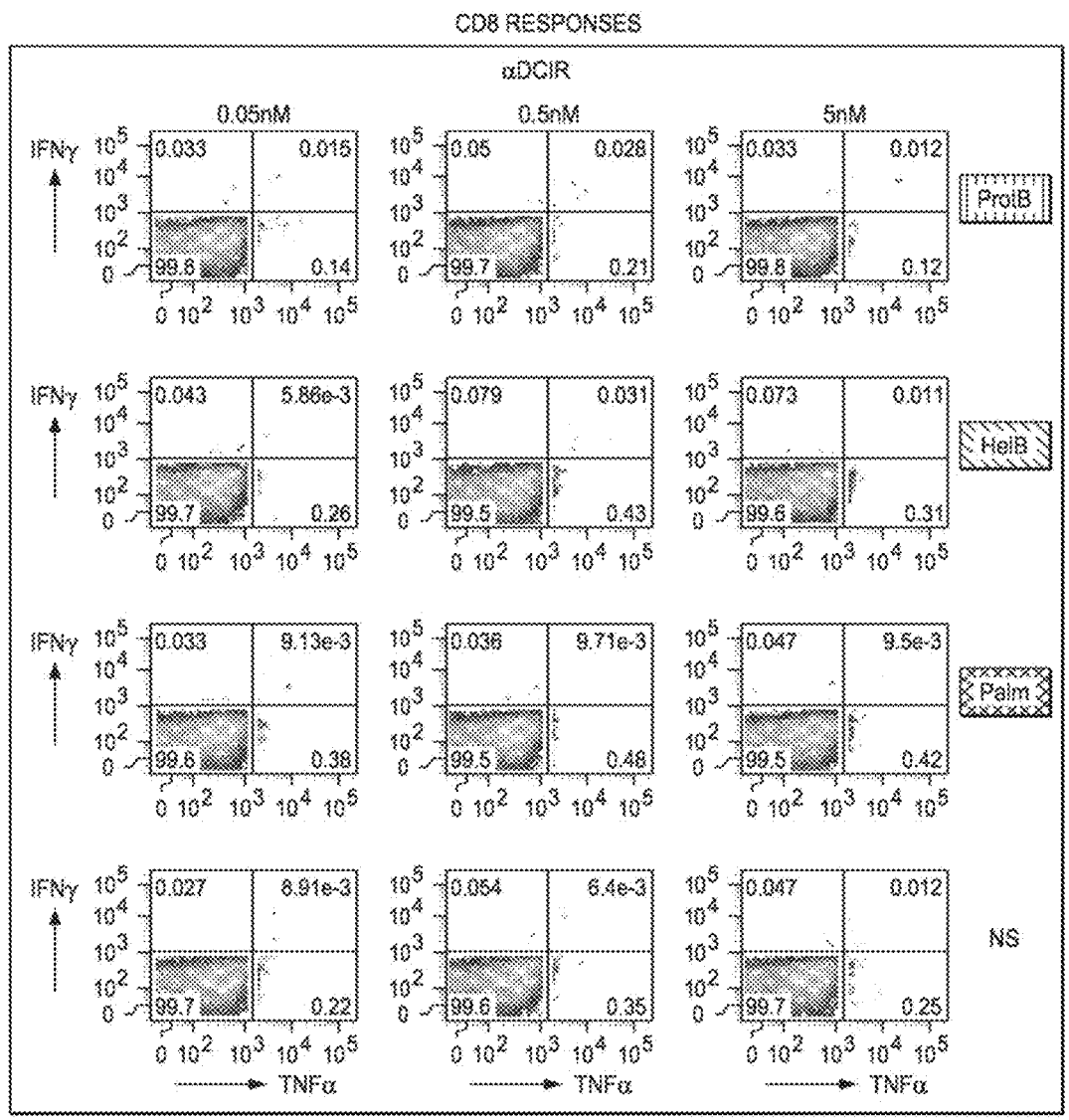
Figure 6C:
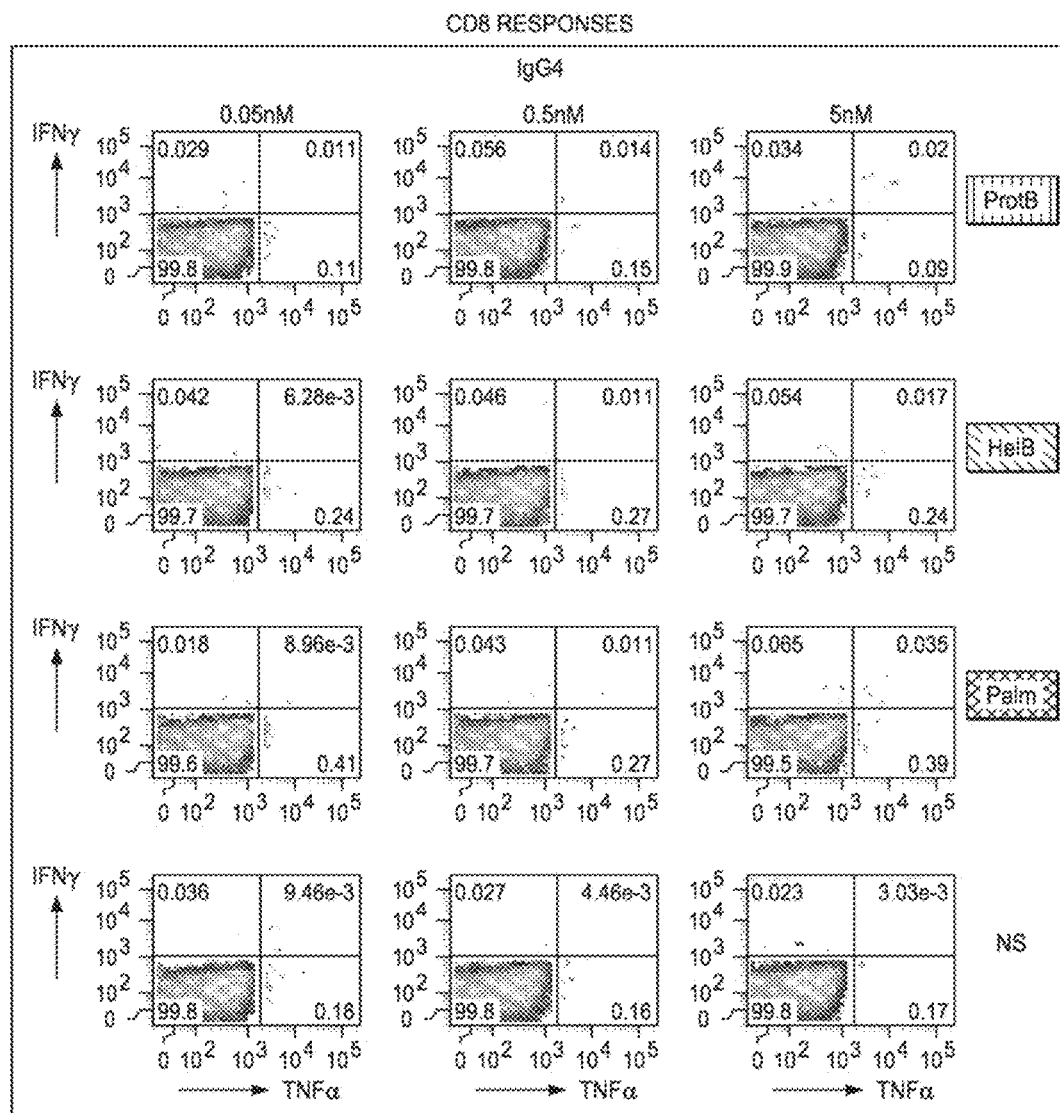
Figure 7B:
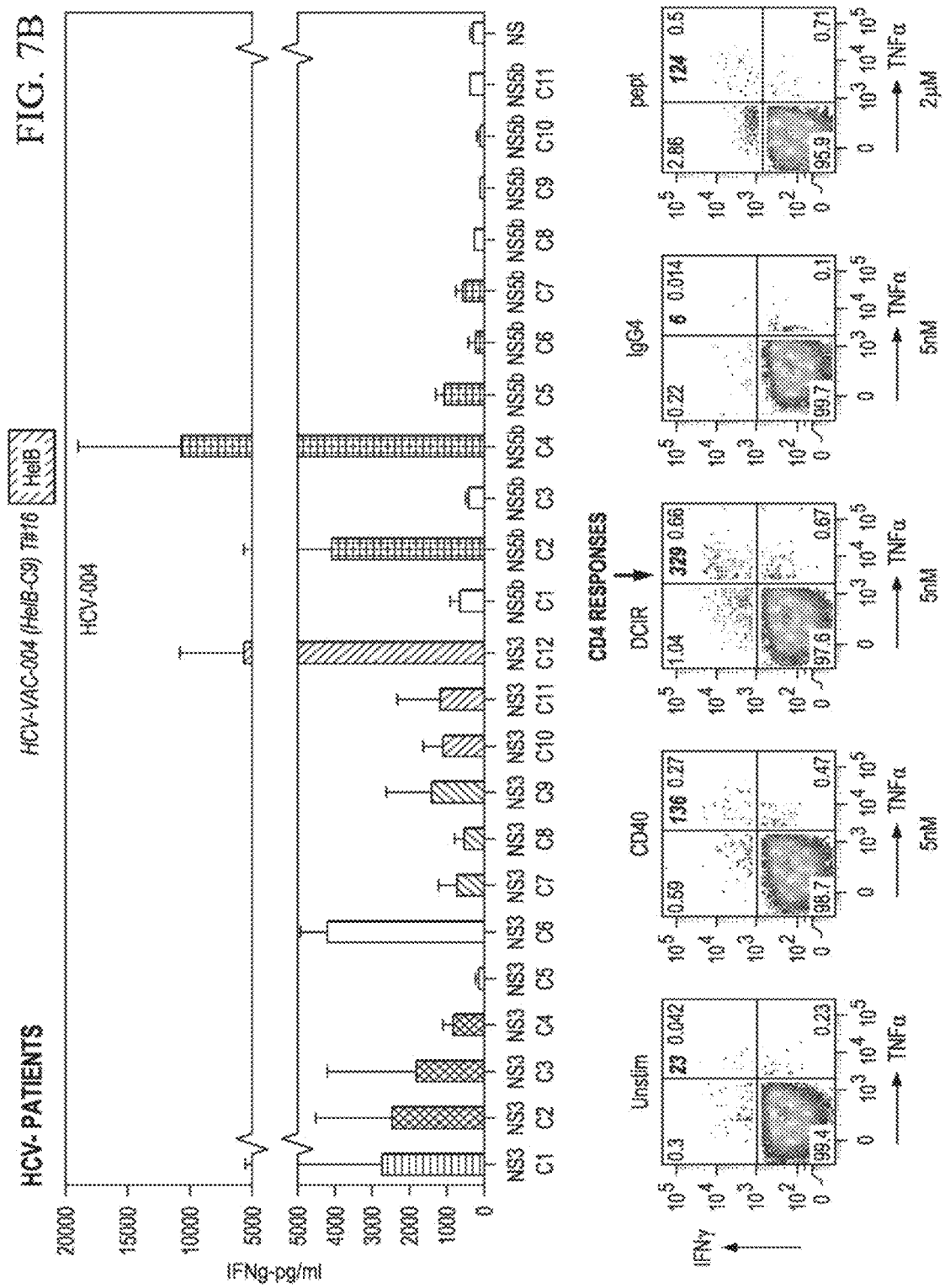
Figure 7D:
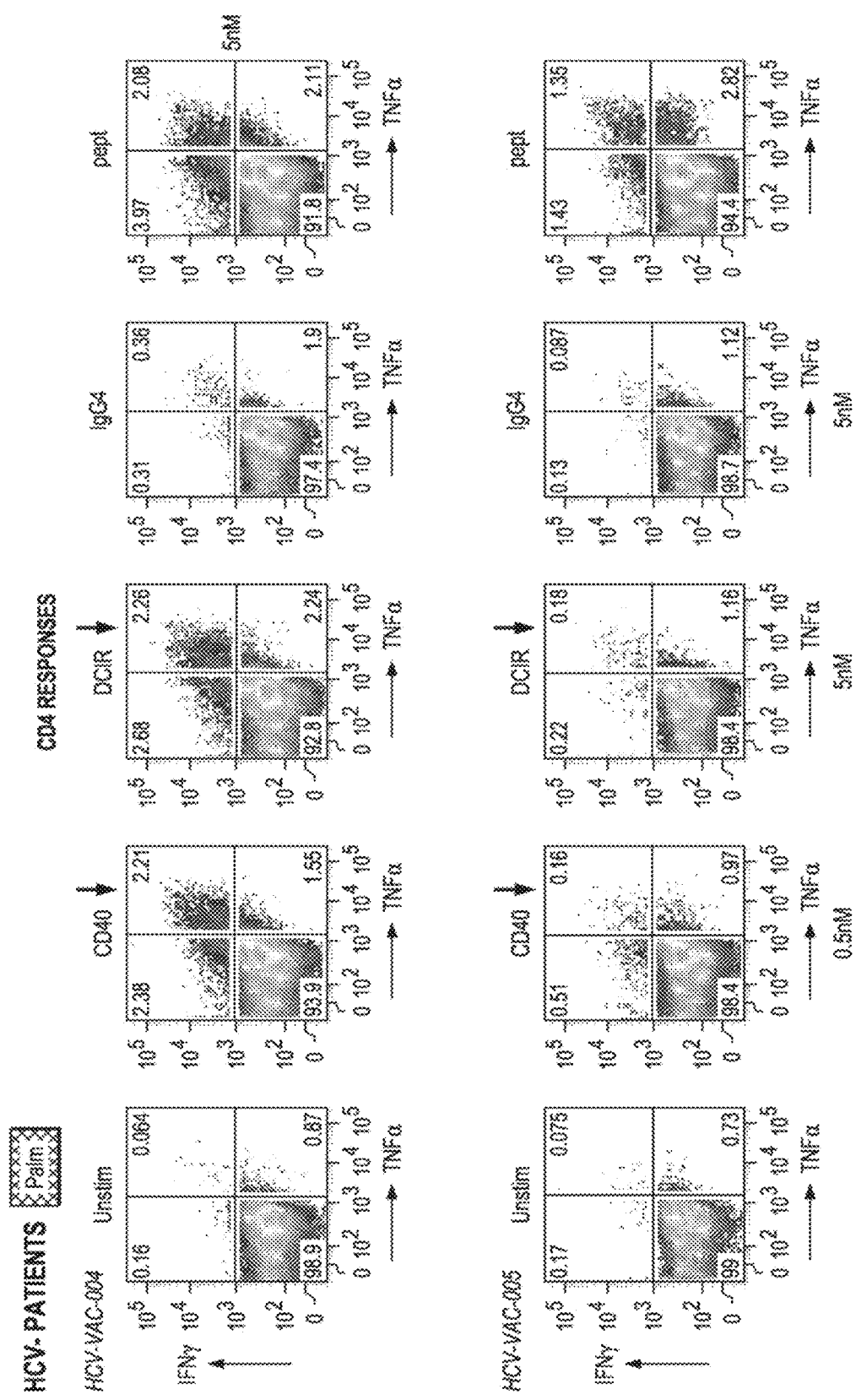
Figure 8A:
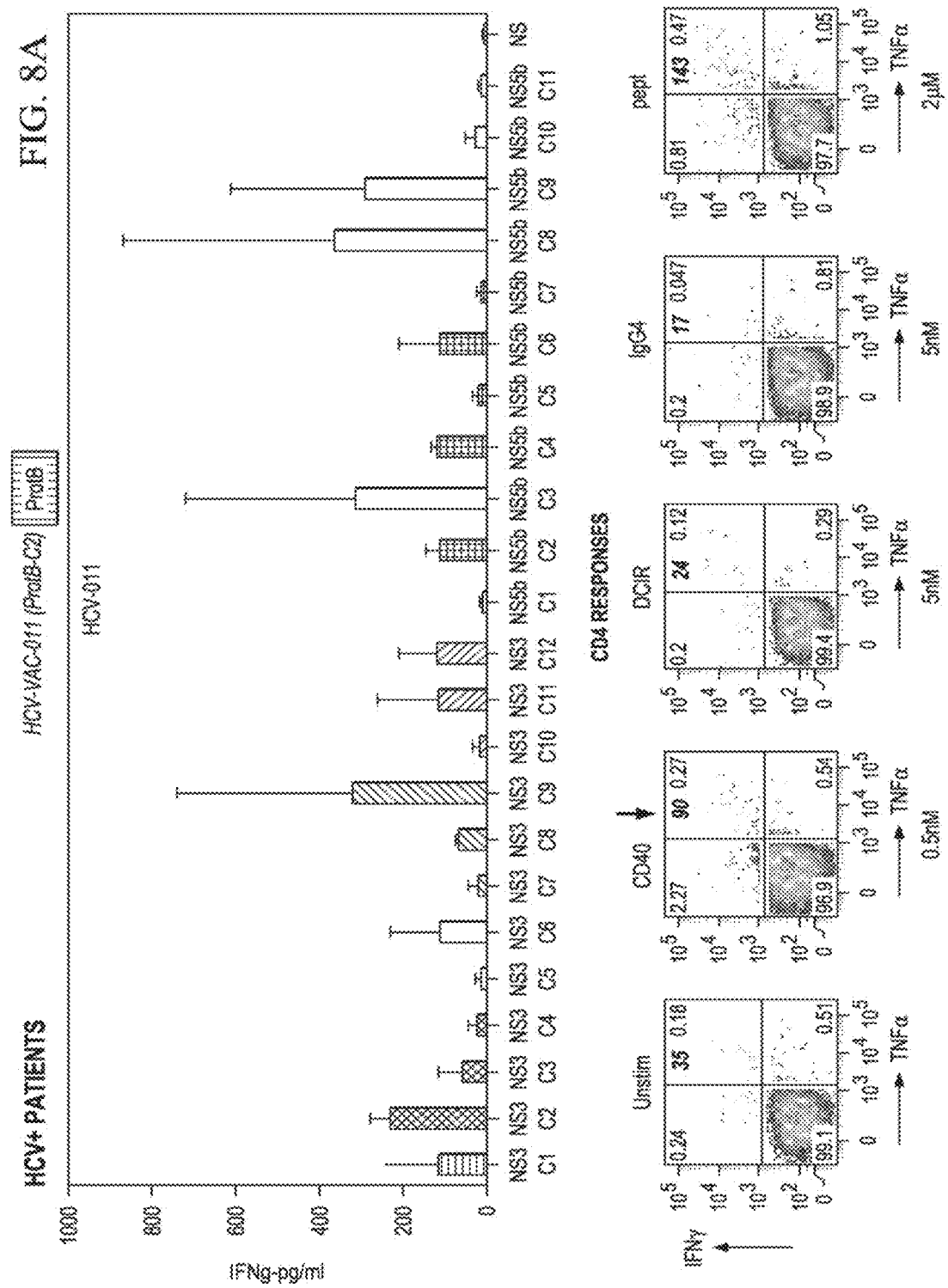
Figure 8B:
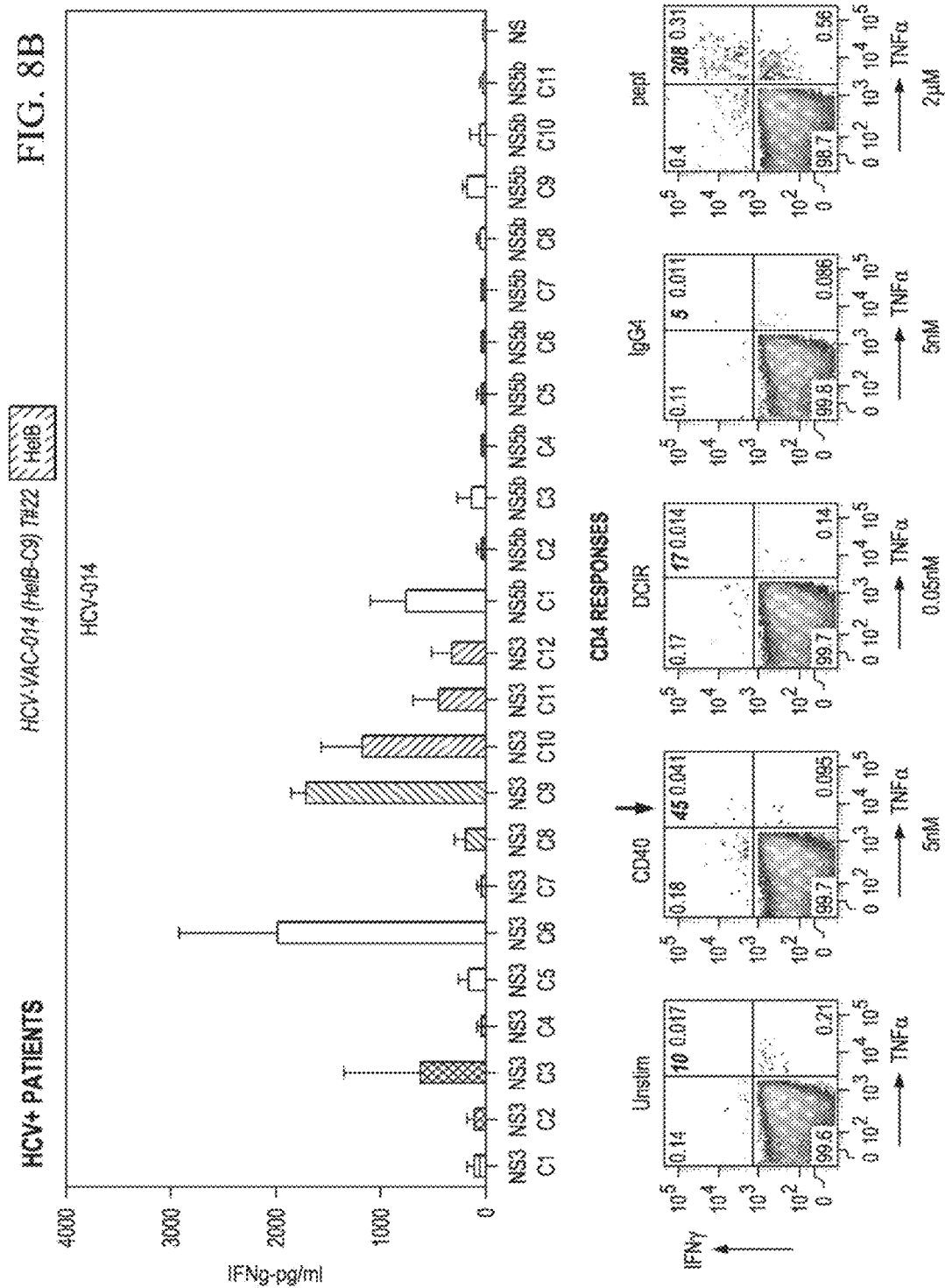
Figure 8C:
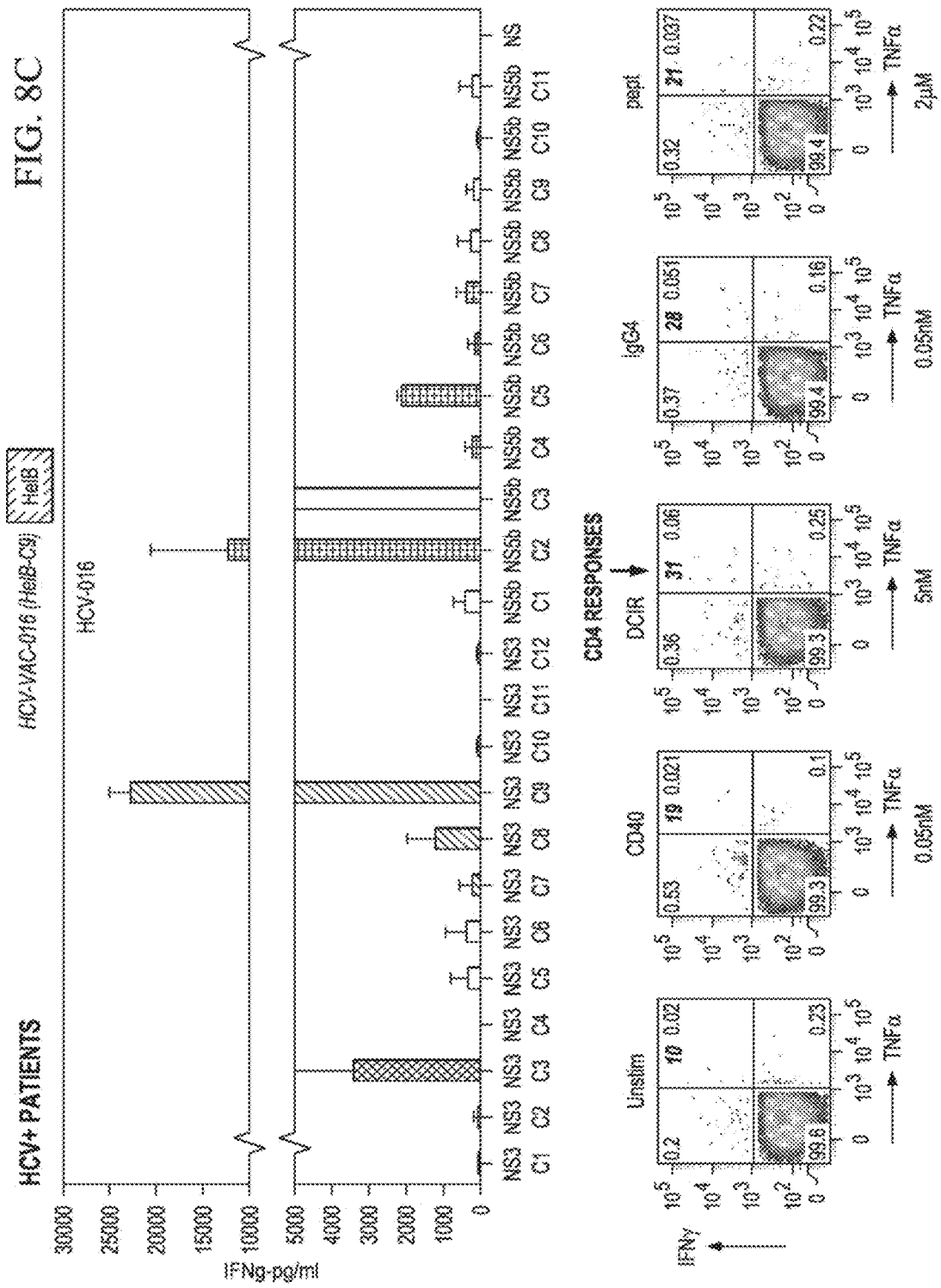

The data in FIGS. 6A to 6C demonstrate that anti-CD40 vaccines bearing HCV NS3HelB NS3ProtB and NS5BPalm antigens can recall a potent memory antigen-specific anti-CD8+ T cell response in vitro using immune cells from HCV infected patients cured after IFN-Ribavirin therapy. This response is directed against multiples HCV epitopes. In this in vitro culture system, dose effect is observed consistent with clear targeting, of DC with an optimum concentration being at 5 nM for anti-CD40 constructs. At these concentrations IgG4 controls induce significantly no CD8+ T cells responses, consistent with antibody targeting of DC.

Similar responses are induced in multiple different chronic HCV infected patients either cured or after therapy or in treatment failure.

The data in FIGS. 7A to 7D show that all chronic HCV infected patients cured after therapy are able to recall CD4+ T cells memory after co-culture of PBMCs with DC targeted with either anti-CD40 or anti-DCIR or both, construct bearing HCV antigens.

The data in FIGS. 8A to 8D shows that all chronic HCV infected patients in treatment failure are able to recall CD4+ T cells memory after co-culture of PBMCs with DC targeted with either anti-CD40 or anti-DCIR or both, construct bearing HCV antigens. Compare to chronic HCV infected patients cured after therapy, responses are low in chronic HCV infected patients in treatment failure and more antigen dependent since for example HCV-VAC-016 patient has no CD4+ T cells memory cells recalled after DC targeting with NS5bPalm construct.

CD8+ antigen specific T cells were obtained after TLR agonist introduction in the co-culture of vaccine with PBMC cells from HCV patients.

The data in FIGS. 9A and 9B show that TLR2 triggering with PAM3 during DC targeting with anti-DCIR vaccines bearing a HCV NS3HelB antigen can recall a potent memory antigen-specific anti-CD4+ and CD8+ T cell response in vitro using immune cells from HCV infected patients. Moderated CD8+ response is also induced by TLR3 triggering and no CD4+ or CD8+ response is induced after TLR7/8 triggering by CL097 in this study. Similar responses are induced in multiple different chronic HCV infected patients either cured or after therapy or in treatment failure.

The data in FIGS. 10A-10D show that TLR2 triggering with PAM3 during DC targeting with anti-CD40 or anti-DCIR vaccines bearing a HCV NS3HelB or HCV NS3ProtB antigen can recall a potent memory antigen-specific anti-CD4+ and CD8+ T cell responses in vitro using immune cells from HCV infected patients. Moderated CD8+ response is also induced by TLR3 triggering in some patients, and cyclic glucan can dramatically increase CD8+ T cells responses in one patient.

FIG. 11 demonstrates the ability of combination of TLR agonists and anti-CD40 HCV-constructs to increase CD4+ T cells responses in chronic HCV infected patients in treatment failure. HCV antigens from NS3 Helicase HelB or from NS3 Protease ProtB constructs were delivered to DCs through CD40 or DCIR. IFNαDCs were targeted with anti-CD40-NS3HelB, anti-DCIR-NS3HelB, anti-CD40-NS3ProtB, anti-DCIR-NS3ProtB, in presence of PAM3 (TLR2 agonist; 200 ng/ml), CL095 (TLR7/8 agonist; 5 µg/ml) or polyIC (TLR3 agonist; 25 µg/ml) or cyclic glucan (TLR4 agonist, 10 µg/ml) before co-culture for 10 days with PBMC cells from chronic HCV infected patients cured after therapy. Cells were stimulated for 6 h with peptide clusters C7 (10 µM; 10 peptides of 15-mers) covering HCV NS3 HelB constructs or with peptide clusters C3 (10 µM; 10 peptides of 15-mers) covering HCV NS3 ProtB constructs. PBMC cells were stained for measuring the frequency of peptide-specific CD4+ intracellular IFNγ+TNFα+ cells, an analyzed by FACS.

All tested HCV patients are able to recall CD4+ and CD8+ HCV specific memory after DC-targeting with HCV vaccine candidates.

FIG. 12A to 12C demonstrate the ability of HCV vaccine candidates to recall CD4+ T cells responses in all chronic HCV infected patients (cured or in treatment failure). HCV antigens from NS3 Helicase HelB, NS5b polymerase Palm or from NS3 Protease ProtB constructs were delivered to DCs through CD40 (FIG. 12B) or DCIR (FIG. 12C). IFNαDCs were targeted with anti-CD40-[NS3HelB~NS3ProtB~NS5bPalm on heavy chain], anti-DCIR-[NS3HelB~NS3ProtB~NS5bPalm on heavy chain] before co-culture for 10 days with PBMC cells from chronic HCV infected patients cured after therapy. Cells were stimulated for 6 h with peptide clusters C7-C9 (10 µM; 10 peptides of 15-mers) covering HCV NS3 HelB domain, with peptide clusters C2-C3-C4 (10 µM; 10 peptides of 15-mers) covering HCV NS3 ProtB domain or with peptide clusters C2-C4-C5-C6-C7 (10 µM; 10 peptides of 15-mers) covering HCV NS5b Palm domain. PBMC cells were stained for measuring the frequency of peptide-specific CD4+ and CD8+ intracellular IFNγ+TNFa+ cells, and analyzed by FACS. The number of CD4+ IFNg+TNFa+ cells induced vaccine candidate is shown.

It was also observed that different combinations of HCV domains on vaccine candidate are equally equivalent to recall CD4+HCV memory. Moreover, HCV antigen combination where two domains are borne on heavy chain and one on light chain is more efficient than having the 3 borne by heavy chain.

FIGS. 13A-13E demonstrate the ability of different HCV antigen combination on vaccine candidate for recall CD4+ T cells responses in chronic HCV infected cured patients. HCV antigens from NS3 Helicase HelB, NS5b polymerase Palm or from NS3 Protease ProtB combination constructs were delivered to DCs through CD40 or DCIR. IFNαDCs were targeted with second-generation vaccines anti-CD40-[NS3HelB on light chain and NS3ProtB~NS5bPalm on heavy chain], anti-DCIR-[NS3HelB on light chain and NS3ProtB~NS5bPalm on heavy chain], or first-generation vaccines anti-CD40-[NS3HelB~NS3ProtB~NS5bPalm on heavy chain], anti-DCIR—[NS3HelB~NS3ProtB~NS5bPalm on heavy chain] before co-culture for 10 days with PBMC cells from chronic HCV infected patients cured after therapy. Cells were stimulated for 6 h with peptide clusters C7 and C9 (10 µM; 10 peptides of 15-mers) covering HCV NS3 HelB domain (shown in green on the figure), with peptide clusters C2-C3-C4 (10 µM; 10 peptides of 15-mers) covering HCV NS3 ProtB domain (shown in pink on the figure) or with peptide clusters C2-C4-C5-C6-C7 (10 µM; 10 peptides of 15-mers) covering HCV NS5b Palm domain (shown in orange in the figure). PBMC cells were stained for measuring the frequency of peptide-specific CD4+ intracellular IFNγ+TNFα+ cells, an analyzed by FACS. The number of CD4+IFNγ+TNFα+ cells induced by first-generation vaccine or second-generation vaccine is compared in the last panel.

The vaccine candidates described in the present invention also showed the ability induce cross reactivity recall memory responses in patients infected with an HCV genotype different from those used to build the vaccine (FIGS. 14A to 14H). FIGS. 14A to 14H demonstrate ability of vaccine candidate to recall CD4+ T cells responses in HCV patients infected with non 1 genotype and HCV-exposed but non infected individual. HCV antigens from NS3 Helicase HelB, NS5b polymerase Palm or from NS3 Protease ProtB combination constructs were delivered to DCs through CD40 or DCIR and DC loaded were co-culture for 10 days with PBMC cells from HCV patients infected with non 1 genotype HCV-infected patients (HCV-015, 2b) and HCV-exposed but non infected individual (HCV-029). Cells were stimulated for 6 h with peptide clusters C7 and C9 (10 µM; 10 peptides of 15-mers) covering HCV NS3 HelB domain, with peptide clusters C2-C3-C4 (10 µM; 10 peptides of 15-mers) covering HCV NS3 ProtB domain or with peptide clusters C2-C4-C5-C6-C7 (10 µM; 10 peptides of 15-mers) covering HCV NS5b Palm domain. PBMC cells were stained for measuring the frequency of peptide-specific CD4+ intracellular IFNγ+TNFα+ cells, an analyzed by FACS.

FIGS. 15A and 15B show the results from a 10 day expansion culture whereby a dose range of 1st generation anti-DCIR-HCV vaccine (left panels) is compared to second generation anti-DCIR-HCV vaccine (right panels). Doses were 0.05 nM, 0.5 nM, and 5 nM and antigen-specific responses were ascertained by stimulation with no peptide (control) or ProtA, HelB, or Palm peptide pools in the presence of Brefeldin, followed by staining for CD3+, CD4+ and intracellular IFNg and TNFa. Samples were analyzed by FACS. Shown are comparable CD4+ HCV antigen-specific responses to the two generations of vaccines.

FIGS. 16A and 16B show the results from a 10 day expansion culture whereby a dose range of 1st generation anti-CD40-HCV vaccine (left panels) is compared to second generation anti-CD40-HCV vaccine (right panels). Doses were 0.05 nM, 0.5 nM, and 5 nM and antigen-specific responses were ascertained by stimulation with no peptide (control) or ProtA, HelB, or Palm peptide pools in the presence of Brefeldin, followed by staining for CD3+, CD4+ and intracellular IFNg and TNFa. Samples were analyzed by FACS. Shown are comparable CD4+ HCV antigen-specific responses to the two generations of vaccines.

Non-limiting examples different DC-specific antibodies or fragments (both nucleotide and protein sequences) that may be used in the preparation of the HCV vaccine of the present invention are shown herein below, the nomenclature corresponding to the target (e.g., Anti_CLEC_6_9B9.2G12_Heavy Hv-V-hIgG4H-C—is an anti-CLEC-6 antibody from the mouse hybridoma clone "9B9.2G12" (which is the source of the anti-CLEC-6 antibody sequence); heavy chain "H" variable region "v" (which can be humanized) heavy and is an IgG4 constant region isotype. The same nomenclature applies to light chains (from mouse Kappa light chains), and the antigens.

```
Anti_CLEC_6_9B9.2G12_Hv-V-hIgG4H-C
(SEQ ID NO: 15):
ATGGGCAGGCTTACTTCTTCATTCTTGCTACTGATTGTCCCTGCATATGT
CCTGTCCCAGGTTACTCTGAAAGAGTCTGGCCCTGGGATATTGCAGCCCT
CCCAGACCCTCAGTCTGACCTGTTCTTTCTCTGGGTTTTCACTGAGCACT
TCTGGTATGAGTGTAGGCTGGATTCGTCAGCCTTCAGGGAAGGGTCTGGA
GTGGCTGGCTCACATTTGGTGGAATGATGATAAGTACTATAATCCAGTCC
TGAAAAGCCGGCTCACAATCTCCAAGGAGACCTCCAACAACCAGGTATTC
CTCAAGATCGCCAGTGTGGTCTCTGCAGATACTGCCACATACTACTGTGC
TCGATTCTATGGTAACTGTCTTGACTACTGGGGCCAAGGCACCACTCTCA
CAGTCTCCTCGGCCAAAACAAAGGGCCCATCCGTCTTCCCCCTGGCGCCC
TGCTCCAGGAGCACCTCCGAGAGCACAGCCGCCCTGGGCTGCCTGGTCAA
GGACTACTTCCCCGAACCGGTGACGGTGTCGTGGAACTCAGGCGCCCTGA
CCAGCGGCGTGCACACCTTCCCGGCTGTCCTACAGTCCTCAGGACTCTAC
TCCCTCAGCAGCGTGGTGACCGTGCCCTCCAGCAGCTTGGGCACGAAGAC
CTACACCTGCAACGTAGATCACAAGCCCAGCAACACCAAGGTGGACAAGA
GAGTTGAGTCCAAATATGGTCCCCCATGCCCACCCTGCCCAGCACCTGAG
TTCGAAGGGGGACCATCAGTCTTCCTGTTCCCCCCAAAACCCAAGGACAC
TCTCATGATCTCCCGGACCCCTGAGGTCACGTGCGTGGTGGTGGACGTGA
GCCAGGAAGACCCCGAGGTCCAGTTCAACTGGTACGTGGATGGCGTGGAG
GTGCATAATGCCAAGACAAAGCCGCGGGAGGAGCAGTTCAACAGCACGTA
CCGTGTGGTCAGCGTCCTCACCGTCCTGCACCAGGACTGGCTGAACGGCA
AGGAGTACAAGTGCAAGGTCTCCAACAAAGGCCTCCCGTCCTCCATCGAG
AAAACCATCTCCAAAGCCAAAGGGCAGCCCCGAGAGCCACAGGTGTACAC
CCTGCCCCCATCCCAGGAGGAGATGACCAAGAACCAGGTCAGCCTGACCT
GCCTGGTCAAAGGCTTCTACCCCAGCGACATCGCCGTGGAGTGGGAGAGC
AATGGGCAGCCGGAGAACAACTACAAGACCACGCCTCCCGTGCTGGACTC
CGACGGCTCCTTCTTCCTCTACAGCAGGCTAACCGTGGACAAGAGCAGGT
GGCAGGAGGGGAATGTCTTCTCATGCTCCGTGATGCATGAGGCTCTGCAC
AACCACTACACACAGAAGAGCCTCTCCCTGTCTCTGGGTAAAGCTAGCTG
ATTAATTAA Anti_CLEC_6_9B9.2G12_Heavy (H)v-V-hIgG4H-C
(SEQ ID NO: 80):
MGRLTSSFLLLIVPAYVLSQVTLKESGPGILQPSQTLSLTCSFSGFSLST
SGMSVGWIRQPSGKGLEWLAHIWWNDDKYYNPVLKSRLTISKETSNNQVF
LKIASVVSADTATYYCARFYGNCLDYWGQGTTLTVSSAKTKGPSVFPLAP
CSRSTSESTAALGCLVKDYFPEPVTVSWNSGALTSGVHTFPAVLQSSGLY
SLSSVVTVPSSSLGTKTYTCNVDHKPSNTKVDKRVESKYGPPCPPCPAPE
FEGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIE
KTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALH
NHYTQKSLSLSLGKAS Anti_CLEC_6_9B9.2G12_Kv-V-hIgGK-C (SEQ ID NO: 16):
ATGATGTCCTCTGCTCAGTTCCTTGGTCTCCTGTTGCTCTGTTTTCAAGG
TACCAGATGTGATATCCAGATGACACAGACTACATCCTCCCTGTCTGCCT
CTCTGGGAGACAGAGTCACCATCAGTTGCAGGGCAAGTCAGGACATTAGC
AATTATTTAAACTGGTATCAGCAGAAACCAGATGGAACTGTTAAACTCCT
GATCTACTACACATCAATATTACAATTAGGAGTCCCATCAAGATTCAGTG
GCAGTGGGTCTGAAACAGATTATTCTCTCACCATTAGCAACCTGGAGCAA
GAAGATATTGCCACTTACTTTTGCCAACAGGGTGATTCGCTTCCATTCAC
GTTCGGCTCGGGGACAAAGCTCGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTATGCCTGCGAAGTCAC
CCATCAGGGCCTGAGCTCGCCCGTCACAAAGAGCTTCAACAGGGGAGAGT
GTTAG
```

-continued

```
Anti_CLEC_6_9B9.2G12_Light (K)v-V-hIgGK-C
(SEQ ID NO: 81):
MMSSAQFLGLLLLCFQGTRCDIQMTQTTSSLSASLGDRVTISCRASQDIS
NYLNWYQQKPDGTVKLLIYYTSILQLGVPSRFSGSGSETDYSLTISNLEQ
EDIATYFCQQGDSLPFTFGSGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC Anti-ASGPR_49C11_7H-LV-hIgG4H-C (SEQ ID NO: 17):
ATGAGAGCGCTGATTCTTTTGTGCCTGTTCACAGCCTTTCCTGGTATCCT
GTCTGATGTGCAGCTTCAGGAGTCAGGACCTGACCTGGTGAAACCTTCTC
AGTCACTTTCACTCACCTGCACTGTCACTGGCTACTCCATCACCAGTGGT
TATAGCTGGCACTGGATCCGGCAGTTTCCAGGAAACAAACTGGAATGGAT
GGGCTACATACTCTTCAGTGGTAGCACTAACTACAACCCATCTCTGAAAA
GTCGAATCTCTATCACTCGAGACACATCCAAGAACCAGTTCTTCCTGCAG
TTGAATTCTGTGACTACTGAGGACACAGCCACATATTTCTGTGCAAGATC
TAACTATGGTTCCTTTGCTTCCTGGGGCCAAGGGACTCTGGTCACTGTCT
CTGCAGCCAAAACAACGGGCCCATCCGTCTTCCCCCTGGCGCCCTGCTCC
AGGAGCACCTCCGAGAGCACAGCCGCCCTGGGCTGCCTGGTCAAGGACTA
CTTCCCCGAACCGGTGACGGTGTCGTGGAACTCAGGCGCCCTGACCAGCG
GCGTGCACACCTTCCCGGCTGTCCTACAGTCCTCAGGACTCTACTCCCTC
AGCAGCGTGGTGACCGTGCCCTCCAGCAGCTTGGGCACGAAGACCTACAC
CTGCAACGTAGATCACAAGCCCAGCAACACCAAGGTGGACAAGAGAGTTG
AGTCCAAATATGGTCCCCCATGCCCACCCTGCCCAGCACCTGAGTTCGAA
GGGGGACCATCAGTCTTCCTGTTCCCCCCAAAACCCAAGGACACTCTCAT
GATCTCCCGGACCCCTGAGGTCACGTGCGTGGTGGTGGACGTGAGCCAGG
AAGACCCCGAGGTCCAGTTCAACTGGTACGTGGATGGCGTGGAGGTGCAT
AATGCCAAGACAAAGCCGCGGGAGGAGCAGTTCAACAGCACGTACCGTGT
GGTCAGCGTCCTCACCGTCCTGCACCAGGACTGGCTGAACGGCAAGGAGT
ACAAGTGCAAGGTCTCCAACAAAGGCCTCCCGTCCTCCATCGAGAAAACC
ATCTCCAAAGCCAAAGGGCAGCCCCGAGAGCCACAGGTGTACACCCTGCC
CCCATCCCAGGAGGAGATGACCAAGAACCAGGTCAGCCTGACCTGCCTGG
TCAAAGGCTTCTACCCCAGCGACATCGCCGTGGAGTGGGAGAGCAATGGG
CAGCCGGAGAACAACTACAAGACCACGCCTCCCGTGCTGGACTCCGACGG
CTCCTTCTTCCTCTACAGCAGGCTAACCGTGGACAAGAGCAGGTGGCAGG
AGGGGAATGTCTTCTCATGCTCCGTGATGCATGAGGCTCTGCACAACCAC
TACACACAGAAGAGCCTCTCCCTGTCTCTGGGTAAAGCTAGCTGATTAAT
TAA Anti-ASGPR_49C11_7H-LV-hIgG4H-C (SEQ ID NO: 82):
MRALILLCLFTAFPGILSDVQLQESGPDLVKPSQSLSLTCTVTGYSITSG
YSWHWIRQFPGNKLEWMGYILFSGSTNYNPSLKSRISITRDTSKNQFFLQ
LNSVTTEDTATYFCARSNYGSFASWGQGTLVTVSAAKTTGPSVFPLAPCS
RSTSESTAALGCLVKDYFPEPVTVSWNSGALTSGVHTFPAVLQSSGLYSL
SSVVTVPSSSLGTKTYTCNVDHKPSNTKVDKRVESKYGPPCPPCPAPEFE
GGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKT
ISKAKGQPREPQVYTLPPSQEEMTKNQVSLTCLVKGFYPSDIAVEWESNG
QPENNYKTTPPVLDSDGSFFLYSRLTVDKSRWQEGNVFSCSVMHEALHNH
YTQKSLSLSLGKAS Anti-ASGPR_49C11_7K-LV-hIgGK-C (SEQ ID NO: 18):
ATGGATTTTCAAGTGCAGATTTTCAGCTTCCTGCTAATCAGTGCCTCAGT
CATAATATCCAGAGGACAAATTGTTCTCACCCAGTCTCCAGCAATCATGT
CTGCATCTCCAGGGGAGAAGGTCACCATGACCTGCAGTGCCAGCTCAAGT
GTAAGTCACATGCACTGGTACCAGCAGAAGTCAGGCACTTCCCCCAAAAG
ATGGATTTATGACACATCCAGACTGGCTTCTGGAGTCCCTGCTCGCTTCA
GTGGCAGTGGGTCTGGGACCTCTTACTCTCTCACAATCAGCAGCATGGAG
GCTGAAGATGCTGCCACTTATTACTGCCAGCAGTGGAGTAGTCACCCATG
GTCGTTCGGTGGAGGCACCAAACTCGAGATCAAACGAACTGTGGCTGCAC
CATCTGTCTTCATCTTCCCGCCATCTGATGAGCAGTTGAAATCTGGAACT
GCCTCTGTTGTGTGCCTGCTGAATAACTTCTATCCCAGAGAGGCCAAAGT
ACAGTGGAAGGTGGATAACGCCCTCCAATCGGGTAACTCCCAGGAGAGTG
TCACAGAGCAGGACAGCAAGGACAGCACCTACAGCCTCAGCAGCACCCTG
ACGCTGAGCAAAGCAGACTACGAGAAACACAAAGTCTATGCCTGCGAAGT
CACCCATCAGGGCCTGAGCTCGCCCGTCACAAAGAGCTTCAACAGGGGAG
AGTGTTAG Anti-ASGPR_49C11_7K-LV-hIgGK-C (SEQ ID NO: 83):
MDFQVQIFSFLLISASVIISRGQIVLTQSPAIMSASPGEKVTMTCSASSS
VSHMHWYQQKSGTSPKRWIYDTSRLASGVPARFSGSGSGTSYSLTISSME
AEDAATYYCQQWSSHPWSFGGGTKLEIKRTVAAPSVFIFPPSDEQLKSGT
ASVVCLLNNFYPREAKVQWKVDNALQSGNSQESVTEQDSKDSTYSLSSTL
TLSKADYEKHKVYACEVTHQGLSSPVTKSFNRGEC Anti-ASGPR_4G2.2_Hv-V-hIgG4H-C (SEQ ID NO: 19):
ATGGCTTGGGTGTGGACCTTGCTATTCCTGATGGCAGCTGCCCAAAGTGC
CCAAGCACAGATCCAGTTGGTGCAGTCTGGACCTGAGCTGAAGAAGCCTG
GAGAGACAGTCAAGATCTCCTGCAAGGCTTCTGGGTATACCTTCACAAAC
TATGGAATGAACTGGGTGAAGCAGGTTCCAGGAAAAGGTTTAAGGTGGAT
GGGCTGGATGGACACCTTCACTGGAGAGCCAACATATGCTGATGACTTCA
```

-continued
AGGGGACGGTTTGCCTTCTCTTTGGAAACCTCTGCCAGCACTGCCTATTTG
CAGATCAACAGCCTCAAAAATGAGGACACGGCTACTTATTTCTGTGCAAG
AGGGGGGATTTTACGACTCAACTACTTTGACTACTGGGGCCAAGGCACCA
CTCTCACAGTCTCCTCAGCCAAAACGAAGGGCCCATCCGTCTTCCCCCTG
GCGCCCTGCTCCAGGAGCACCTCCGAGAGCACAGCCGCCCTGGGCTGCCT
GGTCAAGGACTACTTCCCCGAACCGGTGACGGTGTCGTGGAACTCAGGCG
CCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCAC
GAAGACCTACACCTGCAACGTAGATCACAAGCCCAGCAACACCAAGGTGG
ACAAGAGAGTTGAGTCCAAATATGGTCCCCCATGCCCACCCTGCCCAGCA
CCTGAGTTCGAAGGGGGACCATCAGTCTTCCTGTTCCCCCCAAAACCCAA
GGACACTCTCATGATCTCCCGGACCCCTGAGGTCACGTGCGTGGTGGTGG
ACGTGAGCCAGGAAGACCCCGAGGTCCAGTTCAACTGGTACGTGGATGGC
GTGGAGGTGCATAATGCCAAGACAAAGCCGCGGGAGGAGCAGTTCAACAG
CACGTACCGTGTGGTCAGCGTCCTCACCGTCCTGCACCAGGACTGGCTGA
ACGGCAAGGAGTACAAGTGCAAGGTCTCCAACAAAGGCCTCCCGTCCTCC
ATCGAGAAAACCATCTCCAAAGCCAAAGGGCAGCCCCGAGAGCCACAGGT
GTACACCCTGCCCCCATCCCAGGAGGAGATGACCAAGAACCAGGTCAGCC
TGACCTGCCTGGTCAAAGGCTTCTACCCCAGCGACATCGCCGTGGAGTGG
GAGAGCAATGGGCAGCCGGAGAACAACTACAAGACCACGCCTCCCGTGCT
GGACTCCGACGGCTCCTTCTTCCTCTACAGCAGGCTAACCGTGGACAAGA
GCAGGTGGCAGGAGGGGAATGTCTTCTCATGCTCCGTGATGCATGAGGCT
CTGCACAACCACTACACACAGAAGAGCCTCTCCCTGTCTCTGGGTAAAGC
TAGCTGATTAATTAA Anti-ASGPR_4G2.2_Hv-hIgG4H-C (SEQ ID NO: 84):
MAWVWTLLFLMAAAQSAQAQIQLVQSGPELKKPGETVKISCKASGYTFTN
YGMNWVKQVPGKGLRWMGWMDTFTGEPTYADDFKGRFAFSLETSASTAYL
QINSLKNEDTATYFCARGGILRLNYFDYWGQGTTLTVSSAKTKGPSVFPL
APCSRSTSESTAALGCLVKDYFPEPVTVSWNSGALTSGVHTFPAVLQSSG
LYSLSSVVTVPSSSLGTKTYTCNVDHKPSNTKVDKRVESKYGPPCPPCPA
PEFEGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSS
IEKTISKAKGQPREPQVYTLPPSQEEMTKNQVSLTCLVKGFYPSDIAVEW
ESNGQPENNYKTTPPVLDSDGSFFLYSRLTVDKSRWQEGNVFSCSVMHEA
LHNHYTQKSLSLSLGKAS Anti-ASGPR_4G2.2_Kv-V-hIgGK-C (SEQ ID NO: 20):
ATGAAGTTTCCTTCTCAACTTCTGCTCTTTACTGCTGTTTGGAATCCCAGG
CATGGATATGTGACATCCAGATGACACAATCTTCATCCTCCTTTTCTGTAT
CTCTAGGAGACAGAGTCACCATTACTTGCAAGGCAAGTGAGGACATATAT
AATCGGTTAGGCTGGTATCAGCAGAAACCAGGAAATGCTCCTAGGCTCTT
AATATCTGGTGCAACCAGTTTGGAACTGGGGTTCCTTCAAGATTCAGTG
GCAGTGGATCTGGAAAGGATTACGCTCTCAGCATTACCAGTCTTCAGACT
GAAGATCTTGCTACTTATTACTGTCAACAGTGTTGGACTTCTCCGTACAC
GTTCGGAGGGGGGACCAAGCTCGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTATGCCTGCGAAGTCAC
CCATCAGGGCCTGAGCTCGCCCGTCACAAAGAGCTTCAACAGGGGAGAGT
GTTAG Anti-ASGPR_4G2.2_Kv-V-hIgGK-C (SEQ ID NO: 85):
MKFPSQLLLLLLFGIPGMICDIQMTQSSSFSVSLGDRVTITCKASEDIY
NRLGWYQQKPGNAPRLLISGATSLETGVPSRFSGSGSGKDYALSITSLQT
EDLATYYCQQCWTSPYTFGGGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC Anti-ASGPR_5F10H-LV-hIgG4H-C (SEQ ID NO: 21):
ATGGGATGGAGCTGGATCTTTCTCTTTCTCTTGTCAGGAACTGGAGGTGT
CCTCTCTGAGGTCCAGCTGCAACAGTCTGGACCTGAGCTGGTGAAGCCTG
GGGCTTCAGTGAAGATGTCCTGCAAGGCTTCTGGATACACCTTCACTGAC
TACTACATGAAGTGGGTGAAGCAGAGCATGAAAGAGCCTTGAGTGGAT
TGGAGATATTAATCCTAACTATGGTGATACTTTCTACAACCAGAAGTTCG
AGGGCAAGGCCACATTGACTGTAGACAAATCCTCCAGGACAGCTTATATG
CAGCTCAACAGCCTGACATCTGAGGACTCTGCAGTCTATTATTGTGAAG
AGGGGACTATGGATACTTCGATGTCTGGGGCGCAGGGACCACGGTCACCG
TCTCCTCAGCCAAAACAAAGGGCCCATCCGTCTTCCCCCTGGCGCCCTGC
TCCAGGAGCACCTCCGAGAGCACAGCCGCCCTGGGCTGCCTGGTCAAGGA
CTACTTCCCCGAACCGGTGACGGTGTCGTGGAACTCAGGCGCCCTGACCA
GCGGCGTGCACACCTTCCCGGCTGTCCTACAGTCCTCAGGACTCTACTCC
CTCAGCAGCGTGGTGACCGTGCCCTCCAGCAGCTTGGGCACGAAGACCTA
CACCTGCAACGTAGATCACAAGCCCAGCAACACCAAGGTGGACAAGAGAG
TTGAGTCCAAATATGGTCCCCCATGCCCACCCTGCCCAGCACCTGAGTTC
GAAGGGGGACCATCAGTCTTCCTGTTCCCCCCAAAACCCAAGGACACTCT
CATGATCTCCCGGACCCCTGAGGTCACGTGCGTGGTGGTGGACGTGAGCC
AGGAAGACCCCGAGGTCCAGTTCAACTGGTACGTGGATGGCGTGGAGGTG
CATAATGCCAAGACAAAGCCGCGGGAGGAGCAGTTCAACAGCACGTACCG
TGTGGTCAGCGTCCTCACCGTCCTGCACCAGGACTGGCTGAACGGCAAGG
AGTACAAGTGCAAGGTCTCCAACAAAGGCCTCCCGTCCTCCATCGAGAAA
ACCATCTCCAAAGCCAAAGGGCAGCCCCGAGAGCCACAGGTGTACACCCT
GCCCCCATCCCAGGAGGAGATGACCAAGAACCAGGTCAGCCTGACCTGCC
TGGTCAAAGGCTTCTACCCCAGCGACATCGCCGTGGAGTGGGAGAGCAAT
GGGCAGCCGGAGAACAACTACAAGACCACGCCTCCCGTGCTGGACTCCGA
CGGCTCCTTCTTCCTCTACAGCAGGCTAACCGTGGACAAGAGCAGGTGGC
AGGAGGGGAATGTCTTCTCATGCTCCGTGATGCATGAGGCTCTGCACAAC
CACTACACACAGAAGAGCCTCTCCCTGTCTCTGGGTAAAGCTAGCTGA Anti-ASGPR_5F10H-LV-hIgG4H-C (SEQ ID NO: 86):
MGWSWIFLFLLSGTGGVLSEVQLQQSGPELVKPGASVKMSCKASGYTFTD
YYMKWVKQSHGKSLEWIGDINPNYGDTFYNQKFEGKATLTVDKSSRTAYM
QLNSLTSEDSAVYYCGRGDYGYFDVWGAGTTVTVSSAKTKGPSVFPLAPC
SRSTSESTAALGCLVKDYFPEPVTVSWNSGALTSGVHTFPAVLQSSGLYS
LSSVVTVPSSSLGTKTYTCNVDHKPSNTKVDKRVESKYGPPCPPCPAPEF
EGGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHN
HYTQKSLLSLGKAS Anti-ASGPR_5F10K-LV-hIgGK-C (SEQ ID NO: 22):
ATGGAGACACATTCTCAGGTCTTTGTATACATGTTGCTGTGGTTGTCTGG
TGTTGAAGGAGACATTGTGATGACCCAGTCTCACAAATTCATGTCCACAT
CAGTAGGAGACAGGGTCAGCATCACCTGCAAGGCCAGTCAGGATGTGGGT
ACTGCTGTAGCCTGGTATCAACAGAAACCAGGGCAATCTCCTAAACTACT
GATTTACTGGGCATCCACCCGGCACACTGGAGTCCCTGATCGCTTCACAG
GCAGTGGATCTGGGACAGATTTCACTCTCACCATTAACAATGTGCAGTCT
GAAGACTTGGCAGATTATTTCTGTCAGCAATATAGCAGCAATCCGTACAT
GTTCGGAGGGGGGACCAAGCTCGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTATGCCTGCGAAGTCAC
CCATCAGGGCCTGAGCTCGCCCGTCACAAAGAGCTTCAACAGGGGAGAGT
GTTAG Anti-ASGPR_5F10K-LV-hIgGK-C (SEQ ID NO: 87):
METHSQVFVYMLLWLSGVEGDIVMTQSHKFMSTSVGDRVSITCKASQDVG
TAVAWYQQKPGQSPKLLIYWASTRHTGVPDRFTGSGSGTDFTLTINNVQS
EDLADYFCQQYSSNPYMFGGGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC Anti-ASGPR1H11_H-V-hIgG4H-C (SEQ ID NO: 23):
ATGGGATGGAGCTGGATCTTTCTCTTTCTCCTGTCAGGAACTGCAGGTGT
CCTCTCTGAGGTCCAGCTGCAACAGTCTGGACCTGAGTTGGTGAAGCCTG
GGGCTTCAGTGAAGATATCCTGCAAGACTTCTGGATACACATTCACTGAA
TACACCATGCACTGGGTGAGGCAGAGCCATGGAAAGAGCCTTGAGTGGAT
TGGAGGTATTAATCCTATCAATGGTGGTCCTACCTACAACCAGAAGTTCA
AGGGCAAGGCCACATTGACTGTTGACAAGTCCTCCAGCACAGCCTACATG
GAGCTCCGCAGCCTGACATCTGAGGACTCTGCAGTCTATTACTGTGCAAG
ATGGGACTATGGTAGTCGAGATGTTATGGACTACTGGGGTCAAGGAACCT
CAGTCACCGTCTCCTCAGCCAAAACGAAGGGCCCATCCGTCTTCCCCCTG
GCGCCCTGCTCCAGGAGCACCTCCGAGAGCACAGCCGCCCTGGGCTGCCT
GGTCAAGGACTACTTCCCCGAACCGGTGACGGTGTCGTGGAACTCAGGCG
CCCTGACCAGCGGCGTGCACACCTTCCCGGCTGTCCTACAGTCCTCAGGA
CTCTACTCCCTCAGCAGCGTGGTGACCGTGCCCTCCAGCAGCTT
GGGCACGAAGACCTACACCTGCAACGTAGATCACAAGCCCAGCAACACCA
AGGTGGACAAGAGAGTTGAGTCCAAATATGGTCCCCCATGCCCACCCTGC
CCAGCACCTGAGTTCGAAGGGGGACCATCAGTCTTCCTGTTCCCCCCAAA
ACCCAAGGACACTCTCATGATCTCCCGGACCCCTGAGGTCACGTGCGTGG
TGGTGGACGTGAGCCAGGAAGACCCCGAGGTCCAGTTCAACTGGTACGTG
GATGGCGTGGAGGTGCATAATGCCAAGACAAAGCCGCGGGAGGAGCAGTT
CAACAGCACGTACCGTGTGGTCAGCGTCCTCACCGTCCTGCACCAGGACT
GGCTGAACGGCAAGGAGTACAAGTGCAAGGTCTCCAACAAAGGCCTCCCG
TCCTCCATCGAGAAAACCATCTCCAAAGCCAAAGGGCAGCCCCGAGAGCC
ACAGGTGTACACCCTGCCCCCATCCCAGGAGGAGATGACCAAGAACCAGG
TCAGCCTGACCTGCCTGGTCAAAGGCTTCTACCCCAGCGACATCGCCGTG
GAGTGGGAGAGCAATGGGCAGCCGGAGAACAACTACAAGACCACGCCTCC
CGTGCTGGACTCCGACGGCTCCTTCTTCCTCTACAGCAGGCTAACCGTGG
ACAAGAGCAGGTGGCAGGAGGGGAATGTCTTCTCATGCTCCGTGATGCAT
GAGGCTCTGCACAACCACTACACACAGAAGAGCCTCTCCCTGTCTCTGGG
TAAAGCTAGCTGA Anti-ASGPR1H11_H-V-hIgG4H-C (SEQ ID NO: 88):
MGWSWIFLFLLSGTAGVLSEVQLQQSGPELVKPGASVKISCKTSGYTFTE
YTMHWVRSHGKSLEWIGGINPINGGPTYNQKFKGKATLTVDKSSTAYME
LRSLTSEDSAVYYCARWDYGSRDVMDYWGQGTSVTVSSAKTKGPSVFPLA -continued
PCSRSTSESTAALGCLVKDYFPEPVPVTVSWNSGALTSGVHTFPAVLQSS
GLYSLSSVVTVPSSSLGTKTYTCNVDHKPSNTKVDKRVESKYGPPCPPCP
APEFEGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHE
ALHNHYTQKSLSLSLGKAS Anti-ASGPR1H11K-LV-var2-hIgGK-C (SEQ ID NO: 24):
ATGGAATCACAGACTCTGGTCTTCATATCCATACTGCTCTGGTTATATGG
TGCTGATGGGAACATTGTAATGACTCAATCTCCCAAATCCATGTCCATGT
CAGTAGGGGAGAGGGTCACCTTGAGCTGCAAGGCCAGTGAGAATGTGGGA
ACTTATGTATCCTGGTATCAACAGAGACCAGAACAGTCTCCAAAACTGCT
GATATACGGGGCATCCAACCGGTACACTGGGGTCCCCGATCGCTTCACAG
GCAGTGGATCTGCAACAGATTTCACTCTGACCATCAGCAGTGTGCAGGCT
GAGGACCTTGCAGATTATCACTGTGGACAGACTTACAGCTATATATTCAC
GTTCGGCTCGGGGACAAAGCTCGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTATGCCTGCGAAGTCAC
CCATCAGGGCCTGAGCTCGCCCGTCACAAAGAGCTTCAACAGGGGAGAGT
GTTAG Anti-ASGPR1H11K-LV-var2-hIgGK-C (SEQ ID NO: 89):
METHSQVFVYMLLWLSGVEGNIVMTQSPKSMSMSVGERVTLSCKASENVG
TYVSWYQQRPEQSPKLLIYGASNRYTGVPDRFTGSGSATDFTLTISSVQA
EDLADYHCGQTYSYIFTFGSGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC Anti-CD1d_2B5.3G10_H-V-hIgG4H-C (SEQ ID NO: 25):
ATGGGATGGAGCTGGATCTTTCTCTTCCTCCTGTCAATAACTGCAGGTGT
CCATTGCCAGGTCCAGGTGCAGCAGTCGGGACCTGAGTTGGTGAAGCCTG
GGGCCTCAGTGAAGATTTCCTGCAAAGCCTCTGGCGACGCATTCAGTAGT
TCTTGGATGAACTGGGTGAAGCAGAGGCCTGGACAGGGTCTTGAGTGGAT
TGGACGGATTTATCTTGGAGATGGAGATATTAATTACAATGGGAAGTTCA
AGGGCAGGGCCACACTGACTGCAGACAAATCCTCCAGCACAGCCTACATG
CAGCTCAGCAGCCTGACCTCTGTGGACTCTGCGGTCTATTTCTGCGCGAG
GCAGCTCGGGCTATGGTATGTTATGGACTACTGGGGTCAAGGAACCTCAG
TCACCGTCTCCTCAGCCAAAACAAAGGGCCCATCCGTCTTCCCCCTGGCG
CCCTGCTCCAGGAGCACCTCCGAGAGCACAGCCGCCCTGGGCTGCCTGGT
CAAGGACTACTTCCCCGAACCGGTGACGGTGTCGTGGAACTCAGGCGCCC
TGACCAGCGGCGTGCACACCTTCCCGGCTGTCCTACAGTCCTCAGGACTC
TACTCCCTCAGCAGCGTGGTGACCGTGCCCTCCAGCAGCTTGGGCACGAA
GACCTACACCTGCAACGTAGATCACAAGCCCAGCAACACCAAGGTGGACA
AGAGAGTTGAGTCCAAATATGGTCCCCCATGCCCACCCTGCCCAGCACCT
GAGTTCGAAGGGGGGACCATCAGTCTTCCTGTTCCCCCCAAAACCCAAGGA
CACTCTCATGATCTCCCGGACCCCTGAGGTCACGTGCGTGGTGGTGGACG
TGAGCCAGGAAGACCCCGAGGTCCAGTTCAACTGGTACGTGGATGGCGTG
GAGGTGCATAATGCCAAGACAAAGCCGCGGGAGGAGCAGTTCAACAGCAC
GTACCGTGTGGTCAGCGTCCTCACCGTCCTGCACCAGGACTGGCTGAACG
GCAAGGAGTACAAGTGCAAGGTCTCCAACAAAGGCCTCCCGTCCTCCATC
GAGAAAACCATCTCCAAAGCCAAAGGGCAGCCCCGAGAGCCACAGGTGTA
CACCCTGCCCCCATCCCAGGAGGAGATGACCAAGAACCAGGTCAGCCTGA
CCTGCCTGGTCAAAGGCTTCTACCCCAGCGACATCGCCGTGGAGTGGGAG
AGCAATGGGCAGCCGGAGAACAACTACAAGACCACGCCTCCCGTGCTGGA
CTCCGACGGCTCCTTCTTCCTCTACAGCAGGCTAACCGTGGACAAGAGCA
GGTGGCAGGAGGGGAATGTCTTCTCATGCTCCGTGATGCATGAGGCTCTG
CACAACCACTACACACAGAAGAGCCTCTCCCTGTCTCTGGGTAAAGCTAG
CTGA Anti-CD1d_2B5.3G10_H-V-hIgG4H-C (SEQ ID NO: 90):
MGWSRIFLFLLSITAGVHCQVQVQQSGPELVKPGASVKISCKASGDAFSS
SWMNWVKQRPGQGLEWIGRIYLGDGDINYNGKFKGRATLTADKSSSTAYM
QLSSLTSVDSAVYFCARQLGLWYVMDYWGQGTSVTVSSAKTKGPSVFPLA
PCSRSTSESTAALGCLVKDYFPEPVTVSWNSGALTSGVHTFPAVLQSSGL
YSLSSVVTVPSSSLGTKTYTCNVDHKPSNTKVDKRVESKYGPPCPPCPAP
EFEGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEAL
HNHYTQKSLSLSLGKAS Anti-CD1d_2B5.3G10_K-V-hIgGK-C (SEQ ID NO: 26):
ATGAGTGTGCCCACTCAGGTCCTGGGGTTGCTGCTGCTGTGGCTTACAGG
TGCCAGATGTGACATCCAGATGGCTCAGTCTCCAGCCTCCCTATCTGCAT
CTGTGGGAGAAACTGTCACCATCACATGTCGAGCAAGTGAGAATATTTAC
AGTTATTTAGCATGGTATCAGCAGAAACAGGGAAAATCTCCTCAGCTCCT
GGTCTATAATGCAAAAACCTTAGCAGAAGGTGTGCCATCAAGGTTCAGTG -continued
GCAGTGGATCAGGCACACAGTTTTCTCTGAAGATCAACAGCCTGCAGCCT
GAAGATTTTGGGAGTTATTACTGTCAACATCATTATGGTTTTCCGTGGAC
GTTCGGTGGAGGCACCAAGCTCGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTATGCCTGCGAAGTCAC
CCATCAGGGCCTGAGCTCGCCCGTCACAAAGAGCTTCAACAGGGGAGAGT
GTTAG Anti-CD1d_2B5.3G10_K-V-hIgGK-C (SEQ ID NO: 91):
MSVPTQVLGLLLLWLTGARCDIQMAQSPASLSASVGETVTITCRASENIY
SYLAWYQQKQGKSPQLLVYNAKTLAEGVPSRFSGSGSGTQFSLKINSLQP
EDFGSYYCQHHYGFPWTFGGGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC Anti-CD1d_2H11.2G5_H-V-hIgG4H-C (SEQ ID NO: 27):
ATGAACTTCGGGCTCAGCTTGATTTTCCTTGTCCTCATTTTAAAAGGTGT
CCAGTGTGAGGTCCAGCTGGTGGAGTCTGGGGGAGACTTAGTGAAGCCTG
GAGGGTCCCTGAAACTCTCCTGTGCAGCCTCTGGATTCACTTTCAGTAGC
TATGGCATGTCTTGGGTTCGCCAGACTCCAGACAAGAGGCTGGAGTGGGT
CGCAGTCATTAGTAGTGGTGGAAGTTCCACCTTCTATCCAGACAGTGTGA
AGGGCCGATTCACCATCTCCAGAGACAATGCCAAGAACACCCTGTACCTG
CAAATGAGCAGTCTGAAGTCTGAGGACACAGCCGTGTATTACTGTTCAAG
AGGAGGTTACTACTTTGACTACTGGGGCCAAGGCACCACTCTCACAGTCT
CCGCAGCCAAAACAAAGGGCCCATCCGTCTTCCCCCTGGCGCCCTGCTCC
AGGAGCACCTCCGAGAGCACAGCCGCCCTGGGCTGCCTGGTCAAGGACTA
CTTCCCCGAACCGGTGACGGTGTCGTGGAACTCAGGCGCCCTGACCAGCG
GCGTGCACACCTTCCCGGCTGTCCTACAGTCCTCAGGACTCTACTCCCTC
AGCAGCGTGGTGACCGTGCCCTCCAGCAGCTTGGGCACGAAGACCTACAC
CTGCAACGTAGATCACAAGCCCAGCAACACCAAGGTGGACAAGAGAGTTG
AGTCCAAATATGGTCCCCCATGCCCACCCTGCCCAGCACCTGAGTTCGAA
GGGGGACCATCAGTCTTCCTGTTCCCCCCAAAACCCAAGGACACTCTCAT
GATCTCCCGGACCCCTGAGGTCACGTGCGTGGTGGTGGACGTGAGCCAGG
AAGACCCCGAGGTCCAGTTCAACTGGTACGTGGATGGCGTGGAGGTGCAT
AATGCCAAGACAAAGCCGCGGGAGGAGCAGTTCAACAGCACGTACCGTGT
GGTCAGCGTCCTCACCGTCCTGCACCAGGACTGGCTGAACGGCAAGGAGT
ACAAGTGCAAGGTCTCCAACAAAGGCCTCCCGTCCTCCATCGAGAAAACC
ATCTCCAAAGCCAAAGGGCAGCCCCGAGAGCCACAGGTGTACACCCTGCC
CCCATCCCAGGAGGAGATGACCAAGAACCAGGTCAGCCTGACCTGCCTGG
TCAAAGGCTTCTACCCCAGCGACATCGCCGTGGAGTGGGAGAGCAATGGG
CAGCCGGAGAACAACTACAAGACCACGCCTCCCGTGCTGGACTCCGACGG
CTCCTTCTTCCTCTACAGCAGGCTAACCGTGGACAAGAGCAGGTGGCAGG
AGGGGAATGTCTTCTCATGCTCCGTGATGCATGAGGCTCTGCACAACCAC
TACACACAGAAGAGCCTCTCCCTGTCTCTGGGTAAAGCTAGCTGA Anti-CD1d_2H11.2G5_H-V-hIgG4H-C (SEQ ID NO: 92):
MNFGLSLIFLVLILKGVQCEVQLVESGGDLVKPGGSLKLSCAASGFTFSS
YGMSWVRQTPDKRLEWVAVISSGGSSTFYPDSVKGRFTISRDNAKNTLYL
QMSSLKSEDTAVYYCSRGGYYFDYWGQGTTLTVSAAKTKGPSVFPLAPCS
RSTSESTAALGCLVKDYFPEPVTVSWNSGALTSGVHTFPAVLQSSGLYSL
SSVVTVPSSSLGTKTYTCNVDHKPSNTKVDKRVESKYGPPCPPCPAPEFE
GGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKT
ISKAKGQPREPQVYTLPPSQEEMTKNQVSLTCLVKGFYPSDIAVEWESNG
QPENNYKTTPPVLDSDGSFFLYSRLTVDKSRWQEGNVFSCSVMHEALHNH
YTQKSLSLSLGKAS Anti-CD1d_2H11.2G5_K-V-hIgGK-C (SEQ ID NO: 28):
ATGAGGTTCCAGGTTCAGGTTCTGGGGCTCCTTCTGCTCTGGATATCAGG
TGCCCAGTGTGATGTCCAGATAACCCAGTCTCCATCTTATCTTGCTGCAT
CTCCTGGAGAAACCATTACTATTAATTGCAGGGCAAGCAAGACCATTAGC
AAATATTTAGCCTGGTATCAAGAGAAACCTGAGAAAACTGATAAGCTTCT
TATCTACTCTGGATCCACTTTGCAATCTGGAATTCCATCAAGGTTCAGTG
GCAGTGGATCTGGTACAGATTTCACTCTCACCATCAGTGGCCTGGAGCCT
GAAGATTTTGCAATGTATTACTGTCAACAGCATAATGAATACCCGTGGAC
GTTCGGTGGAGGCACCAAGCTCGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTATGCCTGCGAAGTCAC
CCATCAGGGCCTGAGCTCGCCCGTCACAAAGAGCTTCAACAGGGGAGAGT
GTTAG Anti-CD1d_2H11.2G5_K-V-hIgGK-C (SEQ ID NO: 93):
MRFQVQVLGLLLLWISGAQCDVQITQSPSYLAASPGETITINCRASKTIS
KYLAWYQEKPEKTDKLLIYSGSTLQSGIPSRFSGSGSGTDFTLTISGLEP
EDFAMYYCQQHNEYPWTFGGGTKLEIKRTVAAPSVFIFPPSDEQLKSGTA Anti-CD40_11B6.1C3_H-LV-hIgG4H-C (SEQ ID NO: 29):
ATGGGATGGAGCTGGATCTTTCTCTTCTCCTGTCAGGAACTGCAGGTGT
CCTCTCTGAGGTCCAGCTGCAACAGTCTGGACCTGAGCTGGTGAAGCCTG
GGGCTTCAGTGAAGATATCCTGCAAGGCTTCTGGTTACTCATTCACTGGC
TACTACATGCACTGGGTGAAGCAAAGCCATGTAAAGAGCCTTGAGTGGAT
TGGACGTATTAATCCTTACAATGGTGCTACTAGCTACAACCAGAATTTCA
AGGACAAGGCCAGCTTGACTGTAGATAAGTCCTCCAGCACAGCTTACATG
GAGCTCCACAGCCTGACATCTGAGGACTCTGCAGTCTATTACTGTGCAAG
AGAGGACTACGTCTACTGGGGCCAAGGCACCACTCTCACAGTCTCCTCAG
CCAAAACGAAGGGCCCATCCGTCTTCCCCCTGGCGCCCTGCTCCAGGAGC
ACCTCCGAGAGCACAGCCGCCTGGGCTGCCTGGTCAAGGACTACTTCCC
CGAACCGGTGACGGTGTCGTGGAACTCAGGCGCCCTGACCAGCGGCGTGC
ACACCTTCCCGGCTGTCCTACAGTCCTCAGGACTCTACTCCCTCAGCAGC
GTGGTGACCGTGCCCTCCAGCAGCTTGGGCACGAAGACCTACACCTGCAA
CGTAGATCACAAGCCCAGCAACACCAAGGTGGACAAGAGAGTTGAGTCCA
AATATGGTCCCCCATGCCCACCCTGCCCAGCACCTGAGTTCGAAGGGGGA
CCATCAGTCTTCCTGTTCCCCCCAAAACCCAAGGACACTCTCATGATCTC
CCGGACCCCTGAGGTCACGTGCGTGGTGGTGGACGTGAGCCAGGAAGACC
CCGAGGTCCAGTTCAACTGGTACGTGGATGGCGTGGAGGTGCATAATGCC
AAGACAAAGCCGCGGGAGGAGCAGTTCAACAGCACGTACCGTGTGGTCAG
CGTCCTCACCGTCCTGCACCAGGACTGGCTGAACGGCAAGGAGTACAAGT
GCAAGGTCTCCAACAAAGGCCTCCCGTCCTCCATCGAGAAAACCATCTCC
AAAGCCAAAGGGCAGCCCCGAGAGCCACAGGTGTACACCCTGCCCCCATC
CCAGGAGGAGATGACCAAGAACCAGGTCAGCCTGACCTGCCTGGTCAAAG
GCTTCTACCCCAGCGACATCGCCGTGGAGTGGGAGAGCAATGGGCAGCCG
GAGAACAACTACAAGACCACGCCTCCCGTGCTGGACTCCGACGGCTCCTT
CTTCCTCTACAGCAGGCTAACCGTGGACAAGAGCAGGTGGCAGGAGGGGA
ATGTCTTCTCATGCTCCGTGATGCATGAGGCTCTGCACAACCACTACACA
CAGAAGAGCCTCTCCCTGTCTCTGGGTAAAGCTAGCTGA Anti-CD40_11B6.1C3_H-LV-hIgG4H-C (SEQ ID NO: 94):
MGWSWIFLFLLSGTAGVLSEVQLQQSGPELVKPGASVKISCKASGYSFTG
YYMHWVKQSHVKSLEWIGRINPYNGATSYNQNFKDKASLTVDKSSSTAYM
ELHSLTSEDSAVYYCAREDYVYWGQGTTLTVSSAKTKGPSVFPLAPCSRS
TSESTAALGCLVKDYFPEPVTVSWNSGALTSGVHTFPAVLQSSGLYSLSS
VVTVPSSSLGTKTYTCNVDHKPSNTKVDKRVESKYGPPCPPCPAPEFEGG
PSVFLFPPKPKDTLMISRTPEVTCVVVDVSQEDPEVQFNWYVDGVEHNA
KTKPREEQFNSTYRVVSVLTVLHQDWLNGKEYKCKVSNKGLPSSIEKTIS
KAKGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNHYT
QKSLSLSLGKAS Anti-CD40_11B6.1C3_K-LV-hIgGK-C (SEQ ID NO: 30):
ATGAAGTTGCCTGTTAGGCTGTTGGTGCTGATGTTCTGGATTCCTGCTTC
CAGCAGTGATGTTGTGATGACCCAAACTCCACTCTCCCTGCCTGTCAGTC
TTGGAGATCAAGCCTCCATCTCTTGCAGATCTAGTCAGAGCCTTGTACAC
AGTAATGGAAACACCTATTTACATTGGTACCTGCAGAAGCCAGGCCAGTC
TCCAAAGCTCCTGATCTACAAAGTTTCCAACCGATTTTCTGGGGTCCCAG
ACAGGTTCAGTGGCAGTGGATCAGGGACAGATTTCGCACTCAAGATCAGT
AGAGTGGAGGCTGAGGATCTGGGAGTTTATTTCTGCTCTCAAAGTACACA
TGTTCCGTGGACGTTCGGTGGAGGCACCAAGCTCGAGATCAAACGAACTG
TGGCTGCACCATCTGTCTTCATCTTCCCGCCATCTGATGAGCAGTTGAAA
TCTGGAACTGCCTCTGTTGTGTGCCTGCTGAATAACTTCTATCCCAGAGA
GGCCAAAGTACAGTGGAAGGTGGATAACGCCCTCCAATCGGGTAACTCCC
AGGAGAGTGTCACAGAGCAGGACAGCAAGGACAGCACCTACAGCCTCAGC
AGCACCCTGACGCTGAGCAAAGCAGACTACGAGAAACACAAAGTCTATGC
CTGCGAAGTCACCCATCAGGGCCTGAGCTCGCCCGTCACAAAGAGCTTCA
ACAGGGGAGAGTGTTAG Anti-CD40_11B6.1C3_K-LV-hIgGK-C (SEQ ID NO: 95):
MKLPVRLLVLMFWIPASSSDVVMTQTPLSLPVSLGDQASISCRSSQSLVH
SNGNTYLHWYLQKPGQSPKLLIYKVSNRFSGVPDRFSGSGSGTDFALKIS
RVEAEDLGVYFCSQSTHVPWTFGGGTKLEIKRTVAAPSVFIFPPSDEQLK
SGTASVVCLLNNFYPREAKVQWKVDNALQSGNSQESVTEQDSKDSTYSLS
STLTLSKADYEKHKVYACEVTHQGLSSPVTKSFNRGEC Anti-CD40_12B4.2C10_H-LV-hIgG4H-C (SEQ ID NO: 31):
ATGGAATGGAGTTGGATATTTCTCTTTCTTCTGTCAGGAACTGCAGGTGT
CCACTCTGAGGTCCAGCTGCAGCAGTCTGGACCTGAGCTGGTGAAGCCTG
GGGCTTCAGTGAAGATGTCCTGCAAGGCTTCTGGATACACATTCACTGAC
TATGTTTTGCACTGGGTGAAACAGAAGCCTGGGCAGGGCCTTGAGTGGAT
TGGATATATTAATCCTTACAATGATGGTACTAAGTACAATGAGAAGTTCA
AAGGCAAGGCCACACTGACTTCAGACAAATCTTCCAGCACAGCCTACATG
GAGCTCAGCAGCCTGACCTCTGAGGACTCTGCGGTCTATTACTGTGCAAG
GGGCTATCCGGCCTACTCTGGGTATGCTATGGACTACTGGGGTCAAGGAA
CCTCAGTCACCGTCTCCTCAGCCAAAACGAAGGGCCCATCCGTCTTCCCC
CTGGCGCCCTGCTCCAGGAGCACCTCCGAGAGCACAGCCGCCCTGGGCTG
CCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGG
CACGAAGACCTACACCTGCAACGTAGATCACAAGCCCAGCAACACCAAGG
TGGACAAGAGAGTTGAGTCCAAATATGGTCCCCCATGCCCACCCTGCCCA
GCACCTGAGTTCGAAGGGGGACCATCAGTCTTCCTGTTCCCCCCAAAACC
CAAGGACACTCTCATGATCTCCCGGACCCCTGAGGTCACGTGCGTGGTGG
TGGACGTGAGCCAGGAAGACCCCGAGGTCCAGTTCAACTGGTACGTGGAT
GGCGTGGAGGTGCATAATGCCAAGACAAAGCCGCGGGAGGAGCAGTTCAA
CAGCACGTACCGTGTGGTCAGCGTCCTCACCGTCCTGCACCAGGACTGGC
TGAACGGCAAGGAGTACAAGTGCAAGGTCTCCAACAAAGGCCTCCCGTCC
TCCATCGAGAAAACCATCTCCAAAGCCAAAGGGCAGCCCCGAGAGCCACA
GGTGTACACCCTGCCCCCATCCCAGGAGGAGATGACCAAGAACCAGGTCA
GCCTGACCTGCCTGGTCAAAGGCTTCTACCCCAGCGACATCGCCGTGGAG
TGGGAGAGCAATGGGCAGCCGGAGAACAACTACAAGACCACGCCTCCCGT
GCTGGACTCCGACGGCTCCTTCTTCCTCTACAGCAGGCTAACCGTGGACA
AGAGCAGGTGGCAGGAGGGGAATGTCTTCTCATGCTCCGTGATGCATGAG
GCTCTGCACAACCACTACACACAGAAGAGCCTCTCCCTGTCTCTGGGTAA
AGCTAGCTGA Anti-CD40_12B4.2C10_H-LV-hIgG4H-C (SEQ ID NO: 96):
MEWSWIFLFLLSGTAGVHSEVQLQQSGPELVKPGASVKMSCKASGYTFTD
YVLHWVKQKPGQGLEWIGYINPYNDGTKYNEKFKGKATLTSDKSSSTAYM
ELSSLTSEDSAVYYCARGYPAYSGYAMDYWQGTSVTVSSAKTKGPSVFP
LAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCP
APEFEGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHE
ALHNHYTQKSLSLSLGKAS Anti-CD40_12B4.2C10_K-LV-v2-hIgGK-C
(SEQ ID NO: 32):
ATGATGTCCTCAGTTCCTTGGTCTCCTGTTGCTCTGTTTTCAAGG
TACCAGATGTGATATCCAGATGACACAGACTACATCCTCCCTGTCTGCCT
CTCTGGGAGACAGAGTCACCATCAGTTGCAGGGCAAGTCAGGACATTAGC
AATTATTTAAACTGGTATCAGCAGAAACCAGATGGAACTGTTAAACTCCT
GATCTACTACACATCAAGATTACACTCAGGAGTCCCATCAAGGTTCAGTG
GCAGTGGGTCTGGAACAGATTATTCTCTCACCATTAGCAACCTGGAGCAA
GAAGATATTGCCACTTACTTTTGCCATCATGGTAATACGCTTCCGTGGAC
GTTCGGTGGAGGCACCAAGCTCGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTATGCCTGCGAAGTCAC
CCATCAGGGCCTGAGCTCGCCCGTCACAAAGAGCTTCAACAGGGGAGAGT
GTTAG Anti-CD40_12B4.2C10_K-LV-v2-hIgGK-C
(SEQ ID NO: 97):
MMSSAQFLGLLLLCFQGTRCDIQMTQTTSSLSASLGDRVTISCRASQDIS
NYLNWYQQKPDGTVKLLIYYTSRLHSGVPSRFSGSGSGTDYSLTISNLEQ
EDIATYFCHHGNTLPWTFGGGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC Anti-CD40_12E12.3F3_H-V-hIgG4H-C (SEQ ID NO: 33):
ATGGGTTGGGGCTCAGCTTGATTTTCCTTGTCCTTGTTTTAAAAGGTGT
CCAGTGTGAAGTGAAGCTGGTCGAGTCTGGGGGAGGCTTAGTGCAGCCTG
GAGGGTCCCTGAAACTCTCCTGTGCAACCTCTGGATTCACTTTCAGTGAC
TATTACATGTATTGGGTTCGCCAGACTCCAGAGAAGAGGCTGGAGTGGGT
CGCATACATTAATTCTGGTGGTGGTAGCACCTATTATCCAGACACTGTAA
AGGGCCGATTCACCATCTCCAGAGACAATGCCAAGAACAACCTGTACCTG
CAAATGAGCCGGCTGAAGTCTGAGGACACAGCCATGTATTACTGTGCAAG
ACGGGGGTTACCGTTCCATGCTATGGACTATTGGGGTCAAGGAACCTCAG
TCACCGTCTCCTCAGCCAAAACGAAGGGCCCATCCGTCTTCCCCCTGGCG
CCCTGCTCCAGGAGCACCTCCGAGAGCACAGCCGCCCTGGGCTGCCTGGT
CAAGGACTACTTCCCCGAACCGGTGACGGTGTCGTGGAACTCAGGCGCCC
TGACCAGCGGCGTGCACACCTTCCCGGCTGTCCTACAGTCCTCAGGACTC
TACTCCCTCAGCAGCGTGGTGACCGTGCCCTCCAGCAGCTTGGGCACGAA
GACCTACACCTGCAACGTAGATCACAAGCCCAGCAACACCAAGGTGGACA
AGAGAGTTGAGTCCAAATATGGTCCCCCATGCCCACCCTGCCCAGCACCT
GAGTTCGAAGGGGGACCATCAGTCTTCCTGTTCCCCCCAAAACCCAAGGA
CACTCTCATGATCTCCCGGACCCCTGAGGTCACGTGCGTGGTGGTGGACG
TGAGCCAGGAAGACCCCGAGGTCCAGTTCAACTGGTACGTGGATGGCGTG
GAGGTGCATAATGCCAAGACAAAGCCGCGGGAGGAGCAGTTCAACAGCAC
GTACCGTGTGGTCAGCGTCCTCACCGTCCTGCACCAGGACTGGCTGAACG
GCAAGGAGTACAAGTGCAAGGTCTCCAACAAAGGCCTCCCGTCCTCCATC
GAGAAAACCATCTCCAAAGCCAAAGGGCAGCCCCGAGAGCCACAGGTGTA
CACCCTGCCCCCATCCCAGGAGGAGATGACCAAGAACCAGGTCAGCCTGA

```
CCTGCCTGGTCAAAGGCTTCTACCCCAGCGACATCGCCGTGGAGTGGGAG
AGCAATGGGCAGCCGGAGAACAACTACAAGACCACGCCTCCCGTGCTGGA
CTCCGACGGCTCCTTCTTCCTCTACAGCAGGCTAACCGTGGACAAGAGCA
GGTGGCAGGAGGGGAATGTCTTCTCATGCTCCGTGATGCATGAGGCTCTG
CACAACCACTACACACAGAAGAGCCTCTCCCTGTCTCTGGGTAAAGCTAG
CTGA
```

Anti-CD40_12E12.3F3_H-V-hIgG4H-C (SEQ ID NO: 98):
```
MNLGLSLIFLVLVLKGVQCEVKLVESGGGLVQPGGSLKLSCATSGFTFSD
YYMYWVRQTPEKRLEWVAYINSGGGSTYYPDTVKGRFTISRDNAKNTLYL
QMSRLKSEDTAMYYCARRGLPFHAMDYWGQGTSVTVSSAKTKGPSVFPLA
PCSRSTSESTAALGCLVKDYFPEPVTVSWNSGALTSGVHTFPAVLQSSGL
YSLSSVVTVPSSSLGTKTYTCNVDHKPSNTKVDKRVESKYGPPCPPCPAP
EFEGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEAL
HNHYTQKSLSLSLGKAS
```

Anti-CD40_12E12.3F3_K-LV-hIgGK-C (SEQ ID NO: 34):
```
ATGATGTCCTCTGCTCAGTTCCTTGGTCTCCTGTTGCTCTGTTTTCAAGG
TACCAGATGTGATATCCAGATGACACAGACTACATCCTCCCTGTCTGCCT
CTCTAGGAGACAGAGTCACCATCAGTTGCAGTGCAAGTCAGGGCATTAGC
AATTATTTAAACTGGTATCAGCAGAAACAGATGGAACTGTTAAACTCCT
GATCTATTACACATCAATTTTACACTCAGGAGTCCCATCAAGGTTCAGTG
GCAGTGGGTCTGGGACAGATTATTCTCTCACCATCGGCAACCTGGACCT
GAAGATATTGCCACTTACTATTGTCAGCAGTTTAATAAGCTTCCTCCGAC
GTTCGGTGGAGGCACCAAACTCGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACAAAGTCTATGCCTGCGAAGTCAC
CCATCAGGGCCTGAGCTCGCCCGTCACAAAGAGCTTCAACAGGGGAGAGT
GTTAG
```

Anti-CD40_12E12.3F3_K-LV-hIgGK-C (SEQ ID NO: 99):
```
MMSSAQFLGLLLLCFQGTRCDIQMTQTTSSLSASLGDRVTISCSASQGIS
NYLNWYQQKPDGTVKLLIYYTSILHSGVPSRFSGSGSGTDYSLTIGNLEP
EDIATYYCQQFNKLPPTFGGGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC
```

Anti-DCIR_24A5.4A5_H-V-hIgG4H-C (SEQ ID NO: 35):
```
ATGGATTGGCTGTGGAACTTGCTATTCCTGATGGCAGCTGCCCAAAGTGC
CCAAGCACAGATCCAGTTGGTGCAGTCTGGACCTGAGCTGAAGAAGCCTG
GAGAGACAGTCAAGATCTCCTGCAAGGCTTCTGGTTATTCCTTCACAACA
TATGGAATGAACTGGGTGAAACAGGCTCCAGGAAAGGGTTTAAAGTGGAT
GGGCTGGATAAACACCTACACTGGAGAGTCAACATATGCTGATGACTTCA
AGGGACGGTTTGCCTTCTCTTTGGAAACCTCTGCCAGCACTGCCTATTTG
CAGATCAGTAACCTCAAAAATGAGGACATGGCTACATATTTCTGTGCTAG
AGGGGACTTTAGGTACTACTATTTTGACTACTGGGGCCAAGGCACCACTC
TCACAGGCTCCTCAGCCAAAACGAAGGGCCCATCCGTCTTCCCCCTGGCG
CCCTGCTCCAGGAGCACCTCCGAGAGCACAGCCGCCCTGGGCTGCCTGGT
CAAGGACTACTTCCCCGAACCGGTGACGGTGTCGTGGAACTCAGGCGCCC
TGACCAGCGGCGTGCACACCTTCCCGGCTGTCCTACAGTCCTCAGGACTC
TACTCCCTCAGCAGCGTGGTGACCGTGCCCTCCAGCAGCTTGGGCACGAA
GACCTACACCTGCAACGTAGATCACAAGCCCAGCAACACCAAGGTGGACA
AGAGAGTTGAGTCCAAATATGGTCCCCCATGCCCACCCTGCCCAGCACCT
GAGTTCGAAGGGGGACCATCAGTTTCCTGTTCCCCCCAAAACCCAAGGA
CACTCTCATGATCTCCCGGACCCCTGAGGTCACGTGCGTGGTGGTGGACG
TGAGCCAGGAAGACCCCGAGGTCCAGTTCAACTGGTACGTGGATGGCGTG
GAGGTGCATAATGCCAAGACAAAGCCGCGGGAGGAGCAGTTCAACAGCAC
GTACCGTGTGGTCAGCGTCCTCACCGTCCTGCACCAGGACTGGCTGAACG
GCAAGGAGTACAAGTGCAAGGTCTCCAACAAAGGCCTCCCGTCCTCCATC
GAGAAAACCATCTCCAAAGCCAAAGGGCAGCCCCGAGAGCCACAGGTGTA
CACCCTGCCCCCATCCCAGGAGGAGATGACCAAGAACCAGGTCAGCCTGA
CCTGCCTGGTCAAAGGCTTCTACCCCAGCGACATCGCCGTGGAGTGGGAG
AGCAATGGGCAGCCGGAGAACAACTACAAGACCACGCCTCCCGTGCTGGA
CTCCGACGGCTCCTTCTTCCTCTACAGCAGGCTAACCGTGGACAAGAGCA
GGTGGCAGGAGGGGAATGTCTTCTCATGCTCCGTGATGCATGAGGCTCTG
CACAACCACTACACACAGAAGAGCCTCTCCCTGTCTCTGGGTAAAGCTAG
CTGAT
```

Anti-DCIR_24A5.4A5_H-V-hIgG4H-C (SEQ ID NO: 100):
```
MDWLWNLLFLMAAAQSAQAQIQLVQSGPELKKPGETVKISCKASGYSFTN
YGMNWVKQAPGKGLKWMGWINTYTGESTYADDFKGRFAFSLETSASTAYL
QISNLKNEDMATYFCARGDFRYYFDYWGQGTTLTGSSAKTKGPSVFPLA
PCSRSTSESTAALGCLVKDYFPEPVTVSWNSGALTSGVHTFPAVLQSSGL
YSLSSVVTVPSSSLGTKTYTCNVDHKPSNTKVDKRVESKYGPPCPPCPAP
EFEGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEAL
HNHYTQKSLSLSLGKAS
```

Anti-DCIR_24A5.4A5_K-V-hIgGK-C (SEQ ID NO: 36):
```
ATGAGTGTGCTCACTCAGGTCCTGGCGTTGCTGCTGCTGTGGCTTACAGG
TGCCAGATGTGACATCCAGATGACTCAGTCTCCAGCCTCCCTATCTGCAT
CTGTGGGAGAAACTGTCACCATCACGTGTCGAGCAAGTCGGGAATATTCAC
AATTATTTAGCATGGTATCAGCAGAAACAGGGAAAATCTCCTCAGCTCCT
GGTCTATAATGCAAAAACCTTGGCAGATGGTGTGCCATCAAGGTTCAGTG
GCAGTGGATCAGGAACACAATATTCTCTCAAGATCAACACCCTGCAGCCT
GAAGATTTTGGGAGTTATTACTGTCAACATTTTTGGGATTCTTGGACGTT
CGGTGGAGGCACCAAGCTCGAGATCAAACGAACTGTGGCTGCACCATCTG
TCTTCATCTTCCCGCCATCTGATGAGCAGTTGAAATCTGGAACTGCCTCT
GTTGTGTGCCTGCTGAATAACTTCTATCCCAGAGAGGCCAAAGTACAGTG
GAAGGTGGATAACGCCCTCCAATCGGGTAACTCCCAGGAGAGTGTCACAG
AGCAGGACAGCAAGGACAGCACCTACAGCCTCAGCAGCACCCTGACGCTG
AGCAAAGCAGACTACGAGAAACAAAGTCTATGCCTGCGAAGTCACCCA
TCAGGGCCTGAGCTCGCCCGTCACAAAGAGCTTCAACAGGGGAGAGTGTT
AG
```

Anti-DCIR_24A5.4A5_K-V-hIgGK-C (SEQ ID NO: 101):
```
MSVLTQVLALLLLWLTGARCDIQMTQSPASLSASVGETVTITCRASGNIH
NYLAWYQQKQGKSPQLLVYNAKTLADGVPSRFSGSGSGTQYSLKINTLQP
EDFGSYYCQHFWDSWTFGGGTKLEIKRTVAAPSVFIFPPSDEQLKSGTAS
VVCLLNNFYPREAKVQWKVDNALQSGNSQESVTEQDSKDSTYSLSSTLTL
SKADYEKHKVYACEVTHQGLSSPVTKSFNRGEC
```

Anti-DCIR_24E7.3H9_H-V-hIgG4H-C (SEQ ID NO: 37):
```
ATGGAATGGACCTGGGTCTTTCTCTTCCTCCTGTCAGTAACTGCAGGTGT
CCACTCCCAGGTTCAGCTGCAGCAGTCTGGAGCTGAGCTGATGAAGCCTG
GGGCCTCAGTGAAGATATCCTGCAAGGCTACTGGCTACACATTCAGTAGC
TACTGGATAGAGTGGGTAAAGCAGAGGCCTGGACATGGCCTTGAGTGGAT
TGGAGAGATTTTACCTGGAAGTGGTAGGACTAACGACAATGAGAAGTTCA
AGGGCAAGGCCACATTCACTGCAGATACATCCTCCAAGAAAGCCTACATG
CAACTCAGCAGCCTGACATCTGAGGACTCTGCCGTCTATTATTGTGCAAG
AAGGGGTGGTTACTCCTTTGCTTACTGGGGCCAAGGGACTCTGGTCACTG
TCTCTGCAGCCAAAACAAAGGGCCCATCCGTCTTCCCCCTGGCGCCCTGC
TCCAGGAGCACCTCCGAGAGCACAGCCGCCCTGGGCTGCCTGGTCAAGGA
CTACTTCCCCGAACCGGTGACGGTGTCGTGGAACTCAGGCGCCCTGACCA
GCGGCGTGCACACCTTCCCGGCTGTCCTACAGTCCTCAGGACTCTACTCC
CTCAGCAGCGTGGTGACCGTGCCCTCCAGCAGCTTGGGCACGAAGACCTA
CACCTGCAACGTAGATCACAAGCCCAGCAACACCAAGGTGGACAAGAGAG
TTGAGTCCAAATATGGTCCCCCATGCCCACCCTGCCCAGCACCTGAGTTC
GAAGGGGGACCATCAGTCTTCCTGTTCCCCCCAAAACCCAAGGACACTCT
CATGATCTCCCGGACCCCTGAGGTCACGTGCGTGGTGGTGGACGTGAGCC
AGGAAGACCCCGAGGTCCAGTTCAACTGGTACGTGGATGGCGTGGAGGTG
CATAATGCCAAGACAAAGCCGCGGGAGGAGCAGTTCAACAGCACGTACCG
TGTGGTCAGCGTCCTCACCGTCCTGCACCAGGACTGGCTGAACGGCAAGG
AGTACAAGTGCAAGGTCTCCAACAAAGGCCTCCCGTCCTCCATCGAGAAA
ACCATCTCCAAAGCCAAAGGGCAGCCCCGAGAGCCACAGGTACACCCT
GCCCCCATCCCAGGAGGAGATGACCAAGAACCAGGTCAGCCTGACCTGCC
TGGTCAAAGGCTTCTACCCCAGCGACATCGCCGTGGAGTGGGAGAGCAAT
GGGCAGCCGGAGAACAACTACAAGACCACGCCTCCCGTGCTGGACTCCGA
CGGCTCCTTCTTCCTCTACAGCAGGCTAACCGTGGACAAGAGCAGGTGGC
AGGAGGGGAATGTCTTCTCATGCTCCGTGATGCATGAGGCTCTGCACAAC
CACTACACACAGAAGAGCCTCTCCCTGTCTCTGGGTAAAGCTAGCTGA
```

Anti-DCIR_24E7.3H9_H-V-hIgG4H-C (SEQ ID NO: 102):
```
MEWTWVFLFLLSVTAGVHSQVQLQQSGAELMKPGASVKISCKATGYTFSS
YWIEWVKQRPGHGLEWIGEILPGSGRTNDNEKFKGKATFTADTSSKKAYM
QLSSLTSEDSAVYYCARRGGYSFAYWGQGTLVTVSAAKTKGPSVFPLAPC
SRSTSESTAALGCLVKDYFPEPVTVSWNSGALTSGVHTFPAVLQSSGLYS
LSSVVTVPSSSLGTKTYTCNVDHKPSNTKVDKRVESKYGPPCPPCPAPEF
EGGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHN
HYTQKSLSLSLGKAS
```

Anti-DCIR_24E7.3H9_K-V-hIgGK-C (SEQ ID NO: 38):
```
ATGACCATGTTCTCACTAGCTCTTCTCCTCAGTCTTCTTCCTCTGTGT
CTCTGATTCTAGGGCAGAAACAACTGTGACCCAGTCTATGACCATGTTCT
CACTAGCTCTTCTCCTCAGTCTTCTTCCTCTGTGTCTCTGATTCTAGG
GCAGAAACAACTGTGACCCAGTCTCCAGCATCCCTGTCCATGGCTATAGG
GGAAAAAGTCACCATCAGATGCGTAACAGCACTGATATTGATGATGATG
TGAACTGGTACCAGCAGAAGCCAGGGGAACCTCCTAAACCTTATTTCA
GAAGGCAATACTCTTCGTCCTGGAGTCCCATCCCGATTCTCCAGCAGTGG
CTATGGTACAGATTTTGTTTTTACAATTGAGAACATGCTCTCAGAAGATG
TTGCAGATTACTACTGTTTGCAAAGTGGTAACTTGCCGTACACGTTCGGA
```

-continued
```
GGGGGGACCAAGCTCGAGATCAAACGAACTGTGGCTGCACCATCTGTCTT
CATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCA
GGACAGCAAGGACCACCTACAGCCTCAGCAGCACCCTGACGCTGAGCA
AAGCAGACTACGAGAAACACAAAGTCTATGCCTGCGAAGTCACCCATCAG
GGCCTGAGCTCGCCCGTCACAAAGAGCTTCAACAGGGGAGAGTGTTAGCC
AGCATCCCTGTCCATGGCTATAGGGGAAAAAGTCACCATCAGATGCGTAA
CCAGCACTGATATTGATGATGATGTGAACTGGTACCAGCAGAAGCCAGGG
GAACCTCCTAAACCTCCTTATTTCAGAAGGCAATACTCTTCGTCCTGGAGT
CCCATCCCGATTCTCCAGCAGTGGCTATGGTACAGATTTTGTTTTTACAA
TTGAGAACATGCTCTCAGAAGATGTTGCAGATTACTACTGTTTGCAAAGT
GGTAACTTGCCGTACACGTTCGGAGGGGGGACCAAGCTCGAGATCAAACG
AACTGTGGCTGCACCATCTGTCTTCATCTTCCCGCCATCTGATGAGCAGT
TGAAATCTGGAACTGCCTCTGTTGTGTGCCTGCTGAATAACTTCTATCCC
AGAGAGGCCAAAGTACAGTGGAAGGTGGATAACGCCCTCCAATCGGGTAA
CTCCCAGGAGAGTGTCACAGAGCAGGACAGCAAGGACAGCACCTACAGCC
TCAGCAGCACCCTGACGCTGAGCAAAGCAGACTACGAGAAACACAAAGTC
TATGCCTGCGAAGTCACCCATCAGGGCCTGAGCTCGCCCGTCACAAAGAG
CTTCAACAGGGGAGAGTGTTAG Anti-DCIR_24E7.3H9_K-V-hIgGK-C (SEQ ID NO: 103):
MTMFSLALLLSLLLLCVSDSRAETTVTQSPASLSMAIGEKVTIRCVTSTD
IDDDVNWYQQKPGEPPKLLISEGNTLRPGVPSRFSSSGYGTDFVFTIENM
LSEDVADYYCLQSGNLPYTFGGGTKLEIKRTVAAPSVFIFPPSDEQLKSG
TASVVCLLNNFYPREAKVQWKVDNALQSGNSQESVTEQDSKDSTYSLSST
LTLSKADYEKHKVYACEVTHQGLSSPVTKSFNRGEC Anti-DCIR_29E9.2E2_H-VhIgG4H-C (SEQ ID NO: 39):
ATGGCTTGGGTGTGGACCTTGCTATTCCTGATGGCAGCTGCCCAAAGTGC
CCAAGCACAGATCCAGTTGGTGCAGTCTGGACCTGAGCTGAAGAAGCCTG
GAGAGACAGTCAAGATCTCCTGCAAGGCTTCGGGATATACCTTCACAAAC
TATGGAATGAACTGGGTGAAGCAGGCTCCAGGAAAGGGTTTAAAGTGGGT
GGGCTGGATAAACCTTCACTGGAGAGCCAACATATGTTGATGACTTCA
AGGGACGGTTTGCCTTCTCTTTGGAAAACTCTGCCAGCACTGCCTATTTG
CAGATCAACAACCTCAAAAATGAGGACACGGCTACATATTCTGTGCAAGG
AGGGAATTTTAGGTACTACTACTTTGACTACTGGGGCCAAGGCACCACTC
TCACAGTCTCCTCAGCCAAAACAAAGGGCCCATCCGTCTTCCCCCTGGCG
CCCTGCTCCAGGAGCACCTCCGAGAGCACAGCCGCCCTGGGCTGCCTGGT
CAAGGACTACTTCCCCGAACCGGTGACGGTGTCGTGGAACTCAGGCGCCC
TGACCAGCGGCGTGCACACCTTCCCGGCTGTCCTACAGTCCTCAGGACTC
TACTCCCTCAGCAGCGTGGTGACCGTGCCCTCCAGCAGCTTGGGCACGAA
GACCTACACCTGCAACGTAGATCACAAGCCCAGCAACACCAAGGTGGACA
AGAGAGTTGAGTCCAAATATGGTCCCCCATGCCCACCCTGCCCAGCACCT
GAGTTCGAAGGGGGACCATCAGTCTTCCTGTTCCCCCCAAAACCCAAGGA
CACTCTCATGATCTCCCGGACCCCTGAGGTCACGTGCGTGGTGGTGGACG
TGAGCCAGGAAGACCCCGAGGTCCAGTTCAACTGGTACGTGGATGGCGTG
GAGGTGCATAATGCCAAGACAAAGCCGCGGGAGGAGCAGTTCAACAGCAC
GTACCGTGTGGTCAGCGTCCTCACCGTCCTGCACCAGGACTGGCTGAACG
GCAAGGAGTACAAGTGCAAGGTCTCCAACAAAGGCCTCCCGTCCTCCATC
GAGAAAACCATCTCCAAAGCCAAAGGGCAGCCCCGAGAGCCACAGGTGTA
CACCCTGCCCCCATCCCAGGAGGAGATGACCAAGAACCAGGTCAGCCTGA
CCTGCCTGGTCAAAGGCTTCTACCCCAGCGACATCGCCGTGGAGTGGGAG
AGCAATGGGCAGCCGGAGAACAACTACAAGACCACGCCTCCCGTGCTGGA
CTCCGACGGCTCCTTCTTCCTCTACAGCAGGCTAACCGTGGACAAGAGCA
GGTGGCAGGAGGGGAATGTCTTCTCATGCTCCGTGATGCATGAGGCTCTG
CACAACCACTACACACAGAAGAGCCTCTCCCTGTCTCTGGGTAAAAGCTAG
CTGA Anti-DCIR_29E9.2E2_H-VhIgG4H-C (SEQ ID NO: 104):
MAWVWTLLFLMAAAQSAQAQIQLVQSGPELKKPGETVKISCKASGYTFTN
YGMNWVKQAPGKGLKWVGWINTFTGEPTYVDDFKGRFAFSLETSASTAYL
QINNLKNEDTATYFCARGNFRYYYFDYWQGTTLTVSSAKTKGPSVFPLA
PCSRSTSESTAALGCLVKDYFPEPVTVSWNSGALTSGVHTFPAVLQSSGL
YSLSSVVTVPSSSLGTKTYTCNVDHKPSNTKVDKRVESKYGPPCPPCPAP
EFEGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEAL
HNHYTQKSLSLSLGKAS Anti-DCIR_29E9.2E2_K-V-hIgGK-C (SEQ ID NO: 40):
ATGAGTGTGCTCACTCAGGTCCTGGCGTTGCTGCTGCTGTGGCTTACAGG
TGCCAGATGTGACATCCAGATGACTCAGTCCCCAGCCTCCCTATCTGCAT
CTGTGGGAGAAACTGTCACCATCACATGTCGAACAAGTGGGAATATTCGC
AATTATTTAGCATGGTATCAGCAGAAACCAGGGAAAATCTCCTCAACTCT
GGTCTATAATGCAAAAACCTTAGCAGATGGTGTGCCATCAAGGTTCGGTG
GCAGTGGATCAGGAACACAATATTCTCTCAAGATCAACAGCCTGCAGCCT
GAAGATTTTGGGAATTATTACTGTCAACATTTTTGGAGTAGTCCGTACAC
GTTCGGAGGGGGGACCAAGCTCGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTATGCCTGCGAAGTCAC
CCATCAGGGCCTGAGCTCGCCCGTCACAAAGAGCTTCAACAGGGGAGAGT
GTTAG Anti-DCIR_29E9.2E2_K-V-hIgGK-C (SEQ ID NO: 105):
MSVLTQVLALLLLWLTGARCDIQMTQSPASLSASVGETVTITCRTSGNIR
NYLAWYQQKQGKSPQLLVYNAKTLADGVPSRFGGSGSGTQYSLKINSLQP
EDFGNYYCQHFWSSPYTFGGGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC Anti-DCIR_29G10.3D9_H-V-hIgG4H-C (SEQ ID NO: 41):
ATGATGGGATGGAGCTATATCATCCTCTTTTTGGTAGCAACAGCTACAGA
TGTCCACTCCCAGGTCCAACTGCAGCAGCCTGGGGCTGAACTGGTGAAGC
CTGGGGCTTCAGTGAAGCTGTCCTGCAAGGCTTCTGGCTACACCTTCACC
AGCTACTGGATGCACTGGGTGAAGCAGAGGCCTGGAGAAGGCCTTGAGTG
GATTGGAGAGATTAATCCTAGCTACGGTCGTACTGACTACAATGAGAAGT
TCAAGAACAAGGCCACACTGACTGTAGCCAAATCCTCCAGCACAGCCTAC
ATGCAACTCAGCAGCCTGACATCTGAGGACTCTGCGGTCTATTACTGTGC
AAGAGGAGATTACTACGGTAGTAGCTCGTTTGCTTACTGGGGCCAAGGGA
CTCTGGTCACTGTCTCTGCAGCCAAAACAAAGGGCCCATCCGTCTTCCCC
CTGGCGCCCTGCTCCAGGAGCACCTCCGAGAGCACAGCCGCCCTGGGCTG
CCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGG
CACGAAGACCTACACCTGCAACGTAGATCACAAGCCCAGCAACACCAAGG
TGGACAAGAGAGTTGAGTCCAAATATGGTCCCCCATGCCCACCCTGCCCA
GCACCTGAGTTCGAAGGGGGACCATCAGTCTTCCTGTTCCCCCCAAAACC
CAAGGACACTCTCATGATCTCCCGGACCCCTGAGGTCACGTGCGTGGTGG
TGGACGTGAGCCAGGAAGACCCCGAGGTCCAGTTCAACTGGTACGTGGAT
GGCGTGGAGGTGCATAATGCCAAGACAAAGCCGCGGGAGGAGCAGTTCAA
CAGCACGTACCGTGTGGTCAGCGTCCTCACCGTCCTGCACCAGGACTGGC
TGAACGGCAAGGAGTACAAGTGCAAGGTCTCCAACAAAGGCCTCCCGTCC
TCCATCGAGAAAACCATCTCCAAAGCCAAAGGGCAGCCCCGAGAGCCACA
GGTGTACACCCTGCCCCCATCCCAGGAGGAGATGACCAAGAACCAGGTCA
GCCTGACCTGCCTGGTCAAAGGCTTCTACCCCAGCGACATCGCCGTGGAG
TGGGAGAGCAATGGGCAGCCGGAGAACAACTACAAGACCACGCCTCCCGT
GCTGGACTCCGACGGCTCCTTCTTCCTCTACAGCAGGCTAACCGTGGACA
AGAGCAGGTGGCAGGAGGGGAATGTCTTCTCATGCTCCGTGATGCATGAG
GCTCTGCACAACCACTACACACAGAAGAGCCTCTCCCTGTCTCTGGGTAA
AGCTAGCTGA Anti-DCIR_29G10.3D9_H-V-hIgG4H-C (SEQ ID NO: 106):
MMGWSYIILFLVATATDVHSQVQLQQPGAELVKPGASVKLSCKASGYTFT
SYWMHWVKQRPGEGLEWIGEINPSYGRTDYNEKFKNKATLTVAKSSSTAY
MQLSSLTSEDSAVYYCARGDYYGSSSFAYWGQGTLVTVSAAKTKGPSVFP
LAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCP
APEFEGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPS
```

SIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHE
ALHNHYTQKSLSLSLGKAS

Anti-DCIR_29G10.3D9_K-Var1-V-hIgGK-C
(SEQ ID NO: 42):
ATGGATTTTCAAGTGCAGATTTTCAGCTTCCTGCTAATGAGTGCCTCAGT
CATAATGTCCAGGGGACAAATTGTTCTCACCCAGTCTCCAGCACTCATGT
CTGCATCTCCAGGGGAGAAGGTCACCATGACCTGCAGTGCCAGCTCAAAT
ATAAGTTACATGTACTGGTACCAGCAGAAGCCAAGATCCTCCCCCAAACC
CTGGATTTATCTCACATCCAACCTGGCTTCTGGAGTCCCTGCTCGCTTCA
GTGGCAGTGGGTCTGGGACCTCTTACTCTCTCACAACCAGCAGCATGGAG
GCTGAAGATGCTGCCACTTATTGCTGCCAGCAGTGGAGTAGTAACCCACC
CACGTTCGGTGCTGGGACCAAGCTCGAGATCAAACGAACTGTGGCTGCAC
CATCTGTCTTCATCTTCCCGCCATCTGATGAGCAGTTGAAATCTGGAACT
GCCTCTGTTGTGTGCCTGCTGAATAACTTCTATCCCAGAGAGGCCAAAGT
ACAGTGGAAGGTGGATAACGCCCTCCAATCGGGTAACTCCCAGGAGAGTG
TCACAGAGCAGGACAGCAAGGACAGCACCTACAGCCTCAGCAGCACCCTG
ACGCTGAGCAAAGCAGACTACGAGAAACACAAAGTCTATGCCTGCGAAGT
CACCCATCAGGGCCTGAGCTCGCCCGTCACAAAGAGCTTCAACAGGGGAG
AGTGTTAG Anti-DCIR_29G10.3D9_K-Var1-V-hIgGK-C
(SEQ ID NO: 107):
MDFQVQIFSFLLMSASVIMSRGQIVLTQSPALMSASPGEKVTMTCSASSN
ISYMYWYQQKPRSSPKPWIYLTSNLASGVPARFSGSGSGTSYSLTTSSME
AEDAATYCCQQWSSNPPTFGAGTKLEIKRTVAAPSVFIFPPSDEQLKSGT
ASVVCLLNNFYPREAKVQWKVDNALQSGNSQESVTEQDSKDSTYSLSSTL
TLSKADYEKHKVYACEVTHQGLSSPVTKSFNRGEC Anti-DCIR_29G10.3D9_K-Var2-V-hIgGK-C
(SEQ ID NO: 43):
ATGGATTTTCGAGTGCAGATTTTCAGCTTCCTGCTAATGAGTGCCTCAGT
CATAATGTCCAGGGGACAAATTGTTCTCACCCAGTCTCCAGCACTCATGT
CTGCATCTCCAGGGGAGAAGGTCACCATGACCTGCAGTGCCAGCTCAAAT
ATAAGTTACATGTACTGGTACCAGCAGAAGCCAAGATCCTCCCCCAAACC
CTGGATTTATCTCACATCCAACCTGGCTTCTGGAGTCCCTGCTCGCTTCA
GTGGCAGTGGGTCTGGGACCTCTTACTCTCTCACAATCAGCAGCATGGAG
GCTGAAGATGCTGCCACTTATTACTGCCAGCAGTGGAGTAGTAACCCACC
CACGTTCGGTGCTGGGACCAAGCTCGAGATCAAACGAACTGTGCCTGCAC
CATCTGTCTTCATCTTCCCGCCATCTGATGAGCAGTTGAAATCTGGAACT
GCCTCTGTTGTGTGCCTGCTGAATAACTTCTATCCCAGAGAGGCCAAAGT
ACAGTGGAAGGTGGATAACGCCCTCCAATCGGGTAACTCCCAGGAGAGTG
TCACAGAGCAGGACAGCAAGGACAGCACCTACAGCCTCAGCAGCACCCTG
ACGCTGAGCAAAGCAGACTACGAGAAACACAAAGTCTATGCCTGCGAAGT
CACCCATCAGGGCCTGAGCTCGCCCGTCACAAAGAGCTTCAACAGGGGAG
AGTGTTAG Anti-DCIR_29G10.3D9_K-Var2-V-hIgGK-C
(SEQ ID NO: 108):
MDFRVQIFSFLLMSASVIMSRGQIVLTQSPALMSASPGEKVTMTCSASSN
ISYMYWYQQKPRSSPKPWIYLTSNLASGVPARFSGSGSGTSYSLTISSME
AEDAATYYCQQWSSNPPTFGAGTKLEIKRTVAAPSVFIFPPSDEQLKSGT
ASVVCLLNNFYPREAKVQWKVDNALQSGNSQESVTEQDSKDSTYSLSSTL
TLSKADYEKHKVYACEVTHQGLSSPVTKSFNRGEC Anti-DCIR_2C9K-V-hIgGK-C (SEQ ID NO: 44):
ATGGAGACAGACACACTCCTGCTATGGGTGCTGCTGCTCTGGGTTCCAGG
TTCCACAGGTGACATTGTGCTGATCCAATCTCCAGCTTCTTTGGCTGTGT
CTCTAGGGCAGAGGGCCACCATATCCTGCAGAGCCAGTGAAAGTGTTGAT
AGTTATGTCAATAGTTTTATGCACTGGTACCAGCAGAAACCAGGACAGCC
ACCCAAACTCCTCATCTATCGTGTATCCAACCTAGAATCTGGGATCCCTG
CCAGGTTCAGTGGCAGTGGGTCTAGGACAGACTTCACCCTCACCATTAAT
CCTGTGGAGGCTGATGATGTTGCAACCTATTACTGTCAGCAAAGTAATGA
GGATCCATTCACGTTCGGCTCGGGGACAAAGCTCGAGATCAAACGAACTG
TGGCTGCACCATCTGTCTTCATCTTCCCGCCATCTGATGAGCAGTTGAAA
TCTGGAACTGCCTCTGTTGTGTGCCTGCTGAATAACTTCTATCCCAGAGA
GGCCAAAGTACAGTGGAAGGTGGATAACGCCCTCCAATCGGGTAACTCCC
AGGAGAGTGTCACAGAGCAGGACAGCAAGGACAGCACCTACAGCCTCAGC
AGCACCCTGACGCTGAGCAAAGCAGACTACGAGAAACACAAAGTCTATGC
CTGCGAAGTCACCCATCAGGGCCTGAGCTCGCCCGTCACAAAGAGCTTCA
ACAGGGGAGAGTGTTAG Anti-DCIR_2C9K-V-hIgGK-C (SEQ ID NO: 109):
METDTLLLWVLLLWVPGSTGDIVLIQSPASLAVSLGQRATISCRASESVD
SYVNSFMHWYQQKPGQPPKLLIYRVSNLESGIPARFSGSGSRTDFTLTIN
PVEADDVATYYCQQSNEDPFTFGSGTKLEIKRTVAAPSVFIFPPSDEQLK
SGTASVVCLLNNFYPREAKVQWKVDNALQSGNSQESVTEQDSKDSTYSLS
STLTLSKADYEKHKVYACEVTHQGLSSPVTKSFNRGEC.

Anti-DCIR_31A6.1F5_H-var2-V-hIgG4H-C
(SEQ ID NO: 45):
ATGGAATGTAACTGGATACTTCCTTTTATTCTGTCGGTAATTTCAGGGGT
CTACTCAGAGGTTCAGCTCCAGCAGTCTGGGACTGTGCTGGCAAGGCCTG
GGGCTTCCGTGAATATGTCCTGTAAGGCTGCTGGCTACAGCTTTACCAGT
TACTGGGTGTACTGGGTCAAACAGAGGCCTGGACAGGGTCTGGAATGGAT
TGGTGCTATTTACCCTAAAAATAGTAGAACTAGCTACAACCAGAAGTTCC
AGGACAAGGCCACACTGACTGCAGTCACATCCGCCAGCACTGCCTACATG
GAGCTCAGCAGCCTGACAAATGAGGACTCTGCGGTCTATTACTGTACAAG
ACCTCACTATGATTCGTTTGGTTACTGGGGCCAAGGGACTCTGGTCACTG
TCTCTGCAGCCAAAACAAAGGGCCCATCCGTCTTCCCCCTGGCGCCCTGC
TCCAGGAGCACCTCCGAGAGCACAGCCGCCCTGGGCTGCCTGGTCAAGGA
CTACTTCCCCGAACCGGTGACGGTGTCGTGGAACTCAGGCGCCCTGACCA
GCGGCGTGCACACCTTCCCGGCTGTCCTACAGTCCTCAGGACTCTACTCC
CTCAGCAGCGTGGTGACCGTGCCCTCCAGCAGCTTGGGCACGAAGACCTA
CACCTGCAACGTAGATCACAAGCCCAGCAACACCAAGGTGGACAAGAGAG
TTGAGTCCAAATATGGTCCCCCATGCCCACCCTGCCCAGCACCTGAGTTC
GAAGGGGGACCATCAGTCTTCCTGTTCCCCCCAAAACCCAAGGACACTCT
CATGATCTCCCGGACCCCTGAGGTCACGTGCGTGGTGGTGGACGTGAGCC
AGGAAGACCCCGAGGTCCAGTTCAACTGGTACGTGGATGGCGTGGAGGTG
CATAATGCCAAGACAAAGCCGCGGGAGGAGCAGTTCAACAGCACGTACCG
TGTGGTCAGCGTCCTCACCGTCCTGCACCAGGACTGGCTGAACGGCAAGG
AGTACAAGTGCAAGGTCTCCAACAAAGGCCTCCCGTCCTCCATCGAGAAA
ACCATCTCCAAAGCCAAAGGGCAGCCCCGAGAGCCACAGGTGTACACCCT
GCCCCCATCCCAGGAGGAGATGACCAAGAACCAGGTCAGCCTGACCTGCC
TGGTCAAAGGCTTCTACCCCAGCGACATCGCCGTGGAGTGGGAGAGCAAT
GGGCAGCCGGAGAACAACTACAAGACCACGCCTCCCGTGCTGGACTCCGA
CGGCTCCTTCTTCCTCTACAGCAGGCTAACCGTGGACAAGAGCAGGTGGC
AGGAGGGGAATGTCTTCTCATGCTCCGTGATGCATGAGGCTCTGCACAAC
CACTACACACAGAAGAGCCTCTCCCTGTCTCTGGGTAAAGCTAGCTGA Anti-DCIR_31A6.1F5_H-var2-V-hIgG4H-C
(SEQ ID NO: 110):
MECNWILPFILSVISGVYSEVQLQQSGTVLARPGASVNMSCKAAGYSFTS
YWVYWVKQRPGQGLEWIGAIYPKNSRTSYNQKFQDKATLTAVTSASTAYM
ELSSLTNEDSAVYYCTRPHYDSFGYWGQGTLVTVSAAKTKGPSVFPLAPC
SRSTSESTAALGCLVKDYFPEPVTVSWNSGALTSGVHTFPAVLQSSGLYS
LSSVVTVPSSSLGTKTYTCNVDHKPSNTKVDKRVESKYGPPCPPCPAPEF
EGGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHN
HYTQKSLSLSLGKAS Anti-DCIR_31A6.1F5_K-var2-V-hIgGK-C
(SEQ ID NO: 46):
ATGGAGACAGACACACTCCTGCTATGGGTGCTGCTGCTCTGGGTTCCAGG
TTCCACAGGTGACATTGTGCTGACCCAATCTCCAGCTTCTTTGGCTGTGT
CTCTAGGGCAGAGGGCCACCATATCCTGCAGAGCCAGTGAAAGTGTAGAT
AGTTATGGCATTAGTTTTATGCACTGGTACCAGCAGAAACCAGGACAGCC
ACCCAAACTTCTCATCTATCGTGCATCCAACCAAGAATCTGGGATCCCTG
CCAGGTTCAGTGGCAGTGGGTCTAGGACAGACTTCACCCTCACCATTAAT
CCTGTGGAGGCTGATGATGTTGCAACCTATTACTGTCAGCAAAGTAATGA
GGATCCTACCTTCGGTGCTGGGACCAAGCTCGAGATCAAACGAACTG
TGGCTGCACCATCTGTCTTCATCTTCCCGCCATCTGATGAGCAGTTGAAA
TCTGGAACTGCCTCTGTTGTGTGCCTGCTGAATAACTTCTATCCCAGAGA
GGCCAAAGTACAGTGGAAGGTGGATAACGCCCTCCAATCGGGTAACTCCC
AGGAGAGTGTCACAGAGCAGGACAGCAAGGACAGCACCTACAGCCTCAGC
AGCACCCTGACGCTGAGCAAAGCAGACTACGAGAAACACAAAGTCTATGC
CTGCGAAGTCACCCATCAGGGCCTGAGCTCGCCCGTCACAAAGAGCTTCA
ACAGGGGAGAGTGTTAG Anti-DCIR_31A6.1F5_K-var2-V-hIgGK-C
(SEQ ID NO: 111):
METDTLLLWVLLLWVPGSTGDIVLTQSPASLAVSLGQRATISCRASESVD
SYGISFMHWYQQKPGQPPKLLIYRASNQESGIPARFSGSGSRTDFTLTIN
PVEADDVATYYCQQSNEDPLTFGAGTKLEIKRTVAAPSVFIFPPSDEQLK
SGTASVVCLLNNFYPREAKVQWKVDNALQSGNSQESVTEQDSKDSTYSLS
STLTLSKADYEKHKVYACEVTHQGLSSPVTKSFNRGEC Anti-DCIR_3C2.2D9_H-LV-hIgG4H-C (SEQ ID NO: 47):
ATGAACAGGCTTACTTCCTCATTGCTGCTGCTGATTGTCCCTGCATATGT
CCTGTCCCAGGTTACTCTGAAAGAGTCTGGCCCTGGGATATTGCAGCCCT
CCCAGACCCTCAGTCTGACTTGTTCTTTCTCTGGGTTTTCACTGAGCACT
TCTGGTATGGGTGTGAGCTGGATTCGTCAGCCTTCAGGAAAGGGTCTGGA
GTGGCTGGCACACATTTACTGGGATGATGACAAGCGCTATAATCCATCCC
TGAAGAGCCGGCTCACAATCTTTAAGGATCCCTCCAGCAACCAGGTATTC
CTCAGGATCACCAGTGTGGACACTGCAGATACTGCCACATACTACTGTGC
TCGAAACTCCCATTACTACGGTAGTACTTACGGGGGATACTTCGATGTCT
GGGGCGCAGGGACCACGGTCACCGTCTCCTCAGCCAAAACAAAGGGCCCA -continued TCCGTCTTCCCCCTGGCGCCCTGCTCCAGGAGCACCTCCGAGAGCACAGC
CGCCCTGGGCTGCCTGGTCAAGGACTACTTCCCCGAACCGGTGACGGTGT
CGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTC
CAGCAGCTTGGGCACGAAGACCTACACCTGCAACGTAGATCACAAGCCCA
GCAACACCAAGGTGGACAAGAGAGTTGAGTCCAAATATGGTCCCCCATGC
CCACCCTGCCCAGCACCTGAGTTCGAAGGGGGACCATCAGTCTTCCTGTT
CCCCCCAAAACCCAAGGACACTCTCATGATCTCCCGGACCCCTGAGGTCA
CGTGCGTGGTGGTGGACGTGAGCCAGGAAGACCCCGAGGTCCAGTTCAAC
TGGTACGTGGATGGCGTGGAGGTGCATAATGCCAAGACAAAGCCGCGGGA
GGAGCAGTTCAACAGCACGTACCGTGTGGTCAGCGTCCTCACCGTCCTGC
ACCAGGACTGGCTGAACGGCAAGGAGTACAAGTGCAAGGTCTCCAACAAA
GGCCTCCCGTCCTCCATCGAGAAAACCATCTCCAAAGCCAAAGGGCAGCC
CCGAGAGCCACAGGTGTACACCCTGCCCCCATCCCAGGAGGAGATGACCA
AGAACCAGGTCAGCCTGACCTGCCTGGTCAAAGGCTTCTACCCCAGCGAC
ATCGCCGTGGAGTGGGAGAGCAATGGGCAGCCGGAGAACAACTACAAGAC
CACGCCTCCCGTGCTGGACTCCGACGGCTCCTTCTTCCTCTACAGCAGGC
TAACCGTGGACAAGAGCAGGTGGCAGGAGGGGAATGTCTTCTCATGCTCC
GTGATGCATGAGGCTCTGCACAACCACTACACACAGAAGAGCCTCTCCCT
GTCTCTGGGTAAAGCTAGCTGA Anti-DCIR_3C2.2D9_H-LV-hIgG4H-C (SEQ ID NO: 112):
NRLTSSLLLLIVPAYVLSQQVTLKESGPGILQPSQTLSLTCSFSGFSLST
SGMGVSWIRQPSGKGLEWLAHIYWDDDKRYNPSLKSRLTIFKDPSSNQVF
LRITSVDTADTATYYCARNSHYYGSTYGGYFDVWGAGTTVTVSSAKTKGP
SVFPLAPCSRSTSESTAALGCLVKDYFPEPVTVSWNSGALTSGVHTFPAV
LQSSGLYSLSSVVTVPSSSLGTKTYTCNVDHKPSNTKVDKRVESKYGPPC
PPCPAPEFEGGPSVFLFPPKPKDTLMISRTPEVTCVVVDVSQEDPEVQFN
WYVDGVEVHNAKTKPREEQFNSTYRVVSVLTVLHQDWLNGKEYKCKVSNK
GLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCS
VMHEALHNHYTQKSLSLSLGKAS.

Anti-DCIR_3C2.2D9_K-LV-hIgGK-C (SEQ ID NO: 48):
ATGGAGACAGACACACTCCTGCTATGGGTGCTGCTGCTCTGGGGTTCCAGG
TTCCACAGGTAACATTGTGCTGACCCAGTCTCCAACTTCTTTCACTGTGT
CTCTTGGGCAGAGGGCCACCATATCCTGCAGAGCCAGTGAAAGTGTTCAT
AGTTATGGCAATAGTTTTATGCACTGGTACCAGCAGAAACCAGGGCAGCC
ACCCAAACTCCTCATCTATCTTGCATCCAACGTAGAATCTGGGGTCCCTG
CCAGGTTCAGTGGTAGTGGGTCCAGGACAGACTTCACCCTCACCATTGAT
CCTGTGGAGGCTGATGATGCTGCAACCTATTACTGTCAGCAAAATAGTGA
GGATCCGTGGACGTTCGGTGGAGGCACCAAGCTCGAGATCAAACGAACTG
TGGCTGCACCATCTGTCTTCATCTTCCCGCCATCTGATGAGCAGTTGAAA
TCTGGAACTGCCTCTGTTGTGTGCCTGCTGAATAACTTCTATCCCAGAGA
GGCCAAAGTACAGTGGAAGGTGGATAACGCCCTCCAATCGGGTAACTCCC
AGGAGAGTGTCACAGAGCAGGACAGCAAGGACAGCACCTACAGCCTCAGC
AGCACCCTGACGCTGACGAAAGACAGCTACGAGAAACACAAAGTCTATGC
CTGCGAAGTCACCCATCAGGGCCTGAGCTCGCCCGTCACAAAGAGCTTCA
ACAGGGGAGAGTGTTAG Anti-DCIR_3C2.2D9_K-LV-hIgGK-C (SEQ ID NO: 113):
METDTLLLWVLLLGVPGSTGNIVLTQSPTSFTVSLGQRATISCRASESVH
SYGNSFMHWYQQKPGQPPKLLIYLASNVESGVPARFSGSGSRTDFTLTID
PVEADDAATYYCQQNSEDPWTFGGGTKLEIKRTVAAPSVFIFPPSDEQLK
SGTASVVCLLNNFYPREAKVQWKVDNALQSGNSQESVTEQDSKDSTYSLS
STLTLSKADYEKHKVYACEVTHQGLSSPVTKSFNRGEC Anti-DCIR_6C8.1G9_H-V-hIgG4H-C (SEQ ID NO: 49):
ATGGAATGGACCTGGGTCTTTCTTCCTCCTGTCAGTAACTGCAGGTGT
CCACTCCCAGGTTCAGCTGCAGCAGTCTGGAACTGAGCTGATGAAGCCTG
GGGCCTCAGTGAAGATATCCTGCAAGGCTACTGGCTACACATTCAGTACC
TACTGGATAGAGTGGGTAAAGCAGAGGCCTGGACATGGCCTTGAGTGGAT
TGGAGAGATTTTACCTGGAAGTGGTAGGACTAACGACAATGAGAAGTTCA
AGGGCAAGGCCACAATCACTGCAGATACATCCTCCAAGAAAGCCTACATG
CAACTCAGCAGCCTGACATCTGAGGACTCTGCCGTCTATTACTGTGCAAG
AAGGGGTGGTTACTCCTTTGCTTTCTGGGGCCAAGGGACTCTGGTCTCTG
TCTCTGCAGCCAAAACAAAGGGCCCATCCGTCTTCCCCCTGGCGCCCTGC
TCCAGGAGCACCTCCGAGAGCACAGCGCCCTGGGCTGCCTGGTCAAGGA
CTACTTCCCCGAACCGGTGACGGTGTCGTGGAACTCAGGCGCCCTGACCA
GCGGCGTGCACACCTTCCCGGCTGTCCTACAGTCCTCAGGACTCTACTCC
CTCAGCAGCGTGGTGACCGTGCCCTCCAGCAGCTTGGGCACGAAGACCTA
CACCTGCAACGTAGATCACAAGCCCAGCAACACCAAGGTGGACAAGAGAG
TTGAGTCCAAATATGGTCCCCCATGCCCACCCTGCCCAGCACCTGAGTTC
GAAGGGGGACCATCAGTCTTCCTGTTCCCCCCAAAACCCAAGGACACTCT
CATGATCTCCCGGACCCCTGAGGTCACGTGCGTGGTGGTGGACGTGAGCC
AGGAAGACCCCGAGGTCCAGTTCAACTGGTACGTGGATGGCGTGGAGGTG
CATAATGCCAAGACAAAGCCGCGGGAGGAGCAGTTCAACAGCACGTACCG
TGTGGTCAGCGTCCTCACCGTCCTGCACCAGGACTGGCTGAACGGCAAGG
AGTACAAGTGCAAGGTCTCCAACAAAGGCCTCCCGTCCTCCATCGAGAAA
ACCATCTCCAAAGCCAAAGGGCAGCCCCGAGAGCCACAGGTGTACACCCT
GCCCCCATCCCAGGAGGAGATGACCAAGAACCAGGTCAGCCTGACCTGCC
TGGTCAAAGGCTTCTACCCCAGCGACATCGCCGTGGAGTGGGAGAGCAAT
GGGCAGCCGGAGAACAACTACAAGACCACGCCTCCCGTGCTGGACTCCGA
CGGCTCCTTCTTCCTCTACAGCAGGCTAACCGTGGACAAGAGCAGGTGGC
AGGAGGGGAATGTCTTCTCATGCTCCGTGATGCATGAGGCTCTGCACAAC
CACTACACACAGAAGAGCCTCTCCCTGTCTCTGGGTAAAGCTAGCTGA Anti-DCIR_6C8.1G9_H-V-hIgG4H-C (SEQ ID NO: 114):
MEWTWVFLFLLSVTAGVHSQVQLQQSGTELMKPGASVKISCKATGYTFST
YWIEWVKQRPGHGLEWIGEILPGSGRTNDNEKFKGKATITADTSSKKAYM
QLSSLTSEDSAVYYCARRGGYSFAFWGQGTLVSVSAAKTKGPSVFPLAPC
SRSTSESTAALGCLVKDYFPEPVTVSWNSGALTSGVHTFPAVLQSSGLYS
LSSVVTVPSSSLGTKTYTCNVDHKPSNTKVDKRVESKYGPPCPPCPAPEF
EGGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHN
HYTQKSLSLSLGKAS Anti-DCIR_6C8.1G9_K-V-hIgGK-C (SEQ ID NO: 50):
ATGACCATGTTCTCACTAGCTCTTCTCCTCAGTCTTCTTCTCCTCTGTGT
CTCTGATTCTAGGGCAGAAACAACTGTGACCCAGTCTCCAGCATCCCTGT
CCATGGCTATAGGAGAAAAAGTCACCATCAGATGCGTAACCAGCACTGAT
ATTGATGATGATGTGAACTGGTACCAGCAGAAGCCAGGGGAACCTCCTAA
GCTCCTTATTTCAGAAGGCAATACTCTTCGTGCTGGAGTCCCATCCCGAT
TCTCCAGCAGTGGCTATGGTACAGATTTTGTTTTTACAATTGAGAACATG
CTCTCAGAAGATGTTGCAGATTACTACTGTTTTGCAAAGTGGTAACTTGCC
GTACAGTTCGGAGGGGGGACCAAGCTCGAGATCAAACGAACTGTGGCTG
CACCATCTGTCTTCATCTTCCCGCCATCTGATGAGCAGTTGAAATCTGGA
ACTGCCTCTGTTGTGTGCCTGCTGAATAACTTCTATCCCAGAGAGGCCAA
AGTACAGTGGAAGGTGGATAACGCCCTCCAATCGGGTAACTCCCAGGAGA
GTGTCACAGAGCAGGACAGCAAGGACAGCACCTACAGCCTCAGCAGCACC
CTGACGCTGAGCAAAGCAGACTACGAGAAACACAAAGTCTATGCCTGCGA
AGTCACCCATCAGGGCCTGAGCTCGCCCGTCACAAAGAGCTTCAACAGGG
GAGAGTGTTAG Anti-DCIR_6C8.1G9_K-V-hIgGK-C (SEQ ID NO: 115):
MTMFSLALLLSLLLLCVSDSRAETTVTQSPASLSMAIGEKVTIRCVTSTD
IDDDVNWYQQKPGEPPKLLISEGNTLRAGVPSRFSSSGYGTDFVFTIENM
LSEDVADYYCLQSGNLPYTFGGGTKLEIKRTVAAPSVFIFPPSDEQLKSG
TASVVCLLNNFYPREAKVQWKVDNALQSGNSQESVTEQDSKDSTYSLSST
LTLSKADYEKHKVYACEVTHQGLSSPVTKSFNRGEC Anti-DCIR_9E8.1E3_H-V-hIgG4H-C (SEQ ID NO: 51):
ATGAACAGGCTTACTTCCTCATTGCTGCTGCTGATTGTCCCTGCATATGT
CCTGTCCCAGGTTACTCTGAAAGAGTCTGGCCCTGGGATATTGCAGCCCT
CCCAGACCCTCAGTCTGACTTGTTCTTTCTCTGGGTTTTCACTGAGCACT
TCTGGTATGGGTGTGAGCTGGATTCGTCAGCCTTCAGGAAAGGGTCTGGA
GTGGCTGGCACACATTTACTGGGATGATGACAAGCGCTATAACCCATCCC
TGAAGAGCCGGCTCACAATCTCCAAGGATACCTCCAGCAACCAGGTTTTC
CTCAAGATCACCATTGTGGACACTGCAGATGCTGCCACATACTACTGTGC
TCGAAGCTCCCATTACTACGGTTATGGCTACGGGGGATACTTCGATGTCT
GGGGCGCAGGGACCACGGTCACCGTCTCCTCAGCCAAAACGAAGGGCCCA
TCCGTCTTCCCCCTGGCGCCCTGCTCCAGGAGCACCTCCGAGAGCACAGC
GCCCTGGGCTGCCTGGTCAAGGACTACTTCCCCGAACCGGTGACGGTGT
CGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTC
CAGCAGCTTGGGCACGAAGACCTACACCTGCAACGTAGATCACAAGCCA
GCAACACCAAGGTGGACAAGAGAGTTGAGTCCAAATATGGTCCCCCATGC
CCACCCTGCCCAGCACCTGAGTTCGAAGGGGGACCATCAGTCTTCCTGTT
CCCCCCAAAACCCAAGGACACTCTCATGATCTCCCGGACCCCTGAGGTCA
CGTGCGTGGTGGTGGACGTGAGCCAGGAAGACCCCGAGGTCCAGTTCAAC
TGGTACGTGGATGGCGTGGAGGTGCATAATGCCAAGACAAAGCCGCGGGA
GGAGCAGTTCAACAGCACGTACCGTGTGGTCAGCGTCCTCACCGTCCTGC
ACCAGGACTGGCTGAACGGCAAGGAGTACAAGTGCAAGGTCTCCAACAAA
GGCCTCCCGTCCTCCATCGAGAAAACCATCTCCAAAGCCAAAGGGCAGCC
CCGAGAGCCACAGGTGTACACCCTGCCCCCATCCCAGGAGGAGATGACCA
AGAACCAGGTCAGCCTGACCTGCCTGGTCAAAGGCTTCTACCCCAGCGAC
ATCGCCGTGGAGTGGGAGAGCAATGGGCAGCCGGAGAACAACTACAAGAC
CACGCCTCCCGTGCTGGACTCCGACGGCTCCTTCTTCCTCTACAGCAGGC
TAACCGTGGACAAGAGCAGGTGGCAGGAGGGGAATGTCTTCTCATGCTCC
GTGATGCATGAGGCTCTGCACAACCACTACACACAGAAGAGCCTCTCCCT
GTCTCTGGGTAAAGCTAGCTGA Anti-DCIR_9E8.1E3_H-V-hIgG4H-C (SEQ ID NO: 116):
MNRLTSSLLLLIVPAYVLSQVTLKESGPGILQPSQTLSLTCSFSGFSLST
SGMGVSWIRQPSGKGLEWLAHIYWDDDKRYNPSLKSRLTISKDTSSNQVF
LKITIVDTADAATYYCARSSHYYGYGGYFDVWGAGTTVTVSSAKTKGP
SVFPLAPCSRSTSESTAALGCLVKDYFPEPVTVSWNSGALTSGVHTFPAV
LQSSGLYSLSSVVTVPSSSLGTKTYTCNVDHKPSNTKVDKRVESKYGPPC
PPCPAPEFEGGPSVFLFPPKPKDTLMISRTPEVTCVVVDVSQEDPEVQFN
WYVDGVEVHNAKTKPREEQFNSTYRVVSVLTVLHQDWLNGKEYKCKVSNK -continued
GLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCS
VMHEALHNHYTQKSLSLSLGKAS Anti-DCIR_9E8.1E3_K-LV-hIgGK-C (SEQ ID NO: 52):
ATGGAGACAGACACACTCCTGCTATGGGTGCTGCTGCTCTGGGTTCCAGG
TTCCACAGGTAACATTGTGCTGACCCAATCTCCAGCTTCTTTGGCTGTGT
CTCTAGGGCAGAGGGCCACCATATCCTGCAGAGCCAGTGAAAGTATTCAT
AGTTATGGCAATAGTTTTCTGCACTGGTACCAGCAGAAACCAGGACAGCC
ACCCAAACTCCTCATCTATCTTGCATCCAACCTAGAATCTGGGGTCCCTG
CCAGGTTCAGCGGCAGTGGGTCTAGGACAGACTTCACCCTCACCATTGAT
CCTGTGGAGGCTGATGATGCTGCAACCTATTACTGTCAGCAAAATAATGA
GGATCCGTGGACGTTCGGTGGAGGCACCAAGCTCGAGATCAAACGAACTG
TGGCTGCACCATCTGTCTTCATCTTTCCGCCATCTGATGAGCAGTTGAAA
TCTGGAACTGCCTCTGTTGTGCCTGCTGAATAACTTCTATCCCAGAGA
GGCCAAAGTACAGTGGAAGGTGGATAACGCCCTCCAATCGGGTAACTCCC
AGGAGAGTGTCACAGAGCAGGACAGCAAGGACAGCACCTACAGCCTCAGC
AGCACCCTGACGCTGAGCAAAGCAGACTACGAGAAACACAAAGTCTATGC
CTGCGAAGTCACCCATCAGGGCCTGAGCTCGCCCGTCACAAAGAGCTTCA
ACAGGGGAGAGTGTTAGGCGGCCGCACTAGCGCGGGCCGCATTCGAAGAG
CTCGGTACCCGGGGATCCTCTAGAGTCGACCTGCAGGCATGCAAGCTGGC
CGCGACTCTAGATCATAATCAGC Anti-DCIR_9E8.1E3_K-LV-hIgGK-C (SEQ ID NO: 117):
METDTLLLWVLLLWVPGSTGNIVLTQSPASLAVSLGQRATISCRASESIH
SYGNSFLHWYQQKPGQPPKLLIYLASNLESGVPARFSGSGSRTDFTLTID
PVEADDAATYYCQQNNEDPWTFGGGTKLEIKRTVAAPSVFIFPPSDEQLK
SGTASVVCLLNNFYPREAKVQWKVDNALQSGNSQESVTEQDSKDSTYSLS
STLTLSKADYEKHKVYACEVTHQGLSSPVTKSFNRGEC Anti-DCIR2C9H-LV-hIgG4H-V-hIgG4H-C (SEQ ID NO: 53):
ATGAAATGCAGCTGGGTCATCTTCTTCCTGATGGCAGTGGTTACAGGGGT
CAATTCAGAGGTTCAGCTGCAGCAGTCTGGGGCTGAGCTTGTGAGGCCAG
GGGCCTTAGTCAAGTTGTCCTGCAAAGCTTCTGGCTTCAACATTAATGAC
TACTATATACACTGGGTGAAGCAGCGGCCTGAACAGGGCCTGGAGCGGAT
TGGATGGATTGATCCTGACAATGGTAATACTATATATGACCCGAAGTTCC
AGGGCAAGGCCAGTATAACAGCAGACACATCCCCAACACAGCCTACCTG
CAGCTCAGCAGCCTGACATCTGAGGACACTGCCGTCTATTACTGTGCTAG
AACCCGATCTCCTATGGTTACGACGGGGTTTGTTTACTGGGGCCAAGGGA
CTGTGGTCACTGTCTCTGCAGCCAAAACGAAGGGCCCATCCGTCTTCCCC
CTGGCCGCCCTGCTCAGGAGCACCTCCGAGAGCACAGCCGCCCTGGGCTG
CCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGG
CACGAAGACCTACACCTGCAACGTAGATCACAAGCCCAGCAACACCAAGG
TGGACAAGAGAGTTGAGTCCAAATATGGTCCCCCATGCCCACCCTGCCCA
GCACCTGAGTTCGAAGGGGGACCATCAGTCTTCCTGTTCCCCCCAAAACC
CAAGGACACTCTCATGATCTCCCGGACCCCTGAGGTCACGTGCGTGGTGG
TGGACGTGAGCCAGGAAGACCCCGAGGTCCAGTTCAACTGGTACGTGGAT
GGCGTGGAGGTGCATAATGCCAAGACRAAGCCGCGGGAGGAGCAGTTCAA
CAGCACGTACCGTGTGGTCAGCGTCCTCACCGTCCTGCACCAGGACTGGC
TGAACGGCAAGGAGTACAAGTGCAAGGTCTCCAACAAAGGCCTCCCGTCC
TCCATCGAGAAAACCATCTCCAAAGCCAAAGGGCAGCCCCGAGAGCCACA
GGTGTACACCCTGCCCCCATCCCAGGAGGAGATGACCAAGAACCAGGTCA
GCCTGACCTGCCTGGTCAAAGGCTTCTACCCCAGCGACATCGCCGTGGAG
TGGGAGAGCAATGGGCAGCCGGAGAACAACTACAAGACCACGCCTCCCGT
GCTGGACTCCGACGGCTCCTTCTTCCTCTACAGCAGGCTAACCGTGGACA
AGAGCAGGTGGCAGGAGGGGAATGTCTTCTCATGCTCCGTGATGCATGAG
GCTCTGCACAACCACTACACACAGAAGAGCCTCTCCCTGTCTCTGGGTAA
ATGA Anti-DCIR2C9H-LV-hIgG4H-V-hIgG4H-C
(SEQ ID NO: 118):
MKCSWVIFFLMAVVTGVNSEVQLQQSGAELVRPGALVKLSCKASGFNIND
YYIHWVKQRPEQGLERIGWIDPDNGNTIYDPKFQGKASITADTSPNTAYL
QLSSLTSEDTAVYYCARTRSPMVTTGFVYWGQGTVVTVSAAKTKGPSVFP
LAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCP
APEFEGGPSVFLFPPKPKDTLMISRTPEVTCVVVDVSQEDPEVQFNWYVD
GVEVHNAKXKPREEQFNSTYRVVSVLTVLHQDWLNGKEYKCKVSNKGLPS
SIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHE
ALHNHYTQKSLSLSLGK Anti-DC-SIGNL16E3H (SEQ ID NO: 54):
ATGGAAAGGCACTGGATCTTTCTCTTCCTGTTTTCAGTAACTGCAGGTGT
CCACTCCCAGGTCCAGCTTCAGCAGTCTGGGGCTGAGCTGGCAAAACCTG
GGGCCTCAGTGAAGATGTCCTGCAAGGCTTCTGGCTACACCTTTACTACC
TACTGGATGCACTGGGTAAAACAGAGGCCTGGACAGGGTCTGGAATGGAT
TGGATACATTAATCCTATCACTGGTTATACTGAGTACAATCAGAAGTTCA
AGGACAAGGCCACCTTGACTGCAGACAAATCCTCCAGCACAGCCTACATG CAACTGAGCAGCCTGACATCTGAGGACTCTGCAGTCTATTACTGTGCAAG
AGAGGGTTAAGTGCTATGGACTATTGGGGTCAGGGAACCTCAGTCACCG
TCACCTCAGCCAAAACAACAGCCCCATCGGTCTATCCACTGGCCCCTGTG
TGTGGAGATACAACTGGCTCCTCGGTAACTCTAGGATGCCTGGTCAAGGG
TTATTTCCCTGAGCCAGTGACCTTGACCTGGAACTCTGGATCCCCTGTCA
GTGGTGTGCACACCTTCCCAGCTGTCCTGCAGTCTGACCTCTACACCCTC
AGCAGCTCAGTGACTGTAACCTCGAGCACCTGGCCCAGCCAGACCGTCAC
CTGCAGCGTTGCTCACCCAGCCAGCAGCACCACGGTGGACAAAAAACTTG
AGCCCAGCGGGCCCATTTCAACAATCAACCCCTGTCCTCCATGCAAGGAG
TGTCACAAATGCCCAGCTCCTAACCTCGAGGGTGGACCATCCGTCTTCAT
CTTCCCTCCAAATATCAAGGATGTACTCATGATCTCCCTGACACCCAAGG
TCACGTGTGTGGTGGTGGATGTGAGCGAGGATGACCCAGACGTCCAGATC
AGCTGGTTTGTGAACAACGTGGAAGTACACACAGCTCAGACACAAACCCA
TAGAGAGGATTACAACAGTACTATCCGGGTGGTTGCAGCACCTTCCCCATCC
AGCACCAGGACTGGATGAGTGGCAAGGAGTTCAAATGCAAGGTCAACAAC
AAAGACCTCCCATCACCCATCGAGAGAACCATCTCAAAAATTAAAGGGCT
AGTCAGAGCTCCACAAGTATACATCTTGCCGCCACCAGCAGAGCAGTTGT
CCAGGAAAGATGTCAGTCTTCACTTGCCTGGTCGTGGGCTTCAACCCTGGA
GACATCAGTGTGGAGTGGACCAGCAATGGGCATACAGAGGAGAACTACAA
GGACACCGCACCAGTCCTGGACTCTGACGGTTCTTACTTCATATATAGCA
AGCTCAATATGAAAACAAGCAAGTGGGAGAAAACAGATTCCTTCTCATGC
AACGTTGAGACACGAGGGTCTGAAAAATTACTACCTGAAGAAGACCATCTC
CCGGTCTCCGGGTAAAGCTAGCTGA Anti-DC-SIGNL16E3H (SEQ ID NO: 119):
MERHWIFLFLFSVTAGVHSQVQLQQSGAELAKPGASVKMSCKASGYTFTT
YWMHWVKQRPGQGLEWIGYINPITGYTEYNQKFKDKATLTADKSSSTAYM
QLSSLTSEDSAVYYCAREGLSAMDYWGQGTSVTVTSAKTTAPSVYPLAPV
CGDTTGSSVTLGCLVKGYFPEPVTLTWNSGSLSSGVHTFPAVLQSDLYTL
SSSVTVTSSTWPSQVTVTCSVAHPASSTTVDKKLEPSGPISTINPCPPCKE
CHKCPAPNLEGGPSVFIFPPNIKDVLMISLTPKVTCVVVDVSEDDPDVQI
SWFVNNVEVHTAQTQTHREDYNSTIRVVSTLPIQHQDWMSGKEFKCKVNN
KDLPSPIERTISKIKGLVRAPQVYILPPPAEQLSRKDVSLTCLVVGFNPG
DISVEWTSNGHTEENYKDTAPVLDSDGSYFIYSKLNMKTSKWEKTDSFSC
NVRHEGLKNYYLKKTISRSPGKAS Anti-DC-SIGNL16E3K (SEQ ID NO: 55):
ATGGGCATCAAGATGGAGTCACGGATTCAGGCATTTGTATTCGTGTTTCT
CTGGTTGTCTGGTGTTGGCGGAGACATTGTGATGACCCAGTCTCACAAAT
TCATGTCCACATCAGTAGGAGACAGGGTCAGCGTCACCTGCAAGGCCAGT
CAGGATGTGACTTCTGCTGTAGCCTGGTATCAACAAAAACCAGGGCAATC
TCCTAAACTACTGATTTACTGGGCATCCACCCGGCACACTGGAGTCCCTG
ATCGCTTCACAGGCAGTGGATCTGGGACAGATTATACTCTCACCATCAGC
AGTGTGCAGGCTGAAGACCTGGCACTTTATTACTGTCACCAATATTATAG
CGCTCCTCGGACGTTCGGTGGAGGCACCAAGCTGGAAGTCAAACGGGCTG
ATGCTGCACCAACTGTATCCATCTTCCCACCATCCAGTGAGCAGTTAACA
TCTGGAGGTGCCTCAGTCGTGTGCTTCTTGAACAACTTCTACCCCAAAGA
CATCAATGTCAAGTGGAAGATTGATGGCAGTGAACGACAAAATGGCGTCC
TGAACAGTTGGACTGATCAGGACAGCAAAGACAGCACCTACAGCATGAGC
AGCACCCTCACGTTGACCAAGGACGAGTATGAACGACATAACAGCTATAC
CTGTGAGGCCACTCACAAGACATCAACTTCACCCATCGTCAAGAGCTTCA
ATAGGAATGAGTGTTAG Anti-DC-SIGNL16E3K (SEQ ID NO: 120):
MESRIQAFVFVFLWLSVGGDIVMTQSHKFMSTSVGDRVSVTCKASQDVT
SAVAWYQQKPGQSPKLLIYWASTRHTGVPDRFTGSGSGTDYTLTISSGQA
EDLALYYCHQYYSAPRTFGGGTKLEVKRADAAPTVSIFPPSSEQLTSGGA
SVVCFLNNFYPKDINVKWKIDGSERQNGVLNSWTDQDSKDSTYSMSSTLT
LTKDEYERHNSYTCEATHKTSTSPIVKSFNRNEC Anti-DC-SIGNL16E7H-LV-hIgG4H-C (SEQ ID NO: 56):
ATGGAAAGGCACTGGATCTTTCTCTTCCTGTTTTCAGTAACTGCAGGTGT
CCACTCCCAGGTCCAGCTTCAGCAGTCTGGGGCTGAGCTGGCAAAACCTG
GGGCCTCAGTGAAGATGTCCTGCAAGGCTTCTGGCTACACCTTTACTACC
TACTGGATGCACTGGGTAAAACAGAGGCCTGGACAGGGTCTGGAATGGAT
TGGATACATTAATCCTATCACTGGTTATACTGAGTACAATCAGAAGTTCA
AGGACAAGGCCACCTTGACTGCAGACAAATCCTCCAGCACAGCCTACATG
CAACTGAGCAGCCTGACATCTGAGGACTCTGCAGTCTATTACTGTGCAAG
AGAGGGTTAAGTGCTATGGACTATTGGGGTCAGGGAACCTCAGTCACCG
TCACCTCAGCCAAAACAACGGGCCCATCCGTCTTCCCCCTGGCGCCCTGC
TCCAGGAGCACCTCCGAGAGCACAGCCGCCCTGGGCTGCCTGGTCAAGGA
CTACTTCCCCGAACCGGTGACGGTGTCGTGGAACTCAGGCGCCCTGACCA
GCGGCGTGCACACCTTCCCGGCTGTCCTACAGTCCTCAGGACTCTACTCC
CTCAGCAGCGTGGTGACCGTGCCCTCCAGCAGCTTGGGCACGAAGACCTA
CACCTGCAACGTAGATCACAAGCCCAGCAACACCAAGGTGGACAAGAGAG
TTGAGTCCAAATATGGTCCCCCATGCCCACCCTGCCCAGCACCTGAGTTC
GAAGGGGGACCATCAGTCTTCCTGTTCCCCCCAAAACCCAAGGACACTCT
CATGATCTCCCGGACCCCTGAGGTCACGTGCGTGGTGGTGGACGTGAGCC
AGGAAGACCCCGAGGTCCAGTTCAACTGGTACGTGGATGGCGTGGAGGTG
CATAATGCCAAGACAAAGCCGCGGGAGGAGCAGTTCAACAGCACGTACCG
TGTGGTCAGCGTCCTCACCGTCCTGCACCAGGACTGGCTGAACGGCAAGG -continued AGTACAAGTGCAAGGTCTCCAACAAAGGCCTCCCGTCCTCCATCGAGAAA
ACCATCTCCAAAGCCAAAGGGCAGCCCCGAGAGCCACAGGTGTACACCCT
GCCCCCATCCCAGGAGGAGATGACCAAGAACCAGGTCAGCCTGACCTGCC
TGGTCAAAGGCTTCTACCCCAGCGACATCGCCGTGGAGTGGGAGAGCAAT
GGGCAGCCGGAGAACAACTACAAGACCACGCCTCCCGTGCTGGACTCCGA
CGGCTCCTTCTTCCTCTACAGCAGGCTAACCGTGGACAAGAGCAGGTGGC
AGGAGGGGAATGTCTTCTCATGCTCCGTGATGCATGAGGCTCTGCACAAC
CACTACACACAGAAGAGCCTCTCCCTGTCTCTGGGTAAAGCTAGCTGA Anti-DC-SIGNL16E7H-LV-hIgG4H-C (SEQ ID NO: 121):
MERHWIFLFLFSVTAGVHSQVQLQQSGAELAKPGASVKMSCKASGYTFTT
YWMHWVKQRPGQGLEWIGYINPITGYTEYNQKFKDKATLTADKSSSTAYM
QLSSLTSEDSAVYYCAREGLSAMDYWGQGTSVTVTSAKTTGPSVFPLAPC
SRSTSESTAALGCLVKDYFPEPVTVSWNSGALTSGVHTFPAVLQSSGLYS
LSSVVTVPSSSLGTKTYTCNVDHKPSNTKVDKRVESKYGPPCPPCPAPEF
EGGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHN
HYTQKSLSLSLGKAS.

Anti-DC-SIGNL16E7K-LV-hIgGK-C (SEQ ID NO: 57):
ATGGGGCATCAAGATGGAGTCACAGATTCAGGCATTTGTATTCGTGTTTCT
CTGGTTGTCTGGTGTTGGCGGAGACATTGTGATGACCCAGTCTCACAAAT
TCATGTCCACATCAGTAGGAGACAGGGTCAGCGTCACCTGCAAGGCCAGT
CAGGATGTGACTTCTGCTGTAGTCTGGTATCAACAAAAACCAGGGCAATC
TCCTAAACTACTGATTTACTGGGCATCCACCCGGCACACTGGAGTCCCTG
ATCGCTTCACAGGCAGTGGATCTGGGACAGATTATACTCTCACCATCAGC
AGTGGGCAGGCTGAAGACCTGGCACTTTATTACTGTCACCAATATTATAG
CGCTCCTCGGACGTTCGGTGGAGGCACCAAGCTCGAGATCAAACGAACTG
TGGCTGCACCATCTGTCTTCATCTTCCCGCCATCTGATGAGCAGTTGAAA
TCTGGAACTGCCTCTGTTGTGTGCCTGCTGAATAACTTCTATCCCAGAGA
GGCCAAAGTACAGTGGAAGGTGGATAACGCCCTCCAATCGGGTAACTCCC
AGGAGAGTGTCACAGAGCAGGACAGCAAGGACAGCACCTACAGCCTCAGC
AGCACCCTGACGCTGAGCAAAGCAGACTACGAGAAACACAAAGTCTATGC
CTGCGAAGTCACCCATCAGGGCCTGAGCTCGCCCGTCACAAAGAGCTTCA
ACAGGGGAGAGTGTTAG Anti-DC-SIGNL16E7K-LV-hIgGK-C (SEQ ID NO: 122):
MESQIQAFVFVFLWLSGVGGDIVMTQSHKFMSTSVGDRVSVTCKASQDVT
SAVAWYQQKPGQSPKLLIYWASTRHTGVPDRFTGSGSGTDYTLTISSGQA
EDLALYYCHQYYSAPRTFGGGTKLEIKRTVAAPSVFIFPPSDEQLKSGTA
SVVCLLNNFYPREAKVQWKVDNALQSGNSQESVTEQDSKDSTYSLSSTL
LSKADYEKHKVYACEVTHQGLSSPVTKSFNRGEC Anti-Dectin_1_11B6.4_H-V-hIgG4H-C (SEQ ID NO: 58):
ATGGCTGTCCTGGCACTACTCCTCTGCCTGGTGGCTTTCCCAACTTGTAC
CCTGTCCCAGGTGCAACTGAAGGAGTCAGGACCTGGCCTGGTGGCGCCCT
CACAGAGCCTGTCCATTACCTGCTCTGTCTCTGGGTTCTCATTAAGCAAC
TATGATATAAGCTGGATTCGCCAGCCACCAGGAAAGGGTCTGGAGTGGCT
TGGAGTAATGTGGACTGGTGGAGGCGCAAATTATAATTCAGCTTTCATGT
CCAGACTGAGCATCAACAAGGACAACTCCAAGAGCCAAGTCTTTTTTAAA
ATGAACAATCTGCAAACTGATGACACAGCCATTTATTACTGTGTCAGAGA
TGCGGTGAGGTACTGGAACTTCGATGTCTGGGGCGCAGGGACCACGGTCA
CCGTCTCCTCAGCCAAAACGAAGGGCCCATCCGTCTTCCCCCTGGCGCCC
TGCTCCAGGAGCACCTCCGAGAGCACAGCCGCCCTGGGCTGCCTGGTCAA
GGACTACTTCCCCGAACCGGTGACGGTGTCGTGGAACTCAGGCGCCCTGA
CCAGCGGCGTGCACACCTTCCCGGCTGTCCTACAGTCCTCAGGACTCTAC
TCCCTCAGCAGCGTGGTGACCGTGCCCTCCAGCAGCTTGGGCACGAAGAC
CTACACCTGCAACGTAGATCACAAGCCCAGCAACACCAAGGTGGACAAGA
GAGTTGAGTCCAAATATGGTCCCCCATGCCCACCCTGCCCAGCACCTGAG
TTCGAAGGGGGACCATCAGTCTTCCTGTTCCCCCCAAAACCCAAGGACAC
TCTCATGATCTCCCGGACCCCTGAGGTCACGTGCGTGGTGGTGGACGTGA
GCCAGGAAGACCCCGAGGTCCAGTTCAACTGGTACGTGGATGGCGTGGAG
GTGCATAATGCCAAGACAAAGCCGCGGGAGGAGCAGTTCAACAGCACGTA
CCGTGTGGTCAGCGTCCTCACCGTCCTGCACCAGGACTGGCTGAACGGCA
AGGAGTACAAGTGCAAGGTCTCCAACAAAGGCCTCCCGTCCTCCATCGAG
AAAACCATCTCCAAAGCCAAAGGGCAGCCCCGAGAGCCACAGGTGTACAC
CCTGCCCCCATCCCAGGAGGAGATGACCAAGAACCAGGTCAGCCTGACCT
GCCTGGTCAAAGGCTTCTACCCCAGCGACATCGCCGTGGAGTGGGAGAGC
AATGGGCAGCCGGAGAACAACTACAAGACCACGCCTCCCGTGCTGGACTC
CGACGGCTCCTTCTTCCTCTACAGCAGGCTAACCGTGGACAAGAGCAGGT
GGCAGGAGGGGAATGTCTTCTCATGCTCCGTGATGCATGAGGCTCTGCAC
AACCACTACACACAGAAGAGCCTCTCCCTGTCTCTGGGTAAAGCTAGCTG
A Anti-Dectin_1_11B6.4_H-V-hIgG4H-C
(SEQ ID NO: 123):
MAVLALLLCLVAFPTCTLSQVQLKESGPGLVAPSQSLSITCSVSGFSLSN
YDISWIRQPPGKGLEWLGVMWTGGGANYNSAFMSRLSINKDNSKSQVFLK
MNNLQTDDTAIYYCVRDAVRYWNFDVWGAGTTVTVSSAKTKGPSVFPLAP CSRSTSESTAALGCLVKDYFPEPVTVSWNSGALTSGVHTFPAVLQSSGLY
SLSSVVTVPSSSLGTKTYTCNVDHKPSNTKVDKRVESKYGPPCPPCPAPE
FEGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIE
KTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALH
NHYTQKSLSLSLGKAS Anti-Dectin_1_11B6.4_K-LV-hIgGK-C (SEQ ID NO: 59):
ATGGATTTTCAAGCGCAGATTTTCAGCTTCCTGCTAATCAGTGCTTCAGT
CATAATGTCCAGAGGACAAATTGTTCTCTCCCAGTCACCAGCAATCCTGT
CTGCATCTCCAGGGGAGAAGGTCACAATGACTTGCAGGGCCAGCTCAAGT
GTAAGTTACATACACTGGTACCAGCAGAAGCCAGGATCCTCCCCCAAACC
CTGGATTTATGCCACATCCACCCTGGCTTCTGGAGTCCCTGCTCGCTTCA
GTGGCAGTGGGTCTGGGACCTCTTACTCTCTCACAATCAGCAGAGTGGAG
GCTGAAGATACTGCCACTTATTACTGCCAGCAGTGGAGTAGTAACCCATT
CACGTTCGGCTCGGGGACAAAGCTCGAGATCAAACGAACTGTGGCTGCAC
CATCTGTCTTCATCTTCCCGCCATCTGATGAGCAGTTGAAATCTGGAACT
GCCTCTGTTGTGTGCCTGCTGAATAACTTCTATCCCAGAGAGGCCAAAGT
ACAGTGGAAGGTGGATAACGCCCTCCAATCGGGTAACTCCCAGGAGAGTG
TCACAGAGCAGGACAGCAAGGACAGCACCTACAGCCTCAGCAGCACCCTG
ACGCTGAGCAAAGCAGACTACGAGAAACACAAAGTCTATGCCTGCGAAGT
CACCCATCAGGGCCTGAGCTCGCCCGTCACAAAGAGCTTCAACAGGGGAG
AGTGTTAG Anti-Dectin_1_11B6.4_K-LV-hIgGK-C
(SEQ ID NO: 124):
MDFQAQIFSFLLISASVIMSRGQIVLSQSPAILSASPGEKVTMTCRASSS
VSYIHWYQQKPGSSPKPWIYATSHLASGVPARFSGSGSGTSYSLTISRVE
AEDTATYYCQQWSSNPFTFGSGTKLEIKRTVAAPSVFIFPPSDEQLKSGT
ASVVCLLNNFYPREAKVQWKVDNALQSGNSQESVTEQDSKDSTYSLSSTL
TLSKADYEKHKVYACEVTHQGLSSPVTKSFNRGEC Anti-Dectin_1_15E2.5_H-V-hIgG4H-C (SEQ ID NO: 60):
ATGGAAAGGCACTGGATCTTTCTACTCCTGTTGTCAGTAACTGCAGGTGT
CCACTCCCAGGTCCAGCTGCAGCAGTCTGGGGCTGAACTGGCAAGACCTG
GGGCCTCAGTGAAGATGTCCTGCAAGGCTTCTGGCTACACCTTTACTACC
TACACTATGCACTGGGTAAAACAGAGGCCTGGACAGGGTCTGGAATGGAT
TGGATACATTAATCCTAGCAGTGGTTATACTAATTACAATCAGAAGTTCA
AGGACAAGGCCACATTGACTGCAGACAAATCCTCCAGCACAGCCTCCATG
CAACTGAGCAGCCTGACATCTGAGGACTCTGCAGTCTATTACTGTGCAAG
AGAGAGGGCGGTATTAGTCCCTATGCTATGGACTACTGGGGTCAAGGAA
CCTCAGTCACCGTCTCCTCAGCCAAAACGAAGGGCCCATCCGTCTTCCCC
CTGGCGCCCTGCTCCAGGAGCACCTCCGAGAGCACAGCCGCCCTGGGCTG
CCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGG
CACGAAGACCTACACCTGCAACGTAGATCACAAGCCCAGCAACACCAAGG
TGGACAAGAGAGTTGAGTCCAAATATGGTCCCCCATGCCCACCCTGCCCA
GCACCTGAGTTCGAAGGGGGACCATCAGTCTTCCTGTTCCCCCCAAAACC
CAAGGACACTCTCATGATCTCCCGGACCCCTGAGGTCACGTGCGTGGTGG
TGGACGTGAGCCAGGAAGACCCCGAGGTCCAGTTCAACTGGTACGTGGAT
GGCGTGGAGGTGCATAATGCCAAGACAAAGCCGCGGGAGGAGCAGTTCAA
CAGCACGTACCGTGTGGTCAGCGTCCTCACCGTCCTGCACCAGGACTGGC
TGAACGGCAAGGAGTACAAGTGCAAGGTCTCCAACAAAGGCCTCCCGTCC
TCCATCGAGAAAACCATCTCCAAAGCCAAAGGGCAGCCCCGAGAGCCACA
GGTGTACACCCTGCCCCCATCCCAGGAGGAGATGACCAAGAACCAGGTCA
GCCTGACCTGCCTGGTCAAAGGCTTCTACCCCAGCGACATCGCCGTGGAG
TGGGAGAGCAATGGGCAGCCGGAGAACAACTACAAGACCACGCCTCCCGT
GCTGGACTCCGACGGCTCCTTCTTCCTCTACAGCAGGCTAACCGTGGACA
AGAGCAGGTGGCAGGAGGGGAATGTCTTCTCATGCTCCGTGATGCATGAG
GCTCTGCACAACCACTACACACAGAAGAGCCTCTCCCTGTCTCTGGGTAA
AGCTAGCTGA Anti-Dectin_1_15E2.5_H-V-hIgG4H-C
(SEQ ID NO: 125):
MERHWIFLLLLSVTAGVHSQVQLQQSGAELARPGASVKMSCKASGYTFTT
YTMHWVKQRPGQGLEWIGYINPSSGYTNYNQKFKDKATLTADKSSSTASM
QLSSLTSEDSAVYYCAREARAVLVPYAMDYWGQGTSVTVSSAKTGPSVFP
LAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCP
APEFEGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHE
ALHNHYTQKSLSLSLGKAS Anti-Dectin_1_15E2.5_K-V-hIgGK-C (SEQ ID NO: 61):
ATGCATTTTCAAGTGCAGATTTTCAGCTTCCTGCTAATCAGTGCCTCAGT
CATAATGTCCAGAGGACAAATTGTTCTCACCCAGTCTCCAGCAGTCATGT
CTGCATCTCCAGGGGAGAAGGTCACCATAACCTGCACTGCCAGCTCAAGT -continued TTAAGTTACATGCACTGGTTCCAGCAGAAGCCAGGCACTTCTCCCAAACT
CTGGCTTTATAGCACATCCATCCTGGCTTCTGGAGTCCCTACTCGCTTCA
GTGGCAGTGGATCTGGGACCTCTTACTCTCTCACAATCAGCCGAATGGAG
GCTGAAGATGCTGCCACTTATTACTGCCAGCAAAGGAGTAGTTCCCCATT
CACGTTCGGCTCGGGGACAAAGCTCGAGATCAAACGAACTGTGGCTGCAC
CATCTGTCTTCATCTTCCCGCCATCTGATGAGCAGTTGAAATCTGGAACT
GCCTCTGTTGTGTGCCTGCTGAATAACTTCTATCCCAGAGAGGCCAAAGT
ACAGTGGAAGGTGGATAACGCCCTCCAATCGGGTAACTCCCAGGAGAGTG
TCACAGAGCAGGACAGCAAGGACAGCACCTACAGCCTCAGCAGCACCCTG
ACGCTGAGCAAAGCAGACTACGAGAAACACAAAGTCTATGCCTGCGAAGT
CACCCATCAGGGCCTGAGCTCGCCCGTCACAAAGAGCTTCAACAGGGGAG
AGTGTTAG Anti-Dectin_1_15E2.5_K-V-hIgGK-C (SEQ ID NO: 126):
MHFQVQIFSFLLISASVIMSRGQIVLTQSPAVMSASPGEKVTITCTASSS
LSYMHWFQQKPGTSPKLWLYSTSILASGVPTRFSGSGSGTSYSLTISRME
AEDAATYYCQQRSSSPPFTFGSGTKLEIKRTVAAPSVFIFPPSDEQLKSGT
ASVVCLLNNFYPREAKVQWKVDNALQSGNSQESVTEQDSKDSTYSLSSTL
TLSKADYEKHKVYACEVTHQGLSSPVTKSFNRGEC Anti-Dectin_1_2D8.2D4H-V-hIgG4H-C (SEQ ID NO: 62):
ATGGGATGGACCTGGATCTTTATTTTAATCCTGTCAGTTACTACAGGTGT
CCACTCTGAGGTCCAGCTGCAGCAGTCTGGACCTGAGCTGGAAGAGCCTGGA
GCGCTTCAGTGAAGATATCCTGCAAGGCTTCTGGTTACTCCTTCACTGGC
TACAACATGAACTGGGTGAAACAGAGCAATGGAAAGAGCCTTGAGTGGAT
TGGAAATATTGATCCTTACTATGGTGATAACTACAACCAGAAGTTCA
AGGGCAAGGCCACATTGACTGTAGACAAATCCTCCAGCACAGCCTACATG
CACCTCAAGAGCCTGACATCTGAGGACTCTGCAGTCTATTACTGTGCAAG
ACCCTACGGTAGTGAGGCCTACTTTGCTTACTGGGGCCAAGGGACTCTGG
TCACTGTCTCTGCAGCCAAAACGAAGGGCCCATCCGTCTTCCCCCTGGCG
CCCTGCTCCAGGAGCACCTCCGAGAGCACAGCCGCCCTGGGCTGCCTGGT
CAAGGACTACTTCCCCGAACCGGTGACGGTGTCGTGGAACTCAGGCGCCC
TGACCAGCGGCGTGCACACCTTCCCGGCTGTCCTACAGTCCTCAGGACTC
TACTCCCTCAGCAGCGTGGTGACCGTGCCCTCCAGCAGCTTGGGCACGAA
GACCTACACCTGCAACGTAGATCACAAGCCCAGCAACACCAAGGTGGACA
AGAGAGTTGAGTCCAAATATGGTCCCCCATGCCCACCCTGCCCAGCACCT
GAGTTCGAAGGGGGACCATCAGTCTTCCTGTTCCCCCCAAAACCCAAGGA
CACTCTCATGATCTCCCGGACCCCTGAGGTCACGTGCGTGGTGGTGGACG
TGAGCCAGGAAGACCCCGAGGTCCAGTTCAACTGGTACGTGGATGGCGTG
GAGGTGCATAATGCCAAGACAAAGCCGCGGGAGGAGCAGTTCAACAGCAC
GTACCGTGTGGTCAGCGTCCTCACCGTCCTGCACCAGGACTGGCTGAACG
GCAAGGAGTACAAGTGCAAGGTCTCCAACAAAGGCCTCCCGTCCTCCATC
GAGAAAACCATCTCCAAAGCCAAAGGGCAGCCCCGAGAGCCACAGGTGTA
CACCCTGCCCCCATCCCAGGAGGAGATGACCAAGAACCAGGTCAGCCTGA
CCTGCCTGGTCAAAGGCTTCTACCCCAGCGACATCGCCGTGGAGTGGGAG
AGCAATGGGCAGCCGGAGAACAACTACAAGACCACGCCTCCCGTGCTGGA
CTCCGACGGCTCCTTCTTCCTCTACAGCAGGCTAACCGTGGACAAGAGCA
GGTGGCAGGAGGGGAATGTCTTCTCATGCTCCGTGATGCATGAGGCTCTG
CACAACCACTACACACAGAAGAGCCTCTCCCTGTCTCTGGGTAAAGCTAG
CTGA Anti-Dectin_1_2D8.2D4H-V-hIgG4H-C
(SEQ ID NO: 127):
MGWTWIFILILSVTTGVHSEVQLQQSGPELEKPGASVKISCKASGYSFTG
YNMNWVKQSNGKSLEWIGNIDPYYGDTNYNQKFKGKATLTVDKSSSTAYM
HLKSLTSEDSAVYYCARPYGSEAYFAYWGQGTLVTVSAAKTKGPSVFPLA
PCSRSTSESTAALGCLVKDYFPEPVTVSWNSGALTSGVHTFPAVLQSSGL
YSLSSVVTVPSSSLGTKTYTCNVDHKPSNTKVDKRVESKYGPPCPPCPAP
EFEGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEAL
HNHYTQKSLSLSLGKAS Anti-Dectin_1_2D8.2D4K-V-hIgGK-C (SEQ ID NO: 63):
ATGGTGTCCACTTCTCAGCTCCTTGGACTTTTGCTTTTCTGGACTTCAGC
CTCCAGATGTGACATTGTGATGACTCAGTCTCCAGCCACCCTGTCTGTGA
CTCCAGGAGATAGAGTCTCTCTTTCCTGCAGGGCCAGCCAGAGTATTAGC
GACTACTTACACTGGTATCAACAAAAATCACATGAGTCTCCAAGGCTTCT
CATCAAATATGCTGCCCAATCCATCTCTGGGATCCCCTCCAGGTTCAGTG
GCAGTGGATCAGGGTCAGATTTCACTCTCAGTATCAACGGTGTGGAACCT
GAAGATGTTGGAGTGTATTACTGTCAAAATGGTCACAGCTTTCCGTACAC
GTTCGGAGGGGGGACCAAGCTCGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTATGCCTGCGAAGTCAC
CCATCAGGGCCTGAGCTCGCCCGTCACAAAGAGCTTCAACAGGGGAGAGT
GTTAG Anti-Dectin_1_2D8.2D4K-V-hIgGK-C (SEQ ID NO: 128):
DIVMTQSPATLSVTPGDRVSLSCRASQSISDYLHWYQQKSHESPRLLIKY
AAQSISGIPSRFSGSGSGSDFTLSINGVEPEDVGVYYCQNGHSFPYTFGG
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Anti-Langerin15B10H-LV-hIgG4H-C (SEQ ID NO: 64):
ATGGAATGGAGCTTTCTCTTCATCCTGTCAGGAACTGCAGGTGTCCA
CTCCCAGGTTCAGCTGCGGCAGTCTGGACCTGAGCTGGTGAAGCCTGGGG
CTTCAGTGAAGATGTCCTGCAAGGCTTCTGGATACACATTTACTGACTAT
GTTATAAGTTGGGTGAAGCAGAGAACTGGACAGGGCCTTGAGTGGATTGG
AGATATTTATCCTGGAAGTGGTTATTCTTTCTACAATGAGAACTTCAAGG
GCAAGGCCACACTGACTGCAGACAAATCCTCCACCACAGCCTACATGCAG
CTCAGCAGCCTGACATCTGAGGACTCTGCGGTCTATTTCTGTGCAACCTA
CTATAACTACCCTTTTGCTTACTGGGGCCAAGGGACTCTGGTCACTGTCT
CTGCAGCCAAAACAACGGGCCCATCCGTCTTCCCCCTGGCGCCCTGCTCC
AGGAGCACCTCCGAGAGCACAGCCGCCCTGGGCTGCCTGGTCAAGGACTA
CTTCCCCGAACCGGTGACGGTGTCGTGGAACTCAGGCGCCCTGACCAGCG
GCGTGCACACCTTCCCGGCTGTCCTACAGTCCTCAGGACTCTACTCCCTC
AGCAGCGTGGTGACCGTGCCCTCCAGCAGCTTGGGCACGAAGACCTACAC
CTGCAACGTAGATCACAAGCCCAGCAACACCAAGGTGGACAAGAGAGTTG
AGTCCAAATATGGTCCCCCATGCCCACCCTGCCCAGCACCTGAGTTCGAA
GGGGGACCATCAGTCTTCCTGTTCCCCCCAAAACCCAAGGACACTCTCAT
GATCTCCCGGACCCCTGAGGTCACGTGCGTGGTGGTGGACGTGAGCCAGG
AAGACCCCGAGGTCCAGTTCAACTGGTACGTGGATGGCGTGGAGGTGCAT
AATGCCAAGACAAAGCCGCGGGAGGAGCAGTTCAACAGCACGTACCGTGT
GGTCAGCGTCCTCACCGTCCTGCACCAGGACTGGCTGAACGGCAAGGAGT
ACAAGTGCAAGGTCTCCAACAAAGGCCTCCCGTCCTCCATCGAGAAAACC
ATCTCCAAAGCCAAAGGGCAGCCCCGAGAGCCACAGGTGTACACCCTGCC
CCCATCCCAGGAGGAGATGACCAAGAACCAGGTCAGCCTGACCTGCCTGG
TCAAAGGCTTCTACCCCAGCGACATCGCCGTGGAGTGGGAGAGCAATGGG
CAGCCGGAGAACAACTACAAGACCACGCCTCCCGTGCTGGACTCCGACGG
CTCCTTCTTCCTCTACAGCAGGCTAACCGTGGACAAGAGCAGGTGGCAGG
AGGGGAATGTCTTCTCATGCTCCGTGATGCATGAGGCTCTGCACAACCAC
TACACACAGAAGAGCCTCTCCCTGTCTCTGGGTAAAGCTAGCTGA Anti-Langerin15B10H-LV-hIgG4H-C (SEQ ID NO: 129):
QVQLRQSGPELVKPGASVKMSCKASGYTFTDYVISWVKQRTGQGLEWIGD
IYPGSGYSFYNENFKGKATLTADKSSTTAYMQLSSLTSEDSAVYFCATYY
NYPPAYWGQGTLVTVSAAKTTGPSVFPLAPCSRSTSESTAALGCLVKDYF
PEPVTVSWNSGALTSGVHTFPAVLQSSGLYSLSSVVTVPSSSLGTKTYTC
NVDHKPSNTKVDKRVESKYGPPCPPCPAPEFEGGPSVFLFPPKPKDTLMI
SRTPEVTCVVVDVSQEDPEVQFNWYVDGVEVHNAKTKPREEQFNSTYRVV
SVLTVLHQDWLNGKEYKCKVSNKGLPSSIEKTISKAKGQPREPQVYTLPP
SQEEMTKNQVSLTCLVKGFYPSDIAVEWESNGQPENNYKTTPPVLDSDGS
FFLYSRLTVDKSRWQEGNVFSCSVMHEALHNHYTQKSLSLSLGKAS.

Anti-Langerin15B10K-LV-hIgGK-C (SEQ ID NO: 65):
ATGAAGTTGCCTGTTAGGCTGTTGGTGCTGATGTTCTGGATTCCTGCTTC
CAGCAGTGATGTTGTGATGACCCAAACTCCACTCTCCCTGCCTGTCACTG
TTGGAGATCAAGCCTCCATCTCTTGCAGATCTAGTCAGAGCCTTGTACAC
AGTAATGGAAACACCTATTTACATTGGTACCTGCAGAAGCCAGGCCAGTC
TCCAAAGCTCCTGATCTACAAAGTTTCCAACCGATTTTCTGGGGTCCCAG
ACAGGTTCAGTGGCAGTGGATCAGGGACAAATTTCACACTCAAGATCAGT
AGAGTGGAGGCTGAGGATCTGGGACTTTATTTCTGCTCTCAAAGTACACA
TGTTCCGTACACGTTCGGAGGGGGGACCAAGCTCGAGATCAAACGAACTG
TGGCTGCACCATCTGTCTTCATCTTCCCGCCATCTGATGAGCAGTTGAAA
TCTGGAACTGCCTCTGTTGTGTGCCTGCTGAATAACTTCTATCCCAGAGA
GGCCAAAGTACAGTGGAAGGTGGATAACGCCCTCCAATCGGGTAACTCCC
AGGAGAGTGTCACAGAGCAGGACAGCAAGGACAGCACCTACAGCCTCAGC
AGCACCCTGACGCTGAGCAAAGCAGACTACGAGAAACACAAAGTCTATGC
CTGCGAAGTCACCCATCAGGGCCTGAGCTCGCCCGTCACAAAGAGCTTCA
ACAGGGGAGAGTGTTAG Anti-Langerin15B10K-LV-hIgGK-C (SEQ ID NO: 130):
DVVMTQTPLSLPVRLGDQASISCRSSQSLVHSNGNTYLHWYLQKPGQSPK
LLIYKVSNRFSGVPDRFSGSGSGTNFTLKISRVEAEDLGLYFCSQSTHVP
YTFGGGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC Anti-Langerin2G3H-LV-hIgG4H-C (SEQ ID NO: 66):
ATGACATTGAACATGCTGTTGGGGCTGAGGTGGGTTTCTTTGTTGTTTT
TTATCAAGGTGTGCATTGTGAGGTGCAGCTTGTTGAGTCTGGTGGAGGAT
TGGTGCAGCCTAAAGGGTCATTGAAACTCTCATGTGCAGCCTCTGGATTA
ACCTTCAATATCTACGCCATGAACTGGGTCCGCCAGGCTCCAGGAAAGGG
TTTGGAATGGGTTGCTCGCATAAGAAGTAAAAGTAATAATTATGCAACAT
ATTATGCCGATTCAGTGAAAGACAGGTTCACCATCTCCAGAGATGATTCA
CAAAGCTTGCTCTATCTGCAAATGAACAACTTGAAAACTGAGGACACAGC
CATGTATTACTGTGTGGGACGGGACTGGTTTGATTACTGGGGCCAAGGGA CTCTGGTCACTGTCTCTGCAGCAAAACGAAGGGCCCATCCGTCTTCCCC
CTGGCGCCCTGCTCCAGGAGCACCTCCGAGAGCACAGCCGCCCTGGGCTG
CCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGAG
CACGAAGACCTACACCTGCAACGTAGATCACAAGCCCAGCAACACCAAGG
TGGACAAGAGAGTTGAGTCCAAATATGGTCCCCCATGCCCACCCTGCCCA
GCACCTGAGTTCGAAGGGGGACCATCAGTCTTCCTGTTCCCCCCAAAACC
CAAGGACACTCTCATGATCTCCCGGACCCCTGAGGTCACGTGCGTGGTGG
TGGACGTGAGCCAGGAAGACCCCGAGGTCCAGTTCAACTGGTACGTGGAT
GGCGTGGAGGTGCATAATGCCAAGACAAAGCCGCGGGAGGAGCAGTTCAA
CAGCACGTACCGTGTGGTCAGCGTCCTCACCGTCCTGCACCAGGACTGGC
TGAACGGCAAGGAGTACAAGTGCAAGGTCTCCAACAAAGGCCTCCCGTCC
TCCATCGAGAAAACCATCTCCAAAGCCAAAGGGCAGCCCCGAGAGCCACA
GGTGTACACCCTGCCCCCATCCCAGGAGGAGATGACCAAGAACCAGGTCA
GCCTGACCTGCCTGGTCAAAGGCTTCTACCCCAGCGACATCGCCGTGGAG
TGGGAGAGCAATGGGCAGCCGGAGAACAACTACAAGACCACGCCTCCCGT
GCTGGACTCCGACGGCTCCTTCTTCCTCTACAGCAGGCTAACCGTGGACA
AGAGCAGGTGGCAGGAGGGGAATGTCTTCTCATGCTCCGTGATGCATGAG
GCTCTGCACAACCACTACACAGAAGAGCCTCTCCCTGTCTCTGGGTAA
AGCTAGCTGA Anti-Langerin2G3H-LV-hIgG4H-C (SEQ ID NO: 131):
MTLNMLLGLRWVFFVVPYQGVHCEVQLVESGGGLVQPKGSLKLSCAASGL
TFNIYAMNWVRQAPGKGLEWVARIRNKSNNYATYYADSVKDRFTISRDDS
QSLLYLQMNNLKTEDTAMYYCVGRDWFDYWGQGTLVTVSAAKTKGPSVFP
LAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCP
APEFEGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHE
ALHNHYTQKSLSLSLGKAS Anti-Langerin2G3L-LV-hIgGK-C (SEQ ID NO: 67):
ATGGCCTGGATTTCACTTATACTCTCTCCTGGCTCTCAGCTCAGGGGC
CATTTCCCAGGCTGTTGTGACTCAGGAATCTGCACTCACCACATCACCTG
GTGAAACAGTCACACTCACTTGTCGCTCAAGTACTGGGGCTGTTACAACT
AGTAACTATGCCAACTGGGTCCAAGAAAAACCAGATCATTTATTCACTGG
TCTAATAGGTGGTACCAACAACCGAGTTTCAGGTGTTCCTGCCAGATTCT
CAGGCTCCCTGATTGGAGACAAGGCTGCCCTCACCATCACAGGGCACAG
ACTGAGGATGAGGCAATATATTTCTGTGCTCTATGGTACAGCAACCATTG
GGTGTTCGGTGGAGGAACCAAACTCGAGATCAAACGAACTGTGGCTGCAC
CATCTGTCTTCATCTTCCCGCCATCTGATGAGCAGTTGAAATCTGGAACT
GCCTCTGTTGTGTGCCTGCTGAATAACTTCTATCCCAGAGAGGCCAAAGT
ACAGTGGAAGGTGGATAACGCCCTCCAATCGGGTAACTCCCAGGAGAGTG
TCACAGAGCAGGACAGCAAGGACAGCACCTACAGCCTCAGCAGCACCCTG
ACGCTGAGCAAAGCAGACTACGAGAAACACAAAGTCTATGCCTGCGAAGT
CACCCATCAGGGCCTGAGCTCGCCCGTCACAAAGAGCTTCAACAGGGGAG
AGTGTTAG Anti-Langerin2G3L-LV-hIgGK-C (SEQ ID NO: 132):
MAWISLILSLLALSSGAISQAVVTQESALTTSPGETVTLTCRSSTGAVTT
SNYANWVQEKPDHLFTGLIGGTNNRVSGVPARFSGSLIGDKAALTITGAQ
TEDEAIYFCALWYSNHWVFGGGTKLEIKRTVAAPSVFIFPPSDEQLKSGT
ASVVCLLNNFYPREAKVQWKVDNALQSGNSQESVTEQDSKDSTYSLSSTL
TLSKADYEKHKVYACEVTHQGLSSPVTKSFNRGEC Anti-Lox_1_10F9H-LV-hIgG4H-C (SEQ ID NO: 68):
ATGGAATGGACCTGGGTCTTTCTCTTCCTCCTGTCAGTAACTGCAGGTGT
CCACTCCCAGGTTCAGCTGCAGCAGTCTGGAGCTGAGCTGATGAAGCCTG
GGGCCTCAGTGAAGATATCCTGCAAGGCTACTGGCTACACATTCGGTAGC
TACTGGATAGAGTGGGTAAAGCAGAGGCCTGGACATGGCCTTGAGTGGAT
TGGAGAGATTTTACCTGGAAGTGGTAATACTAACTACAATGAGAACTTCA
AGGGCAAGGCCACATTCACTGCAGATACATCCTCCAACACAGCCTACATG
CAACTCACCAGTCTGACATCTGAGGACTCTGCCGTCTATTACTGTGCTAG
GGCGGGGATTTATTGGGGCCAAGGGACTCTGGTCACTGTCTCTGCAGCCA
AAACGAAGGGCCCATCCGTCTTCCCCCTGGCGCCCTGCTCCAGGAGCACC
TCCGAGAGCACAGCCGCCCTGGGCTGCCTGGTCAAGGACTACTTCCCCGA
ACCGGTGACGGTGTCGTGGAACTCAGGCGCCCTGACCAGCGGCGTGCACA
CCTTCCCGGCTGTCCTACAGTCCTCAGGACTCTACTCCCTCAGCAGCGTG
GTGACCGTGCCCTCCAGCAGCTTGGGCACGAAGACCTACACCTGCAACGT
AGATCACAAGCCCAGCAACACCAAGGTGGACAAGAGAGTTGAGTCCAAAT
ATGGTCCCCCATGCCCACCCTGCCCAGCACCTGAGTTCGAAGGGGGACCA
TCAGTCTTCCTGTTCCCCCCAAAACCCAAGGACACTCTCATGATCTCCCG
GACCCCTGAGGTCACGTGCGTGGTGGTGGACGTGAGCCAGGAAGACCCCG
AGGTCCAGTTCAACTGGTACGTGGATGGCGTGGAGGTGCATAATGCCAAG
ACAAAGCCGCGGGAGGAGCAGTTCAACAGCACGTACCGTGTGGTCAGCGT
CCTCACCGTCCTGCACCAGGACTGGCTGAACGGCAAGGAGTACAAGTGCA
AGGTCTCCAACAAAGGCCTCCCGTCCTCCATCGAGAAAACCATCTCCAAA
GCCAAAGGGCAGCCCCGAGAGCCACAGGTGTACACCCTGCCCCCATCCCA
GGAGGAGATGACCAAGAACCAGGTCAGCCTGACCTGCCTGGTCAAAGGCT
TCTACCCCAGCGACATCGCCGTGGAGTGGGAGAGCAATGGGCAGCCGGAG
AACAACTACAAGACCACGCCTCCCGTGCTGGACTCCGACGGCTCCTTCTT
CCTCTACAGCAGGCTAACCGTGGACAAGAGCAGGTGGCAGGAGGGGAATG
TCTTCTCATGCTCCGTGATGCATGAGGCTCTGCACAACCACTACACACAG
AAGAGCCTCTCCCTGTCTCTGGGTAAAGCTAGCTGA Anti-Lox_1_10F9H-LV-hIgG4H-C (SEQ ID NO: 133):
MEWTWVFLFLLSVTAGVHSQVQLQQSGAELMKPGASVKISCKATGYTFGS
YWIEWVKQRPGHGLEWIGEILPGSGNTNYNENFKGKATFTADTSSNTAYM
QLTSLTSEDSAVYYCARAGIYWGQGTLVTVSAAKTKGPSVFPLAPCSRST
SESTAALGCLVKDYFPEPVTVSWNSGALTSGVHTFPAVLQSSGLYSLSSV
VTVPSSSLGTKTYTCNVDHKPSNTKVDKRVESKYGPPCPPCPAPEFEGGP
SVFLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPE
NNYKTTPPVLDSDGSFFLYSRLTVDKSRWQEGNVFSCSVMHEALHNHYTQ
KSLSLSLGKAS Anti-Lox_1_10F9K-LV-hIgGK-C (SEQ ID NO: 69):
ATGGAGAAAGACACACTCCTGCTATGGGTCCTGCTTCTCTGGGTTCCAGG
TTCCACAGGTGACATTGTGCTGACCCAATCTCCAGCTTTTTTGGCTGTGT
CTCTAGGGCAGAGGGCCACCATCTCCTGCAGAGCCAGCGAAAGTGTTGAT
AATTATGGCATTAGTTTTATGAACTGGTTCCAACAGAAACCAGGACAGCC
ACCCAAACTCCTCATCTATGTTGCATCCAAGCAAGGATCCGGGGTCCCTG
CCAGGTTTAGTGGCAGTGGGTCTGGGACAGACTTCAGCCTCAACATCCAT
CCTATGGAGGAGGATGATACTGCAATGTATTTCTGTCAGCAAAGTAAGGA
GGTTCCTCGGACGTTCGGTGGAGGCACCAAGCTCGAGATCAAACGAACTG
TGGCTGCACCATCTGTCTTCATCTTCCCGCCATCTGATGAGCAGTTGAAA
TCTGGAACTGCCTCTGTTGTGTGCCTGCTGAATAACTTCTATCCCAGAGA
GGCCAAAGTACAGTGGAAGGTGGATAACGCCCTCCAATCGGGTAACTCCC
AGGAGAGTGTCACAGAGCAGGACAGCAAGGACAGCACCTACAGCCTCAGC
AGCACCCTGACGCTGAGCAAAGCAGACTACGAGAAACACAAAGTCTATGC
CTGCGAAGTCACCCATCAGGGCCTGAGCTCGCCCGTCACAAAGAGCTTCA
ACAGGGGAGAGTGTTAG Anti-Lox_1_10F9K-LV-hIgGK-C (SEQ ID NO: 134):
MEKDTLLLWVLLLWVPGSTGDIVLTQSPAFLAVSLGQRATISCRASESVD
NYGISFMNWFQQKPGQPPKLLIYVASKQGSGVPARFSGSGSGTDFSLNIH
PMEEDDTAMYFCQQSKEVPRTFGGGTKLEIKRTVAAPSVFIFPPSDEQLK
SGTASVVCLLNNFYPREAKVQWKVDNALQSGNSQESVTEQDSKDSTYSLS
STLTLSKADYEKHKVYACEVTHQGLSSPVTKSFNRGEC Anti-LOX-111C8H-LV-hIgG4H-C (SEQ ID NO: 70):
ATGGAATGTAACTGGATACTTCCTTTTATTCTGTCGGTAACTTCAGGGGT
CTACTCAGAGGTTCAGCTCCAGCAGTCTGGGACTGTGCTGGCAAGGCCTG
GGGCTTCAGTGAAGATGTCCTGCAAGGCTTCTGGCTACACCTTTACCAGC
TACTGGATGCACTGGGTAAAACAGAGGCCTGGACAGGGTCTGGAATGGAT
TGGCGCTATTTATCCTGGAAATAGTGATACTACCTACAACCAGAAGTTCA
AGGGCAAGGCCAAACTGACTGCAGTCACATCCACCAGCACTGCCTACATG
GAGCTCAGCAGCCTGACAAATGAGGACTCTGCGGTCTATTACTGTACACC
TACTTACTACTTTGACTACTGGGGCCAAGGCACCTCTCTCACAGTCTCCT
CAGCCAAAACGAAGGGCCCATCCGTCTTCCCCCTGGCGCCCTGCTCCAGG
AGCACCTCCGAGAGCACAGCCGCCCTGGGCTGCCTGGTCAAGGACTACTT
CCCCGAACCGGTGACGGTGTCGTGGAACTCAGGCGCCCTGACCAGCGGCG
TGCACACCTTCCCGGCTGTCCTACAGTCCTCAGGACTCTACTCCCTCAGC
AGCGTGGTGACCGTGCCCTCCAGCAGCTTGGGCACGAAGACCTACACCTG
CAACGTAGATCACAAGCCCAGCAACACCAAGGTGGACAAGAGAGTTGAGT
CCAAATATGGTCCCCCATGCCCACCCTGCCCAGCACCTGAGTTCGAAGGG
GGACCATCAGTCTTCCTGTTCCCCCCAAAACCCAAGGACACTCTCATGAT
CTCCCGGACCCCTGAGGTCACGTGCGTGGTGGTGGACGTGAGCCAGGAAG
ACCCCGAGGTCCAGTTCAACTGGTACGTGGATGGCGTGGAGGTGCATAAT
GCCAAGACAAAGCCGCGGGAGGAGCAGTTCAACAGCACGTACCGTGTGGT
CAGCGTCCTCACCGTCCTGCACCAGGACTGGCTGAACGGCAAGGAGTACA
AGTGCAAGGTCTCCAACAAAGGCCTCCCGTCCTCCATCGAGAAAACCATC
TCCAAAGCCAAAGGGCAGCCCCGAGAGCCACAGGTGTACACCCTGCCCCC
ATCCCAGGAGGAGATGACCAAGAACCAGGTCAGCCTGACCTGCCTGGTCA
AAGGCTTCTACCCCAGCGACATCGCCGTGGAGTGGGAGAGCAATGGGCAG
CCGGAGAACAACTACAAGACCACGCCTCCCGTGCTGGACTCCGACGGCTC
CTTCTTCCTCTACAGCAGGCTAACCGTGGACAAGAGCAGGTGGCAGGAGG
GGAATGTCTTCTCATGCTCCGTGATGCATGAGGCTCTGCACAACCACTAC
ACACAGAAGAGCCTCTCCCTGTCTCTGGGTAAAGCTAGCTGA Anti-LOX-111C8H-LV-hIgG4H-C (SEQ ID NO: 135):
MECNWILPFILSVTSGVYSEVQLQQSGTVLARPGASVKMSCKASGYTFTS
YWMHWVKQRPGQGLEWIGAIYPGNSDTTYNQKFKGKAKLTAVTSTSTAYM
ELSSLTNEDSAVYYCTPTYYFDYWGQGTSLTVSSAKTKGPSVFPLAPCSR
STSESTAALGCLVKDYFPEPVTVSWNSGALTSGVHTFPAVLQSSGLYSLS
SVVTVPSSSLGTKTYTCNVDHKPSNTKVDKRVESKYGPPCPPCPAPEFEG
GPSVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTI -continued
SKAKGQPREPQVYTLPPSQEEMTKNQVSLTCLVKGFYPSDIAVEWESNGQ
PENNYKTTPPVLDSDGSFFLYSRLTVDKSRWQEGNVFSCSVMHEALHNHY
TQKSLSLSLGKAS Anti-LOX-111C8K-LV-hIgGK-C (SEQ ID NO: 71):
ATGAGTCCTGCCCAATTCCTGTTTCTGTTAGTGCTCTGGATTCGGGAAAC
AACGGTGATGTTGTGATGACCCAGACTCCACTCACTTTGTCGGTTACCA
TTGGACAACCAGCCTCCATCTCTTGCAAGTCAAGTCAGAGCCTCTTAGAT
AGTGATGGAAAGACATATTTGAATTGGTTCTTACAGAGGCCAGGCCAGTC
TCCAAAGCGCCTAATCTATCTGGTGTCTAAACTGGACTCTGGAGTCCCTG
ACAGGTTCACTGGCAGTGGATCAGGGACAGATTTCACACTGAAAATCAGC
AGAGTGGAGGCTGAGGATTTGGGAGTTTATTATTGCTGGCAAGGTACACA
TTTTCCGTGGACGTTCGGTGGAGGCACCAAGCTCGAGATCAAACGAACTG
TGGCTGCACCATCTGTCTTCATCTTCCCGCCATCTGATGAGCAGTTGAAA
TCTGGAACTGCCTCTGTTGTGTGCCTGCTGAATAACTTCTATCCCAGAGA
GGCCAAAGTACAGTGGAAGGTGGATAACGCCCTCCAATCGGGTAACTCCC
AGGAGAGTGTCACAGAGCAGGACAGCAAGGACAGCACCTACAGCCTCAGC
AGCACCCTGACGCTGAGCAAAGCAGACTACGAGAAACACAAAGTCTATGC
CTGCGAAGTCACCCATCAGGGCCTGAGCTCGCCCGTCACAAAGAGCTTCA
ACAGGGGAGAGTGTTAG Anti-LOX-111C8K-LV-hIgGK-C (SEQ ID NO: 136):
MSPAQFLFLLVLWIRETNGDVVMTQTPLTLSVTIGQPASISCKSSQSLLD
SDGKTYLNWFLQRPGQSPKRLIYLVSKLDSGVPDRFTGSGSGTDFTLKIS
RVEAEDLGVYYCWQGTHFPWTFGGGTKLEIKRTVAAPSVFIFPPSDEQLK
SGTASVVCLLNNFYPREAKVQWKVDNALQSGNSQESVTEQDSKDSTYSLS
STLTLSKADYEKHKVYACEVTHQGLSSPVTKSFNRGEC Anti-LOX-115C4H-LV-hIgG4H-C (SEQ ID NO: 72):
ATGGGAGGGATCTGGATCTTTCTCTTCCTCCTGTCAGGAACTGCAGGTGC
CCACTCTGAGATCCAGCTGCAGCAGACTGGACCTGAGCTGGTGAAGCCTG
GGGCTTCAGTGAAGATATCCTGCAAGGCTTCTGGTTATCCATTCACTGAC
TACATCATGGTCTGGGTGAAGCAGAGCCATGGAAAGAGCCTTGAGTGGAT
TGGAAATATTAGTCCTTACTATGGTACTACTAACTACAATCTGAAGTTCA
AGGGCAAGGCCACATTGACTGTAGACAAATCTTCCAGCACAGCCTACATG
CAGCTCAACAGTCTGACATCTGAGGACTCTGCAGTCTATTACTGTGCAAG
ATCCCCTAACTGGGACGGGGCCTGGTTTGCTCACTGGGGCCAAGGGGCTC
TGGTCACTGTCTCTGCAGCCAAAACAAAGGGCCCATCCGTCTTCCCCCTG
GCGCCCTGCTCCAGGAGCACCTCCGAGAGCACAGCCGCCCTGGGCTGCCT
GGTCAAGGACTACTTCCCCGAACCGGTGACGGTGTCGTGGAACTCAGGCG
CCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCAC
GAAGACCTACACCTGCAACGTAGATCACAAGCCCAGCAACACCAAGGTGG
ACAAGAGAGTTGAGTCCAAATATGGTCCCCCATGCCCACCCTGCCCAGCA
CCTGAGTTCGAAGGGGGACCATCAGTCTTCCTGTTCCCCCCAAAACCCAA
GGACACTCTCATGATCTCCCGGACCCCTGAGGTCACGTGCGTGGTGGTGG
ACGTGAGCCAGGAAGACCCCGAGGTCCAGTTCAACTGGTACGTGGATGGC
GTGGAGGTGCATAATGCCAAGACAAAGCCGCGGGAGGAGCAGTTCAACAG
CACGTACCGTGTGGTCAGCGTCCTCACCGTCCTGCACCAGGACTGGCTGA
ACGGCAAGGAGTACAAGTGCAAGGTCTCCAACAAAGGCCTCCCGTCCTCC
ATCGAGAAAACCATCTCCAAAGCCAAAGGGCAGCCCCGAGAGCCACAGGT
GTACACCCTGCCCCCATCCCAGGAGGAGATGACCAAGAACCAGGTCAGCC
TGACCTGCCTGGTCAAAGGCTTCTACCCCAGCGACATCGCCGTGGAGTGG
GAGAGCAATGGGCAGCCGGAGAACAACTACAAGACCACGCCTCCCGTGCT
GGACTCCGACGGCTCCTTCTTCCTCTACAGCAGGCTAACCGTGGACAAGA
GCAGGTGGCAGGAGGGGAATGTCTTCTCATGCTCCGTGATGCATGAGGCT
CTGCACAACCACTACACACAGAAGAGCCTCTCCCTGTCTCTGGGTAAAGC
TAGCTGATTAATTAA Anti-LOX-115C4H-LV-hIgG4H-C (SEQ ID NO: 137):
MGGIWIFLFLLSGTAGAHSEIQLQQTGPELVKPGASVKISCKASGYPFTD
YIMVWVKQSHGKSLEWIGNISPYYGTTNYNLKFKGKATLTVDKSSSTAYM
QLNSLTSEDSAVYYCARSPNWDGAWFAHWGQGALVTVSAAKTKGPSVFPL
APCSRSTSESTAALGCLVKDYFPEPVTVSWNSGALTSGVHTFPAVLQSSG
LYSLSSVVTVPSSSLGTKTYTCNVDHKPSNTKVDKRVESKYGPPCPPCPA
PEFEGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSS
IEKTISKAKGQPREPQVYTLPPSQEEMTKNQVSLTCLVKGFYPSDIAVEW
ESNGQPENNYKTTPPVLDSDGSFFLYSRLTVDKSRWQEGNVFSCSVMHEA
LHNHYTQKSLSLSLGKAS Anti-LOX-115C4K-LV-hIgGK-C (SEQ ID NO: 73):
ATGGAGACAGACACAATCCTGCTATGGGTGCTGCTGCTCTGGGTTCCAGG
CTCCACTGGTGACATTGTGCTGACCCAATCTCCAGCTTCTTTGGCTGTGT
CTCTAGGGCAGAGGGCCACCATCTCCTGCAAGGCCAGCCAAAGTGTTGAT
TATGATGGTGATAGTTATATGAACTGGTTCCAACAGAAACCAGGACAGCC
ACCCAAACTCCTCATCTATGCTGCATCCAATCTAGAATCTGGGATCCCAG
CCAGGTTTAGTGGCAGTGGGTCTGGGACAGACTTCACCCTCAACATCCAT
CCTGTGGAGGAGGAGGATGCTGCAACCTATTACTGTCAGCAAAGTAATGA
GGATCCATTCACGTTCGGCTCGGGGACAAAGCTCGAGATCAAACGAACTG
TGGCTGCACCATCTGTCTTCATCTTCCCGCCATCTGATGAGCAGTTGAAA
TCTGGAACTGCCTCTGTTGTGTGCCTGCTGAATAACTTCTATCCCAGAGA
GGCCAAAGTACAGTGGAAGGTGGATAACGCCCTCCAATCGGGTAACTCCC
AGGAGAGTGTCACAGAGCAGGACAGCAAGGACAGCACCTACAGCCTCAGC
AGCACCCTGACGCTGAGCAAAGCAGACTACGAGAAACACAAAGTCTATGC
CTGCGAAGTCACCCATCAGGGCCTGAGCTCGCCCGTCACAAAGAGCTTCA
ACAGGGGAGAGTGTTAG Anti-LOX-115C4K-LV-hIgGK-C (SEQ ID NO: 138):
METDTILLWVLLLWVPGSTGDIVLTQSPASLAVSLGQRATISCKASQSVD
YDGDSYMNWFQQKPGQPPKLLIYAASNLESGIPARFSGSGSGTDFTLNIH
PVEEEDAATYYCQQSNEDPFTFGSGTKLEIKRTVAAPSVFIFPPSDEQLK
SGTASVVCLLNNFYPREAKVQWKVDNALQSGNSQESVTEQDSKDSTYSLS
STLTLSKADYEKHKVYACEVTHQGLSSPVTKSFNRGEC Anti-Marco_10B7.3G4H-LV-hIgG4H-C (SEQ ID NO: 74):
ATGGCTGTCCTGGGGCTGCTTCTCTGCCTGGTGACGTTCCCAAGCTGTGT
CCTGTCCCAGGTGCAGCTGAAGGAGTCAGGACCTGGCCTGGTGGCACCCT
CACAGAGCCTGTCCATCACATGCACTGTCTCTGGGTTCTCATTATCCAGA
TATAGTGTATTTTGGGTTCGCCAGCCTCCAGGAAAGGGTCTGGAGTGGCT
GGGAGTTGATATGGGTGGTGGAAGCACAGACTATAATTCAGCTCTCAAAT
CCAGACTGAGCATCAGCAAGGACAACTCCAAGAGCCAAGTTTTCTTAAAA
ATGAACAGTCTGCAAACTGATGACACAGCCATGTACTACTGTGCCAGAAT
CTACTTTGATTACGACGGGGATGGACTACTGGGGTCAAGGAACCTCAG
TCACCGTCTCCTCAGCCAAAACAACGGGCCCATCCGTCTTCCCCCTGGCG
CCCTGCTCCAGGAGCACCTCCGAGAGCACAGCCGCCCTGGGCTGCCTGGT
CAAGGACTACTTCCCCGAACCGGTGACGGTGTCGTGGAACTCAGGCGCCC
TGACCAGCGGCGTGCACACCTTCCCGGCTGTCCTACAGTCCTCAGGACTC
TACTCCCTCAGCAGCGTGGTGACCGTGCCCTCCAGCAGCTTGGGCACGAA
GACCTACACCTGCAACGTAGATCACAAGCCCAGCAACACCAAGGTGGACA
AGAGAGTTGAGTCCAAATATGGTCCCCCATGCCCACCCTGCCCAGCACCT
GAGTTCGAAGGGGGACCATCAGTCTTCCTGTTCCCCCCAAAACCCAAGGA
CACTCTCATGATCTCCCGGACCCCTGAGGTCACGTGCGTGGTGGTGGACG
TGAGCCAGGAAGACCCCGAGGTCCAGTTCAACTGGTACGTGGATGGCGTG
GAGGTGCATAATGCCAAGACAAAGCCGCGGGAGGAGCAGTTCAACAGCAC
GTACCGTGTGGTCAGCGTCCTCACCGTCCTGCACCAGGACTGGCTGAACG
GCAAGGAGTACAAGTGCAAGGTCTCCAACAAAGGCCTCCCGTCCTCCATC
GAGAAAACCATCTCCAAAGCCAAAGGGCAGCCCCGAGAGCCACAGGTGTA
CACCCTGCCCCCATCCCAGGAGGAGATGACCAAGAACCAGGTCAGCCTGA
CCTGCCTGGTCAAAGGCTTCTACCCCAGCGACATCGCCGTGGAGTGGGAG
AGCAATGGGCAGCCGGAGAACAACTACAAGACCACGCCTCCCGTGCTGGA
CTCCGACGGCTCCTTCTTCCTCTACAGCAGGCTAACCGTGGACAAGAGCA
GGTGGCAGGAGGGGAATGTCTTCTCATGCTCCGTGATGCATGAGGCTCTG
CACAACCACTACACACAGAAGAGCCTCTCCCTGTCTCTGGGTAAAGCTAG
CTG Anti-Marco_10B7.3G4H-LV-hIgG4H-C (SEQ ID NO: 139):
MAVLGLLLCLVTFPSCVLSQVQLKESGPGLVAPSQSLSITCTVSGFSLSR
YSVFWVRQPPGKGLEWLGLIWGGGSTDYNSALKSRLSISKDNSKSQVFLK
MNSLQTDDTAMYYCARIYFDYDGAMDYWGQGTSVTVSSAKTTGPSVFPLA
PCSRSTSESTAALGCLVKDYFPEPVTVSWNSGALTSGVHTFPAVLQSSGL
YSLSSVVTVPSSSLGTKTYTCNVDHKPSNTKVDKRVESKYGPPCPPCPAP
EFEGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEAL
HNHYTQKSLSLSLGKAS AntiMarco_10B7.3G4K_H-V-hIgGK-C (SEQ ID NO: 75):
ATGCATCGCACCAGCATGGGCATCAAGATGGAGTCACGGATTCAGGCATT
TGTATTCGTGTTTCTCTGGTTGTCTGGTGTTGGCGGAGACATTGTGATGA
CCCAGTCTCACAAATTCATGTCCACATCAGTAGGAGACAGGGTCAGCGTC
ACCTGCAAGGCCAGTCAGGATGTGACTTCTGCTGTAGCCTGGTATCAACA
AAAACCAGGGCAATCTCCTAAACTACTGATTTACTGGGCATCCACCCGGC
ACACTGGAGTCCCTGATCGCTTCACAGGCAGTGGATCTGGGACAGATTAT
ACTCTCACCATCAGCAGTGGGCAGGCTGAAGACCTGGCACTTTATTACTG
TCACCAATATTATAGCGCTCCTCGGACGTTCGGTGGAGGCACCAAGCTCG
AGATCAAACGAACTGTGGCTGCACCATCTGTCTTCATCTTCCCGCCATCT
GATGAGCAGTTGAAATCTGGAACTGCCTCTGTTGTGTGCCTGCTGAATAA
CTTCTATCCCAGAGAGGCCAAAGTACAGTGGAAGGTGGATAACGCCCTCC
AATCGGGTAACTCCCAGGAGAGTGTCACAGAGCAGGACAGCAAGGACAGC
ACCTACAGCCTCAGCAGCACCCTGACGCTGAGCAAAGCAGACTACGAGAA
ACACAAAGTCTATGCCTGCGAAGTCACCCATCAGGGCCTGAGCTCGCCCG
TCACAAAGAGCTTCAACAGGGGAGAGTGTTAG AntiMarco_10B7.3G4K_H-V-hIgGK-C (SEQ ID NO: 140):
MHRTSMGIKMESRIQAFVFVFLWLSGVGGDIVMTQSHKFMSTSVGDRVSV
TCKASQDVTSAVAWYQQKPGQSPKLLIYWASTRHTGVPDRFTGSGSGTDY
TLTISSGQAEDLALYYCHQYYSAPRTFGGGTKLEIKRTVAAPSVFIFPPS
DEQLKSGTASVVCLLNNFYPREAKVQWKVDNALQSGNSQESVTEQDSKDS
TYSLSSTLTLSKADYEKHKVYACEVTHQGLSSPVTKSFNRGEC -continued Anti-Marco_11A8.3C9_H-V-hIgG4H-C (SEQ ID NO: 76):
ATGGAATGGAACTGGGTCGTTCTCTTCCTCCTGTCATTAACTGCAGGTGT
CTATGCCCAGGGTCAGATGCAGCAGTCTGGAGCTGAGCTGGTGAAGCCTG
GGGCTTCAGTGAAGCTGTCCTGCAAGACTTCTGGCTTCACCTTCAGCAGT
AACTATATAAGTTGGTGAAGCAAAAGCCTGGACAGAGTCTTGAGTGGAT
TGCATGGATTTATGCTGGAACTGGTGGTATTACCTATAATCAGAAGTTCA
GAGGCAGGGCCCAACTGACTGTAGACACATCCTCCAGCACAGCCTACATG
CAGTTCAGCAGCCTGACAACTGATGACTCTGCCATCTATTACTGTGCAAG
ACACGTGAGGGGTTACCATCCATGGACTACTGGGGTCAAGGAACCTCAG
TCACCGTCTCCTCAGCCAAAACGAAGGGCCCATCCGTCTTCCCCCTGGCG
CCCTGCTCCAGGAGCACCTCCGAGAGCACAGCCGCCCTGGGCTGCCTGGT
CAAGGACTACTTCCCCGAACCGGTGACGGTGTCGTGGAACTCAGGCGCCC
TGACCAGCGGCGTGCACACCTTCCCGGCTGTCCTACAGTCCTCAGGACTC
TACTCCCTCAGCAGCGTGGTGACCGTGCCCTCCAGCAGCTTGGGCACGAA
GACCTACACCTGCAACGTAGATCACAAGCCCAGCAACACCAAGGTGGACA
AGAGAGTTGAGTCCAAATATGGTCCCCCATGCCCACCCTGCCCAGCACCT
GAGTTCGAAGGGGGACCATCAGTCTTCCTGTTCCCCCCAAAACCCAAGGA
CACTCTCATGATCTCCCGGACCCCTGAGGTCACGTGCGTGGTGGTGGCAG
TGAGCCAGGAAGACCCCGAGGTCCAGTTCAACTGGTACGTGGATGGCGTG
GAGGTGCATAATGCCAAGACAAAGCCGCGGGAGGAGCAGTTCAACAGCAC
GTACCGTGTGGTCAGCGTCCTCACCGTCCTGCACCAGGACTGGCTGAACG
GCAAGGAGTACAAGTGCAAGGTCTCCAACAAAGGCCTCCCGTCCTCCATC
GAGAAAACCATCTCCAAAGCCAAAGGGCAGCCCCGAGAGCCACAGGTGTA
CACCCTGCCCCCATCCCAGGAGGATGACCAAGAACCAGGTCAGCCTGA
CCTGCCTGGTCAAAGGCTTCTACCCCAGCGACATCGCCGTGGAGTGGGAG
AGCAATGGGCAGCCGGAGAACAACTACAAGACCACGCCTCCCGTGCTGGA
CTCCGACGGCTCCTTCTTCCTCTACAGCAGGCTAACCGTGGACAAGAGCA
GGTGGCAGGAGGGGAATGTCTTCTCATGCTCCGTGATGCATGAGGCTCTG
CACAACCACTACACACAGAAGAGCCTCTCCCTGTCTCTGGGTAAAGCTAG
CTGA Anti-Marco_11A8.3C9_H-V-hIgG4H-C (SEQ ID NO: 141):
MEWNWVVLFLLSLTAGVYAQGQMQQSGAELVKPGASVKLSCKTSGFTFSS
NYISWLKQKPGQSLEWIAWIYAGTGGIYNQKFRGRAQLTVDTSSSTAYM
QFSSLTTDDSAIYYCARHVRGYHPMDYWGQGTSVTVSSAKTKGPSVFPLA
PCSRSTSESTAALGCLVKDYFPEPVTVSWNSGALTSGVHTFPAVLQSSGL
YSLSSVVTVPSSSLGTKTYTCNVDHKPSNTKVDKRVESKYGPPCPPCPAP
EFEGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEAL
HNHYTQKSLSLSLGKAS Anti-Marco_11A8.3C9_H-V-hIgGK-C (SEQ ID NO: 77):
ATGGAGTCACAGACTCAGGTCTTTGTATACATGTTGCTGTGGTTGTCTGG
TGTTGATGGAGACATTGTGATGACCCAGTCTCAAAAATTCATGTCCGCAT
CAGTAGGGGACAGGGTCAGCGTCACCTGCAGGGCCAGTCAGAATGTGGTT
ACTAATGTAGGCTGGTATCAACAGAAACCAGGGCAATCTCCTAAAGTACT
GATTTACTCGGCATCCTTCCGGTACAGTGGAGTCCCTGATCGCTTCACAG
GCAGTGGATCTGGGACAGATTTCACTCTCACCATCACCAATGTGCAGTCT
GAAGACTTGGCAGAGTATTTCTGTCAGCAATATAACAACTATCCGTACAC
GTTCGGAGGGGGACCAAGCTCGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACAAAGTCTATGCCTGCAAGTCAC
CCATCAGGGCCTGAGCTCGCCCGTCACAAAGAGCTTCAACAGGGGAGAGT
GTTAG Anti-Marco_11A8.3C9_H-V-hIgGK-C (SEQ ID NO: 142):
MESQTQVFVYMLLWLSGVDGDIVMTQSQKFMSASVGDRVSVTCRASQNVV
TNVGWYQQKPGQSPKVLIYSASFRYSGVPDRFTGSGSGTDFTLTITNVQS
EDLAEYFCQQYNNYPYTFGGGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC Anti-Marco_3H10.1F3_H-V-hIgG4H-C (SEQ ID NO: 78):
ATGGGATGGAGCTATATCATCCTCTTTTTGGTAGCAACAGCTACAGATGT
CCACTCCCAGGTCCAACTGCAGCAGCCTGGGGCTGAACTGGTGAAGCCTG
GGGCTTCAGTGAAGCTGTCCTGCAAGGCTTCTGGCTACACCTTCACCAGC
TACTGGATGCACTGGGTGAAGCAGAGGCCTGGAGAAGGCCTTGAGTGGAT
TGGAGAGATTAATCCTAGCTACGGTCGTACTGACTACAATGGGAAGTTCA
AGAACAAGGCCACACTGACTGTAGCAAATCCTCCAGCACAGCCTACATG
CAACTCAGCAGCCTGACATCTGAGGACTCTGCGGTCTATTACTGTGCAAG
AGGAGATTACTACGGTAGTAGCTCGTTTGCTTACTGGGGCCAAGGGACTC
TGGTCACTGTCTCTGCAGCCAAAACAAAGGGCCCATCCGTCTTCCCCCTG
GCGCCCTGCTCCAGGAGCACCTCCGAGAGCACAGCCGCCCTGGGCTGCCT
GGTCAAGGACTACTTCCCCGAACCGGTGACGGTGTCGTGGAACTCAGGCG
CCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCAC GAAGACCTACACCTGCAACGTAGATCACAAGCCCAGCAACACCAAGGTGG
ACAAGAGAGTTGAGTCCAAATATGGTCCCCCATGCCCACCCTGCCCAGCA
CCTGAGTTCGAAGGGGGACCATCAGTCTTCCTGTTCCCCCCAAAACCCAA
GGACACTCTCATGATCTCCCGGACCCCTGAGGTCACGTGCGTGGTGGTGG
ACGTGAGCCAGGAAGACCCCGAGGTCCAGTTCAACTGGTACGTGGATGGC
GTGGAGGTGCATAATGCCAAGACAAAGCCGCGGGAGGAGCAGTTCAACAG
CACGTACCGTGTGGTCAGCGTCCTCACCGTCCTGCACCAGGACTGGCTGA
ACGGCAAGGAGTACAAGTGCAAGGTCTCCAACAAAGGCCTCCCGTCCTCC
ATCGAGAAAACCATCTCCAAAGCCAAAGGGCAGCCCCGAGAGCCACAGGT
GTACACCCTGCCCCCATCCCAGGAGGAGATGACCAAGAACCAGGTCAGCC
TGACCTGCCTGGTCAAAGGCTTCTACCCCAGCGACATCGCCGTGGAGTGG
GAGAGCAATGGGCAGCCGGAGAACAACTACAAGACCACGCCTCCCGTGCT
GGACTCCGACGGCTCCTTCTTCCTCTACAGCAGGCTAACCGTGGACAAGA
GCAGGTGGCAGGAGGGGAATGTCTTCTCATGCTCCGTGATGCATGAGGCT
CTGCACAACCACTACACACAGAAGAGCCTCTCCCTGTCTCTGGGTAAAGC
TAGCTGA Anti-Marco_3H10.1F3_H-V-hIgG4H-C (SEQ ID NO: 143):
MGWSYIILFLVATATDVHSQVQLQQPGAELVKPGASVKLSCKASGYTFTS
YWMHWVKQRPGEGLEWIGEINPSYGRTDYNGKFKNKATLTVAKSSSTAYM
QLSSLTSEDSAVYYCARGDYYGSSSFAYWGQGTLVTVSAAKTKGPSVFPL
APCSRSTSESTAALGCLVKDYFPEPVTVSWNSGALTSGVHTFPAVLQSSG
LYSLSSVVTVPSSSLGTKTYTCNVDHKPSNTKVDKRVESKYGPPCPPCPA
PEFEGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSS
IEKTISKAKGQPREPQVYTLPPSQEEMTKNQVSLTCLVKGFYPSDIAVEW
ESNGQPENNYKTTPPVLDSDGSFFLYSRLTVDKSRWQEGNVFSCSVMHEA
LHNHYTQKSLSLSLGKAS Anti-Marco_3H10.1F3_K-V-hIgGK-C (SEQ ID NO: 79):
ATGGAGTCACAGACTCAGGTCTTTGTATACATGTTGCTGTGGTTGTCTGG
TGTTGATGGAGACATTGTGATGACCCAGTCTCAAAAATTCATGTCCACAT
CATTAGGAGACAGGGTCAGCGTCACCTGCAAGGCCAGTCAGAATGTGGGT
ACTAATGTAGCCTGGTATCAACAGAAACCAGGGCACTCTCCTAAAGCACT
GATTTACTCGGCATCCTACCGGTACAGTGGAGTCCCTGATCGCTTCACAG
GCAGTGGATCTGGGACAGATTTCACTCTCACCATCAGCAATGTGCAGTCT
GAAGACTTGGCAGAGTTTTTCTGTCAGCAATATAACAACTATCCGTACAC
GTTCGGAGGGGGGACCACGCTCGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTATGCCTGCGAAGTCAC
CCATCAGGGCCTGAGCTCGCCCGTCACAAAGAGCTTCAACAGGGGAGAGT
GTTAG Anti-Marco_3H10.1F3_K-V-hIgGK-C (SEQ ID NO: 144):
MESQTQVFVYMLLWLSGVDGDIVMTQSQKFMSTSLGDRVSVTCKASQNVG
TNVAWYQQKPGHSPKALIYSASYRYSGVPDRFTGSGSGTDFTLTISNVQS
EDLAEFFCQQYNNYPYTFGGGTTLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC Humanized anti-CD40-HCV vaccine is: hAnti-CD40VK2-LV-hIgGK-C×hAnti-CD40VH3-LV-hIgG4H-C-Flex-v1-HelB-f1-ProtB-f2-NS5BPalm, wherein the portion of HelB are underlined, the portions of ProtB are bold and the portions of NS5BPalm are italicized. The linker sequence (in bold italics) is flanked by the transition sequence "AS" that bracket the linker sequences

[hAnti-CD40VK2-LV-hIgGK-C]
(SEQ ID NO: 158)
DIQMTQSPSSLSASVGDRVTITCSASQGISNYLNWYQQKPGKAVKLLIYY
TSILHSGVPSRFSGSGSGTDYTLTISSLQPEDFATYYCQQFNKLPPTFGG
GTKLEIKRTVAAPSVFIFPPSDEQLKSGTASVVCLLNNFYPREAKVQWK
VDNALQSGNSQESVTEQDSKDSTYSLSSTLTLSKADYEKHKVYACEV
THQGLSSPVTKSFNRGEC hAnti-CD40VH3-LV-hIgG4H-C-Flex-v1-HelB-f1-ProtB-f2-NS5BPalm
(SEQ ID NO: 159)
EVQLVESGGGLVQPGGSLKLSCATSGFTFSDYYMYWVRQAPGKGLEW
VAYINSGGGSTYYPDTVKGRFTISRDNAKNTLYLQMNSLRAEDTAVYYCA
RRGLPFHAMDYWGQGTLVTVSSAKTKGPSVFPLAPCSRSTSESTAAL
GCLVKDYFPEPVTVSWNSGALTSGVHTFPAVLQSSGLYSLSSVVTVP
SSSLGTKTYTCNVDHKPSNTKVDKRVESKYGPPCPPCPAPEFEGGP
SVFLFPPKPKDTLMISRTPEVTCVVVDVSQEDPEVQFNWYVDGVEV -continued
HNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEW
ESNGQPENNYKTTPPVLDSDGSFFLYSRLTVDKSRWQEGNVFSCSV
MHEALHNHYTQKSLSLSLGKAS *QTPTNTISVTPTNNSTP*
*TNNSNPKPNP* ASVTVPHPNI
EEVALSTTGEIPFYGKAIPLEVIKGGRHLIFCHSKKKCDELAAKLVAL
GINAVAYYRGLDVSVIPTSGVVVVATDALMTGFTGDFDSVIDCNTC
VTQTVDFSLDPTFTIETTTLPQDAVSRTQRRGRTGRGKPGIYRFVAP
GERAS SSVSPTTSVHPTPTSVPPTPTKSSP ASTPCTCGSSDLYL-
VTRHADVIPVRRRGDS
RGSLLSPRPISYLKGSSGGPLLCPAGHAVGIFRAAVCTRGVAKAVD
FIPVENLETTMRSPVFTDNSSPPAVPQSAS
PTSTPADSSTITPTATPTATPTIKG ASVLDS
HYQDVLKEVKAAASKVKANALYDVVSKLPLAVMGSSYGFQYSPGQ
RVEFLVQAWKSKKTPMGFSYDTRCFDSTVTESDIRTEEAIYQCCDL
DPQAFVAIKSLTERLYVGRCRASGVLTTSCGNTLTCYIKARAACRAA
GLQDCTMLVCGDDLVVICESAGVQEDAASLRAFTEAMTRYSAPPG
DPPQPEYDLELITAS Humanized anti-DCIR-HCV 1$^{st}$ generation vaccine is: [hAnti-DCIRVK4-LV-hIgGK-C]×[hAnti-DCIRVH1-LV-hIgG4H-C (SEQ ID NO.: 168); TNGSITVAATAPTVTPTVNATPSAA (SEQ ID NO.: 169) or QTPTNTISVTPTNNSTPTNNSNPKPNP (SEQ ID NO:170).

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Patent Application Publication No. 2009/0238822: Chimeric HCV Antigens for Eliciting an Immune Response.

U.S. Patent Application Publication No. 2008/0241170: Vaccines Based on Targeting Antigen to DCIR Expressed on Antigen-Presenting Cells.

U.S. Patent Application Publication No. 2010/0239575: Anti-CD-40 Antibodies and Uses Thereof.

What is claimed is:

1. A method for increasing effectiveness of Hepatitis C virus (HCV) antigen presentation by an antigen presenting cell (APC) comprising the steps of:

administering to a subject in need thereof a composition comprising an antibody conjugate that includes:

(i) a recombinant antibody having a light chain L and a heavy chain H, wherein said recombinant antibody binds to a CD40 receptor or a DCIR receptor;

(ii) two or three HCV antigens fused at a C-terminal position of said heavy chain H of said recombinant antibody;

(iii) one HCV antigen fused at a C-terminal position of said light chain L of said recombinant antibody;

wherein the antibody conjugate has a general structure given by:

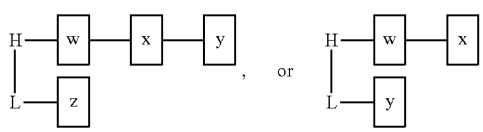

wherein w, x, y, and z represent one or more HCV antigens or domains selected from the group consisting of protein E1, envelope protein E2, non-structural protein NS3, non-structural protein NS4b, non-structural protein NS5b, or any combinations thereof.

2. The method of claim 1, wherein the antigen presenting cell comprises a dendritic cell (DC).

3. The method of claim 1, wherein the one or more native or engineered HCV antigenic peptide is selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 14, E1b, and variants that have 95% identity with any one of the listed sequences.

4. The method of claim 1, wherein the DC-antibody is humanized.

5. The method of claim 1, wherein the composition further comprises one or more agents selected from the group consisting of an agonistic anti-CD40 antibody, an agonistic anti-CD40 antibody fragment, a CD40 ligand (CD40L) polypeptide, a CD40L polypeptide fragment, anti-4-1BB antibody, an anti-4-1BB antibody fragment, 4-1BB ligand polypeptide, a 4-1BB ligand polypeptide fragment, IFN-γ, TNF-α, type 1 cytokines, type 2 cytokines and combinations and modifications thereof.

6. The method of claim 1, wherein the HCV antigenic peptide is selected from the group consisting of protein E1, envelope protein E2, non-structural protein NS3, non-structural protein NS4b, non-structural protein NS5b, and a fragment thereof.

7. The method of claim 1, wherein the one or more HCV antigenic peptide is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and variants that have 95% identity with any one of the listed sequences.

8. The method of claim 1, wherein the HCV antigenic peptide is SEQ ID NO: 3 or an antigenic domain thereof.

9. The method of claim 1, wherein the antibody or antigen-binding fragment is selected from the group consisting of an antibody and antigen-binding fragment that binds to CD40.

10. The method of claim 1, wherein the antibody or antigen-binding fragment is selected from the group consisting of an antibody and antigen-binding fragment that binds to DCIR.

11. The method of claim 1, wherein the antibody conjugate comprises

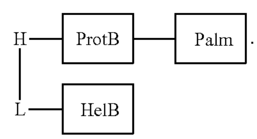

12. The method of claim 1, wherein the antibody conjugate comprises

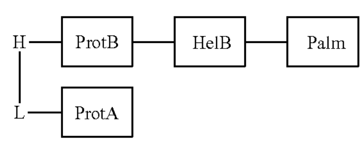

13. The method of claim 1, wherein the antibody conjugate has a general structure given by:

and wherein the antibody conjugate more effectively stimulates antigen presentation than an antibody conjugate having a general structure given by:

14. The method of claim 1, wherein the antibody conjugate has a general structure given by:
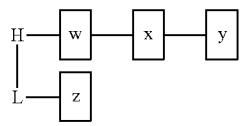
and wherein the antibody conjugate more effectively stimulates antigen presentation than an antibody conjugate having a general structure given by:
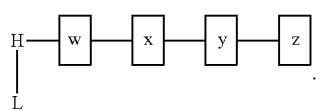
* * * * *

SEQUENCE LISTING

```
<160> NUMBER OF SEQ ID NOS: 170

<210> SEQ ID NO 1
<211> LENGTH: 191
<212> TYPE: PRT
<213> ORGANISM: Hepatitis C virus

<400> SEQUENCE: 1

Tyr Gln Val Arg Asn Ser Ser Gly Leu Tyr His Val Thr Asn Asp Cys
1               5                   10                  15

Pro Asn Ser Ser Ile Val Tyr Glu Ala Ala Asp Ala Ile Leu His Thr
            20                  25                  30

Pro Gly Cys Val Pro Cys Val Arg Glu Gly Asn Ala Ser Arg Cys Trp
        35                  40                  45

Val Ala Val Thr Pro Thr Val Ala Thr Arg Asp Gly Lys Leu Pro Thr
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95
```

```
Gly Gln Leu Phe Thr Phe Ser Pro Arg Arg His Trp Thr Thr Gln Asp
                100                 105                 110

Cys Asn Cys Ser Ile Tyr Pro Gly His Ile Thr Gly His Arg Met Ala
            115                 120                 125

Trp Asp Met Met Met Asn Trp Ser Pro Thr Thr Ala Val Val Ala Gln
        130                 135                 140

Leu Leu Arg Ile Pro Gln Ala Ile Leu Asp Met Ile Ala Gly Ala His
145                 150                 155                 160

Trp Gly Val Leu Ala Gly Ile Ala Tyr Phe Ser Met Val Gly Asn Trp
                165                 170                 175

Ala Lys Val Leu Val Val Leu Leu Leu Phe Ala Gly Val Asp Ala
            180                 185                 190

<210> SEQ ID NO 2
<211> LENGTH: 363
<212> TYPE: PRT
<213> ORGANISM: Hepatitis C virus

<400> SEQUENCE: 2

Glu Thr His Val Thr Gly Gly Ser Ala Ala Arg Thr Thr Ala Gly Leu
1               5                   10                  15

Ala Gly Leu Phe Thr Pro Gly Ala Lys Gln Asn Ile Gln Leu Ile Asn
                20                  25                  30

Thr Asn Gly Ser Trp His Ile Asn Arg Thr Ala Leu Asn Cys Asn Asp
            35                  40                  45

Ser Leu Asn Thr Gly Trp Val Ala Gly Leu Phe Tyr Tyr His Lys Phe
        50                  55                  60

Asn Ser Ser Gly Cys Pro Glu Arg Leu Ala Ser Cys Arg Pro Leu Thr
65                  70                  75                  80

Asp Phe Asp Gln Gly Trp Gly Pro Ile Ser Tyr Ala Asn Gly Ser Gly
                85                  90                  95

Pro Asp Gln Arg Pro Tyr Cys Trp His Tyr Pro Pro Lys Pro Cys Gly
                100                 105                 110

Ile Val Pro Ala Lys Ser Val Cys Gly Pro Val Tyr Cys Phe Thr Pro
            115                 120                 125

Ser Pro Val Val Gly Thr Thr Asp Arg Ser Gly Ala Pro Thr Tyr
        130                 135                 140

Asn Trp Gly Glu Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
            180                 185                 190

Asn Asn Thr Leu His Cys Pro Thr Asp Cys Phe Arg Lys His Pro Glu
        195                 200                 205

Ala Thr Tyr Ser Arg Cys Gly Ser Gly Pro Trp Ile Thr Pro Arg Cys
    210                 215                 220

Leu Val Asp Tyr Pro Tyr Arg Leu Trp His Tyr Pro Cys Thr Ile Asn
225                 230                 235                 240

Tyr Thr Ile Phe Lys Ile Arg Met Tyr Val Gly Gly Val Glu His Arg
                245                 250                 255

Leu Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Gln
        275                 280                 285
```

Trp Gln Val Leu Pro Cys Ser Phe Thr Thr Leu Pro Ala Leu Ser Thr
            290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys Trp Glu Tyr Val
                325                 330                 335

Val Leu Leu Phe Leu Leu Leu Ala Asp Ala Arg Val Cys Ser Cys Leu
            340                 345                 350

Trp Met Met Leu Leu Ile Ser Gln Ala Glu Ala
            355                 360

<210> SEQ ID NO 3
<211> LENGTH: 631
<212> TYPE: PRT
<213> ORGANISM: Hepatitis C virus

<400> SEQUENCE: 3

Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Ile Val Ser Thr Ala Ala Gln Thr Phe Leu Ala Thr Cys Ile
        35                  40                  45

Asn Gly Val Cys Trp Thr Val Tyr His Gly Ala Gly Thr Arg Thr Ile
50                  55                  60

Ala Ser Pro Lys Gly Pro Val Ile Gln Met Tyr Thr Asn Val Asp Gln
65                  70                  75                  80

Asp Leu Val Gly Trp Pro Ala Pro Gln Gly Ala Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

Pro Arg Pro Ile Ser Tyr Leu Lys Gly Ser Ser Gly Gly Pro Leu Leu
130                 135                 140

Cys Pro Ala Gly His Ala Val Gly Ile Phe Arg Ala Ala Val Cys Thr
145                 150                 155                 160

Arg Gly Val Ala Lys Ala Val Asp Phe Ile Pro Val Glu Asn Leu Glu
                165                 170                 175

Thr Thr Met Arg Ser Pro Val Phe Thr Asp Asn Ser Ser Pro Pro Ala
            180                 185                 190

Val Pro Gln Ser Phe Gln Val Ala His Leu His Ala Pro Thr Gly Ser
        195                 200                 205

Gly Lys Ser Thr Lys Val Pro Ala Ala Tyr Ala Ala Gln Gly Tyr Lys
210                 215                 220

Val Leu Val Leu Asn Pro Ser Val Ala Ala Thr Leu Gly Phe Gly Ala
225                 230                 235                 240

Tyr Met Ser Lys Ala His Gly Ile Asp Pro Asn Ile Arg Thr Gly Val
                245                 250                 255

Arg Thr Ile Thr Thr Gly Ser Pro Ile Thr Tyr Ser Thr Tyr Gly Lys
            260                 265                 270

Phe Leu Ala Asp Gly Gly Cys Ser Gly Gly Ala Tyr Asp Ile Ile Ile
        275                 280                 285

Cys Asp Glu Cys His Ser Thr Asp Ala Thr Ser Ile Leu Gly Ile Gly

```
        290                 295                 300
Thr Val Leu Asp Gln Ala Glu Thr Ala Gly Ala Arg Leu Val Val Leu
305                 310                 315                 320

Ala Thr Ala Thr Pro Pro Gly Ser Val Thr Val Pro His Pro Asn Ile
            325                 330                 335

Glu Glu Val Ala Leu Ser Thr Thr Gly Glu Ile Pro Phe Tyr Gly Lys
            340                 345                 350

Ala Ile Pro Leu Glu Val Ile Lys Gly Gly Arg His Leu Ile Phe Cys
            355                 360                 365

His Ser Lys Lys Cys Asp Glu Leu Ala Ala Lys Leu Val Ala Leu
    370                 375                 380

Gly Ile Asn Ala Val Ala Tyr Tyr Arg Gly Leu Asp Val Ser Val Ile
385                 390                 395                 400

Pro Thr Ser Gly Val Val Val Val Ala Thr Asp Ala Leu Met Thr
            405                 410                 415

Gly Phe Thr Gly Asp Phe Asp Ser Val Ile Asp Cys Asn Thr Cys Val
            420                 425                 430

Thr Gln Thr Val Asp Phe Ser Leu Asp Pro Thr Phe Thr Ile Glu Thr
        435                 440                 445

Thr Thr Leu Pro Gln Asp Ala Val Ser Arg Thr Gln Arg Arg Gly Arg
    450                 455                 460

Thr Gly Arg Gly Lys Pro Gly Ile Tyr Arg Phe Val Ala Pro Gly Glu
465                 470                 475                 480

Arg Pro Ser Gly Met Phe Asp Ser Ser Val Leu Cys Glu Cys Tyr Asp
            485                 490                 495

Ala Gly Cys Ala Trp Tyr Glu Leu Thr Pro Ala Glu Thr Thr Val Arg
            500                 505                 510

Leu Arg Ala Tyr Met Asn Thr Pro Gly Leu Pro Val Cys Gln Asp His
        515                 520                 525

Leu Glu Phe Trp Glu Gly Val Phe Thr Gly Leu Thr His Ile Asp Ala
    530                 535                 540

His Phe Leu Ser Gln Thr Lys Gln Ser Gly Glu Asn Leu Pro Tyr Leu
545                 550                 555                 560

Val Ala Tyr Gln Ala Thr Val Cys Ala Arg Ala Gln Ala Pro Pro Pro
            565                 570                 575

Ser Trp Asp Gln Met Trp Lys Cys Leu Ile Arg Leu Lys Pro Thr Leu
            580                 585                 590

His Gly Pro Thr Pro Leu Leu Tyr Arg Leu Gly Ala Val Gln Asn Glu
        595                 600                 605

Val Thr Leu Thr His Pro Ile Thr Lys Tyr Ile Met Thr Cys Met Ser
    610                 615                 620

Ala Asp Leu Glu Val Val Thr
625                 630

<210> SEQ ID NO 4
<211> LENGTH: 196
<212> TYPE: PRT
<213> ORGANISM: Hepatitis C virus

<400> SEQUENCE: 4

Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30
```

```
Val Gln Ile Val Ser Thr Ala Ala Gln Thr Phe Leu Ala Thr Cys Ile
             35                  40                  45

Asn Gly Val Cys Trp Thr Val Tyr His Gly Ala Gly Thr Arg Thr Ile
 50                  55                  60

Ala Ser Pro Lys Gly Pro Val Ile Gln Met Tyr Thr Asn Val Asp Gln
 65                  70                  75                  80

Asp Leu Val Gly Trp Pro Ala Pro Gln Gly Ala Arg Ser Leu Thr Pro
                 85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

Pro Arg Pro Ile Ser Tyr Leu Lys Gly Ser Ser Gly Gly Pro Leu Leu
130                 135                 140

Cys Pro Ala Gly His Ala Val Gly Ile Phe Arg Ala Ala Val Cys Thr
145                 150                 155                 160

Arg Gly Val Ala Lys Ala Val Asp Phe Ile Pro Val Glu Asn Leu Glu
                165                 170                 175

Thr Thr Met Arg Ser Pro Val Phe Thr Asp Asn Ser Ser Pro Pro Ala
            180                 185                 190

Val Pro Gln Ser
        195

<210> SEQ ID NO 5
<211> LENGTH: 435
<212> TYPE: PRT
<213> ORGANISM: Hepatitis C virus

<400> SEQUENCE: 5

Phe Gln Val Ala His Leu His Ala Pro Thr Gly Ser Gly Lys Ser Thr
 1               5                  10                  15

Lys Val Pro Ala Ala Tyr Ala Ala Gln Gly Tyr Lys Val Leu Val Leu
             20                  25                  30

Asn Pro Ser Val Ala Ala Thr Leu Gly Phe Gly Ala Tyr Met Ser Lys
         35                  40                  45

Ala His Gly Ile Asp Pro Asn Ile Arg Thr Gly Val Arg Thr Ile Thr
 50                  55                  60

Thr Gly Ser Pro Ile Thr Tyr Ser Thr Tyr Gly Lys Phe Leu Ala Asp
 65                  70                  75                  80

Gly Gly Cys Ser Gly Gly Ala Tyr Asp Ile Ile Ile Cys Asp Glu Cys
                 85                  90                  95

His Ser Thr Asp Ala Thr Ser Ile Leu Gly Ile Gly Thr Val Leu Asp
            100                 105                 110

Gln Ala Glu Thr Ala Gly Ala Arg Leu Val Val Leu Ala Thr Ala Thr
        115                 120                 125

Pro Pro Gly Ser Val Thr Val Pro His Pro Asn Ile Glu Glu Val Ala
130                 135                 140

Leu Ser Thr Thr Gly Glu Ile Pro Phe Tyr Gly Lys Ala Ile Pro Leu
145                 150                 155                 160

Glu Val Ile Lys Gly Gly Arg His Leu Ile Phe Cys His Ser Lys Lys
                165                 170                 175

Lys Cys Asp Glu Leu Ala Ala Lys Leu Val Ala Leu Gly Ile Asn Ala
            180                 185                 190

Val Ala Tyr Tyr Arg Gly Leu Asp Val Ser Val Ile Pro Thr Ser Gly
        195                 200                 205
```

```
Val Val Val Val Ala Thr Asp Ala Leu Met Thr Gly Phe Thr Gly
            210                 215                 220

Asp Phe Asp Ser Val Ile Asp Cys Asn Thr Cys Val Thr Gln Thr Val
225                 230                 235                 240

Asp Phe Ser Leu Asp Pro Thr Phe Thr Ile Glu Thr Thr Thr Leu Pro
                245                 250                 255

Gln Asp Ala Val Ser Arg Thr Gln Arg Arg Gly Arg Thr Gly Arg Gly
                260                 265                 270

Lys Pro Gly Ile Tyr Arg Phe Val Ala Pro Gly Glu Arg Pro Ser Gly
                275                 280                 285

Met Phe Asp Ser Ser Val Leu Cys Glu Cys Tyr Asp Ala Gly Cys Ala
    290                 295                 300

Trp Tyr Glu Leu Thr Pro Ala Glu Thr Thr Val Arg Leu Arg Ala Tyr
305                 310                 315                 320

Met Asn Thr Pro Gly Leu Pro Val Cys Gln Asp His Leu Glu Phe Trp
                325                 330                 335

Glu Gly Val Phe Thr Gly Leu Thr His Ile Asp Ala His Phe Leu Ser
                340                 345                 350

Gln Thr Lys Gln Ser Gly Glu Asn Leu Pro Tyr Leu Val Ala Tyr Gln
    355                 360                 365

Ala Thr Val Cys Ala Arg Ala Gln Ala Pro Pro Pro Ser Trp Asp Gln
370                 375                 380

Met Trp Lys Cys Leu Ile Arg Leu Lys Pro Thr Leu His Gly Pro Thr
385                 390                 395                 400

Pro Leu Leu Tyr Arg Leu Gly Ala Val Gln Asn Glu Val Thr Leu Thr
                405                 410                 415

His Pro Ile Thr Lys Tyr Ile Met Thr Cys Met Ser Ala Asp Leu Glu
                420                 425                 430

Val Val Thr
        435

<210> SEQ ID NO 6
<211> LENGTH: 591
<212> TYPE: PRT
<213> ORGANISM: Hepatitis C virus

<400> SEQUENCE: 6

Ser Met Ser Tyr Ser Trp Thr Gly Ala Leu Val Thr Pro Cys Ala Ala
1               5                   10                  15

Glu Glu Gln Lys Leu Pro Ile Asn Ala Leu Ser Asn Ser Leu Leu Arg
                20                  25                  30

His His Asn Leu Val Tyr Ser Thr Thr Ser Arg Ser Ala Cys Gln Arg
            35                  40                  45

Gln Lys Lys Val Thr Phe Asp Arg Leu Gln Val Leu Asp Ser His Tyr
    50                  55                  60

Gln Asp Val Leu Lys Glu Val Lys Ala Ala Ser Lys Val Lys Ala
65                  70                  75                  80

Asn Leu Leu Ser Val Glu Glu Ala Cys Ser Leu Thr Pro Pro His Ser
                85                  90                  95

Ala Lys Ser Lys Phe Gly Tyr Gly Ala Lys Asp Val Arg Cys His Ala
                100                 105                 110

Arg Lys Ala Val Asn His Ile Asn Ser Val Trp Lys Asp Leu Leu Glu
            115                 120                 125

Asp Ser Val Thr Pro Ile Asp Thr Thr Ile Met Ala Lys Asn Glu Val
```

-continued

```
            130                 135                 140
Phe Cys Val Gln Pro Glu Lys Gly Gly Arg Lys Pro Ala Arg Leu Ile
145                 150                 155                 160
Val Phe Pro Asp Leu Gly Val Arg Val Cys Glu Lys Met Ala Leu Tyr
                    165                 170                 175
Asp Val Val Ser Lys Leu Pro Leu Ala Val Met Gly Ser Ser Tyr Gly
                180                 185                 190
Phe Gln Tyr Ser Pro Gly Gln Arg Val Glu Phe Leu Val Gln Ala Trp
            195                 200                 205
Lys Ser Lys Lys Thr Pro Met Gly Phe Ser Tyr Asp Thr Arg Cys Phe
210                 215                 220
Asp Ser Thr Val Thr Glu Ser Asp Ile Arg Thr Glu Glu Ala Ile Tyr
225                 230                 235                 240
Gln Cys Cys Asp Leu Asp Pro Gln Ala Arg Val Ala Ile Lys Ser Leu
                    245                 250                 255
Thr Glu Arg Leu Tyr Val Gly Gly Pro Leu Thr Asn Ser Arg Gly Glu
                260                 265                 270
Asn Cys Gly Tyr Arg Arg Cys Arg Ala Ser Gly Val Leu Thr Thr Ser
            275                 280                 285
Cys Gly Asn Thr Leu Thr Cys Tyr Ile Lys Ala Arg Ala Ala Cys Arg
290                 295                 300
Ala Ala Gly Leu Gln Asp Cys Thr Met Leu Val Cys Gly Asp Asp Leu
305                 310                 315                 320
Val Val Ile Cys Glu Ser Ala Gly Val Gln Glu Asp Ala Ala Ser Leu
                    325                 330                 335
Arg Ala Phe Thr Glu Ala Met Thr Arg Tyr Ser Ala Pro Pro Gly Asp
                340                 345                 350
Pro Pro Gln Pro Glu Tyr Asp Leu Glu Leu Ile Thr Ser Cys Ser Ser
            355                 360                 365
Asn Val Ser Val Ala His Asp Gly Ala Gly Lys Arg Val Tyr Tyr Leu
370                 375                 380
Thr Arg Asp Pro Thr Thr Pro Leu Ala Arg Ala Ala Trp Glu Thr Ala
385                 390                 395                 400
Arg His Thr Pro Val Asn Ser Trp Leu Gly Asn Ile Ile Met Phe Ala
                    405                 410                 415
Pro Thr Leu Trp Ala Arg Met Ile Leu Met Thr His Phe Phe Ser Val
                420                 425                 430
Leu Ile Ala Arg Asp Gln Leu Glu Gln Ala Leu Asp Cys Glu Ile Tyr
            435                 440                 445
Gly Ala Cys Tyr Ser Ile Glu Pro Leu Asp Leu Pro Pro Ile Ile Gln
450                 455                 460
Arg Leu His Gly Leu Ser Ala Phe Ser Leu His Ser Tyr Ser Pro Gly
465                 470                 475                 480
Glu Ile Asn Arg Val Ala Ala Cys Leu Arg Lys Leu Gly Val Pro Pro
                    485                 490                 495
Leu Arg Ala Trp Arg His Arg Ala Arg Ser Val Arg Ala Arg Leu Leu
                500                 505                 510
Ser Arg Gly Gly Arg Ala Ala Ile Cys Gly Lys Tyr Leu Phe Asn Trp
            515                 520                 525
Ala Val Arg Thr Lys Leu Lys Leu Thr Pro Ile Ala Ala Ala Gly Gln
530                 535                 540
Leu Asp Leu Ser Gly Trp Phe Thr Ala Gly Tyr Ser Gly Gly Asp Ile
545                 550                 555                 560
```

```
Tyr His Ser Val Ser His Ala Arg Pro Arg Trp Phe Trp Phe Cys Leu
                565                 570                 575
Leu Leu Leu Ala Ala Gly Val Gly Ile Tyr Leu Leu Pro Asn Arg
            580                 585                 590

<210> SEQ ID NO 7
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Thr Ser Val Gly Gln Leu Phe Thr Phe Ser Pro Arg Arg His Trp Thr
1               5                   10                  15
Thr Gln Asp Cys Asn Cys Ser Ile Tyr Pro Gly His Ile Thr Gly His
            20                  25                  30
Arg Met Ala Trp Asp Met Met Met Asn Trp Ser Pro Thr Thr Ala Val
        35                  40                  45
Val Ala Gln Leu Leu Arg Ile Pro Gln Ala Ile Leu Asp Met Ile Ala
    50                  55                  60
Gly Ala Ser
65

<210> SEQ ID NO 8
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Thr Ser Glu Thr His Val Thr Gly Gly Ser Ala Ala Arg Thr Thr Ala
1               5                   10                  15
Gly Leu Ala Gly Leu Phe Thr Pro Gly Ala Lys Gln Asn Ile Gln Leu
            20                  25                  30
Ile Asn Thr Asn Gly Ser Trp His Ile Asn Arg Thr Ala Leu Asn Cys
        35                  40                  45
Asn Asp Ser Leu Asn Thr Gly Trp Val Ala Gly Leu Phe Tyr Tyr His
    50                  55                  60
Lys Phe Asn Ser Ser Gly Cys Pro Glu Arg Leu Ala Ser Cys Arg Pro
65                  70                  75                  80
Leu Thr Asp Phe Asp Gln Gly Trp Gly Pro Ile Ser Tyr Ala Asn Gly
                85                  90                  95
Ser Gly Pro Asp Gln Arg Pro Tyr Cys Trp His Tyr Pro Pro Lys Pro
            100                 105                 110
Cys Gly Ile Val Pro Ala Lys Ser Val Cys Gly Pro Val Tyr Cys Phe
        115                 120                 125
Thr Pro Ser Pro Val Val Val Gly Thr Thr Asp Arg Ser Gly Ala Pro
    130                 135                 140
Thr Tyr Asn Trp Gly Glu Asn Asp Thr Asp Val Phe Val Leu Asn Asn
145                 150                 155                 160
Thr Arg Pro Pro Leu Gly Asn Trp Phe Gly Cys Thr Trp Met Asn Ser
                165                 170                 175
Thr Gly Phe Thr Lys Val Cys Gly Ala Pro Pro Cys Val Ile Gly Gly
            180                 185                 190
```

```
Val Gly Asn Asn Thr Leu His Cys Pro Thr Asp Cys Phe Arg Lys His
        195                 200                 205
Pro Glu Ala Thr Tyr Ser Arg Cys Gly Ser Gly Pro Trp Ile Thr Pro
    210                 215                 220
Arg Cys Leu Val Asp Tyr Pro Tyr Arg Leu Trp His Tyr Pro Cys Thr
225                 230                 235                 240
Ile Asn Tyr Thr Ile Phe Lys Ile Arg Met Tyr Val Gly Gly Val Glu
                245                 250                 255
His Arg Leu Glu Ala Ala Cys Asn Trp Thr Arg Gly Glu Arg Cys Asp
            260                 265                 270
Leu Glu Asp Arg Asp Arg Ser Glu Leu Ser Pro Leu Leu Leu Ser Thr
        275                 280                 285
Thr Gln Trp Gln Val Leu Pro Cys Ser Phe Thr Thr Leu Pro Ala Leu
    290                 295                 300
Ser Thr Gly Leu Ile His Leu His Gln Asn Ile Val Asp Val Gln Tyr
305                 310                 315                 320
Leu Tyr Gly Val Gly Ser Ser Ile Ala Ser Trp Ala Ile Lys Trp Glu
                325                 330                 335
Tyr Val Val Leu Leu Phe Leu Leu Ala Ser
                340                 345

<210> SEQ ID NO 9
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Thr Ser Ala Pro Ile Thr Ala Tyr Ala Gln Gln Thr Arg Gly Leu Leu
1               5                   10                  15
Gly Cys Ile Ile Thr Ser Leu Thr Gly Arg Asp Lys Asn Gln Val Glu
                20                  25                  30
Gly Glu Val Gln Ile Val Ser Thr Ala Ala Gln Thr Phe Leu Ala Thr
            35                  40                  45
Cys Ile Asn Gly Val Cys Trp Thr Val Tyr His Gly Ala Gly Thr Arg
        50                  55                  60
Thr Ile Ala Ser
65

<210> SEQ ID NO 10
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Thr Ser Thr Pro Cys Thr Cys Gly Ser Ser Asp Leu Tyr Leu Val Thr
1               5                   10                  15
Arg His Ala Asp Val Ile Pro Val Arg Arg Arg Gly Asp Ser Arg Gly
                20                  25                  30
Ser Leu Leu Ser Pro Arg Pro Ile Ser Tyr Leu Lys Gly Ser Ser Gly
            35                  40                  45
Gly Pro Leu Leu Cys Pro Ala Gly His Ala Val Gly Ile Phe Arg Ala
        50                  55                  60
```

```
Ala Val Cys Thr Arg Gly Val Ala Lys Ala Val Asp Phe Ile Pro Val
 65                  70                  75                  80

Glu Asn Leu Glu Thr Thr Met Arg Ser Pro Val Phe Thr Asp Asn Ser
                 85                  90                  95

Ser Pro Pro Ala Val Pro Gln Ser Ala Ser
            100                 105

<210> SEQ ID NO 11
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Thr Ser Phe Gln Val Ala His Leu His Ala Pro Thr Gly Ser Gly Lys
  1               5                  10                  15

Ser Thr Lys Val Pro Ala Ala Tyr Ala Ala Gln Gly Tyr Lys Val Leu
                 20                  25                  30

Val Leu Asn Pro Ser Val Ala Ala Thr Leu Gly Phe Gly Ala Tyr Met
             35                  40                  45

Ser Lys Ala His Gly Ile Asp Pro Asn Ile Arg Thr Gly Val Arg Thr
 50                  55                  60

Ile Thr Thr Gly Ser Pro Ile Thr Tyr Ser Thr Tyr Gly Lys Phe Leu
 65                  70                  75                  80

Ala Asp Gly Gly Cys Ser Gly Gly Ala Tyr Asp Ile Ile Ile Cys Asp
                 85                  90                  95

Glu Cys His Ser Thr Asp Ala Thr Ser Ile Leu Gly Ile Gly Thr Val
            100                 105                 110

Leu Asp Gln Ala Glu Thr Ala Gly Ala Arg Leu Val Val Leu Ala Thr
        115                 120                 125

Ala Thr Pro Pro Gly Ser Ala Ser
    130                 135

<210> SEQ ID NO 12
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr Ser Val Thr Val Pro His Pro Asn Ile Glu Glu Val Ala Leu Ser
  1               5                  10                  15

Thr Thr Gly Glu Ile Pro Phe Tyr Gly Lys Ala Ile Pro Leu Glu Val
                 20                  25                  30

Ile Lys Gly Gly Arg His Leu Ile Phe Cys His Ser Lys Lys Lys Cys
             35                  40                  45

Asp Glu Leu Ala Ala Lys Leu Val Ala Leu Gly Ile Asn Ala Val Ala
         50                  55                  60

Tyr Tyr Arg Gly Leu Asp Val Ser Val Ile Pro Thr Ser Gly Val Val
 65                  70                  75                  80

Val Val Val Ala Thr Asp Ala Leu Met Thr Gly Phe Thr Gly Asp Phe
                 85                  90                  95

Asp Ser Val Ile Asp Cys Asn Thr Cys Val Thr Gln Thr Val Asp Phe
            100                 105                 110
```

```
Ser Leu Asp Pro Thr Phe Thr Ile Glu Thr Thr Leu Pro Gln Asp
        115                 120                 125

Ala Val Ser Arg Thr Gln Arg Gly Arg Thr Gly Arg Gly Lys Pro
    130                 135                 140

Gly Ile Tyr Arg Phe Val Ala Pro Gly Glu Arg Ala Ser
145                 150                 155

<210> SEQ ID NO 13
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Thr Ser Pro Ser Gly Met Phe Asp Ser Ser Val Leu Cys Glu Cys Tyr
1               5                   10                  15

Asp Ala Gly Cys Ala Trp Tyr Glu Leu Thr Pro Ala Glu Thr Thr Val
            20                  25                  30

Arg Leu Arg Ala Tyr Met Asn Thr Pro Gly Leu Pro Val Cys Gln Asp
        35                  40                  45

His Leu Glu Phe Trp Glu Gly Val Phe Thr Gly Leu Thr His Ile Asp
    50                  55                  60

Ala His Phe Leu Ser Gln Thr Lys Gln Ser Gly Glu Asn Leu Pro Tyr
65                  70                  75                  80

Leu Val Ala Tyr Gln Ala Thr Val Cys Ala Arg Ala Gln Ala Pro Pro
                85                  90                  95

Pro Ser Trp Asp Gln Met Trp Lys Cys Leu Ile Arg Leu Lys Pro Thr
            100                 105                 110

Leu His Gly Pro Thr Pro Leu Leu Tyr Arg Leu Gly Ala Val Gln Asn
        115                 120                 125

Glu Val Thr Leu Thr His Pro Ile Thr Lys Tyr Ile Met Thr Cys Met
    130                 135                 140

Ser Ala Asp Leu Glu Val Val Thr Ala Ser
145                 150

<210> SEQ ID NO 14
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Thr Ser Val Leu Asp Ser His Tyr Gln Asp Val Leu Lys Glu Val Lys
1               5                   10                  15

Ala Ala Ala Ser Lys Val Lys Ala Asn Ala Leu Tyr Asp Val Val Ser
            20                  25                  30

Lys Leu Pro Leu Ala Val Met Gly Ser Ser Tyr Gly Phe Gln Tyr Ser
        35                  40                  45

Pro Gly Gln Arg Val Glu Phe Leu Val Gln Ala Trp Lys Ser Lys Lys
    50                  55                  60

Thr Pro Met Gly Phe Ser Tyr Asp Thr Arg Cys Phe Asp Ser Thr Val
65                  70                  75                  80

Thr Glu Ser Asp Ile Arg Thr Glu Glu Ala Ile Tyr Gln Cys Cys Asp
                85                  90                  95
```

```
Leu Asp Pro Gln Ala Arg Val Ala Ile Lys Ser Leu Thr Glu Arg Leu
            100                 105                 110

Tyr Val Gly Arg Cys Arg Ala Ser Gly Val Leu Thr Thr Ser Cys Gly
        115                 120                 125

Asn Thr Leu Thr Cys Tyr Ile Lys Ala Arg Ala Ala Cys Arg Ala Ala
    130                 135                 140

Gly Leu Gln Asp Cys Thr Met Leu Val Cys Gly Asp Asp Leu Val Val
145                 150                 155                 160

Ile Cys Glu Ser Ala Gly Val Gln Glu Asp Ala Ala Ser Leu Arg Ala
                165                 170                 175

Phe Thr Glu Ala Met Thr Arg Tyr Ser Ala Pro Pro Gly Asp Pro Pro
            180                 185                 190

Gln Pro Glu Tyr Asp Leu Glu Leu Ile Thr Ala Ser
        195                 200
```

<210> SEQ ID NO 15
<211> LENGTH: 1409
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
atgggcaggc ttacttcttc attcttgcta ctgattgtcc ctgcatatgt cctgtcccag    60
gttactctga aagagtctgg ccctgggata ttgcagccct cccagaccct cagtctgacc   120
tgttctttct ctgggttttc actgagcact tctggtatga gtgtaggctg gattcgtcag   180
ccttcaggga agggtctgga gtggctggct cacatttggt ggaatgatga taagtactat   240
aatccagtcc tgaaaagccg gctcacaatc tccaaggaga cctccaacaa ccaggtattc   300
ctcaagatcg ccagtgtggt ctctgcagat actgccacat actactgtgc tcgattctat   360
ggtaactgtc ttgactactg ggccaaggca accactctca cagtctcctc ggccaaaaca   420
aagggcccat ccgtcttccc cctggcgccc tgctccagga gcacctccga gagcacagcc   480
gccctgggct gcctggtcaa ggactacttc cccgaaccgg tgacggtgtc gtggaactca   540
ggcgccctga ccagcggcgt gcacaccttc ccggctgtcc tacagtcctc aggactctac   600
tccctcagca gcgtggtgac cgtgccctcc agcagcttgg gcacgaagac ctacacctgc   660
aacgtagatc acaagcccag caacaccaag gtggacaaga gagttgagtc caaatatggt   720
cccccatgcc cacctgccc agcacctgag ttcgagggg accatcagt cttcctgttc   780
ccccaaaac ccaaggacac tctcatgatc tcccggaccc ctgaggtcac gtgcgtggtg   840
gtggacgtga gccaggaaga cccgaggtc cagttcaact ggtacgtgga tggcgtggag   900
gtgcataatg ccaagacaaa gccgcgggag gagcagttca acagcacgta ccgtgtggtc   960
agcgtcctca ccgtcctgca ccaggactgg ctgaacggca aggagtacaa gtgcaaggtc  1020
tccaacaaag gcctcccgtc ctccatcgag aaaaccatct ccaaagccaa agggcagccc  1080
cgagagccac aggtgtacac cctgccccca tcccaggagg agatgaccaa gaaccaggtc  1140
agcctgacct gcctggtcaa aggcttctac cccagcgaca tcgccgtgga gtgggagagc  1200
aatgggcagc cggagaacaa ctacaagacc acgcctcccg tgctggactc cgacggctcc  1260
ttcttcctct acagcaggct aaccgtggac aagagcaggt ggcagagggg gaatgtcttc  1320
tcatgctccg tgatgcatga ggctctgcac aaccactaca cacagaagag cctctccctg  1380
```
tctctgggta aagctagctg attaattaa                                       1409

<210> SEQ ID NO 16
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atgatgtcct ctgctcagtt ccttggtctc ctgttgctct gttttcaagg taccagatgt     60
gatatccaga tgacacagac tacatcctcc ctgtctgcct ctctgggaga cagagtcacc    120
atcagttgca gggcaagtca ggacattagc aattatttaa actggtatca gcagaaacca    180
gatggaactg ttaaactcct gatctactac acatcaatat acaattagg agtcccatca     240
agattcagtg gcagtgggtc tgaaacagat tattctctca ccattagcaa cctggagcaa    300
gaagatattg ccacttactt tgccaacag ggtgattcgc ttccattcac gttcggctcg     360
gggacaaagc tcgagatcaa cgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctatgcct gcgaagtcac ccatcagggc    660
ctgagctcgc ccgtcacaaa gagcttcaac aggggagagt gttag                    705

<210> SEQ ID NO 17
<211> LENGTH: 1403
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atgagagcgc tgattctttt gtgcctgttc acagcctttc tggtatcct gtctgatgtg      60
cagcttcagg agtcaggacc tgacctggtg aaaccttctc agtcacttc actcacctgc     120
actgtcactg ctactccat caccagtggt tatagctggc actggatccg gcagtttcca     180
ggaaacaaac tggaatggat gggctacata ctcttcagtg gtagcactaa ctacaaccca    240
tctctgaaaa gtcgaatctc tatcactcga gacacatcca agaaccagtt cttcctgcag    300
ttgaattctg tgactactga ggacacagcc acatatttct gtgcaagatc taactatggt    360
tcctttgctt cctggggcca agggactctg gtcactgtct ctgcagccaa acaacgggc     420
ccatccgtct tccccctggc gccctgctcc aggagcacct ccgagagcac agccgccctg    480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgg tgaccgtgcc ctccagcagc ttgggcacga gacctacac ctgcaacgta     660
gatcacaagc ccagcaacac caaggtggac aagagagttg agtccaaata tggtccccca    720
tgcccaccct gcccagcacc tgagttcgaa ggggaccat cagtcttcct gttcccccca     780
aaacccaagg acactctcat gatctcccgg acccctgagg tcacgtgcgt ggtggtggac    840
gtgagccagg aagaccccga ggtccagttc aactggtacg tggatggcgt ggaggtgcat    900
aatgccaaga caaagccgcg ggaggagcag ttcaacagca cgtaccgtgt ggtcagcgtc    960

```
ctcaccgtcc tgcaccagga ctggctgaac ggcaaggagt acaagtgcaa ggtctccaac    1020
aaaggcctcc cgtcctccat cgagaaaacc atctccaaag ccaagggca gccccgagag     1080 ccacaggtgt acaccctgcc cccatcccag gaggagatga ccaagaacca ggtcagcctg    1140
acctgcctgg tcaaaggctt ctaccccagc gacatcgccg tggagtggga gagcaatggg    1200
cagccggaga caactacaa gaccacgcct cccgtgctgg actccgacgg ctccttcttc     1260
ctctacagca ggctaaccgt ggacaagagc aggtggcagg aggggaatgt cttctcatgc    1320
tccgtgatgc atgaggctct gcacaaccac tacacacaga gagcctctc cctgtctctg     1380 ggtaaagcta gctgattaat taa                                            1403
```

<210> SEQ ID NO 18
<211> LENGTH: 708
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 18

```
atggattttc aagtgcagat tttcagcttc ctgctaatca gtgcctcagt cataatatcc    60
agaggacaaa ttgttctcac ccagtctcca gcaatcatgt ctgcatctcc aggggagaag   120
gtcaccatga cctgcagtgc cagctcaagt gtaagtcaca tgcactggta ccagcagaag   180
tcaggcactt cccccaaaag atggatttat gacacatcca actggcttc tggagtccct    240 gctcgcttca gtggcagtgg gtctgggacc tcttactctc tcacaatcag cagcatggag   300
gctgaagatg ctgccactta ttactgccag cagtggagta gtcacccatg gtcgttcggt   360
ggaggcacca aactcgagat caaacgaact gtggctgcac catctgtctt catcttcccg   420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac cgagaaacac aaagtctatg cctgcgaagt cacccatcag    660
ggcctgagct cgcccgtcac aaagagcttc aacaggggag agtgttag                  708
```

<210> SEQ ID NO 19
<211> LENGTH: 1415
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 19

```
atggcttggg tgtggaccct gctattcctg atggcagctg cccaaagtgc ccaagcacag    60
atccagttgg tgcagtctgg acctgagctg aagaagcctg agagacagt caagatctcc     120 tgcaaggctt ctgggtatac cttcacaaac tatggaatga actgggtgaa gcaggttcca    180
ggaaaaggtt taaggtggat gggctggatg gacaccttca ctggagagcc aacatatgct    240
gatgacttca agggacggtt tgccttctct ttggaaacct ctgccagcac tgcctatttg    300
cagatcaaca gcctcaaaaa tgaggacacg gctacttatt tctgtgcaag agggggggatt    360 ttacgactca actactttga ctactggggc caaggcacca ctctcacagt ctcctcagcc    420
aaaacgaagg gcccatccgt cttccccctg gcgccctgct ccaggagcac ctccgagagc    480
```

```
acagccgccc tgggctgcct ggtcaaggac tacttccccg aaccggtgac ggtgtcgtgg      540
aactcaggcg ccctgaccag cggcgtgcac accttcccgg ctgtcctaca gtcctcagga      600
ctctactccc tcagcagcgt ggtgaccgtg ccctccagca gcttgggcac gaagacctac      660
acctgcaacg tagatcacaa gcccagcaac accaaggtgg acaagagagt tgagtccaaa      720
tatggtcccc catgcccacc ctgcccagca cctgagttcg aaggggggacc atcagtcttc     780 ctgttccccc caaaacccaa ggacactctc atgatctccc ggacccctga ggtcacgtgc      840
gtggtggtgg acgtgagcca ggaagacccc gaggtccagt tcaactggta cgtggatggc      900
gtggaggtgc ataatgccaa gacaaagccg cgggaggagc agttcaacag cacgtaccgt      960
gtggtcagcg tcctcaccgt cctgcaccag gactggctga acggcaagga gtacaagtgc     1020
aaggtctcca acaaaggcct cccgtcctcc atcgagaaaa ccatctccaa agccaaaggg     1080
cagccccgag agccacaggt gtacaccctg cccccatccc aggaggagat gaccaagaac     1140
caggtcagcc tgacctgcct ggtcaaaggc ttctacccca gcgacatcgc cgtggagtgg     1200
gagagcaatg ggcagccgga gaacaactac aagaccacgc ctcccgtgct ggactccgac     1260
ggctccttct tcctctacag caggctaacc gtggacaaga gcaggtggca ggaggggaat     1320
gtcttctcat gctccgtgat gcatgaggct ctgcacaacc actacacaca gaagagcctc     1380
tccctgtctc tgggtaaagc tagctgatta attaa                                1415
```

<210> SEQ ID NO 20
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
atgaagtttc cttctcaact tctgctctta ctgctgtttg gaatcccagg catgatatgt       60
gacatccaga tgacacaatc ttcatcctcc ttttctgtat ctctaggaga cagagtcacc      120
attacttgca aggcaagtga ggacatatat aatcggttag ctggtatcca gcagaaacca      180
ggaaatgctc ctaggctctt aatatctggt gcaaccagtt tggaaactgg ggttccttca      240
agattcagtg gcagtggatc tggaaaggat tacgctctca gcattaccag tcttcagact      300
gaagatcttc tacttatta ctgtcaacag tgttggactt ctccgtacac gttcggaggg      360
gggaccaagc tcgagatcaa acgaactgtg gctgcaccat ctgtcttcat cttcccgcca      420
tctgatgagc agttgaaatc tggaactgcc tctgttgtgt gcctgctgaa taacttctat      480
cccagagagg ccaaagtaca gtggaaggtg gataacgccc tccaatcggg taactcccag      540
gagagtgtca cagagcagga cagcaaggac agcacctaca gcctcagcag caccctgacg      600
ctgagcaaag cagactacga gaaacacaaa gtctatgcct gcgaagtcac ccatcagggc      660
ctgagctcgc ccgtcacaaa gagcttcaac aggggagagt gttag                     705
```

<210> SEQ ID NO 21
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
atgggatgga gctggatctt tctctttctc ttgtcaggaa ctggaggtgt cctctctgag       60
```

```
gtccagctgc aacagtctgg acctgagctg gtgaagcctg gggcttcagt gaagatgtcc    120
tgcaaggctt ctggatacac cttcactgac tactacatga agtgggtgaa gcagagccat    180
ggaaagagcc ttgagtggat tggagatatt aatcctaact atggtgatac tttctacaac    240
cagaagttcg agggcaaggc cacattgact gtagacaaat cctccaggac agcctacatg    300
cagctcaaca gcctgacatc tgaggactct gcagtctatt attgtggaag aggggactat    360
ggatacttcg atgtctgggg cgcagggacc acggtcaccg tctcctcagc caaaacaaag    420
ggcccatccg tcttcccct ggcgccctgc tccaggagca cctccgagag cacagccgcc    480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcttgggca cgaagaccta cacctgcaac    660
gtagatcaca agcccagcaa caccaaggtg gacaagagag ttgagtccaa atatggtccc    720
ccatgcccac cctgcccagc acctgagttc aagggggac catcagtctt cctgttcccc    780
ccaaaaccca aggacactct catgatctcc cggacccctg aggtcacgtg cgtggtggtg    840
gacgtgagcc aggaagaccc cgaggtccag ttcaactggt acgtggatgg cgtggaggtg    900
cataatgcca agacaaagcc gcgggaggag cagttcaaca gcacgtaccg tgtggtcagc    960
gtcctcaccg tcctgcacca ggactggctg aacggcaagg agtacaagtg caaggtctcc   1020
aacaaaggcc tcccgtcctc catcgagaaa accatctcca aagccaaagg gcagccccga   1080
gagccacagg tgtacaccct gccccatcc caggaggaga tgaccaagaa ccaggtcagc   1140
ctgacctgcc tggtcaaagg cttctacccc agcgacatcg ccgtggagtg ggagagcaat   1200
gggcagccgg agaacaacta caagaccacg cctcccgtgc tggactccga cggctccttc   1260
ttcctctaca gcaggctaac cgtggacaag agcaggtggc aggaggggaa tgtcttctca   1320
tgctccgtga tgcatgaggc tctgcacaac cactacacac agaagagcct ctccctgtct   1380
ctgggtaaag ctagctga                                                  1398
```

<210> SEQ ID NO 22
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
atggagacac attctcaggt ctttgtatac atgttgctgt ggttgtctgg tgttgaagga     60
gacattgtga tgacccagtc tcacaaattc atgtccacat cagtaggaga cagggtcagc    120
atcacctgca aggccagtca ggatgtgggt actgctgtag cctggtatca acagaaacca    180
gggcaatctc ctaaactact gatttactgg gcatccaccc ggcacactgg agtccctgat    240
cgcttcacag gcagtggatc tgggacagat ttcactctca ccattaacaa tgtgcagtct    300
gaagacttgg cagattattt ctgtcagcaa tatagcagca tccgtacat gttcggaggg    360 gggaccaagc tcgagatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctatgcct gcgaagtcac ccatcagggc    660
```

```
ctgagctcgc ccgtcacaaa gagcttcaac aggggagagt gttag              705
```

<210> SEQ ID NO 23
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atgggatgga gctggatctt tctctttctc ctgtcaggaa ctgcaggtgt cctctctgag    60
gtccagctgc aacagtctgg acctgagttg gtgaagcctg ggcttcagt gaagatatcc    120
tgcaagactt ctggatacac attcactgaa taccatgc actgggtgag gcagagccat    180
ggaaagagcc ttgagtggat tggaggtatt aatcctatca atggtggtcc tacctacaac    240
cagaagttca aggcaaggc acattgact gttgacaagt cctccagcac agcctacatg    300
gagctccgca gcctgacatc tgaggactct gcagtctatt actgtgcaag atgggactat    360
ggtagtcgag atgttatgga ctactggggt caaggaacct cagtcaccgt ctcctcagcc    420
aaaacgaagg gcccatccgt cttccccctg gcgccctgct ccaggagcac ctccgagagc    480
acagccgccc tgggctgcct ggtcaaggac tacttccccg aaccggtacc ggtgacggtg    540
tcgtggaact caggcgccct gaccagcggc gtgcacacct tcccggctgt cctacagtcc    600
tcaggactct actccctcag cagcgtggtg accgtgccct ccagcagctt gggcacgaag    660
acctacacct gcaacgtaga tcacaagccc agcaacacca aggtggacaa gagagttgag    720
tccaaatatg gtcccccatg cccacccctgc ccagcacctg agttcgaagg ggaccatca    780
gtcttcctgt tccccccaaa acccaaggac actctcatga tctcccggac ccctgaggtc    840
acgtgcgtgg tggtggacgt gagccaggaa gaccccgagg tccagttcaa ctggtacgtg    900
gatggcgtgg aggtgcataa tgccaagaca aagccgcggg aggagcagtt caacagcacg    960
taccgtgtgg tcagcgtcct caccgtcctg caccaggact ggctgaacgg caaggagtac    1020
aagtgcaagg tctccaacaa aggcctcccg tcctccatcg agaaaaccat ctccaaagcc    1080
aaagggcagc cccgagagcc acaggtgtac accctgcccc catcccagga ggagatgacc    1140
aagaaccagg tcagcctgac ctgcctggtc aaaggcttct accccagcga catcgccgtg    1200
gagtgggaga gcaatgggca gccggagaac aactacaaga ccacgcctcc cgtgctggac    1260
tccgacggct ccttcttcct ctacagcagg ctaaccgtgg acaagagcag gtggcaggag    1320
gggaatgtct tctcatgctc cgtgatgcat gaggctctgc acaaccacta cacacagaag    1380
agcctctccc tgtctctggg taaagctagc tga                                  1413
```

<210> SEQ ID NO 24
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
atggaatcac agactctggt cttcatatcc atactgctct ggttatatgg tgctgatggg    60
aacattgtaa tgactcaatc tcccaaatcc atgtccatgt cagtagggga gagggtcacc    120
ttgagctgca aggccagtga gaatgtggga acttatgtat cctggtatca acagagacca    180
```

| | |
|---|---:|
| gaacagtctc caaaactgct gatatacggg gcatccaacc ggtacactgg ggtccccgat | 240 |
| cgcttcacag gcagtggatc tgcaacagat ttcactctga ccatcagcag tgtgcaggct | 300 |
| gaggaccttg cagattatca ctgtggacag acttacagct atatattcac gttcggctcg | 360 |
| gggacaaagc tcgagatcaa acgaactgtg gctgcaccat ctgtcttcat cttcccgcca | 420 |
| tctgatgagc agttgaaatc tggaactgcc tctgttgtgt gcctgctgaa taacttctat | 480 |
| cccagagagg ccaaagtaca gtggaaggtg gataacgccc tccaatcggg taactcccag | 540 |
| gagagtgtca cagagcagga cagcaaggac agcacctaca gcctcagcag caccctgacg | 600 |
| ctgagcaaag cagactacga gaaacacaaa gtctatgcct gcgaagtcac ccatcagggc | 660 |
| ctgagctcgc ccgtcacaaa gagcttcaac aggggagagt gttag | 705 |

<210> SEQ ID NO 25
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

| | |
|---|---:|
| atgggatgga gccggatctt tctcttcctc ctgtcaataa ctgcaggtgt ccattgccag | 60 |
| gtccaggtgc agcagtcggg acctgagttg gtgaagcctg ggcctcagt gaagatttcc | 120 |
| tgcaaagcct ctggcgacgc attcagtagt tcttggatga actgggtgaa gcagaggcct | 180 |
| ggacagggtc ttgagtggat tggacggatt tatcttggag atggagatat taattacaat | 240 |
| gggaagttca agggcagggc cacactgact gcagacaaat cctccagcac agcctacatg | 300 |
| cagctcagca gcctgacctc tgtggactct gcggtctatt tctgcgcgag gcagctcggg | 360 |
| ctatggtatg ttatggacta ctggggtcaa ggaacctcag tcaccgtctc ctcagccaaa | 420 |
| acaaagggcc catccgtctt ccccctggcg ccctgctcca ggagcacctc cgagagcaca | 480 |
| gccgccctgg gctgcctggt caaggactac ttccccgaac cggtgacggt gtcgtggaac | 540 |
| tcaggcgccc tgaccagcgg cgtgcacacc ttcccggctg tcctacagtc ctcaggactc | 600 |
| tactccctca gcagcgtggt gaccgtgccc tccagcagct gggcacgaa gacctacacc | 660 |
| tgcaacgtag atcacaagcc cagcaacacc aaggtggaca agagagttga gtccaaatat | 720 |
| ggtcccccat gcccacctg cccagcacct gagttcgaag ggggaccatc agtcttcctg | 780 |
| ttccccccaa aacccaagga cactctcatg atctcccgga cccctgaggt cacgtgcgtg | 840 |
| gtggtggacg tgagccagga agaccccgag gtccagttca actggtacgt ggatggcgtg | 900 |
| gaggtgcata atgccaagac aaagccgcgg gaggagcagt tcaacagcac gtaccgtgtg | 960 |
| gtcagcgtcc tcaccgtcct gcaccaggac tggctgaacg gcaaggagta caagtgcaag | 1020 |
| gtctccaaca aaggcctccc gtcctccatc gagaaaacca tctccaaagc caaagggcag | 1080 |
| ccccgagagc cacaggtgta caccctgccc ccatcccagg aggagatgac caagaaccag | 1140 |
| gtcagcctga cctgcctggt caaaggcttc taccccagcg acatcgccgt ggagtgggag | 1200 |
| agcaatgggc agccggagaa caactacaag accacgcctc ccgtgctgga ctccgacggc | 1260 |
| tccttcttcc tctacagcag gctaaccgtg gacaagagca ggtggcagga ggggaatgtc | 1320 |
| ttctcatgct ccgtgatgca tgaggctctg cacaaccact acacacagaa gagcctctcc | 1380 |
| ctgtctctgg gtaaagctag ctga | 1404 |

<210> SEQ ID NO 26

```
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
atgagtgtgc ccactcaggt cctggggttg ctgctgctgt ggcttacagg tgccagatgt      60
gacatccaga tggctcagtc tccagcctcc ctatctgcat ctgtgggaga aactgtcacc     120
atcacatgtc gagcaagtga gaatatttac agttatttag catggtatca gcagaaacag     180
ggaaaatctc ctcagctcct ggtctataat gcaaaaacct tagcagaagg tgtgccatca     240
aggttcagtg gcagtggatc aggcacacag ttttctctga gatcaacagc ctgcagcct      300 gaagattttg ggagttatta ctgtcaacat cattatggtt ttccgtggac gttcggtgga     360
ggcaccaagc tcgagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctatgcct gcgaagtcac ccatcagggc     660
ctgagctcgc ccgtcacaaa gagcttcaac aggggagagt gttag                     705

<210> SEQ ID NO 27
<211> LENGTH: 1395
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atgaacttcg ggctcagctt gattttcctt gtcctcattt taaaaggtgt ccagtgtgag      60
gtgcagctgg tggagtctgg gggagactta gtgaagcctg agggtccct gaaactctcc     120 tgtgcagcct ctggattcac tttcagtagc tatggcatgt cttgggttcg ccagactcca     180
gacaagaggc tggagtgggt cgcagtcatt agtagtggtg gaagttccac cttctatcca     240
gacagtgtga aggggcgatt caccatctcc agagacaatg ccaagaacac cctgtacctg     300
caaatgagca gtctgaagtc tgaggacaca gccgtgtatt actgttcaag aggaggttac     360
tactttgact actggggcca aggcaccact ctcacagtct ccgcagccaa aacaaagggc     420
ccatccgtct tccccctggc gccctgctcc aggagcacct ccgagagcac agccgccctg     480
ggctgcctgg tcaaggacta cttccccgaa ccggtgacgg tgtcgtggaa ctcaggcgcc     540
ctgaccagcg gcgtgcacac cttcccggct gtcctacagt cctcaggact ctactccctc     600
agcagcgtgg tgaccgtgcc ctccagcagc ttgggcacga gacctacac ctgcaacgta      660 gatcacaagc ccagcaacac caaggtggac aagagagttg agtccaaata tggtccccca     720
tgcccaccct gcccagcacc tgagttcgaa ggggaccat cagtcttcct gttcccccca      780
aaacccaagg acactctcat gatctcccgg acccctgagg tcacgtgcgt ggtggtggac     840
gtgagccagg aagaccccga ggtccagttc aactggtacg tggatggcgt ggaggtgcat     900
aatgccaaga caaagccgcg ggaggagcag ttcaacagca cgtaccgtgt ggtcagcgtc     960
ctcaccgtcc tgcaccagga ctggctgaac ggcaaggagt acaagtgcaa ggtctccaac    1020
aaaggcctcc cgtcctccat cgagaaaacc atctccaaag ccaaagggca gccccgagag    1080
```

```
ccacaggtgt acaccctgcc cccatcccag gaggagatga ccaagaacca ggtcagcctg    1140
acctgcctgg tcaaaggctt ctaccccagc gacatcgccg tggagtggga gagcaatggg    1200
cagccggaga caactacaa gaccacgcct cccgtgctgg actccgacgg ctccttcttc    1260
ctctacagca ggctaaccgt ggacaagagc aggtggcagg aggggaatgt cttctcatgc    1320
tccgtgatgc atgaggctct gcacaaccac tacacacaga gagcctctc cctgtctctg    1380 ggtaaagcta gctga                                                     1395

<210> SEQ ID NO 28
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
atgaggttcc aggttcaggt tctggggctc cttctgctct ggatatcagg tgcccagtgt      60
gatgtccaga taacccagtc tccatcttat cttgctgcat ctcctggaga aaccattact     120
attaattgca gggcaagcaa gaccattagc aaatatttag cctggtatca agagaaacct     180
gagaaaactg ataagcttct tatctactct ggatccactt tgcaatctgg aattccatca     240
aggttcagtg gcagtggatc tggtacagat ttcactctca ccatcagtgg cctggagcct     300
gaagattttg caatgtatta ctgtcaacag cataatgaat accgtggac gttcggtgga     360 ggcaccaagc tcgagatcaa cgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacctgacg    600 ctgagcaaag cagactacga aaacacaaa gtctatgcct gcgaagtcac ccatcagggc     660
ctgagctcgc ccgtcacaaa gagcttcaac aggggagagt gttag                    705

<210> SEQ ID NO 29
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
atgggatgga gctggatctt tctctttctc ctgtcaggaa ctgcaggtgt cctctctgag      60
gtccagctgc aacagtctgg acctgagctg gtgaagcctg ggcttcagt gaagatatcc     120 tgcaaggctt ctggttactc attcactggc tactacatgc actgggtgaa gcaaagccat     180
gtaaagagcc ttgagtggat tggacgtatt aatccttaca atggtgctac tagctacaac     240
cagaatttca ggacaaggc cagcttgact gtagataagt cctccagcac agcctacatg     300
gagctccaca gcctgacatc tgaggactct gcagtctatt actgtgcaag agaggactac     360
gtctactggg gccaaggcac cactctcaca gtctcctcag ccaaaacgaa gggcccatcc     420
gtcttccccc tggcgccctg ctccaggagc acctccgaga gcacagccgc cctgggctgc     480
ctggtcaagg actacttccc cgaaccggtg acggtgtcgt ggaactcagg cgccctgacc     540
agcggcgtgc acaccttccc ggctgtccta cagtcctcag gactctactc cctcagcagc     600
```

```
gtggtgaccg tgccctccag cagcttgggc acgaagacct acacctgcaa cgtagatcac      660
aagcccagca acaccaaggt ggacaagaga gttgagtcca aatatggtcc cccatgccca      720
ccctgcccag cacctgagtt cgaagggggga ccatcagtct tcctgttccc cccaaaaccc    780
aaggacactc tcatgatctc ccggacccct gaggtcacgt gcgtggtggt ggacgtgagc     840
caggaagacc ccgaggtcca gttcaactgg tacgtggatg gcgtggaggt gcataatgcc     900
aagacaaagc cgcgggagga gcagttcaac agcacgtacc gtgtggtcag cgtcctcacc     960
gtcctgcacc aggactggct gaacggcaag gagtacaagt gcaaggtctc caacaaaggc    1020
ctcccgtcct ccatcgagaa aaccatctcc aaagccaaag gcagccccg agagccacag     1080 gtgtacaccc tgcccccatc ccaggaggag atgaccaaga accaggtcag cctgacctgc    1140
ctggtcaaag gcttctaccc cagcgacatc gccgtggagt gggagagcaa tgggcagccg    1200
gagaacaact acaagaccac gcctcccgtg ctggactccg acggctcctt cttcctctac    1260
agcaggctaa ccgtggacaa gagcaggtgg caggagggga atgtcttctc atgctccgtg    1320
atgcatgagg ctctgcacaa ccactacaca cagaagagcc tctccctgtc tctgggtaaa    1380
gctagctga                                                             1389

<210> SEQ ID NO 30
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
atgaagttgc ctgttaggct gttggtgctg atgttctgga ttcctgcttc cagcagtgat       60
gttgtgatga cccaaactcc actctccctg cctgtcagtc ttggagatca agcctccatc     120
tcttgcagat ctagtcagag ccttgtacac agtaatggaa acacctattt acattggtac     180
ctgcagaagc caggccagtc tccaaagctc ctgatctaca agtttccaa ccgattttct      240 ggggtcccag acaggttcag tggcagtgga tcagggacag atttcgcact caagatcagt    300
agagtggagg ctgaggatct gggagtttat ttctgctctc aaagtacaca tgttccgtgg    360
acgttcggtg gaggcaccaa gctcgagatc aaacgaactg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctatgc ctgcgaagtc      660 acccatcagg gcctgagctc gcccgtcaca aagagcttca caggggaga gtgttag        717

<210> SEQ ID NO 31
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
atggaatgga gttggatatt tctctttctt ctgtcaggaa ctgcaggtgt ccactctgag       60
gtccagctgc agcagtctgg acctgagctg gtaaagcctg gggcttcagt gaagatgtcc     120
tgcaaggctt ctggatacac attcactgac tatgttttgc actgggtgaa acagaagcct    180
```

```
gggcagggcc ttgagtggat tggatatatt aatccttaca atgatggtac taagtacaat      240
gagaagttca aaggcaaggc cacactgact tcagacaaat cctccagcac agcctacatg      300
gagctcagca gcctgacctc tgaggactct gcggtctatt actgtgcaag gggctatccg      360
gcctactctg gtatgctat ggactactgg ggtcaaggaa cctcagtcac cgtctcctca       420
gccaaaacga agggcccatc cgtcttcccc ctggcgccct gctccaggag cacctccgag      480
agcacagccg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacgaagacc      660
tacacctgca acgtagatca caagcccagc aacaccaagg tggacaagag agttgagtcc      720
aaatatggtc cccatgccc accctgccca gcacctgagt tcgaagggg accatcagtc        780 ttcctgttcc ccccaaaacc caaggacact ctcatgatct cccggacccc tgaggtcacg      840
tgcgtggtgg tggacgtgag ccaggaagac cccgaggtcc agttcaactg gtacgtggat      900
ggcgtggagg tgcataatgc caagacaaag ccgcgggagg agcagttcaa cagcacgtac      960
cgtgtggtca gcgtcctcac cgtcctgcac caggactggc tgaacggcaa ggagtacaag     1020
tgcaaggtct ccaacaaagg cctcccgtcc tccatcgaga aaaccatctc caaagccaaa     1080
gggcagcccc gagagccaca ggtgtacacc ctgcccccat cccaggagga gatgaccaag     1140
aaccaggtca gcctgacctg cctggtcaaa ggcttctacc ccagcgacat cgccgtggag     1200
tgggagagca atgggcagcc ggagaacaac tacaagacca cgcctcccgt gctggactcc     1260
gacggctcct tcttcctcta cagcaggcta accgtggaca agagcaggtg gcaggagggg     1320
aatgtcttct catgctccgt gatgcatgag gctctgcaca accactacac acagaagagc     1380
ctctccctgt ctctgggtaa agctagctga                                      1410
```

<210> SEQ ID NO 32
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
atgatgtcct ctgctcagtt ccttggtctc ctgttgctct gttttcaagg taccagatgt       60
gatatccaga tgacacagac tacatcctcc ctgtctgcct ctctgggaga cagagtcacc      120
atcagttgca gggcaagtca ggacattagc aattatttaa actggtatca gcagaaacca      180
gatggaactg ttaaactcct gatctactac acatcaagat acactcagg agtcccatca       240 aggttcagtg gcagtgggtc tggaacagat tattctctca ccattagcaa cctggagcaa      300
gaagatattg ccacttactt ttgccatcat ggtaatacgc ttccgtggac gttcggtgga     360
ggcaccaagc tcgagatcaa acgaactgtg gctgcaccat ctgtcttcat cttcccgcca      420
tctgatgagc agttgaaatc tggaactgcc tctgttgtgt gcctgctgaa taacttctat      480
cccagagagg ccaaagtaca gtggaaggtg gataacgccc tccaatcggg taactcccag      540
gagagtgtca cagagcagga cagcaaggac agcacctaca gcctcagcag cacc ctgacg     600 ctgagcaaag cagactacga gaaacacaaa gtctatgcct gcgaagtcac ccatcagggc      660
ctgagctcgc ccgtcacaaa gagcttcaac aggggagagt gttag                      705
```

<210> SEQ ID NO 33
<211> LENGTH: 1404
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

| | |
|---|---|
| atgaacttgg ggctcagctt gattttcctt gtccttgttt taaaaggtgt ccagtgtgaa | 60 |
| gtgaagctgg tggagtctgg gggaggctta gtgcagcctg agggtccct gaaactctcc | 120 |
| tgtgcaacct ctggattcac tttcagtgac tattacatgt attgggttcg ccagactcca | 180 |
| gagaagaggc tggagtgggt cgcatacatt aattctggtg gtggtagcac ctattatcca | 240 |
| gacactgtaa agggccgatt caccatctcc agagacaatg ccaagaacac cctgtacctg | 300 |
| caaatgagcc ggctgaagtc tgaggacaca gccatgtatt actgtgcaag acggggtta | 360 |
| ccgttccatg ctatggacta ttgggtcaa ggaacctcag tcaccgtctc ctcagccaaa | 420 |
| acgaagggcc catccgtctt cccctggcg ccctgctcca ggagcacctc cgagagcaca | 480 |
| gccgccctgg gctgcctggt caaggactac ttccccgaac cggtgacggt gtcgtggaac | 540 |
| tcaggcgccc tgaccagcgg cgtgcacacc ttcccggctg tcctacagtc ctcaggactc | 600 |
| tactccctca gcagcgtggt gaccgtgccc tccagcagct gggcacgaa gacctacacc | 660 |
| tgcaacgtag atcacaagcc cagcaacacc aaggtggaca gagagttga gtccaaatat | 720 |
| ggtcccccat gcccaccctg cccagcacct gagttcgaag gggaccatc agtcttcctg | 780 |
| ttccccccaa acccaaggga cactctcatg atctcccgga cccctgaggt cacgtgcgtg | 840 |
| gtggtggacg tgagccagga agaccccgag gtccagttca actggtacgt ggatggcgtg | 900 |
| gaggtgcata atgccaagac aaagccgcgg gaggagcagt tcaacagcac gtaccgtgtg | 960 |
| gtcagcgtcc tcaccgtcct gcaccaggac tggctgaacg gcaaggagta caagtgcaag | 1020 |
| gtctccaaca aaggcctccc gtcctccatc gagaaaacca tctccaaagc caagggcag | 1080 |
| ccccgagagc cacaggtgta caccctgccc catcccagg aggagatgac caagaaccag | 1140 |
| gtcagcctga cctgcctggt caaaggcttc taccccagcg acatcgccgt ggagtgggag | 1200 |
| agcaatgggc agccggagaa caactacaag accacgcctc ccgtgctgga ctccgacggc | 1260 |
| tccttcttcc tctacagcag gctaaccgtg gacaagagca ggtggcagga ggggaatgtc | 1320 |
| ttctcatgct ccgtgatgca tgaggctctg cacaaccact acacacagaa gagcctctcc | 1380 |
| ctgtctctgg gtaaagctag ctga | 1404 |

<210> SEQ ID NO 34
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

| | |
|---|---|
| atgatgtcct ctgctcagtt ccttggtctc ctgttgctct gttttcaagg taccagatgt | 60 |
| gatatccaga tgacacagac tacatcctcc ctgtctgcct ctctaggaga cagagtcacc | 120 |
| atcagttgca gtgcaagtca gggcattagc aattatttaa actggtatca gcagaaacca | 180 |
| gatggaactg ttaaactcct gatctattac acatcaattt tacactcagg agtcccatca | 240 |
| aggttcagtg gcagtgggtc tgggacagat tattctctca ccatcggcaa cctggaacct | 300 |

```
gaagatattg ccacttacta ttgtcagcag tttaataagc ttcctccgac gttcggtgga      360
ggcaccaaac tcgagatcaa acgaactgtg gctgcaccat ctgtcttcat cttcccgcca      420
tctgatgagc agttgaaatc tggaactgcc tctgttgtgt gcctgctgaa taacttctat      480
cccagagagg ccaaagtaca gtggaaggtg gataacgccc tccaatcggg taactcccag      540
gagagtgtca cagagcagga cagcaaggac agcacctaca gcctcagcag cacctgacg      600 ctgagcaaag cagactacga gaaacacaaa gtctatgcct gcgaagtcac ccatcagggc      660
ctgagctcgc ccgtcacaaa gagcttcaac aggggagagt gttag                     705
```

<210> SEQ ID NO 35
<211> LENGTH: 1405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
atggattggc tgtggaactt gctattcctg atggcagctg cccaaagtgc ccaagcacag       60
atccagttgg tgcagtctgg acctgagctg aagaagcctg gagagacagt caagatctcc      120
tgcaaggctt ctgggtattc cttcacaaac tatggaatga actgggtgaa acaggctcca      180
ggaaagggtt taaagtggat gggctggata aacacctaca ctggagagtc aacatatgct      240
gatgacttca agggacggtt tgccttctct ttggaaacct ctgccagcac tgcctatttg      300
cagatcagta acctcaaaaa tgaggacatg gctacatatt tctgtgctag aggggacttt      360
aggtactact atttgacta ctggggccaa ggcaccactc tcacaggctc ctcagccaaa       420
acgaagggcc catccgtctt cccctggcg ccctgctcca ggagcacctc cgagagcaca      480
gccgccctgg gctgcctggt caaggactac ttcccgaac cggtgacggt gtcgtggaac      540
tcaggcgccc tgaccagcgg cgtgcacacc ttcccggctg tcctacagtc ctcaggactc      600
tactccctca gcagcgtggt gaccgtgccc tccagcagct gggcacgaa gacctacacc      660 tgcaacgtag atcacaagcc cagcaacacc aaggtggaca agagagttga gtccaaatat      720
ggtcccccat gcccaccctg cccagcacct gagttcgaag ggggaccatc agtcttcctg      780
ttccccccaa aacccaagga cactctcatg atctccgga cccctgaggt cacgtgcgtg      840
gtggtggacg tgagccagga agaccccgag gtccagttca actggtacgt ggatggcgtg      900
gaggtgcata atgccaagac aaagccgcgg gaggagcagt tcaacagcac gtaccgtgtg      960
gtcagcgtcc tcaccgtcct gcaccaggac tggctgaacg gcaaggagta caagtgcaag     1020
gtctccaaca aaggcctccc gtcctccatc gagaaaacca tctccaaagc caaagggcag     1080
ccccgagagc cacaggtgta caccctgccc ccatcccagg aggagatgac caagaaccag     1140
gtcagcctga cctgcctggt caaaggcttc taccccagcg acatcgccgt ggagtgggag     1200
agcaatgggc agccggagaa caactacaag accacgcctc ccgtgctgga ctccgacggc     1260
tccttcttcc tctacagcag gctaaccgtg gacaagagca ggtggcagga ggggaatgtc     1320
ttctcatgct ccgtgatgca tgaggctctg cacaaccact acacacagaa gagcctctcc     1380
ctgtctctgg gtaaagctag ctgat                                          1405
```

<210> SEQ ID NO 36
<211> LENGTH: 702
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 36

```
atgagtgtgc tcactcaggt cctggcgttg ctgctgctgt ggcttacagg tgccagatgt      60
gacatccaga tgactcagtc tccagcctcc ctatctgcat ctgtgggaga aactgtcacc     120
atcacgtgtc gagcaagtgg gaatattcac aattatttag catggtatca gcagaaacag     180
ggaaaatctc ctcagctcct ggtctataat gcaaaaacct tggcagatgg tgtgccatca     240
aggttcagtg gcagtggatc aggaacacaa tattctctca gatcaacacc ctgcagcct      300
gaagattttg ggagttatta ctgtcaacat ttttgggatt cttggacgtt cggtggaggc     360
accaagctcg agatcaaacg aactgtggct gcaccatctg tcttcatctt cccgccatct     420
gatgagcagt tgaaatctgg aactgcctct gttgtgtgcc tgctgaataa cttctatccc     480
agagaggcca agtacagtg aaggtggat aacgccctcc aatcgggtaa ctcccaggag        540
agtgtcacag agcaggacag caaggacagc acctacagcc tcagcagcac cctgacgctg     600
agcaaagcag actacgagaa acacaaagtc tatgcctgcg aagtcaccca tcagggcctg     660
agctcgcccg tcacaaagag cttcaacagg ggagagtgtt ag                        702
```

<210> SEQ ID NO 37
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
atggaatgga cctgggtctt tctcttcctc ctgtcagtaa ctgcaggtgt ccactcccag      60
gttcagctgc agcagtctgg agctgagctg atgaagcctg gggcctcagt gaagatatcc     120
tgcaaggcta ctggctacac attcagtagc tactggatag agtgggtaaa gcagaggcct     180
ggacatggcc ttgagtggat tggagagatt ttacctggaa gtggtaggac taacgacaat     240
gagaagttca agggcaaggc cacattcact gcagatacat cctccaagaa agcctacatg     300
caactcagca gcctgacatc tgaggactct gccgtctatt attgtgcaag aagggggtggt    360
tactcctttg cttactgggg ccaagggact ctggtcactg tctctgcagc caaaacaaag     420
ggcccatccg tcttccccct ggcgccctgc tccaggagca cctccgagag cacagccgcc     480
ctgggctgcc tggtcaagga ctacttcccc gaaccggtga cggtgtcgtg aactcaggc      540
gccctgacca gcggcgtgca caccttcccg gctgtcctac agtcctcagg actctactcc     600
ctcagcagcg tggtgaccgt gccctccagc agcttgggca cgaagaccta cacctgcaac     660
gtagatcaca agcccagcaa caccaaggtg gacaagagag ttgagtccaa atatggtccc     720
ccatgcccac cctgcccagc acctgagttc aagggggac atcagtcttc ctgttccc       780
ccaaaaccca aggacactct catgatctcc cggacccctg aggtcacgtg cgtggtggtg     840
gacgtgagcc aggaagaccc cgaggtccag ttcaactggt acgtggatgg cgtggaggtg     900
cataatgcca agacaaagcc gcgggaggag cagttcaaca gcacgtaccg tgtggtcagc     960
gtcctcaccg tcctgcacca ggactggctg aacggcaagg agtacaagtg caaggtctcc    1020
aacaaaggcc tcccgtcctc catcgagaaa accatctcca agccaaagg gcagccccga    1080
gagccacagg tgtacaccct gcccccatcc caggaggaga tgaccaagaa ccaggtcagc    1140
ctgacctgcc tggtcaaagg cttctacccc agcgacatcg ccgtggagtg ggagagcaat    1200
```

| | |
|---|---|
| gggcagccgg agaacaacta caagaccacg cctcccgtgc tggactccga cggctccttc | 1260 |
| ttcctctaca gcaggctaac cgtggacaag agcaggtggc aggagggaa tgtcttctca | 1320 |
| tgctccgtga tgcatgaggc tctgcacaac cactacacac agaagagcct ctccctgtct | 1380 |
| ctgggtaaag ctagctga | 1398 |

<210> SEQ ID NO 38
<211> LENGTH: 1422
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 38

| | |
|---|---|
| atgaccatgt tctcactagc tcttctcctc agtcttcttc cctctgtgt ctctgattct | 60 |
| agggcagaaa caactgtgac ccagtctatg accatgttct cactagctct tctcctcagt | 120 |
| cttcttctcc tctgtgtctc tgattctagg gcagaaacaa ctgtgaccca gtctccagca | 180 |
| tccctgtcca tggctatagg ggaaaaagtc accatcagat gcgtaaccag cactgatatt | 240 |
| gatgatgatg tgaactggta ccagcagaag ccaggggaac ctcctaaaact ccttatttca | 300 |
| gaaggcaata ctcttcgtcc tggagtccca tcccgattct ccagcagtgg ctatggtaca | 360 |
| gattttgttt ttacaattga aacatgctc tcagaagatg ttgcagatta ctactgtttg | 420 |
| caaagtggta acttgccgta cacgttcgga ggggggacca agctcgagat caaacgaact | 480 |
| gtggctgcac catctgtctt catcttcccg ccatctgatg agcagttgaa atctggaact | 540 |
| gcctctgttg tgtgcctgct gaataacttc tatcccagag aggccaaagt acagtggaag | 600 |
| gtggataacg ccctccaatc gggtaactcc caggagagtg tcacagagca ggacagcaag | 660 |
| gacagcacct acagcctcag cagcaccctg acgctgagca agcagacta cgagaaacac | 720 |
| aaagtctatg cctgcgaagt cacccatcag ggcctgagct cgcccgtcac aaagagcttc | 780 |
| aacaggggag agtgttagcc agcatccctg tccatggcta gggggaaaa agtcaccatc | 840 |
| agatgcgtaa ccagcactga tattgatgat gatgtgaact ggtaccagca gaagccaggg | 900 |
| gaacctccta aactccttat tcagaaggc aatactcttc gtcctggagt cccatcccga | 960 |
| ttctccagca gtggctatgg tacagatttt gttttacaa ttgagaacat gctctcagaa | 1020 |
| gatgttgcag attactactg tttgcaaagt ggtaacttgc cgtacacgtt cggagggggg | 1080 |
| accaagctcg agatcaaacg aactgtggct gcaccatctg tcttcatctt cccgccatct | 1140 |
| gatgagcagt tgaaatctgg aactgcctct gttgtgtgcc tgctgaataa cttctatccc | 1200 |
| agagaggcca aagtacagtg gaaggtggat aacgccctcc aatcgggtaa ctcccaggag | 1260 |
| agtgtcacag agcaggacag caaggacagc acctacagcc tcagcagcac cctgacgctg | 1320 |
| agcaaagcag actacgagaa acacaaagtc tatgcctgcg aagtcaccca tcagggcctg | 1380 |
| agctcgcccg tcacaaagag cttcaacagg ggagagtgtt ag | 1422 |

<210> SEQ ID NO 39
<211> LENGTH: 1404
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 39

| | |
|---|---|
| atggcttggg tgtggacctt gctattcctg atggcagctg cccaaagtgc ccaagcacag | 60 |
| atccagttgg tgcagtctgg acctgagctg aagaagcctg agagacagt caagatctcc | 120 |
| tgcaaggctt ctgggtatac cttcacaaac tatggaatga actgggtgaa gcaggctcca | 180 |
| ggaaaggggtt taaagtgggt gggctggata acaccttca ctggagagcc aacatatgtt | 240 |
| gatgacttca agggacggtt tgccttctct ttggaaacct ctgccagcac tgcctatttg | 300 |
| cagatcaaca acctcaaaaa tgaggacacg gctacatatt tctgtgcaag agggaatttt | 360 |
| aggtactact actttgacta ctggggccaa ggcaccactc tcacagtctc ctcagccaaa | 420 |
| acaaagggcc catccgtctt ccccctggcg ccctgctcca ggagcacctc cgagagcaca | 480 |
| gccgccctgg gctgcctggt caaggactac ttccccgaac cggtgacggt gtcgtggaac | 540 |
| tcaggcgccc tgaccagcgg cgtgcacacc ttcccggctg tcctacagtc ctcaggactc | 600 |
| tactccctca gcagcgtggt gaccgtgccc tccagcagct gggcacgaa gacctacacc | 660 |
| tgcaacgtag atcacaagcc cagcaacacc aaggtggaca gagagttga gtccaaatat | 720 |
| ggtcccccat gcccaccctg cccagcacct gagttcgaag gggaccatc agtcttcctg | 780 |
| ttccccccaa aacccaagga cactctcatg atctcccgga cccctgaggt cacgtgcgtg | 840 |
| gtggtggacg tgagccagga agaccccgag gtccagttca actggtacgt ggatggcgtg | 900 |
| gaggtgcata atgccaagac aaagccgcgg gaggagcagt tcaacagcac gtaccgtgtg | 960 |
| gtcagcgtcc tcaccgtcct gcaccaggac tggctgaacg gcaaggagta caagtgcaag | 1020 |
| gtctccaaca aaggcctccc gtcctccatc gagaaaacca tctccaaagc caaagggcag | 1080 |
| ccccgagagc cacaggtgta caccctgccc ccatcccagg aggagatgac caagaaccag | 1140 |
| gtcagcctga cctgcctggt caaaggcttc taccccagcg acatcgccgt ggagtgggag | 1200 |
| agcaatgggc agccggagaa caactacaag accacgcctc ccgtgctgga ctccgacggc | 1260 |
| tccttcttcc tctacagcag gctaaccgtg gacaagagca ggtggcagga ggggaatgtc | 1320 |
| ttctcatgct ccgtgatgca tgaggctctg cacaaccact acacacagaa gagcctctcc | 1380 |
| ctgtctctgg gtaaagctag ctga | 1404 |

<210> SEQ ID NO 40
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

| | |
|---|---|
| atgagtgtgc tcactcaggt cctggcgttg ctgctgctgt ggcttacagg tgccagatgt | 60 |
| gacatccaga tgactcagtc cccagcctcc ctatctgcat ctgtgggaga aactgtcacc | 120 |
| atcacatgtc gaacaagtgg gaatattcgc aattatttag catggtatca gcagaaacag | 180 |
| ggaaaatctc ctcaactcct ggtctataat gcaaaaacct tagcagatgg tgtgccatca | 240 |
| aggttcggtg gcagtggatc aggaacacaa tattctctca agatcaacag cctgcagcct | 300 |
| gaagattttg ggaattatta ctgtcaacat ttttggagta gtccgtacac gttcggaggg | 360 |
| gggaccaagc tcgagatcaa acgaactgtg gctgcaccat ctgtcttcat cttcccgcca | 420 |
| tctgatgagc agttgaaatc tggaactgcc tctgttgtgt gcctgctgaa taacttctat | 480 |
| cccagagagg ccaaagtaca gtggaaggtg gataacgccc tccaatcggg taactcccag | 540 |
| gagagtgtca cagagcagga cagcaaggac agcacctaca gcctcagcag cacccttgacg | 600 |

| | |
|---|---|
| ctgagcaaag cagactacga gaaacacaaa gtctatgcct gcgaagtcac ccatcagggc | 660 |
| ctgagctcgc ccgtcacaaa gagcttcaac aggggagagt gttag | 705 |

<210> SEQ ID NO 41
<211> LENGTH: 2811
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

| | |
|---|---|
| atgatgggat ggagctatat catcctcttt ttggtagcaa cagctacaga tgtccactcc | 60 |
| caggtccaac tgcagcagcc tggggctgaa ctggtgaagc ctggggcttc agtgaagctg | 120 |
| tcctgcaagg cttctggcta caccttcacc agctactgga tgcactgggt gaagcagagg | 180 |
| cctggagaag gccttgagtg gattggagag attaatccta gctacggtcg tactgactac | 240 |
| aatgagaagt tcaagaacaa ggccacactg actgtagcca aatcctccag cacagcctac | 300 |
| atgcaactca gcagcctgac atctgaggac tctgcggtct attactgtgc aagaggagat | 360 |
| tactacggta gtagctcgtt tgcttactgg ggccaaggga ctctggtcac tgtctctgca | 420 |
| gccaaaacaa agggcccatc cgtcttcccc ctggcgccct gctccaggag cacctccgag | 480 |
| agcacagccg ccctgggctg cctggtcaag gactacttcc ccgaaccggt gacggtgtcg | 540 |
| tggaactcag gcgccctgac cagcggcgtg cacaccttcc cggctgtcct acagtcctca | 600 |
| ggactctact ccctcagcag cgtggtgacc gtgccctcca gcagcttggg cacgaagacc | 660 |
| tacacctgca acgtagatca caagcccagc aacaccaagg tggacaagag agttgagtcc | 720 |
| aaatatggtc cccatgccc accctgccca gcacctgagt tcgaaggggg accatcagtc | 780 |
| ttcctgttcc ccccaaaacc caaggacact ctcatgatct cccggacccc tgaggtcacg | 840 |
| tgcgtggtgg tggacgtgag ccaggaagac cccgaggtcc agttcaactg gtacgtggat | 900 |
| ggcgtggagg tgcataatgc caagacaaag ccgcgggagg agcagttcaa cagcacgtac | 960 |
| cgtgtggtca gcgtcctcac cgtcctgcac caggactggc tgaacggcaa ggagtacaag | 1020 |
| tgcaaggtct ccaacaaagg cctcccgtcc tccatcgaga aaaccatctc caaagccaaa | 1080 |
| gggcagcccc gagagccaca ggtgtacacc ctgcccccat cccaggagga tgaccaag | 1140 |
| aaccaggtca gcctgacctg cctggtcaaa ggcttctacc ccagcgacat cgccgtggag | 1200 |
| tgggagagca atgggcagcc ggagaacaac tacaagacca cgcctcccgt gctggactcc | 1260 |
| gacggctcct tcttcctcta cagcaggcta accgtggaca agagcaggtg gcaggagggg | 1320 |
| aatgtcttct catgctccgt gatgcatgag gctctgcaca accactacac acagaagagc | 1380 |
| ctctcccctgt ctctgggtaa agctagcgga tggagctata tcatcctctt tttggtagca | 1440 |
| acagctacag atgtccactc ccaggtccaa ctgcagcagc ctggggctga actggtgaag | 1500 |
| cctggggctt cagtgaagct gtcctgcaag gcttctggct acaccttcac cagctactgg | 1560 |
| atgcactggg tgaagcagag gcctggagaa ggccttgagt ggattggaga gattaatcct | 1620 |
| agctacggtc gtactgacta caatgggaag ttcaagaaca aggccacact gactgtagcc | 1680 |
| aaatcctcca gcacagccta catgcaactc agcagcctga catctgagga ctctgcggtc | 1740 |
| tattactgtg caagaggaga ttactacggt agtagctcgt ttgcttactg gggccaaggg | 1800 |
| actctggtca ctgtctctgc agccaaaaca aagggcccat ccgtcttccc cctggcgccc | 1860 |
| tgctccagga gcacctccga gagcacagcc gccctgggct gcctggtcaa ggactacttc | 1920 |

```
cccgaaccgg tgacggtgtc gtggaactca ggcgccctga ccagcggcgt gcacaccttc    1980
ccggctgtcc tacagtcctc aggactctac tccctcagca gcgtggtgac cgtgccctcc    2040
agcagcttgg gcacgaagac ctacacctgc aacgtagatc acaagcccag caacaccaag    2100
gtggacaaga gagttgagtc caaatatggt cccccatgcc caccctgccc agcacctgag    2160
ttcgaagggg gaccatcagt cttcctgttc cccccaaaac caaggacac tctcatgatc    2220 tcccggaccc ctgaggtcac gtgcgtggtg gtggacgtga gccaggaaga ccccgaggtc    2280
cagttcaact ggtacgtgga tggcgtggag gtgcataatg ccaagacaaa gccgcgggag    2340
gagcagttca acagcacgta ccgtgtggtc agcgtcctca ccgtcctgca ccaggactgg    2400
ctgaacggca aggagtacaa gtgcaaggtc tccaacaaag gcctcccgtc ctccatcgag    2460
aaaaccatct ccaaagccaa agggcagccc cgagagccac aggtgtacac cctgccccca    2520
tcccaggagg agatgaccaa gaaccaggtc agcctgacct gcctggtcaa aggcttctac    2580
cccagcgaca tcgccgtgga gtgggagagc aatgggcagc cggagaacaa ctacaagacc    2640
acgcctcccg tgctggactc cgacggctcc ttcttcctct acagcaggct aaccgtggac    2700
aagagcaggt ggcaggaggg gaatgtcttc tcatgctccg tgatgcatga ggctctgcac    2760
aaccactaca cacagaagag cctctcccctg tctctgggta aagctagctg a             2811
```

<210> SEQ ID NO 42
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
atggattttc aagtgcagat tttcagcttc ctgctaatga gtgcctcagt cataatgtcc      60
aggggacaaa ttgttctcac ccagtctcca gcactcatgt ctgcatctcc aggggagaag    120
gtcaccatga cctgcagtgc cagctcaaat ataagttaca tgtactggta ccagcagaag    180
ccaagatcct cccccaaacc ctggatttat ctcacatcca acctggcttc tggagtccct    240
gctcgcttca gtggcagtgg gtctgggacc tcttactctc tcacaaccag cagcatggag    300
gctgaagatg ctgccactta ttgctgccag cagtggagta gtaacccacc cacgttcggt    360
gctgggacca agctcgagat caaacgaact gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctatg cctgcgaagt cacccatcag    660
ggcctgagct cgcccgtcac aaagagcttc aacaggggag agtgttag               708
```

<210> SEQ ID NO 43
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
atggattttc gagtgcagat tttcagcttc ctgctaatga gtgcctcagt cataatgtcc      60
aggggacaaa ttgttctcac ccagtctcca gcactcatgt ctgcatctcc aggggagaag    120
```

```
gtcaccatga cctgcagtgc cagctcaaat ataagttaca tgtactggta ccagcagaag      180
ccaagatcct cccccaaacc ctggatttat ctcacatcca acctggcttc tggagtccct      240
gctcgcttca gtggcagtgg gtctgggacc tcttactctc tcacaatcag cagcatggag      300
gctgaagatg ctgccactta ttactgccag cagtggagta gtaacccacc cacgttcggt      360
gctgggacca agctcgagat caaacgaact gtggctgcac catctgtctt catcttcccg      420
ccatctgatg agcagttgaa atctggaact gcctctgttg tgtgcctgct gaataacttc      480
tatcccagag aggccaaagt acagtggaag gtggataacg ccctccaatc gggtaactcc      540
caggagagtg tcacagagca ggacagcaag gacagcacct acagcctcag cagcaccctg      600
acgctgagca agcagactac gagaaacac aaagtctatg cctgcgaagt cacccatcag      660
ggcctgagct cgcccgtcac aaagagcttc aacaggggag agtgttag                  708
```

```
<210> SEQ ID NO 44
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atggagacag acacactcct gctatgggtg ctgctgctct gggttccagg ttccacaggt       60
gacattgtgc tgatccaatc tccagcttct ttggctgtgt ctctagggca gagggccacc      120
atatcctgca gagccagtga aagtgttgat agttatgtca atagttttat gcactggtac      180
cagcagaaac caggacagcc acccaaactc ctcatctatc gtgtatccaa cctagaatct      240
gggatccctg ccaggttcag tggcagtggg tctaggacag acttcaccct caccattaat      300
cctgtggagg ctgatgatgt tgcaacctat tactgtcagc aaagtaatga ggatccattc      360
acgttcggct cggggacaaa gctcgagatc aaacgaactg tggctgcacc atctgtcttc      420
atcttcccgc catctgatga gcagttgaaa tctggaactg cctctgttgt gtgcctgctg      480
aataacttct atcccagaga ggccaaagta cagtggaagg tggataacgc cctccaatcg      540
ggtaactccc aggagagtgt cacagagcag gacagcaagg acagcaccta cagcctcagc      600
agcaccctga cgctgagcaa agcagactac gagaaacaca aagtctatgc ctgcgaagtc      660
acccatcagg gcctgagctc gcccgtcaca aagagcttca acaggggaga gtgttag        717
```

```
<210> SEQ ID NO 45
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
atggaatgta ctggatatct cctttttatt ctgtcggtaa tttcaggggt ctactcagag       60
gttcagctcc agcagtctgg gactgtgctg gcaaggcctg ggcttccgt gaatatgtcc      120 tgtaaggctg ctggctacag ctttaccagt tactgggtga ctgggtcaa acagaggcct      180 ggacagggtc tggaatggat tggtgctatt tacccctaaaa atagtagaac tagctacaac      240
cagaagttcc aggacaaggc cacactgact gcagtcacat ccgccagcac tgcctacatg      300
gagctcagca gcctgacaaa tgaggactct gcggtctatt actgtacaag acctcactat      360
```

```
gattcgtttg gttactgggg ccaagggact ctggtcactg tctctgcagc caaaacaaag    420
ggcccatccg tcttccccct ggcgccctgc tccaggagca cctccgagag cacagccgcc    480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcttgggca cgaagaccta cacctgcaac    660
gtagatcaca agcccagcaa caccaaggtg gacaagagag ttgagtccaa atatggtccc    720
ccatgcccac cctgcccagc acctgagttc gaaggggac catcagtctt cctgttcccc     780
ccaaaaccca aggacactct catgatctcc cggacccctg aggtcacgtg cgtggtggtg    840
gacgtgagcc aggaagaccc cgaggtccag ttcaactggt acgtggatgg cgtggaggtg    900
cataatgcca agacaaagcc gcgggaggag cagttcaaca gcacgtaccg tgtggtcagc    960
gtcctcaccg tcctgcacca ggactggctg aacggcaagg agtacaagtg caaggtctcc   1020
aacaaaggcc tcccgtcctc catcgagaaa accatctcca agccaaaggg cagcccccga   1080
gagccacagg tgtacaccct gccccatcc caggaggaga tgaccaagaa ccaggtcagc    1140
ctgacctgcc tggtcaaagg cttctacccc agcgacatcg ccgtggagtg ggagagcaat   1200
gggcagccgg agaacaacta caagaccacg cctcccgtgc tggactccga cggctccttc   1260
ttcctctaca gcaggctaac cgtggacaag agcaggtggc aggaggggaa tgtcttctca   1320
tgctccgtga tgcatgaggc tctgcacaac cactacacac agaagagcct ctccctgtct   1380
ctgggtaaag ctagctga                                                 1398

<210> SEQ ID NO 46
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
atggagacag acacactcct gctatgggtg ctgctgctct ggttccaggt ttccacaggt     60
gacattgtgc tgacccaatc tccagcttct ttggctgtgt ctctagggca gagggccacc    120
atatcctgca gagccagtga aagtgtagat agttatggca ttagttttat gcactggtac    180
cagcagaaac aggacagcc acccaaactc ctcatctatc gtgcatccaa ccaagaatct    240
gggatccctg ccaggttcag tggcagtggg tctaggacag acttcaccct caccattaat    300
cctgtggagg ctgatgatgt tgcaacctat tactgtcagc aaagtaatga ggatccgctc    360
acgttcggtg ctgggaccaa gctcgagatc aaacgaactg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctatgc ctgcgaagtc    660
acccatcagg gcctgagctc gcccgtcaca aagagcttca caggggaga gtgttag        717

<210> SEQ ID NO 47
<211> LENGTH: 1422
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 47

```
atgaacaggc ttacttcctc attgctgctg ctgattgtcc ctgcatatgt cctgtcccag      60
gttactctga aagagtctgg ccctgggata ttgcagccct cccagaccct cagtctgact     120
tgttctttct ctgggttttc actgagcact tctggtatgg gtgtgagctg gattcgtcag     180
ccttcaggaa agggtctgga gtggctggca cacatttact gggatgatga caagcgctat     240
aatccatccc tgaagagccg gctcacaatc tttaaggatc cctccagcaa ccaggtattc     300
ctcaggatca ccagtgtgga cactgcagat actgccacat actactgtgc tcgaaactcc     360
cattactacg gtagtactta cggggggatac ttcgatgtct ggggcgcagg gaccacggtc     420
accgtctcct cagccaaaac aaagggccca tccgtcttcc ccctggcgcc ctgctccagg     480
agcacctccg agagcacagc cgccctgggc tgcctggtca aggactactt ccccgaaccg     540
gtgacggtgt cgtggaactc aggcgccctg accagcggcg tgcacacctt cccggctgtc     600
ctacagtcct caggactcta ctccctcagc agcgtggtga ccgtgccctc cagcagcttg     660
ggcacgaaga cctacacctg caacgtagat cacaagccca gcaacaccaa ggtggacaag     720
agagttgagt ccaaatatgg tcccccatgc ccacccctgcc cagcacctga gttcgaaggg     780
ggaccatcag tcttcctgtt ccccccaaaa cccaaggaca ctctcatgat ctcccggacc     840
cctgaggtca cgtgcgtggt ggtggacgtg agccaggaag accccgaggt ccagttcaac     900
tggtacgtgg atggcgtgga ggtgcataat gccaagacaa agccgcggga ggagcagttc     960
aacagcacgt accgtgtggt cagcgtcctc accgtcctgc accaggactg gctgaacggc    1020
aaggagtaca agtgcaaggt ctccaacaaa ggcctcccgt cctccatcga gaaaaccatc    1080
tccaaagcca aagggcagcc ccgagagcca caggtgtaca ccctgccccc atcccaggag    1140
gagatgacca agaaccaggt cagcctgacc tgcctggtca aaggcttcta ccccagcgac    1200
atcgccgtgg agtgggagag caatgggcag ccggagaaca actacaagac cacgcctccc    1260
gtgctggact ccgacggctc cttcttcctc tacagcaggc taaccgtgga caagagcagg    1320
tggcaggagg ggaatgtctt ctcatgctcc gtgatgcatg aggctctgca caaccactac    1380
acacagaaga gcctctccct gtctctgggt aaagctagct ga                       1422
```

<210> SEQ ID NO 48
<211> LENGTH: 717
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
atggagacag acacactcct gctatgggtg ctgctgctcg gggttccagg ttccacaggt      60
aacattgtgc tgacccagtc tccaacttct ttcactgtgt ctcttgggca gagggccacc     120
atatcctgca gagccagtga aagtgttcat agttatggca atagtttat gcactggtac     180
cagcagaaac cagggcagcc acccaaactc ctcatctatc ttgcatccaa cgtagaatct     240
ggggtccctg ccaggttcag tggtagtggg tccaggacag acttcaccct caccattgat     300
cctgtggagg ctgatgatgc tgcaacctat tactgtcagc aaaatagtga ggatccgtgg     360
acgttcggtg gaggcaccaa gctcgagatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
```

```
ggtaactccc aggagagtgt cacagagcag acagcaagg acagcaccta cagcctcagc    600
agcaccctga cgctgagcaa agcagactac gagaaacaca aagtctatgc ctgcgaagtc    660
acccatcagg gcctgagctc gcccgtcaca aagagcttca cagggaga gtgttag        717
```

<210> SEQ ID NO 49
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
atggaatgga cctgggtctt tctcttcctc ctgtcagtaa ctgcaggtgt ccactcccag     60
gttcagctgc agcagtctgg aactgagctg atgaagcctg gggcctcagt gaagatatcc    120
tgcaaggcta ctggctacac attcagtacc tactggatag agtgggtaaa gcagaggcct    180
ggacatggcc ttgagtggat tggagagatt ttacctggaa gtggtaggac taacgacaat    240
gagaagttca gggcaaggc cacaatcact gcagatacat cctccaagaa agcctacatg    300
caactcagca gcctgacatc tgaggactct gccgtctatt actgtgcaag aaggggtggt    360 tactccttg ctttctgggg ccaagggact ctggtctctg tctctgcagc caaaacaaag    420
ggcccatccg tcttccccct ggcgccctgc tccaggagca cctccgagag cacagccgcc    480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcttgggca cgaagaccta cacctgcaac    660
gtagatcaca agcccagcaa caccaaggtg gacaagagag ttgagtccaa atatggtccc    720
ccatgcccac cctgcccagc acctgagttc gaaggggac catcagtctt cctgttcccc    780
ccaaaaccca aggacactct catgatctcc cggacccctg aggtcacgtg cgtggtggtg    840
gacgtgagcc aggaagaccc cgaggtccag ttcaactggt acgtggatgg cgtggaggtg    900
cataatgcca agacaaagcc gcgggaggag cagttcaaca gcacgtaccg tgtggtcagc    960
gtcctcaccg tcctgcacca ggactggctg aacggcaagg agtacaagtg caaggtctcc    1020
aacaaaggcc tcccgtcctc catcgagaaa accatctcca aagccaaagg gcagccccga    1080
gagccacagg tgtacaccct gcccccatcc caggaggaga tgaccaagaa ccaggtcagc    1140
ctgacctgcc tggtcaaagg cttctacccc agcgacatcg ccgtggagtg ggagagcaat    1200
gggcagccgg agaacaacta caagaccacg cctcccgtgc tggactccga cggctccttc    1260
ttcctctaca gcaggctaac cgtggacaag agcaggtggc aggagggaa tgtcttctca    1320 tgctccgtga tgcatgaggc tctgcacaac cactacacac agaagagcct ctccctgtct    1380
ctgggtaaag ctagctga                                                 1398
```

<210> SEQ ID NO 50
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
atgaccatgt tctcactagc tcttctcctc agtcttcttc tcctctgtgt ctctgattct     60
```

| | |
|---|---|
| agggcagaaa caactgtgac ccagtctcca gcatccctgt ccatggctat aggagaaaaa | 120 |
| gtcaccatca gatgcgtaac cagcactgat attgatgatg atgtgaactg gtaccagcag | 180 |
| aagccagggg aacctcctaa gctccttatt tcagaaggca atactcttcg tgctggagtc | 240 |
| ccatcccgat tctccagcag tggctatggt acagattttg tttttacaat tgagaacatg | 300 |
| ctctcagaag atgttgcaga ttactactgt ttgcaaagtg gtaacttgcc gtacacgttc | 360 |
| ggagggggga ccaagctcga gatcaaacga actgtggctg caccatctgt cttcatcttc | 420 |
| ccgccatctg atgagcagtt gaaatctgga actgcctctg ttgtgtgcct gctgaataac | 480 |
| ttctatccca gagaggccaa agtacagtgg aaggtggata cgccctcca atcgggtaac | 540 |
| tcccaggaga gtgtcacaga gcaggacagc aaggacagca cctacagcct cagcagcacc | 600 |
| ctgacgctga gcaaagcaga ctacgagaaa cacaaagtct atgcctgcga agtcacccat | 660 |
| cagggcctga gctcgcccgt cacaaagagc ttcaacaggg gagagtgtta g | 711 |

<210> SEQ ID NO 51
<211> LENGTH: 1422
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

| | |
|---|---|
| atgaacaggc ttacttcctc attgctgctg ctgattgtcc ctgcatatgt cctgtcccag | 60 |
| gttactctga aagagtctgg ccctgggata ttgcagccct cccagaccct cagtctgact | 120 |
| tgttctttct ctgggttttc actgagcact tctggtatgg gtctgagctg gattcgtcag | 180 |
| ccttcaggaa agggtctgga gtggctggca cacatttact gggatgatga caagcgctat | 240 |
| aacccatccc tgaagagccg gctcacaatc tccaaggata cctccagcaa ccaggttttc | 300 |
| ctcaagatca ccattgtgga cactgcagat gctgccacat actgtgtgc tcgaagctcc | 360 |
| cattactacg gttatggcta cggggggatac ttcgatgtct ggggcgcagg gaccacggtc | 420 |
| accgtctcct cagccaaaac gaagggccca tccgtcttcc ccctggcgcc ctgctccagg | 480 |
| agcacctccg agagcacagc cgccctgggc tgcctggtca aggactactt ccccgaaccg | 540 |
| gtgacggtgt cgtggaactc aggcgccctg accagcggcg tgcacacctt cccggctgtc | 600 |
| ctacagtcct caggactcta ctccctcagc agcgtggtga ccgtgccctc agcagcttg | 660 |
| ggcacgaaga cctacacctg caacgtagat cacaagccca gcaacaccaa ggtggacaag | 720 |
| agagttgagt ccaaatatgg tcccccatgc ccaccctgcc cagcacctga gttcgaaggg | 780 |
| ggaccatcag tcttcctgtt ccccccaaaa cccaaggaca ctctcatgat ctcccggacc | 840 |
| cctgaggtca cgtgcgtggt ggtggacgtg agccaggaag accccgaggt ccagttcaac | 900 |
| tggtacgtgg atggcgtgga ggtgcataat gccaagacaa agccgcggga ggagcagttc | 960 |
| aacagcacgt accgtgtggt cagcgtcctc accgtcctgc accaggactg gctgaacggc | 1020 |
| aaggagtaca agtgcaaggt ctccaacaaa ggcctcccgt cctccatcga gaaaaccatc | 1080 |
| tccaaagcca aagggcagcc ccgagagcca caggtgtaca ccctgccccc atcccaggag | 1140 |
| gagatgacca agaaccaggt cagcctgacc tgcctggtca aaggcttcta ccccagcgac | 1200 |
| atcgccgtgg agtgggagag caatgggcag ccggagaaca actacaagac cacgcctccc | 1260 |
| gtgctggact ccgacggctc cttcttcctc tacagcaggc taaccgtgga caagagcagg | 1320 |
| tggcaggagg ggaatgtctt ctcatgctcc gtgatgcatg aggctctgca caaccactac | 1380 |

```
acacagaaga gcctctccct gtctctgggt aaagctagct ga                         1422
```

<210> SEQ ID NO 52
<211> LENGTH: 823
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
atggagacag acacactcct gctatgggtg ctgctgctct ggttccagg ttccacaggt         60
aacattgtgc tgacccaatc tccagcttct ttggctgtgt ctctagggca gagggccacc      120
atatcctgca gagccagtga aagtattcat agttatggca atagttttct gcactggtac      180
cagcagaaac aggacagcc acccaaactc ctcatctatc ttgcatccaa cctagaatct       240
ggggtccctg ccaggttcag cggcagtggg tctaggacag acttcaccct caccattgat      300
cctgtggagc tgatgatgc tgcaacctat tactgtcagc aaaataatga ggatccgtgg       360
acgttcggtg gaggcaccaa gctcgagatc aaacgaactg tggctgcacc atctgtcttc      420
atcttcccgc catctgatga gcagttgaaa tctggaactg cctctgttgt gtgcctgctg      480
aataacttct atcccagaga ggccaaagta cagtggaagg tggataacgc cctccaatcg      540
ggtaactccc aggagagtgt cacagagcag gacagcaagg acagcaccta cagcctcagc      600
agcaccctga cgctgagcaa agcagactac gagaaacaca agtctatgc ctgcgaagtc       660
acccatcagg gcctgagctc gcccgtcaca aagagcttca caggggaga gtgttaggcg       720
gccgcactag cgcgggccgc attcgaagag ctcggtaccc ggggatcctc tagagtcgac      780
ctgcaggcat gcaagctggc cgcgactcta gatcataatc agc                         823
```

<210> SEQ ID NO 53
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
atgaaatgca gctgggtcat cttcttcctg atggcagtgg ttacaggggt caattcagag        60
gttcagctgc agcagtctgg ggctgagctt gtgaggccag ggccttagt caagttgtcc       120
tgcaaagctt ctggcttcaa cattaatgac tactatatcc actgggtgaa gcagcggcct      180
gaacagggcc tggagcggat tggatggatt gatcctgaca atggtaatac tatatatgac      240
ccgaagttcc agggcaaggc cagtataaca gcagacacat cccccaacac agcctacctg      300
cagctcagca gcctgacatc tgaggacact gccgtctatt actgtgctag aacccgatct      360
cctatggtta cgacgggtt tgtttactgg ggccaaggga ctgtggtcac tgtctctgca      420
gccaaaacga agggcccatc cgtcttcccc ctggcgccct gctccaggag cacctccgag      480
agcacagccg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacgaagacc      660
tacacctgca acgtagatca caagcccagc aacaccaagg tggacaagag agttgagtcc      720
aaatatggtc cccatgccc accctgccca gcacctgagt tcgaagggg accatcagtc       780
ttcctgttcc ccccaaaacc caaggacact ctcatgatct cccggacccc tgaggtcacg      840
```

```
tgcgtggtgg tggacgtgag ccaggaagac cccgaggtcc agttcaactg gtacgtggat    900
ggcgtggagg tgcataatgc caagacaagg ccgcggagg agcagttcaa cagcacgtac    960
cgtgtggtca gcgtcctcac cgtcctgcac caggactggc tgaacggcaa ggagtacaag   1020
tgcaaggtct ccaacaaagg cctcccgtcc tccatcgaga aaaccatctc caaagccaaa   1080
gggcagcccc gagagccaca ggtgtacacc ctgcccccat cccaggagga tgaccaag     1140 aaccaggtca gcctgacctg cctggtcaaa ggcttctacc ccagcgacat cgccgtggag   1200
tgggagagca atgggcagcc ggagaacaac tacaagacca cgcctcccgt gctggactcc   1260
gacggctcct tcttcctcta cagcaggcta accgtggaca gagcaggtg gcaggagggg    1320 aatgtcttct catgctccgt gatgcatgag gctctgcaca accactacac acagaagagc   1380
ctctccctgt ctctgggtaa atga                                          1404
```

<210> SEQ ID NO 54
<211> LENGTH: 1425
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
atggaaaggc actggatctt tctcttcctg ttttcagtaa ctgcaggtgt ccactcccag     60
gtccagcttc agcagtctgg ggctgagctg gcaaaacctg gggcctcagt gaagatgtcc    120
tgcaaggctt ctggctacac ctttactacc tactggatgc actgggtaaa acagaggcct    180
ggacagggtc tggaatggat tggatacatt aatcctatca ctggttatac tgagtacaat    240
cagaagttca aggacaaggc caccttgact gcagacaaat cctccagcac agcctacatg    300
caactgagca gcctgacatc tgaggactct gcagtctatt actgtgcaag agagggttta    360
agtgctatgg actattgggg tcagggaacc tcagtcaccg tcacctcagc caaaacaaca    420
gccccatcgg tctatccact ggcccctgtg tgtggagata aactggctc ctcggtaact     480 ctaggatgcc tggtcaaggg ttatttccct gagccagtga ccttgacctg gaactctgga    540
tccctgtcca gtggtgtgca caccttccca gctgtcctgc agtctgacct ctacaccctc    600
agcagctcag tgactgtaac ctcgagcacc tggcccagcc agaccgtcac ctgcagcgtt    660
gctcacccag ccagcagcac cacggtggac aaaaaacttg agcccagcgg gcccatttca    720
acaatcaacc cctgtcctcc atgcaaggag tgtcacaaat gcccagctcc taaccctgag    780
ggtggaccat ccgtcttcat cttccctcca aatatcaagg atgtactcat gatctccctg    840
acacccaagg tcacgtgtgt ggtggtggat gtgagcgagg atgacccaga cgtccagatc    900
agctggtttg tgaacaacgt ggaagtacac acagctcaga cacaaaccca tagagaggat    960
tacaacagta ctatccgggt ggtcagcacc ctccccatcc agcaccagga ctggatgagt   1020
ggcaaggagt tcaaatgcaa ggtcaacaac aaagacctcc catcacccat cgagagaacc   1080
atctcaaaaa ttaaagggct agtcagagct ccacaagtat acatcttgcc gccaccagca   1140
gagcagttgt ccaggaaaga tgtcagtctc acttgcctgg tcgtgggctt caaccctgga   1200
gacatcagtg tggagtggac cagcaatggg catacagagg agaactacaa ggacaccgca   1260
ccagtcctgg actctgacgg ttcttacttc atatatagca agctcaatat gaaaacaagc   1320
aagtgggaga aaacagattc cttctcatgc aacgtgagac acgagggtct gaaaaattac   1380
tacctgaaga agaccatctc ccggtctccg ggtaaagcta gctga                   1425
```

<210> SEQ ID NO 55
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
atgggcatca agatggagtc acggattcag gcatttgtat tcgtgtttct ctggttgtct      60
ggtgttggcg gagacattgt gatgacccag tctcacaaat tcatgtccac atcagtagga    120
gacagggtca gcgtcacctg caaggccagt caggatgtga cttctgctgt agcctggtat    180
caacaaaaac cagggcaatc tcctaaacta ctgatttact gggcatccac ccggcacact    240
ggagtccctg atcgcttcac aggcagtgga tctgggacag attatactct caccatcagc    300
agtgggcagg ctgaagacct ggcactttat tactgtcacc aatattatag cgctcctcgg    360
acgttcggtg gaggcaccaa gctggaagtc aaacggctg atgctgcacc aactgtatcc     420
atcttcccac catccagtga gcagttaaca tctggaggtg cctcagtcgt gtgcttcttg    480
aacaacttct accccaaaga catcaatgtc aagtggaaga ttgatggcag tgaacgacaa    540
aatggcgtcc tgaacagttg gactgatcag gacagcaaag acagcaccta cagcatgagc    600
agcaccctca cgttgaccaa ggacgagtat gaacgacata cagctatac ctgtgaggcc      660
actcacaaga catcaacttc acccatcgtc aagagcttca ataggaatga gtgttag       717
```

<210> SEQ ID NO 56
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
atggaaaggc actggatctt tctcttcctg ttttcagtaa ctgcaggtgt ccactcccag      60
gtccagcttc agcagtctgg ggctgagctg gcaaaacctg gggcctcagt gaagatgtcc    120
tgcaaggctt ctggctacac ctttactacc tactggatgc actgggtaaa acagaggcct    180
ggacagggtc tggaatggat tggatacatt aatcctatca ctggttatac tgagtacaat    240
cagaagttca aggacaaggc caccttgact gcagacaaat cctccagcac agcctacatg    300
caactgagca gcctgacatc tgaggactct gcagtctatt actgtgcaag agagggttta    360
agtgctatgg actattgggg tcagggaacc tcagtcaccg tcacctcagc caaaacaacg    420
ggcccatccg tcttcccct ggcgccctgc tccaggagca cctccgagag cacagccgcc     480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcttgggca cgaagaccta cacctgcaac    660
gtagatcaca gcccagcaa caccaaggtg gacaagagag ttgagtccaa atatggtccc     720
ccatgcccac cctgcccagc acctgagttc aaggggggac catcagtctt cctgttcccc    780
ccaaaaccca aggacactct catgatctcc cggacccctg aggtcacgtg cgtggtggtg    840
gacgtgagcc aggaagaccc cgaggtccag ttcaactggt acgtggatgg cgtggaggtg    900
cataatgcca agacaaagcc gcgggaggag cagttcaaca gcacgtaccg tgtggtcagc    960
```

```
gtcctcaccg tcctgcacca ggactggctg aacggcaagg agtacaagtg caaggtctcc      1020
aacaaaggcc tcccgtcctc catcgagaaa accatctcca agccaaagg gcagccccga       1080 gagccacagg tgtacaccct gcccccatcc caggaggaga tgaccaagaa ccaggtcagc      1140
ctgacctgcc tggtcaaagg cttctacccc agcgacatcg ccgtggagtg ggagagcaat     1200
gggcagccgg agaacaacta caagaccacg cctcccgtgc tggactccga cggctccttc     1260
ttcctctaca gcaggctaac cgtggacaag agcaggtggc aggagggaa tgtcttctca      1320 tgctccgtga tgcatgaggc tctgcacaac cactacacag agaagagcct ctccctgtct     1380
ctgggtaaag ctagctga                                                   1398
```

<210> SEQ ID NO 57
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
atgggcatca agatggagtc acagattcag gcatttgtat tcgtgtttct ctggttgtct      60
ggtgttggcg gagacattgt gatgacccag tctcacaaat tcatgtccac atcagtagga    120
gacagggtca gcgtcacctg caaggccagt caggatgtga cttctgctgt agcctggtat    180
caacaaaaac cagggcaatc tcctaaacta ctgatttact gggcatccac ccggcacact    240
ggagtccctg atcgcttcac aggcagtgga tctgggacag attatactct caccatcagc    300
agtgggcagg ctgaagacct ggcactttat tactgtcacc aatattatag cgctcctcgg    360
acgttcggtg gaggcaccaa gctcgagatc aaacgaactg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca aagtctatgc ctgcgaagtc    660
acccatcagg gcctgagctc gcccgtcaca aagagcttca caggggaga gtgttag       717
```

<210> SEQ ID NO 58
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
atggctgtcc tggcactact cctctgcctg gtggctttcc caacttgtac cctgtcccag      60
gtgcaactga aggagtcagg acctggcctg gtggcgccct cacagagcct gtccattacc    120
tgctctgtct ctgggttctc attaagcaac tatgatataa gctggattcg ccagccacca    180
ggaaagggtc tggagtggct tggagtaatg tggactggtg gaggcgcaaa ttataattca    240
gctttcatgt ccagactgag catcaacaag gacaactcca gagccaagt tttttaaaa     300 atgaacaatc tgcaaactga tgacacagcc atttattact gtgtcagaga tgcggtgagg    360
tactggaact tcgatgtctg gggcgcaggg accacggtca ccgtctcctc agccaaaacg    420
aagggcccat ccgtcttccc cctggcgccc tgctccagga gcacctccga gagcacagcc    480
gccctgggct gcctggtcaa ggactacttc cccgaaccgg tgacggtgtc gtggaactca    540
```

```
ggcgccctga ccagcggcgt gcacaccttc ccggctgtcc tacagtcctc aggactctac    600
tccctcagca gcgtggtgac cgtgccctcc agcagcttgg gcacgaagac ctacacctgc    660
aacgtagatc acaagcccag caacaccaag gtggacaaga gagttgagtc caaatatggt    720
cccccatgcc caccctgccc agcacctgag ttcaagggga ccatcagt cttcctgttc      780 cccccaaaac ccaaggacac tctcatgatc tcccggaccc ctgaggtcac gtgcgtggtg    840
gtggacgtga gccaggaaga ccccgaggtc cagttcaact ggtacgtgga tggcgtggag    900
gtgcataatg ccaagacaaa gccgcgggag gagcagttca acagcacgta ccgtgtggtc    960
agcgtcctca ccgtcctgca ccaggactgg ctgaacggca aggagtacaa gtgcaaggtc   1020
tccaacaaag gcctcccgtc ctccatcgag aaaaccatct ccaaagccaa agggcagccc   1080
cgagagccac aggtgtacac cctgcccccc tcccaggagg agatgaccaa gaaccaggtc   1140
agcctgacct gcctggtcaa aggcttctac cccagcgaca tcgccgtgga gtgggagagc   1200
aatgggcagc cggagaacaa ctacaagacc acgcctcccg tgctggactc cgacggctcc   1260
ttcttcctct acagcaggct aaccgtggac aagagcaggt ggcaggaggg gaatgtcttc   1320
tcatgctccg tgatgcatga ggctctgcac aaccactaca cacagaagag cctctccctg   1380
tctctgggta aagctagctg a                                             1401

<210> SEQ ID NO 59
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
atggattttc aagcgcagat tttcagcttc ctgctaatca gtgcttcagt cataatgtcc     60
agaggacaaa ttgttctctc ccagtcacca gcaatcctgt ctgcatctcc aggggagaag    120
gtcacaatga cttgcagggc cagctcaagt gtaagttaca tacactggta ccagcagaag    180
ccaggatcct cccccaaacc ctggatttat gccacatccc acctggcttc tggagtccct    240
gctcgcttca gtggcagtgg gtctgggacc tcttactctc tcacaatcag cagagtggag    300
gctgaagata ctgccactta ttactgccag cagtggagta gtaacccatt cacgttcggc    360
tcggggacaa agctcgagat caaacgaact gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctatg cctgcgaagt cacccatcag    660
ggcctgagct cgcccgtcac aaagagcttc aacaggggag agtgttag                708

<210> SEQ ID NO 60
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
atggaaaggc actggatctt tctactcctg ttgtcagtaa ctgcaggtgt ccactcccag     60
```

| | |
|---|---|
| gtccagctgc agcagtctgg ggctgaactg gcaagacctg gggcctcagt gaagatgtcc | 120 |
| tgcaaggctt ctggctacac ctttactacc tacactatgc actgggtaaa acagaggcct | 180 |
| ggacagggtc tggaatggat tggatacatt aatcctagca gtggttatac taattacaat | 240 |
| cagaagttca aggacaaggc cacattgact gcagacaaat cctccagcac agcctccatg | 300 |
| caactgagca gcctgacatc tgaggactct gcagtctatt actgtgcaag agagagggcg | 360 |
| gtattagtcc cctatgctat ggactactgg ggtcaaggaa cctcagtcac cgtctcctca | 420 |
| gccaaaacaa agggcccatc cgtcttcccc ctggcgccct gctccaggag cacctccgag | 480 |
| agcacagccg ccctgggctg cctggtcaag gactacttcc ccgaaccggt gacggtgtcg | 540 |
| tggaactcag gcgccctgac cagcggcgtg cacaccttcc cggctgtcct acagtcctca | 600 |
| ggactctact ccctcagcag cgtggtgacc gtgccctcca gcagcttggg cacgaagacc | 660 |
| tacacctgca acgtagatca caagcccagc aacaccaagg tggacaagag agttgagtcc | 720 |
| aaatatggtc ccccatgccc acctgccca gcacctgagt tcgaagggg accatcagtc | 780 |
| ttcctgttcc cccaaaacc caaggacact ctcatgatct cccggaccc tgaggtcacg | 840 |
| tgcgtggtgg tggacgtgag ccaggaagac cccgaggtcc agttcaactg gtacgtggat | 900 |
| ggcgtggagg tgcataatgc caagacaaag ccgcgggagg agcagttcaa cagcacgtac | 960 |
| cgtgtggtca gcgtcctcac cgtcctgcac caggactggc tgaacggcaa ggagtacaag | 1020 |
| tgcaaggtct ccaacaaagg cctcccgtcc tccatcgaga aaaccatctc caaagccaaa | 1080 |
| gggcagcccc gagagccaca ggtgtacacc ctgcccccat cccaggagga tgaccaag | 1140 |
| aaccaggtca gcctgacctg cctggtcaaa ggcttctacc ccagcgacat cgccgtggag | 1200 |
| tgggagagca atgggcagcc ggagaacaac tacaagacca cgcctcccgt gctggactcc | 1260 |
| gacggctcct tcttcctcta cagcaggcta accgtggaca agagcaggtg gcaggagggg | 1320 |
| aatgtcttct catgctccgt gatgcatgag gctctgcaca accactacac acagaagagc | 1380 |
| ctctccctgt ctctgggtaa agctagctga | 1410 |

<210> SEQ ID NO 61
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

| | |
|---|---|
| atgcattttc aagtgcagat tttcagcttc ctgctaatca gtgcctcagt cataatgtcc | 60 |
| agaggacaaa ttgttctcac ccagtctcca gcagtcatgt ctgcatctcc aggggagaag | 120 |
| gtcaccataa cctgcactgc cagctcaagt ttaagttaca tgcactggtt ccagcagaag | 180 |
| ccaggcactt ctcccaaact ctggctttat agcacatcca tcctggcttc tggagtccct | 240 |
| actcgcttca gtggcagtgg atctgggacc tcttactctc tcacaatcag ccgaatggag | 300 |
| gctgaagatg ctgccactta ttactgccag caaaggagta gttccccatt cacgttcggc | 360 |
| tcggggacaa agctcgagat caaacgaact gtggctgcac catctgtctt catcttcccg | 420 |
| ccatctgatg agcagttgaa atctggaact gcctctgttg tgtgcctgct gaataacttc | 480 |
| tatcccagag aggccaaagt acagtggaag gtggataacg ccctccaatc gggtaactcc | 540 |
| caggagagtg tcacagagca ggacagcaag gacagcacct acagcctcag cagcaccctg | 600 |
| acgctgagca agcagactac gagaaacac aaagtctatg cctgcgaagt cacccatcag | 660 |

```
ggcctgagct cgcccgtcac aaagagcttc aacaggggag agtgttag            708
```

<210> SEQ ID NO 62
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
atgggatgga cctggatctt tattttaatc ctgtcagtta ctacaggtgt ccactctgag     60
gtccagctgc agcagtctgg acctgagctg gagaagcctg gcgcttcagt gaagatatcc    120
tgcaaggctt ctggttactc cttcactggc tacaacatga actgggtgaa acagagcaat    180
ggaaagagcc ttgagtggat tggaaatatt gatccttact atggtgatac taactacaac    240
cagaagttca agggcaaggc cacattgact gtagacaaat cctccagcac agcctacatg    300
cacctcaaga gcctgacatc tgaggactct gcagtctatt actgtgcaag accctacggt    360
agtgaggcct actttgctta ctggggccaa gggactctgg tcactgtctc tgcagccaaa    420
acgaagggcc catccgtctt ccccctggcg ccctgctcca ggagcacctc cgagagcaca    480
gccgccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcacgaa gacctacacc     660
tgcaacgtag atcacaagcc cagcaacacc aaggtggaca gagagttga gtccaaatat     720
ggtcccccat gcccaccctg cccagcacct gagttcgaag ggggaccatc agtcttcctg    780
ttccccccaa aacccaagga cactctcatg atctcccgga cccctgaggt cacgtgcgtg    840
gtggtggacg tgagccagga agaccccgag gtccagttca actggtacgt ggatggcgtg    900
gaggtgcata atgccaagac aaagccgcgg gaggagcagt tcaacagcac gtaccgtgtg    960
gtcagcgtcc tcaccgtcct gcaccaggac tggctgaacg gcaaggagta caagtgcaag   1020
gtctccaaca aaggcctccc gtcctccatc gagaaaacca tctccaaagc caaagggcag   1080
ccccgagagc cacaggtgta caccctgccc ccatcccagg aggagatgac caagaaccag   1140
gtcagcctga cctgcctggt caaaggcttc taccccagcg acatcgccgt ggagtgggag   1200
agcaatgggc agccggagaa caactacaag accacgcctc ccgtgctgga ctccgacggc   1260
tccttcttcc tctacagcag gctaaccgtg gacaagagca ggtggcagga ggggaatgtc   1320
ttctcatgct ccgtgatgca tgaggctctg cacaaccact acacacagaa gagcctctcc   1380
ctgtctctgg gtaaagctag ctga                                          1404
```

<210> SEQ ID NO 63
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
atggtgtcca cttctcagct ccttggactt ttgcttttct ggacttcagc ctccagatgt     60
gacattgtga tgactcagtc tccagccacc ctgtctgtga ctccaggaga tagagtctct    120
ctttcctgca gggccagcca gagtattagc gactacttac actggtatca acaaaaatca    180
catgagtctc caaggcttct catcaaatat gctgcccaat ccatctctgg gatcccctcc    240
```

```
aggttcagtg gcagtggatc agggtcagat ttcactctca gtatcaacgg tgtggaacct    300
gaagatgttg gagtgtatta ctgtcaaaat ggtcacagct ttccgtacac gttcggaggg    360
gggaccaagc tcgagatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctatgcct gcgaagtcac ccatcagggc    660
ctgagctcgc ccgtcacaaa gagcttcaac aggggagagt gttag                    705

<210> SEQ ID NO 64
<211> LENGTH: 1395
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
atggaatgga ggatctttct cttcatcctg tcaggaactg caggtgtcca ctcccaggtt     60
cagctgcggc agtctggacc tgagctggtg aagcctgggg cttcagtgaa gatgtcctgc    120
aaggcttctg gatacacatt tactgactat gttataagtt gggtgaagca gagaactgga    180
cagggccttg agtggattgg agatatttat cctggaagtg gttattcttt ctacaatgag    240
aacttcaagg gcaaggccac actgactgca gacaaatcct ccaccacagc ctacatgcag    300
ctcagcagcc tgacatctga ggactctgcg gtctatttct gtgcaaccta ctataactac    360 cctttttgctt actggggcca agggactctg gtcactgtct ctgcagccaa acaacgggc    420 ccatccgtct tccccctggc gccctgctcc aggagcacct ccgagagcac agccgccctg    480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgt gaccgtgcc ctccagcagc ttgggcacga agacctacac ctgcaacgta    660
gatcacaagc ccagcaacac caaggtggac aagagagttg agtccaaata tggtccccca    720 tgcccacccct gcccagcacc tgagttcgaa ggggaccat cagtcttcct gttccccca    780 aaacccaagg acactctcat gatctcccgg acccctgagg tcacgtgcgt ggtggtggac    840
gtgagccagg aagaccccga ggtccagttc aactggtacg tggatggcgt ggaggtgcat    900
aatgccaaga caaagccgcg ggaggagcag ttcaacagca cgtaccgtgt ggtcagcgtc    960
ctcaccgtcc tgcaccagga ctggctgaac ggcaaggagt acaagtgcaa ggtctccaac   1020
aaaggcctcc cgtcctccat cgagaaaacc atctccaaag ccaaagggca gccccgagag   1080
ccacaggtgt acaccctgcc cccatcccag gaggagatga ccaagaacca ggtcagcctg   1140
acctgcctgg tcaaaggctt ctaccccagc gacatcgccg tggagtggga gagcaatggg   1200
cagccggaga acaactacaa gaccacgcct cccgtgctgg actccgacgg ctccttcttc   1260
ctctacagca ggctaaccgt ggacaagagc aggtggcagg aggggaatgt cttctcatgc   1320
tccgtgatgc atgaggctct gcacaaccac tacacacaga gagcctctc cctgtctctg   1380 ggtaaagcta gctga                                                    1395

<210> SEQ ID NO 65
<211> LENGTH: 717
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
atgaagttgc ctgttaggct gttggtgctg atgttctgga ttcctgcttc cagcagtgat      60
gttgtgatga cccaaactcc actctccctg cctgtccgtc ttggagatca agcctccatc     120
tcttgcagat ctagtcagag ccttgtacac agtaatggaa acacctattt acattggtac     180
ctgcagaagc caggccagtc tccaaagctc ctgatctaca agtttccaa ccgatttttct      240
ggggtcccag acaggttcag tggcagtgga tcaggacaa atttcacact caagatcagc      300
agagtggagg ctgaggatct gggactttat ttctgctctc aaagtacaca tgttccgtac      360
acgttcggag gggggaccaa gctcgagatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctatgc ctgcgaagtc      660
acccatcagg gcctgagctc gcccgtcaca aagagcttca caggggaga gtgttag        717
```

<210> SEQ ID NO 66
<211> LENGTH: 1410
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

```
atgacattga acatgctgtt ggggctgagg tgggttttct tgttgtttt ttatcaaggt       60
gtgcattgtg aggtgcagct tgttgagtct ggtggaggat tggtgcagcc taagggtca      120
ttgaaactct catgtgcagc ctctggatta accttcaata tctacgccat gaactgggtc     180
cgccaggctc caggaaaggg tttggaatgg gttgctcgca taagaaataa agtaataat      240
tatgcaacat attatgccga ttcagtgaaa gacaggttca ccatctccag agatgattca     300
caaagcttgc tctatctgca aatgaacaac ttgaaaactg aggacacagc catgtattac     360
tgtgtgggac gggactggtt tgattactgg ggccaaggga ctctggtcac tgtctctgca    420
gccaaaacga gggcccatcg tcttcccc ctggcgccct gctccaggag cacctccgag       480
agcacagccg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacgaagacc     660
tacacctgca acgtagatca caagcccagc aacaccaagg tggacaagag agttgagtcc     720
aaatatggtc cccatgccc accctgccca gcacctgagt cgaagggg accatcagtc       780
ttcctgttcc ccccaaaacc caaggacact ctcatgatct cccggacccc tgaggtcacg     840
tgcgtggtgg tggacgtgag ccaggaagac cccgaggtcc agttcaactg gtacgtggat     900
ggcgtggagg tgcataatgc caagacaaag ccgcgggagg agcagttcaa cagcacgtac     960
cgtgtggtca gcgtcctcac cgtcctgcac caggactggc tgaacggcaa ggagtacaag    1020
tgcaaggtct ccaacaaagg cctcccgtcc tccatcgaga aaaccatctc caaagccaaa    1080
```

```
gggcagcccc gagagccaca ggtgtacacc ctgcccccat cccaggagga gatgaccaag    1140
aaccaggtca gcctgacctg cctggtcaaa ggcttctacc ccagcgacat cgccgtggag    1200
tgggagagca atgggcagcc ggagaacaac tacaagacca cgcctcccgt gctggactcc    1260
gacggctcct tcttcctcta cagcaggcta accgtggaca agagcaggtg gcaggagggg    1320
aatgtcttct catgctccgt gatgcatgag gctctgcaca accactacac acagaagagc    1380
ctctccctgt ctctgggtaa agctagctga                                    1410

<210> SEQ ID NO 67
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
atggcctgga tttcacttat actctctctc ctggctctca gctcagggc catttcccag     60 gctgttgtga ctcaggaatc tgcactcacc acatcacctg gtgaaacagt cacactcact    120
tgtcgctcaa gtactggggc tgttacaact agtaactatg ccaactgggt ccaagaaaaa    180
ccagatcatt tattcactgg tctaataggt ggtaccaaca ccgagtttc aggtgttcct    240 gccagattct caggctccct gattggagac aaggctgccc tcaccatcac aggggcacag    300
actgaggatg aggcaatata tttctgtgct ctatggtaca gcaaccattg ggtgttcggt    360
ggaggaacca aactcgagat caaacgaact gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctatg cctgcgaagt cacccatcag    660
ggcctgagct cgcccgtcac aaagagcttc aacaggggag agtgttag                708

<210> SEQ ID NO 68
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
atggaatgga cctgggtctt tctcttcctc ctgtcagtaa ctgcaggtgt ccactcccag     60
gttcagctgc agcagtctgg agctgagctg atgaagcctg gggcctcagt gaagatatcc    120
tgcaaggcta ctggctacac attcggtagc tactggatag agtgggtaaa gcagaggcct    180
ggacatggcc ttgagtggat tggagagatt ttacctggaa gtggtaatac taactacaat    240
gagaacttca gggcaaggc cacattcact gcagatacat cctccaacac agcctacatg    300
caactcacca gtctgacatc tgaggactct gccgtctatt actgtgctag ggcggggatt    360
tattggggcc aagggactct ggtcactgtc tctgcagcca aaacgaaggg cccatccgtc    420
ttccccctgg cgccctgctc caggagcacc tccgagagca gccgccct gggctgcctg    480 gtcaaggact acttccccga accggtgacg gtgtcgtgga actcaggcgc cctgaccagc    540
ggcgtgcaca ccttccggc tgtcctacag tcctcaggac tctactccct cagcagcgtg    600
gtgaccgtgc cctccagcag cttgggcacg aagacctaca cctgcaacgt agatcacaag    660
```

```
cccagcaaca ccaaggtgga caagagagtt gagtccaaat atggtccccc atgcccaccc    720
tgcccagcac ctgagttcga aggggggacca tcagtcttcc tgttcccccc aaaacccaag    780
gacactctca tgatctcccg accccctgag gtcacgtgcg tggtggtgga cgtgagccag    840 gaagacccccg aggtccagtt caactggtac gtggatggcg tggaggtgca taatgccaag    900
acaaagccgc gggaggagca gttcaacagc acgtaccgtg tggtcagcgt cctcaccgtc    960
ctgcaccagg actggctgaa cggcaaggag tacaagtgca aggtctccaa caaaggcctc   1020
ccgtcctcca tcgagaaaac catctccaaa gccaagggc agccccgaga gccacaggtg    1080
tacaccctgc ccccatccca ggaggagatg accaagaacc aggtcagcct gacctgcctg   1140
gtcaaaggct tctaccccag cgacatcgcc gtggagtggg agagcaatgg gcagccggag   1200
aacaactaca agaccacgcc tcccgtgctg gactccgacg gctccttctt cctctacagc   1260
aggctaaccg tggacaagag caggtggcag gaggggaatg tcttctcatg ctccgtgatg   1320
catgaggctc tgcacaacca ctacacacag aagagcctct ccctgtctct gggtaaagct   1380
agctga                                                               1386
```

```
<210> SEQ ID NO 69
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
atggagaaag acacactcct gctatgggtc ctgcttctct gggttccagg ttccacaggt     60
gacattgtgc tgacccaatc tccagctttt ttggctgtgt ctctagggca gagggccacc    120
atctcctgca gagccagcga aagtgttgat aattatggca ttagttttat gaactggttc    180
caacagaaac caggacagcc acccaaactc ctcatctatg ttgcatccaa gcaaggatcc    240
ggggtccctg ccaggtttag tggcagtggg tctgggacag acttcagcct caacatccat    300
cctatggagg aggatgatac tgcaatgtat ttctgtcagc aaagtaagga ggttcctcgg    360
acgttcggtg gaggcaccaa gctcgagatc aaacgaactg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca aagtctatgc ctgcgaagtc    660
acccatcagg gcctgagctc gcccgtcaca aagagcttca acaggggaga gtgttag     717
```

```
<210> SEQ ID NO 70
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
atggaatgta actggatact tcctttttatt ctgtcggtaa cttcagggt ctactcagag      60 gttcagctcc agcagtctgg gactgtgctg gcaaggcctg ggcttcagt gaagatgtcc    120 tgcaaggctt ctggctacac ctttaccagc tactggatgc actgggtaaa acagaggcct    180
```

```
ggacagggtc tggaatggat tggcgctatt tatcctggaa atagtgatac tacctacaac    240
cagaagttca agggcaaggc caaactgact gcagtcacat ccaccagcac tgcctacatg    300
gagctcagca gcctgacaaa tgaggactct gcggtctatt actgtacacc tacttactac    360
tttgactact ggggccaagg cacctctctc acagtctcct cagccaaaac gaagggccca    420
tccgtcttcc ccctggcgcc ctgctccagg agcacctccg agcacagc gccctgggc      480 tgcctggtca aggactactt ccccgaaccg gtgacggtgt cgtggaactc aggcgccctg    540
accagcggcg tgcacacctt cccggctgtc ctacagtcct caggactcta ctccctcagc    600
agcgtggtga ccgtgccctc cagcagcttg ggcacgaaga cctacacctg caacgtagat    660
cacaagccca gcaacaccaa ggtggacaag agagttgagt ccaaatatgg tcccccatgc    720 ccacctgcc cagcacctga gttcgaaggg ggaccatcag tcttcctgtt ccccccaaaa    780
cccaaggaca ctctcatgat ctcccggacc cctgaggtca cgtgcgtggt ggtggacgtg    840
agccaggaag accccgaggt ccagttcaac tggtacgtgg atggcgtgga ggtgcataat    900
gccaagacaa agccgcggga ggagcagttc aacagcacgt accgtgtggt cagcgtcctc    960
accgtcctgc accaggactg gctgaacggc aaggagtaca agtgcaaggt ctccaacaaa    1020
ggcctcccgt cctccatcga gaaaaccatc tccaaagcca agggcagcc ccgagagcca    1080 caggtgtaca ccctgccccc atcccaggag gagatgacca gaaccaggt cagcctgacc    1140 tgcctggtca aaggcttcta ccccagcgac atcgccgtgg agtgggagag caatgggcag    1200
ccggagaaca actacaagac cacgcctccc gtgctggact ccgacggctc cttcttcctc    1260
tacagcaggc taaccgtgga caagagcagg tggcaggagg ggaatgtctt ctcatgctcc    1320
gtgatgcatg aggctctgca caaccactac acacagaaga gcctctccct gtctctgggt    1380
aaagctagct ga                                                        1392

<210> SEQ ID NO 71
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
atgagtcctg cccaattcct gtttctgtta gtgctctgga ttcgggaaac caacggtgat     60
gttgtgatga cccagactcc actcactttg tcggttacca ttggacaacc agcctccatc    120
tcttgcaagt caagtcagag cctcttagat agtgatggaa agacatattt gaattggttc    180
ttacagaggc caggccagtc tccaaagcgc ctaatctatc tggtgtctaa actggactct    240
ggagtccctg acaggttcac tggcagtgga tcagggacag atttcacact gaaaatcagc    300
agagtggagg ctgaggattt gggagtttat tattgctggc aaggtacaca ttttccgtgg    360
acgttcggtg gaggcaccaa gctcgagatc aaacgaactg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctatgc ctgcgaagtc    660 acccatcagg gcctgagctc gcccgtcaca aagagcttca caggggaga gtgttag       717

<210> SEQ ID NO 72
```

<211> LENGTH: 1415
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

| | | | | |
|---|---|---|---|---|
| atgggaggga | tctggatctt | tctcttcctc | ctgtcaggaa | ctgcaggtgc | ccactctgag | 60 |
| atccagctgc | agcagactgg | acctgagctg | gtgaagcctg | ggcttcagt | gaagatatcc | 120 |
| tgcaaggctt | ctggttatcc | attcactgac | tacatcatgg | tctgggtgaa | gcagagccat | 180 |
| ggaaagagcc | ttgagtggat | tggaaatatt | agtccttact | atggtactac | taactacaat | 240 |
| ctgaagttca | agggcaaggc | cacattgact | gtagacaaat | cttccagcac | agcctacatg | 300 |
| cagctcaaca | gtctgacatc | tgaggactct | gcagtctatt | actgtgcaag | atcccctaac | 360 |
| tgggacgggg | cctggtttgc | tcactgggggc | caaggggctc | tggtcactgt | ctctgcagcc | 420 |
| aaaacaaagg | gcccatccgt | cttccccctg | gcgccctgct | ccaggagcac | ctccgagagc | 480 |
| acagccgccc | tgggctgcct | ggtcaaggac | tacttcccccg | aaccggtgac | ggtgtcgtgg | 540 |
| aactcaggcg | ccctgaccag | cggcgtgcac | accttcccgg | ctgtcctaca | gtcctcagga | 600 |
| ctctactccc | tcagcagcgt | ggtgaccgtg | ccctccagca | gcttgggcac | gaagacctac | 660 |
| acctgcaacg | tagatcacaa | gcccagcaac | accaaggtgg | acaagagagt | tgagtccaaa | 720 |
| tatggtcccc | catgcccacc | ctgcccagca | cctgagttcg | aaggggggacc | atcagtcttc | 780 |
| ctgttcccccc | caaaacccaa | ggacactctc | atgatctccc | ggacccctga | ggtcacgtgc | 840 |
| gtggtggtgg | acgtgagcca | ggaagacccc | gaggtccagt | tcaactggta | cgtggatggc | 900 |
| gtggaggtgc | ataatgccaa | gacaaagccg | cgggaggagc | agttcaacag | cacgtaccgt | 960 |
| gtggtcagcg | tcctcaccgt | cctgcaccag | gactggctga | acggcaagga | gtacaagtgc | 1020 |
| aaggtctcca | acaaaggcct | cccgtcctcc | atcgagaaaa | ccatctccaa | agccaaaggg | 1080 |
| cagccccgag | agccacaggt | gtacaccctg | ccccccatccc | aggaggagat | gaccaagaac | 1140 |
| caggtcagcc | tgacctgcct | ggtcaaaggc | ttctacccca | gcgacatcgc | cgtggagtgg | 1200 |
| gagagcaatg | ggcagccgga | gaacaactac | aagaccacgc | ctcccgtgct | ggactccgac | 1260 |
| ggctccttct | tcctctacag | caggctaacc | gtggacaaga | gcaggtggca | ggagggggaat | 1320 |
| gtcttctcat | gctccgtgat | gcatgaggct | ctgcacaacc | actacacaca | gaagagcctc | 1380 |
| tccctgtctc | tgggtaaagc | tagctgatta | attaa | | | 1415 |

<210> SEQ ID NO 73
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

| | | | | |
|---|---|---|---|---|
| atggagacag | acacaatcct | gctatgggtg | ctgctgctct | gggttccagg | ctccactggt | 60 |
| gacattgtgc | tgacccaatc | tccagcttct | ttggctgtgt | ctctagggca | gagggccacc | 120 |
| atctcctgca | aggccagcca | agtgttgat | tatgatggtg | atagttatat | gaactggttc | 180 |
| caacagaaac | caggacagcc | acccaaactc | ctcatctatg | ctgcatccaa | tctagaatct | 240 |
| gggatcccag | ccaggtttag | tggcagtggg | tctgggacag | acttcaccct | caacatccat | 300 |
| cctgtggagg | aggaggatgc | tgcaacctat | tactgtcagc | aaagtaatga | ggatccattc | 360 |

```
acgttcggct cggggacaaa gctcgagatc aaacgaactg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca aagtctatgc ctgcgaagtc    660
acccatcagg gcctgagctc gcccgtcaca aagagcttca caggggaga gtgttag       717
```

<210> SEQ ID NO 74
<211> LENGTH: 1403
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 74

```
atggctgtcc tggggctgct tctctgcctg gtgacgttcc caagctgtgt cctgtcccag     60
gtgcagctga aggagtcagg acctggcctg gtggcaccct cacagagcct gtccatcaca    120
tgcactgtct ctgggttctc attatccaga tatagtgtat tttgggttcg ccagcctcca    180
ggaaagggtc tggagtggct gggattgata tggggtggtg gaagcacaga ctataattca    240
gctctcaaat ccagactgag catcagcaag gacaactcca agagccaagt tttcttaaaa    300
atgaacagtc tgcaaactga tgacacagcc atgtactact gtgccagaat ctactttgat    360
tacgacgggg ctatggacta ctggggtcaa ggaacctcag tcaccgtctc ctcagccaaa    420
acaacgggcc catccgtctt ccccctggcg ccctgctcca ggagcacctc cgagagcaca    480
gccgccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcacgaa gacctacacc    660 tgcaacgtag atcacaagcc cagcaacacc aaggtggaca gagagttga gtccaaatat    720 ggtcccccat gcccacccctg cccagcacct gagttcgaag gggaccatc agtcttcctg    780 ttccccccaa aacccaagga cactctcatg atctcccgga ccccctgaggt cacgtgcgtg    840 gtggtggacg tgagccagga agaccccgag gtccagttca actggtacgt ggatggcgtg    900
gaggtgcata atgccaagac aaagccgcgg gaggagcagt tcaacagcac gtaccgtgtg    960
gtcagcgtcc tcaccgtcct gcaccaggac tggctgaacg gcaaggagta caagtgcaag   1020
gtctccaaca aaggcctccc gtcctccatc gagaaaacca tctccaaagc caaagggcag   1080
ccccgagagc cacaggtgta caccctgccc ccatcccagg aggagatgac caagaaccag   1140
gtcagcctga cctgcctggt caaaggcttc taccccagcg acatcgccgt ggagtgggag   1200
agcaatgggc agccggagaa caactacaag accacgcctc ccgtgctgga ctccgacggc   1260
tccttcttcc tctacagcag gctaaccgtg gacaagagca ggtggcagga ggggaatgtc   1320
ttctcatgct ccgtgatgca tgaggctctg cacaaccact acacacagaa gagcctctcc   1380
ctgtctctgg gtaaagctag ctg                                           1403
```

<210> SEQ ID NO 75
<211> LENGTH: 732
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

| atgcatcgca | ccagcatggg | catcaagatg | gagtcacgga | ttcaggcatt | tgtattcgtg | 60 |
| tttctctggt | tgtctggtgt | tggcggagac | attgtgatga | cccagtctca | caaattcatg | 120 |
| tccacatcag | taggagacag | ggtcagcgtc | acctgcaagg | ccagtcagga | tgtgacttct | 180 |
| gctgtagcct | ggtatcaaca | aaaccaggg | caatctccta | aactactgat | ttactgggca | 240 |
| tccacccggc | acactggagt | ccctgatcgc | ttcacaggca | gtggatctgg | gacagattat | 300 |
| actctcacca | tcagcagtgg | gcaggctgaa | gacctggcac | tttattactg | tcaccaatat | 360 |
| tatagcgctc | tcggacgtt | cggtggaggc | accaagctcg | agatcaaacg | aactgtggct | 420 |
| gcaccatctg | tcttcatctt | cccgccatct | gatgagcagt | tgaaatctgg | aactgcctct | 480 |
| gttgtgtgcc | tgctgaataa | cttctatccc | agagaggcca | aagtacagtg | gaaggtggat | 540 |
| aacgccctcc | aatcgggtaa | ctcccaggag | agtgtcacag | agcaggacag | caaggacagc | 600 |
| acctacagcc | tcagcagcac | cctgacgctg | agcaaagcag | actacgagaa | acacaaagtc | 660 |
| tatgcctgcg | aagtcaccca | tcagggcctg | agctcgcccg | tcacaaagag | cttcaacagg | 720 |
| ggagagtgtt | ag | | | | | 732 |

<210> SEQ ID NO 76
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

| atggaatgga | actgggtcgt | tctcttcctc | ctgtcattaa | ctgcaggtgt | ctatgcccag | 60 |
| ggtcagatgc | agcagtctgg | agctgagctg | gtgaagcctg | ggcttcagt | gaagctgtcc | 120 |
| tgcaagactt | ctggcttcac | cttcagcagt | aactatataa | gttggttgaa | gcaaaagcct | 180 |
| ggacagagtc | ttgagtggat | tgcatggatt | tatgctggaa | ctggtggtat | tacctataat | 240 |
| cagaagttca | gaggcagggc | caactgact | gtagacacat | cctccagcac | agcctacatg | 300 |
| cagttcagca | gcctgacaac | tgatgactct | gccatctatt | actgtgcaag | acacgtgagg | 360 |
| ggttaccatc | ctatggacta | ctggggtcaa | ggaacctcag | tcaccgtctc | ctcagccaaa | 420 |
| acgaagggcc | catccgtctt | cccctggcg | ccctgctcca | ggagcacctc | cgagagcaca | 480 |
| gccgccctgg | gctgcctggt | caaggactac | ttccccgaac | cggtgacggt | gtcgtggaac | 540 |
| tcaggcgccc | tgaccagcgg | cgtgcacacc | ttcccggctg | tcctacagtc | ctcaggactc | 600 |
| tactccctca | gcagcgtggt | gaccgtgccc | tccagcagct | tgggcacgaa | gacctacacc | 660 |
| tgcaacgtag | atcacaagcc | cagcaacacc | aaggtggaca | agagagttga | gtccaaatat | 720 |
| ggtcccccat | gcccacccctg | cccagcacct | gagttcgaag | ggggaccatc | agtcttcctg | 780 |
| ttccccccaa | aacccaagga | cactctcatg | atctcccgga | cccctgaggt | cacgtgcgtg | 840 |
| gtggtggacg | tgagccagga | agaccccgag | gtccagttca | actggtacgt | ggatggcgtg | 900 |
| gaggtgcata | atgccaagac | aaagccgcgg | gaggagcagt | tcaacagcac | gtaccgtgtg | 960 |
| gtcagcgtcc | tcaccgtcct | gcaccaggac | tggctgaacg | gcaaggagta | caagtgcaag | 1020 |
| gtctccaaca | aaggcctccc | gtcctccatc | gagaaaacca | tctccaaagc | caagggcag | 1080 |
| ccccgagagc | cacaggtgta | caccctgccc | ccatcccagg | aggagatgac | caagaaccag | 1140 |

| | |
|---|---|
| gtcagcctga cctgcctggt caaaggcttc tacccagcg acatcgccgt ggagtgggag | 1200 |
| agcaatgggc agccggagaa caactacaag accacgcctc ccgtgctgga ctccgacggc | 1260 |
| tccttcttcc tctacagcag gctaaccgtg gacaagagca ggtggcagga ggggaatgtc | 1320 |
| ttctcatgct ccgtgatgca tgaggctctg cacaaccact acacacagaa gagcctctcc | 1380 |
| ctgtctctgg gtaaagctag ctga | 1404 |

<210> SEQ ID NO 77
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77

| | |
|---|---|
| atggagtcac agactcaggt ctttgtatac atgttgctgt ggttgtctgg tgttgatgga | 60 |
| gacattgtga tgacccagtc tcaaaaattc atgtccgcat cagtagggga cagggtcagc | 120 |
| gtcacctgca gggccagtca gaatgtggtt actaatgtag ctggtatca acagaaacca | 180 |
| gggcaatctc ctaaagtact gatttactcg gcatccttcc ggtacagtgg agtccctgat | 240 |
| cgcttcacag gcagtggatc tgggacagat ttcactctca ccatcaccaa tgtgcagtct | 300 |
| gaagacttgg cagagtattt ctgtcagcaa tataacaact atccgtacac gttcggaggg | 360 |
| gggaccaagc tcgagatcaa acgaactgtg gctgcaccat ctgtcttcat cttcccgcca | 420 |
| tctgatgagc agttgaaatc tggaactgcc tctgttgtgt gcctgctgaa taacttctat | 480 |
| cccagagagg ccaaagtaca gtggaaggtg gataacgccc tccaatcggg taactcccag | 540 |
| gagagtgtca cagagcagga cagcaaggac agcacctaca gcctcagcag caccctgacg | 600 |
| ctgagcaaag cagactacga gaaacacaaa gtctatgcct gcgaagtcac ccatcagggc | 660 |
| ctgagctcgc ccgtcacaaa gagcttcaac aggggagagt gttag | 705 |

<210> SEQ ID NO 78
<211> LENGTH: 1407
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78

| | |
|---|---|
| atgggatgga gctatatcat cctcttttg gtagcaacag ctacagatgt ccactcccag | 60 |
| gtccaactgc agcagcctgg ggctgaactg gtgaagcctg ggcttcagt gaagctgtcc | 120 |
| tgcaaggctt ctggctacac cttcaccagc tactggatgc actgggtgaa gcagaggcct | 180 |
| ggagaaggcc ttgagtggat tggagagatt aatcctagct acggtcgtac tgactacaat | 240 |
| gggaagttca agaacaaggc cacactgact gtagccaaat cctccagcac agcctacatg | 300 |
| caactcagca gcctgacatc tgaggactct gcggtctatt actgtgcaag aggagattac | 360 |
| tacggtagta gctcgtttgc ttactggggc caagggactc tggtcactgt ctctgcagcc | 420 |
| aaaacaaagg gccatccgt cttcccctg gcgccctgct ccaggagcac ctccgagagc | 480 |
| acagccgccc tgggctgcct ggtcaaggac tacttccccg aaccggtgac ggtgtcgtgg | 540 |
| aactcaggcg ccctgaccag cggcgtgcac accttcccgg ctgtcctaca gtcctcagga | 600 |
| ctctactccc tcagcagcgt ggtgaccgtg ccctccagca gcttgggcac gaagacctac | 660 |
| acctgcaacg tagatcacaa gcccagcaac accaaggtgg acaagagagt tgagtccaaa | 720 |

```
tatggtcccc catgcccacc ctgcccagca cctgagttcg aaggggggacc atcagtcttc      780 ctgttccccc caaaacccaa ggacactctc atgatctccc ggacccctga ggtcacgtgc      840
gtggtggtgg acgtgagcca ggaagacccc gaggtccagt tcaactggta cgtggatggc      900
gtggaggtgc ataatgccaa gacaaagccg cggaggagc agttcaacag cacgtaccgt      960
gtggtcagcg tcctcaccgt cctgcaccag gactggctga acggcaagga gtacaagtgc     1020
aaggtctcca acaaaggcct cccgtcctcc atcgagaaaa ccatctccaa agccaaaggg     1080
cagccccgag agccacaggt gtacaccctg cccccatccc aggaggagat gaccaagaac     1140
caggtcagcc tgacctgcct ggtcaaaggc ttctacccca gcgacatcgc cgtggagtgg     1200
gagagcaatg ggcagccgga gaacaactac aagaccacgc ctcccgtgct ggactccgac     1260
ggctccttct cctctacag caggctaacc gtggacaaga gcaggtggca ggaggggaat     1320
gtcttctcat gctccgtgat gcatgaggct ctgcacaacc actacacaca gaagagcctc     1380
tccctgtctc tgggtaaagc tagctga                                         1407
```

<210> SEQ ID NO 79
<211> LENGTH: 705
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 79

```
atggagtcac agactcaggt ctttgtatac atgttgctgt ggttgtctgg tgttgatgga       60
gacattgtga tgacccagtc tcaaaaattc atgtccacat cattaggaga cagggtcagc      120
gtcacctgca aggccagtca gaatgtgggt actaatgtag cctggtatca acagaaacca      180
gggcactctc ctaaagcact gatttactcg gcatcctacc ggtacagtgg agtccctgat      240
cgcttcacag gcagtggatc tgggacagat ttcactctca ccatcagcaa tgtgcagtct      300
gaagacttgg cagagttttt ctgtcagcaa tataacaact atccgtacac gttcggaggg      360
gggaccacgc tcgagatcaa acgaactgtg gctgcaccat ctgtcttcat cttcccgcca      420
tctgatgagc agttgaaatc tggaactgcc tctgttgtgt gcctgctgaa taacttctat      480
cccagagagg ccaaagtaca gtggaaggtg gataacgccc tccaatcggg taactcccag      540
gagagtgtca cagagcagga cagcaaggac agcacctaca gcctcagcag caccctgacg      600
ctgagcaaag cagactacga gaaacacaaa gtctatgcct gcgaagtcac ccatcagggc      660
ctgagctcgc ccgtcacaaa gagcttcaac aggggagagt gttag                     705
```

<210> SEQ ID NO 80
<211> LENGTH: 466
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 80

Met Gly Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

```
Ser Thr Ser Gly Met Ser Val Gly Trp Ile Arg Gln Pro Ser Gly Lys
 50                  55                  60

Gly Leu Glu Trp Leu Ala His Ile Trp Trp Asn Asp Lys Tyr Tyr
 65                  70                  75                  80

Asn Pro Val Leu Lys Ser Arg Leu Thr Ile Ser Lys Glu Thr Ser Asn
                     85                  90                  95

Asn Gln Val Phe Leu Lys Ile Ala Ser Val Ser Ala Asp Thr Ala
                100                 105                 110

Thr Tyr Tyr Cys Ala Arg Phe Tyr Gly Asn Cys Leu Asp Tyr Trp Gly
             115                 120                 125

Gln Gly Thr Thr Leu Thr Val Ser Ser Ala Lys Thr Lys Gly Pro Ser
 130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
             165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Ser Leu Gly Thr Lys Thr Tyr Thr Cys Asn Val Asp His
        210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Glu Gly Gly Pro Ser
                245                 250                 255

Val Phe Leu Phe Pro Pro Lys Pro Lys Asp Thr Leu Met Ile Ser Arg
                260                 265                 270

Thr Pro Glu Val Thr Cys Val Val Val Asp Val Ser Gln Glu Asp Pro
            275                 280                 285

Glu Val Gln Phe Asn Trp Tyr Val Asp Gly Val Glu Val His Asn Ala
290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
    450                 455                 460
```

Ala Ser
465

<210> SEQ ID NO 81
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Met Ser Ser Ala Gln Phe Leu Gly Leu Leu Leu Cys Phe Gln
1               5                   10                  15

Gly Thr Arg Cys Asp Ile Gln Met Thr Gln Thr Ser Ser Leu Ser
                20                  25                  30

Ala Ser Leu Gly Asp Arg Val Thr Ile Ser Cys Arg Ala Ser Gln Asp
                35                  40                  45

Ile Ser Asn Tyr Leu Asn Trp Tyr Gln Gln Lys Pro Asp Gly Thr Val
            50                  55                  60

Lys Leu Leu Ile Tyr Tyr Thr Ser Ile Leu Gln Leu Gly Val Pro Ser
65              70                  75                  80

Arg Phe Ser Gly Ser Gly Ser Glu Thr Asp Tyr Ser Leu Thr Ile Ser
                85                  90                  95

Asn Leu Glu Gln Glu Asp Ile Ala Thr Tyr Phe Cys Gln Gln Gly Asp
                100                 105                 110

Ser Leu Pro Phe Thr Phe Gly Ser Gly Thr Lys Leu Glu Ile Lys Arg
                115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145             150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225             230

<210> SEQ ID NO 82
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Arg Ala Leu Ile Leu Leu Cys Leu Phe Thr Ala Phe Pro Gly Ile
1               5                   10                  15

Leu Ser Asp Val Gln Leu Gln Glu Ser Gly Pro Asp Leu Val Lys Pro
                20                  25                  30

Ser Gln Ser Leu Ser Leu Thr Cys Thr Val Thr Gly Tyr Ser Ile Thr
                35                  40                  45

```
Ser Gly Tyr Ser Trp His Trp Ile Arg Gln Phe Pro Gly Asn Lys Leu
    50                  55                  60

Glu Trp Met Gly Tyr Ile Leu Phe Ser Gly Ser Thr Asn Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Phe Cys Ala Arg Ser Asn Tyr Gly Ser Phe Ala Ser Trp Gly Gln Gly
        115                 120                 125

Thr Leu Val Thr Val Ser Ala Ala Lys Thr Thr Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Pro Cys Pro Ala Pro Glu Phe Glu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Ser Leu Ser Leu Gly Lys Ala Ser
    450                 455                 460
```

```
<210> SEQ ID NO 83
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Asp Phe Gln Val Gln Ile Phe Ser Phe Leu Leu Ile Ser Ala Ser
1               5                   10                  15

Val Ile Ile Ser Arg Gly Gln Ile Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Val Ser His Met His Trp Tyr Gln Gln Lys Ser Gly Thr Ser
    50                  55                  60

Pro Lys Arg Trp Ile Tyr Asp Thr Ser Arg Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser His Pro Trp Ser Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 84
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Ala Trp Val Trp Thr Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Val Pro Gly Lys Gly Leu
    50                  55                  60

Arg Trp Met Gly Trp Met Asp Thr Phe Thr Gly Glu Pro Thr Tyr Ala
```

```
                65                  70                  75                  80
Asp Asp Phe Lys Gly Arg Phe Ala Phe Ser Leu Glu Thr Ser Ala Ser
                    85                  90                  95

Thr Ala Tyr Leu Gln Ile Asn Ser Leu Lys Asn Glu Asp Thr Ala Thr
            100                 105                 110

Tyr Phe Cys Ala Arg Gly Gly Ile Leu Arg Leu Asn Tyr Phe Asp Tyr
        115                 120                 125

Trp Gly Gln Gly Thr Thr Leu Thr Val Ser Ser Ala Lys Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Glu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys Ala Ser
465

<210> SEQ ID NO 85
```

<211> LENGTH: 234
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

Met Lys Phe Pro Ser Gln Leu Leu Leu Leu Leu Phe Gly Ile Pro
1               5                   10                  15

Gly Met Ile Cys Asp Ile Gln Met Thr Gln Ser Ser Ser Phe Ser
                20                  25                  30

Val Ser Leu Gly Asp Arg Val Thr Ile Thr Cys Lys Ala Ser Glu Asp
            35                  40                  45

Ile Tyr Asn Arg Leu Gly Trp Tyr Gln Gln Lys Pro Gly Asn Ala Pro
50                  55                  60

Arg Leu Leu Ile Ser Gly Ala Thr Ser Leu Glu Thr Gly Val Pro Ser
65                  70                  75                  80

Arg Phe Ser Gly Ser Gly Ser Gly Lys Asp Tyr Ala Leu Ser Ile Thr
                85                  90                  95

Ser Leu Gln Thr Glu Asp Leu Ala Thr Tyr Tyr Cys Gln Gln Cys Trp
            100                 105                 110

Thr Ser Pro Tyr Thr Phe Gly Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 86
<211> LENGTH: 464
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

Met Gly Trp Ser Trp Ile Phe Leu Phe Leu Leu Ser Gly Thr Gly Gly
1               5                   10                  15

Val Leu Ser Glu Val Gln Leu Gln Gln Ser Gly Pro Glu Leu Val Lys
                20                  25                  30

Pro Gly Ala Ser Val Lys Met Ser Cys Lys Ala Ser Gly Tyr Thr Phe
            35                  40                  45

Thr Asp Tyr Tyr Met Lys Trp Val Lys Gln Ser His Gly Lys Ser Leu
        50                  55                  60

Glu Trp Ile Gly Asp Ile Asn Pro Asn Tyr Gly Asp Thr Phe Tyr Asn
65                  70                  75                  80

-continued

Gln Lys Phe Glu Gly Lys Ala Thr Leu Thr Val Asp Lys Ser Ser Arg
                85                  90                  95

Thr Ala Tyr Met Gln Leu Asn Ser Leu Thr Ser Glu Asp Ser Ala Val
            100                 105                 110

Tyr Tyr Cys Gly Arg Gly Asp Tyr Gly Tyr Phe Asp Val Trp Gly Ala
        115                 120                 125

Gly Thr Thr Val Thr Val Ser Ser Ala Lys Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Glu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Gln Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
        435                 440                 445

His Asn His Tyr Thr Gln Lys Ser Leu Leu Ser Leu Gly Lys Ala Ser
    450                 455                 460

<210> SEQ ID NO 87
<211> LENGTH: 234
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 87

Met Glu Thr His Ser Gln Val Phe Val Tyr Met Leu Leu Trp Leu Ser
1               5                   10                  15

Gly Val Glu Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Gly Thr Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Asn
                85                  90                  95

Asn Val Gln Ser Glu Asp Leu Ala Asp Tyr Phe Cys Gln Gln Tyr Ser
            100                 105                 110

Ser Asn Pro Tyr Met Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 88
<211> LENGTH: 469
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 88

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Thr Ser Gly Tyr Thr Phe
        35                  40                  45

Thr Glu Tyr Thr Met His Trp Val Arg Ser His Gly Lys Ser Leu Glu
    50                  55                  60

Trp Ile Gly Gly Ile Asn Pro Ile Asn Gly Gly Pro Thr Tyr Asn Gln
65                  70                  75                  80

Lys Phe Lys Gly Lys Ala Thr Leu Thr Val Asp Lys Ser Ser Ser Thr
                85                  90                  95

Ala Tyr Met Glu Leu Arg Ser Leu Thr Ser Glu Asp Ser Ala Val Tyr
            100                 105                 110

Tyr Cys Ala Arg Trp Asp Tyr Gly Ser Arg Asp Val Met Asp Tyr Trp
        115                 120                 125

Gly Gln Gly Thr Ser Val Thr Val Ser Ser Ala Lys Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Glu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys Ala Ser
465

<210> SEQ ID NO 89
<211> LENGTH: 234
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 89

Met Glu Thr His Ser Gln Val Phe Val Tyr Met Leu Leu Trp Leu Ser
1               5                   10                  15

Gly Val Glu Gly Asn Ile Val Met Thr Gln Ser Pro Lys Ser Met Ser
            20                  25                  30

Met Ser Val Gly Glu Arg Val Thr Leu Ser Cys Lys Ala Ser Glu Asn
        35                  40                  45

Val Gly Thr Tyr Val Ser Trp Tyr Gln Gln Arg Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Thr Tyr
            100                 105                 110

Ser Tyr Ile Phe Thr Phe Gly Ser Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 90
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Gly Trp Ser Arg Ile Phe Leu Phe Leu Leu Ser Ile Thr Ala Gly
1               5                   10                  15

Val His Cys Gln Val Gln Val Gln Gln Ser Gly Pro Glu Leu Val Lys
            20                  25                  30

Pro Gly Ala Ser Val Lys Ile Ser Cys Lys Ala Ser Gly Asp Ala Phe
        35                  40                  45

Ser Ser Ser Trp Met Asn Trp Val Lys Gln Arg Pro Gly Gln Gly Leu
    50                  55                  60

Glu Trp Ile Gly Arg Ile Tyr Leu Gly Asp Gly Asp Ile Asn Tyr Asn
65                  70                  75                  80

Gly Lys Phe Lys Gly Arg Ala Thr Leu Thr Ala Asp Lys Ser Ser Ser
                85                  90                  95

Thr Ala Tyr Met Gln Leu Ser Ser Leu Thr Ser Val Asp Ser Ala Val 100                 105                 110
Tyr Phe Cys Ala Arg Gln Leu Gly Leu Trp Tyr Val Met Asp Tyr Trp
            115                 120                 125

Gly Gln Gly Thr Ser Val Thr Val Ser Ser Ala Lys Thr Lys Gly Pro
        130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Glu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys Ala Ser
465

<210> SEQ ID NO 91
<211> LENGTH: 234
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 91

```
Met Ser Val Pro Thr Gln Val Leu Gly Leu Leu Leu Trp Leu Thr
1               5                   10                  15

Gly Ala Arg Cys Asp Ile Gln Met Ala Gln Ser Pro Ala Ser Leu Ser
            20                  25                  30

Ala Ser Val Gly Glu Thr Val Thr Ile Thr Cys Arg Ala Ser Glu Asn
        35                  40                  45

Ile Tyr Ser Tyr Leu Ala Trp Tyr Gln Gln Lys Gln Gly Lys Ser Pro
    50                  55                  60

Gln Leu Leu Val Tyr Asn Ala Lys Thr Leu Ala Glu Gly Val Pro Ser
65                  70                  75                  80

Arg Phe Ser Gly Ser Gly Ser Gly Thr Gln Phe Ser Leu Lys Ile Asn
                85                  90                  95

Ser Leu Gln Pro Glu Asp Phe Gly Ser Tyr Tyr Cys Gln His His Tyr
            100                 105                 110

Gly Phe Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 92
<211> LENGTH: 464
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

Glu Trp Val Ala Val Ile Ser Ser Gly Gly Ser Ser Thr Phe Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Val
            100                 105                 110
```

Tyr Tyr Cys Ser Arg Gly Gly Tyr Tyr Phe Asp Tyr Trp Gly Gln Gly
            115                 120                 125

Thr Thr Leu Thr Val Ser Ala Ala Lys Thr Lys Gly Pro Ser Val Phe
        130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
210                 215                 220

Ser Asn Thr Lys Val Asp Lys Arg Val Glu Ser Lys Tyr Gly Pro Pro
225                 230                 235                 240

Cys Pro Pro Cys Pro Ala Pro Glu Phe Glu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Ser Leu Ser Leu Gly Lys Ala Ser
    450                 455                 460

<210> SEQ ID NO 93
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Met Arg Phe Gln Val Gln Val Leu Gly Leu Leu Leu Leu Trp Ile Ser

```
            1               5                  10                 15
Gly Ala Gln Cys Asp Val Gln Ile Thr Gln Ser Pro Ser Tyr Leu Ala
                20                 25                 30

Ala Ser Pro Gly Glu Thr Ile Thr Ile Asn Cys Arg Ala Ser Lys Thr
                35                 40                 45

Ile Ser Lys Tyr Leu Ala Trp Tyr Gln Glu Lys Pro Glu Lys Thr Asp
 50                 55                 60

Lys Leu Leu Ile Tyr Ser Gly Ser Thr Leu Gln Ser Gly Ile Pro Ser
 65                 70                 75                 80

Arg Phe Ser Gly Ser Gly Ser Gly Thr Asp Phe Thr Leu Thr Ile Ser
                85                 90                 95

Gly Leu Glu Pro Glu Asp Phe Ala Met Tyr Tyr Cys Gln Gln His Asn
                100                105                110

Glu Tyr Pro Trp Thr Phe Gly Gly Gly Thr Lys Leu Glu Ile Lys Arg
                115                120                125

Thr Val Ala Ala Pro Ser Val Phe Ile Phe Pro Pro Ser Asp Glu Gln
                130                135                140

Leu Lys Ser Gly Thr Ala Ser Val Val Cys Leu Leu Asn Asn Phe Tyr
145                 150                155                160

Pro Arg Glu Ala Lys Val Gln Trp Lys Val Asp Asn Ala Leu Gln Ser
                165                170                175

Gly Asn Ser Gln Glu Ser Val Thr Glu Gln Asp Ser Lys Asp Ser Thr
                180                185                190

Tyr Ser Leu Ser Ser Thr Leu Thr Leu Ser Lys Ala Asp Tyr Glu Lys
                195                200                205

His Lys Val Tyr Ala Cys Glu Val Thr His Gln Gly Leu Ser Ser Pro
                210                215                220

Val Thr Lys Ser Phe Asn Arg Gly Glu Cys
225                 230

<210> SEQ ID NO 94
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Gly Trp Ser Trp Ile Phe Leu Phe Leu Leu Ser Gly Thr Ala Gly
 1               5                  10                 15

Val Leu Ser Glu Val Gln Leu Gln Gln Ser Gly Pro Glu Leu Val Lys
                20                 25                 30

Pro Gly Ala Ser Val Lys Ile Ser Cys Lys Ala Ser Gly Tyr Ser Phe
                35                 40                 45

Thr Gly Tyr Tyr Met His Trp Val Lys Gln Ser His Val Lys Ser Leu
 50                 55                 60

Glu Trp Ile Gly Arg Ile Asn Pro Tyr Asn Gly Ala Thr Ser Tyr Asn
 65                 70                 75                 80

Gln Asn Phe Lys Asp Lys Ala Ser Leu Thr Val Asp Lys Ser Ser Ser
                85                 90                 95

Thr Ala Tyr Met Glu Leu His Ser Leu Thr Ser Glu Asp Ser Ala Val
                100                105                110

Tyr Tyr Cys Ala Arg Glu Asp Tyr Val Tyr Trp Gly Gln Gly Thr Thr
                115                120                125
```

```
Leu Thr Val Ser Ser Ala Lys Thr Lys Gly Pro Ser Val Phe Pro Leu
        130                 135                 140

Ala Pro Cys Ser Arg Ser Thr Ser Glu Ser Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Lys Thr Tyr Thr Cys Asn Val Asp His Lys Pro Ser Asn
    210                 215                 220

Thr Lys Val Asp Lys Arg Val Glu Ser Lys Tyr Gly Pro Pro Cys Pro
225                 230                 235                 240

Pro Cys Pro Ala Pro Glu Phe Glu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Gly Leu Pro Ser Ser Ile Glu Lys Thr Ile Ser Lys Ala
            340                 345                 350

Lys Gly Gln Pro Arg Glu Pro Gln Val Tyr Thr Leu Pro Pro Ser Gln
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Arg Leu Thr Val Asp Lys Ser Arg Trp Gln Glu
            420                 425                 430

Gly Asn Val Phe Ser Cys Ser Val Met His Glu Ala Leu His Asn His
        435                 440                 445

Tyr Thr Gln Lys Ser Leu Ser Leu Ser Leu Gly Lys Ala Ser
    450                 455                 460

<210> SEQ ID NO 95
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30
```

```
Ser Leu Gly Asp Gln Ala Ser Ile Ser Cys Arg Ser Ser Gln Ser Leu
            35                  40                  45

Val His Ser Asn Gly Asn Thr Tyr Leu His Trp Tyr Leu Gln Lys Pro
 50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Ala
                 85                  90                  95

Leu Lys Ile Ser Arg Val Glu Ala Glu Asp Leu Gly Val Tyr Phe Cys
            100                 105                 110

Ser Gln Ser Thr His Val Pro Trp Thr Phe Gly Gly Gly Thr Lys Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 96
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Glu Trp Ser Trp Ile Phe Leu Phe Leu Leu Ser Gly Thr Ala Gly
 1               5                  10                  15

Val His Ser Glu Val Gln Leu Gln Gln Ser Gly Pro Glu Leu Val Lys
             20                  25                  30

Pro Gly Ala Ser Val Lys Met Ser Cys Lys Ala Ser Gly Tyr Thr Phe
         35                  40                  45

Thr Asp Tyr Val Leu His Trp Val Lys Gln Lys Pro Gly Gln Gly Leu
 50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Lys Ser Ser Ser
                 85                  90                  95

Thr Ala Tyr Met Glu Leu Ser Ser Leu Thr Ser Glu Asp Ser Ala Val
            100                 105                 110

Tyr Tyr Cys Ala Arg Gly Tyr Pro Ala Tyr Ser Gly Tyr Ala Met Asp
        115                 120                 125

Tyr Trp Gly Gln Gly Thr Ser Val Thr Val Ser Ala Lys Thr Lys
130                 135                 140

Gly Pro Ser Val Phe Pro Leu Ala Pro Cys Ser Arg Ser Thr Ser Glu
```

```
                145                 150                 155                 160
        Ser Thr Ala Ala Leu Gly Cys Leu Val Lys Asp Tyr Phe Pro Glu Pro
                        165                 170                 175

Val Thr Val Ser Trp Asn Ser Gly Ala Leu Thr Ser Gly Val His Thr
                        180                 185                 190

Phe Pro Ala Val Leu Gln Ser Ser Gly Leu Tyr Ser Leu Ser Ser Val
                        195                 200                 205

Val Thr Val Pro Ser Ser Leu Gly Thr Lys Thr Tyr Thr Cys Asn
                        210                 215                 220

Val Asp His Lys Pro Ser Asn Thr Lys Val Asp Lys Arg Val Glu Ser
        225                 230                 235                 240

Lys Tyr Gly Pro Pro Cys Pro Pro Cys Pro Ala Pro Glu Phe Glu Gly
                        245                 250                 255

Gly Pro Ser Val Phe Leu Phe Pro Pro Lys Pro Lys Asp Thr Leu Met
                        260                 265                 270

Ile Ser Arg Thr Pro Glu Val Thr Cys Val Val Val Asp Val Ser Gln
                        275                 280                 285

Glu Asp Pro Glu Val Gln Phe Asn Trp Tyr Val Asp Gly Val Glu Val
                        290                 295                 300

His Asn Ala Lys Thr Lys Pro Arg Glu Glu Gln Phe Asn Ser Thr Tyr
        305                 310                 315                 320

Arg Val Val Ser Val Leu Thr Val Leu His Gln Asp Trp Leu Asn Gly
                        325                 330                 335

Lys Glu Tyr Lys Cys Lys Val Ser Asn Lys Gly Leu Pro Ser Ser Ile
                        340                 345                 350

Glu Lys Thr Ile Ser Lys Ala Lys Gly Gln Pro Arg Glu Pro Gln Val
                        355                 360                 365

Tyr Thr Leu Pro Pro Ser Gln Glu Glu Met Thr Lys Asn Gln Val Ser
                        370                 375                 380

Leu Thr Cys Leu Val Lys Gly Phe Tyr Pro Ser Asp Ile Ala Val Glu
        385                 390                 395                 400

Trp Glu Ser Asn Gly Gln Pro Glu Asn Asn Tyr Lys Thr Thr Pro Pro
                        405                 410                 415

Val Leu Asp Ser Asp Gly Ser Phe Phe Leu Tyr Ser Arg Leu Thr Val
                        420                 425                 430

Asp Lys Ser Arg Trp Gln Glu Gly Asn Val Phe Ser Cys Ser Val Met
                        435                 440                 445

His Glu Ala Leu His Asn His Tyr Thr Gln Lys Ser Leu Ser Leu Ser
        450                 455                 460

Leu Gly Lys Ala Ser
        465

<210> SEQ ID NO 97
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
                20                  25                  30
```

```
Ala Ser Leu Gly Asp Arg Val Thr Ile Ser Cys Arg Ala Ser Gln Asp
         35                   40                  45

Ile Ser Asn Tyr Leu Asn Trp Tyr Gln Gln Lys Pro Asp Gly Thr Val
 50                      55                  60

Lys Leu Leu Ile Tyr Tyr Thr Ser Arg Leu His Ser Gly Val Pro Ser
 65                  70                  75                  80

Arg Phe Ser Gly Ser Gly Ser Gly Thr Asp Tyr Ser Leu Thr Ile Ser
             85                  90                  95

Asn Leu Glu Gln Glu Asp Ile Ala Thr Tyr Phe Cys His His Gly Asn
            100                 105                 110

Thr Leu Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 98
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Asn Leu Gly Leu Ser Leu Ile Phe Leu Val Leu Val Leu Lys Gly
 1               5                  10                  15

Val Gln Cys Glu Val Lys Leu Val Glu Ser Gly Gly Gly Leu Val Gln
             20                  25                  30

Pro Gly Gly Ser Leu Lys Leu Ser Cys Ala Thr Ser Gly Phe Thr Phe
         35                  40                  45

Ser Asp Tyr Tyr Met Tyr Trp Val Arg Gln Thr Pro Glu Lys Arg Leu
 50                  55                  60

Glu Trp Val Ala Tyr Ile Asn Ser Gly Gly Ser Thr Tyr Tyr Pro
 65                  70                  75                  80

Asp Thr Val Lys Gly Arg Phe Thr Ile Ser Arg Asp Asn Ala Lys Asn
             85                  90                  95

Thr Leu Tyr Leu Gln Met Ser Arg Leu Lys Ser Glu Asp Thr Ala Met
            100                 105                 110

Tyr Tyr Cys Ala Arg Arg Gly Leu Pro Phe His Ala Met Asp Tyr Trp
        115                 120                 125

Gly Gln Gly Thr Ser Val Thr Val Ser Ser Ala Lys Thr Lys Gly Pro
130                 135                 140

Ser Val Phe Pro Leu Ala Pro Cys Ser Arg Ser Thr Ser Glu Ser Thr
145                 150                 155                 160
```

```
Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Glu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys Ala Ser
465

<210> SEQ ID NO 99
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Ser Ala Ser Gln Gly
```

```
                35                  40                  45
Ile Ser Asn Tyr Leu Asn Trp Tyr Gln Gln Lys Pro Asp Gly Thr Val
 50                  55                  60

Lys Leu Leu Ile Tyr Tyr Thr Ser Ile Leu His Ser Gly Val Pro Ser
 65                  70                  75                  80

Arg Phe Ser Gly Ser Gly Ser Gly Thr Asp Tyr Ser Leu Thr Ile Gly
                 85                  90                  95

Asn Leu Glu Pro Glu Asp Ile Ala Thr Tyr Tyr Cys Gln Gln Phe Asn
                100                 105                 110

Lys Leu Pro Pro Thr Phe Gly Gly Gly Thr Lys Leu Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 100
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Asp Trp Leu Trp Asn Leu Leu Phe Leu Met Ala Ala Ala Gln Ser
 1               5                  10                  15

Ala Gln Ala Gln Ile Gln Leu Val Gln Ser Gly Pro Glu Leu Lys Lys
                20                  25                  30

Pro Gly Glu Thr Val Lys Ile Ser Cys Lys Ala Ser Gly Tyr Ser Phe
            35                  40                  45

Thr Asn Tyr Gly Met Asn Trp Val Lys Gln Ala Pro Gly Lys Gly Leu
 50                  55                  60

Lys Trp Met Gly Trp Ile Asn Thr Tyr Thr Gly Glu Ser Thr Tyr Ala
 65                  70                  75                  80

Asp Asp Phe Lys Gly Arg Phe Ala Phe Ser Leu Glu Thr Ser Ala Ser
                 85                  90                  95

Thr Ala Tyr Leu Gln Ile Ser Asn Leu Lys Asn Glu Asp Met Ala Thr
                100                 105                 110

Tyr Phe Cys Ala Arg Gly Asp Phe Arg Tyr Tyr Phe Asp Tyr Trp
            115                 120                 125

Gly Gln Gly Thr Thr Leu Thr Gly Ser Ser Ala Lys Thr Lys Gly Pro
        130                 135                 140

Ser Val Phe Pro Leu Ala Pro Cys Ser Arg Ser Thr Ser Glu Ser Thr
145                 150                 155                 160
```

Ala Ala Leu Gly Cys Leu Val Lys Asp Tyr Phe Pro Glu Pro Val Thr
            165                 170                 175

Val Ser Trp Asn Ser Gly Ala Leu Thr Ser Gly Val His Thr Phe Pro
        180                 185                 190

Ala Val Leu Gln Ser Ser Gly Leu Tyr Ser Leu Ser Ser Val Val Thr
    195                 200                 205

Val Pro Ser Ser Ser Leu Gly Thr Lys Thr Tyr Thr Cys Asn Val Asp
210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Glu Gly Gly Pro
            245                 250                 255

Ser Val Phe Leu Phe Pro Pro Lys Pro Lys Asp Thr Leu Met Ile Ser
        260                 265                 270

Arg Thr Pro Glu Val Thr Cys Val Val Val Asp Val Ser Gln Glu Asp
    275                 280                 285

Pro Glu Val Gln Phe Asn Trp Tyr Val Asp Gly Val Glu Val His Asn
290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
            325                 330                 335

Tyr Lys Cys Lys Val Ser Asn Lys Gly Leu Pro Ser Ser Ile Glu Lys
        340                 345                 350

Thr Ile Ser Lys Ala Lys Gly Gln Pro Arg Glu Pro Gln Val Tyr Thr
    355                 360                 365

Leu Pro Pro Ser Gln Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Arg Leu Thr Val Asp Lys
        420                 425                 430

Ser Arg Trp Gln Glu Gly Asn Val Phe Ser Cys Ser Val Met His Glu
    435                 440                 445

Ala Leu His Asn His Tyr Thr Gln Lys Ser Leu Ser Leu Ser Leu Gly
450                 455                 460

Lys Ala Ser
465

<210> SEQ ID NO 101
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Ile His Asn Tyr Leu Ala Trp Tyr Gln Gln Lys Gln Gly Lys Ser Pro
 50                  55                  60

Gln Leu Leu Val Tyr Asn Ala Lys Thr Leu Ala Asp Gly Val Pro Ser
 65                  70                  75                  80

Arg Phe Ser Gly Ser Gly Ser Gly Thr Gln Tyr Ser Leu Lys Ile Asn
                 85                  90                  95

Thr Leu Gln Pro Glu Asp Phe Gly Ser Tyr Tyr Cys Gln His Phe Trp
             100                 105                 110

Asp Ser Trp Thr Phe Gly Gly Gly Thr Lys Leu Glu Ile Lys Arg Thr
         115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 102
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Ile Ser Cys Lys Ala Thr Gly Tyr Thr Phe
        35                  40                  45

Ser Ser Tyr Trp Ile Glu Trp Val Lys Gln Arg Pro Gly His Gly Leu
    50                  55                  60

Glu Trp Ile Gly Glu Ile Leu Pro Gly Ser Gly Arg Thr Asn Asp Asn
65                  70                  75                  80

Glu Lys Phe Lys Gly Lys Ala Thr Phe Thr Ala Asp Thr Ser Ser Lys
                85                  90                  95

Lys Ala Tyr Met Gln Leu Ser Ser Leu Thr Ser Glu Asp Ser Ala Val
            100                 105                 110

Tyr Tyr Cys Ala Arg Arg Gly Gly Tyr Ser Phe Ala Tyr Trp Gly Gln
        115                 120                 125

Gly Thr Leu Val Thr Val Ser Ala Ala Lys Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser

```
                 165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Glu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Gln Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
        435                 440                 445

His Asn His Tyr Thr Gln Lys Ser Leu Ser Leu Ser Leu Gly Lys Ala
    450                 455                 460

Ser
465

<210> SEQ ID NO 103
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Met Thr Met Phe Ser Leu Ala Leu Leu Leu Ser Leu Leu Leu Leu Cys
1               5                   10                  15

Val Ser Asp Ser Arg Ala Glu Thr Thr Val Thr Gln Ser Pro Ala Ser
            20                  25                  30

Leu Ser Met Ala Ile Gly Glu Lys Val Thr Ile Arg Cys Val Thr Ser
        35                  40                  45
```

```
Thr Asp Ile Asp Asp Val Asn Trp Tyr Gln Gln Lys Pro Gly Glu
 50                  55                  60

Pro Pro Lys Leu Leu Ile Ser Glu Gly Asn Thr Leu Arg Pro Gly Val
 65                  70                  75                  80

Pro Ser Arg Phe Ser Ser Gly Tyr Gly Thr Asp Phe Val Phe Thr
                 85                  90                  95

Ile Glu Asn Met Leu Ser Glu Asp Val Ala Asp Tyr Tyr Cys Leu Gln
                100                 105                 110

Ser Gly Asn Leu Pro Tyr Thr Phe Gly Gly Gly Thr Lys Leu Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 104
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Ala Trp Val Trp Thr Leu Leu Phe Leu Met Ala Ala Ala Gln Ser
 1               5                  10                  15

Ala Gln Ala Gln Ile Gln Leu Val Gln Ser Gly Pro Glu Leu Lys Lys
                20                  25                  30

Pro Gly Glu Thr Val Lys Ile Ser Cys Lys Ala Ser Gly Tyr Thr Phe
             35                  40                  45

Thr Asn Tyr Gly Met Asn Trp Val Lys Gln Ala Pro Gly Lys Gly Leu
 50                  55                  60

Lys Trp Val Gly Trp Ile Asn Thr Phe Thr Gly Glu Pro Thr Tyr Val
 65                  70                  75                  80

Asp Asp Phe Lys Gly Arg Phe Ala Phe Ser Leu Glu Thr Ser Ala Ser
                 85                  90                  95

Thr Ala Tyr Leu Gln Ile Asn Asn Leu Lys Asn Glu Asp Thr Ala Thr
                100                 105                 110

Tyr Phe Cys Ala Arg Gly Asn Phe Arg Tyr Tyr Phe Asp Tyr Trp
            115                 120                 125

Gly Gln Gly Thr Thr Leu Thr Val Ser Ser Ala Lys Thr Lys Gly Pro
130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175
```

```
Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Cys Pro Ala Pro Glu Phe Glu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
            325                 330                 335

Tyr Lys Cys Lys Val Ser Asn Lys Gly Leu Pro Ser Ser Ile Glu Lys
        340                 345                 350

Thr Ile Ser Lys Ala Lys Gly Gln Pro Arg Glu Pro Gln Val Tyr Thr
    355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Arg Leu Thr Val Asp Lys
        420                 425                 430

Ser Arg Trp Gln Glu Gly Asn Val Phe Ser Cys Ser Val Met His Glu
    435                 440                 445

Ala Leu His Asn His Tyr Thr Gln Lys Ser Leu Ser Leu Ser Leu Gly
    450                 455                 460

Lys Ala Ser
465

<210> SEQ ID NO 105
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Thr Ser Gly Asn
        35                  40                  45

Ile Arg Asn Tyr Leu Ala Trp Tyr Gln Gln Lys Gln Gly Lys Ser Pro
```

```
           50                  55                  60
Gln Leu Leu Val Tyr Asn Ala Lys Thr Leu Ala Asp Gly Val Pro Ser
 65                  70                  75                  80

Arg Phe Gly Gly Ser Gly Ser Gly Thr Gln Tyr Ser Leu Lys Ile Asn
                 85                  90                  95

Ser Leu Gln Pro Glu Asp Phe Gly Asn Tyr Tyr Cys Gln His Phe Trp
            100                 105                 110

Ser Ser Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 106
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Met Gly Trp Ser Tyr Ile Ile Leu Phe Leu Val Ala Thr Ala Thr
  1               5                  10                  15

Asp Val His Ser Gln Val Gln Leu Gln Gln Pro Gly Ala Glu Leu Val
                 20                  25                  30

Lys Pro Gly Ala Ser Val Lys Leu Ser Cys Lys Ala Ser Gly Tyr Thr
             35                  40                  45

Phe Thr Ser Tyr Trp Met His Trp Val Lys Gln Arg Pro Gly Glu Gly
         50                  55                  60

Leu Glu Trp Ile Gly Glu Ile Asn Pro Ser Tyr Gly Arg Thr Asp Tyr
 65                  70                  75                  80

Asn Glu Lys Phe Lys Asn Lys Ala Thr Leu Thr Val Ala Lys Ser Ser
                 85                  90                  95

Ser Thr Ala Tyr Met Gln Leu Ser Ser Leu Thr Ser Glu Asp Ser Ala
            100                 105                 110

Val Tyr Tyr Cys Ala Arg Gly Asp Tyr Tyr Gly Ser Ser Ser Phe Ala
        115                 120                 125

Tyr Trp Gly Gln Gly Thr Leu Val Thr Val Ser Ala Ala Lys Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175
```

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Glu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys Ala Ser
465

<210> SEQ ID NO 107
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Met Asp Phe Gln Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
            20                  25                  30

Met Ser Ala Ser Pro Gly Glu Lys Val Thr Met Thr Cys Ser Ala Ser
        35                  40                  45

Ser Asn Ile Ser Tyr Met Tyr Trp Tyr Gln Gln Lys Pro Arg Ser Ser
    50                  55                  60

Pro Lys Pro Trp Ile Tyr Leu Thr Ser Asn Leu Ala Ser Gly Val Pro
65                  70                  75                  80

Ala Arg Phe Ser Gly Ser Gly Ser Gly Thr Ser Tyr Ser Leu Thr Thr
                85                  90                  95

Ser Ser Met Glu Ala Glu Asp Ala Ala Thr Tyr Cys Cys Gln Gln Trp
            100                 105                 110

Ser Ser Asn Pro Pro Thr Phe Gly Ala Gly Thr Lys Leu Glu Ile Lys
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 108
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Asp Phe Arg Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
            20                  25                  30

Met Ser Ala Ser Pro Gly Glu Lys Val Thr Met Thr Cys Ser Ala Ser
        35                  40                  45

Ser Asn Ile Ser Tyr Met Tyr Trp Tyr Gln Gln Lys Pro Arg Ser Ser
    50                  55                  60

Pro Lys Pro Trp Ile Tyr Leu Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Pro Thr Phe Gly Ala Gly Thr Lys Leu Glu Ile Lys
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser

```
                180             185             190
Thr Tyr Ser Leu Ser Ser Thr Leu Thr Leu Ser Lys Ala Asp Tyr Glu
                195             200             205
Lys His Lys Val Tyr Ala Cys Glu Val Thr His Gln Gly Leu Ser Ser
        210             215             220
Pro Val Thr Lys Ser Phe Asn Arg Gly Glu Cys
225             230             235
```

<210> SEQ ID NO 109
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Met Glu Thr Asp Thr Leu Leu Leu Trp Val Leu Leu Leu Trp Val Pro
1               5                   10                  15
Gly Ser Thr Gly Asp Ile Val Leu Ile Gln Ser Pro Ala Ser Leu Ala
                20                  25                  30
Val Ser Leu Gly Gln Arg Ala Thr Ile Ser Cys Arg Ala Ser Glu Ser
            35                  40                  45
Val Asp Ser Tyr Val Asn Ser Phe Met His Trp Tyr Gln Gln Lys Pro
        50                  55                  60
Gly Gln Pro Pro Lys Leu Leu Ile Tyr Arg Val Ser Asn Leu Glu Ser
65                  70                  75                  80
Gly Ile Pro Ala Arg Phe Ser Gly Ser Gly Ser Arg Thr Asp Phe Thr
                85                  90                  95
Leu Thr Ile Asn Pro Val Glu Ala Asp Asp Val Ala Thr Tyr Tyr Cys
                100                 105                 110
Gln Gln Ser Asn Glu Asp Pro Phe Thr Phe Gly Ser Gly Thr Lys Leu
            115                 120                 125
Glu Ile Lys Arg Thr Val Ala Ala Pro Ser Val Phe Ile Phe Pro Pro
        130                 135                 140
Ser Asp Glu Gln Leu Lys Ser Gly Thr Ala Ser Val Val Cys Leu Leu
145                 150                 155                 160
Asn Asn Phe Tyr Pro Arg Glu Ala Lys Val Gln Trp Lys Val Asp Asn
                165                 170                 175
Ala Leu Gln Ser Gly Asn Ser Gln Glu Ser Val Thr Glu Gln Asp Ser
            180                 185                 190
Lys Asp Ser Thr Tyr Ser Leu Ser Ser Thr Leu Thr Leu Ser Lys Ala
        195                 200                 205
Asp Tyr Glu Lys His Lys Val Tyr Ala Cys Glu Val Thr His Gln Gly
    210                 215                 220
Leu Ser Ser Pro Val Thr Lys Ser Phe Asn Arg Gly Glu Cys
225                 230                 235
```

<210> SEQ ID NO 110
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

```
Met Glu Cys Asn Trp Ile Leu Pro Phe Ile Leu Ser Val Ile Ser Gly
```

-continued

```
1               5                   10                  15
Val Tyr Ser Glu Val Gln Leu Gln Gln Ser Gly Thr Val Leu Ala Arg
            20                  25                  30
Pro Gly Ala Ser Val Asn Met Ser Cys Lys Ala Ala Gly Tyr Ser Phe
            35                  40                  45
Thr Ser Tyr Trp Val Tyr Trp Val Lys Gln Arg Pro Gly Gln Gly Leu
        50                  55                  60
Glu Trp Ile Gly Ala Ile Tyr Pro Lys Asn Ser Arg Thr Ser Tyr Asn
65                  70                  75                  80
Gln Lys Phe Gln Asp Lys Ala Thr Leu Thr Ala Val Thr Ser Ala Ser
                85                  90                  95
Thr Ala Tyr Met Glu Leu Ser Ser Leu Thr Asn Glu Asp Ser Ala Val
                100                 105                 110
Tyr Tyr Cys Thr Arg Pro His Tyr Asp Ser Phe Gly Tyr Trp Gly Gln
            115                 120                 125
Gly Thr Leu Val Thr Val Ser Ala Ala Lys Thr Lys Gly Pro Ser Val
        130                 135                 140
Phe Pro Leu Ala Pro Cys Ser Arg Ser Thr Ser Glu Ser Thr Ala Ala
145                 150                 155                 160
Leu Gly Cys Leu Val Lys Asp Tyr Phe Pro Glu Pro Val Thr Val Ser
                165                 170                 175
Trp Asn Ser Gly Ala Leu Thr Ser Gly Val His Thr Phe Pro Ala Val
                180                 185                 190
Leu Gln Ser Ser Gly Leu Tyr Ser Leu Ser Ser Val Val Thr Val Pro
            195                 200                 205
Ser Ser Ser Leu Gly Thr Lys Thr Tyr Thr Cys Asn Val Asp His Lys
        210                 215                 220
Pro Ser Asn Thr Lys Val Asp Lys Arg Val Glu Ser Lys Tyr Gly Pro
225                 230                 235                 240
Pro Cys Pro Pro Cys Pro Ala Pro Glu Phe Glu Gly Gly Pro Ser Val
                245                 250                 255
Phe Leu Phe Pro Pro Lys Pro Lys Asp Thr Leu Met Ile Ser Arg Thr
                260                 265                 270
Pro Glu Val Thr Cys Val Val Val Asp Val Ser Gln Glu Asp Pro Glu
            275                 280                 285
Val Gln Phe Asn Trp Tyr Val Asp Gly Val Glu Val His Asn Ala Lys
        290                 295                 300
Thr Lys Pro Arg Glu Glu Gln Phe Asn Ser Thr Tyr Arg Val Val Ser
305                 310                 315                 320
Val Leu Thr Val Leu His Gln Asp Trp Leu Asn Gly Lys Glu Tyr Lys
                325                 330                 335
Cys Lys Val Ser Asn Lys Gly Leu Pro Ser Ser Ile Glu Lys Thr Ile
                340                 345                 350
Ser Lys Ala Lys Gly Gln Pro Arg Glu Pro Gln Val Tyr Thr Leu Pro
            355                 360                 365
Pro Ser Gln Glu Glu Met Thr Lys Asn Gln Val Ser Leu Thr Cys Leu
        370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Val Leu Asp Ser
                405                 410                 415
Asp Gly Ser Phe Phe Leu Tyr Ser Arg Leu Thr Val Asp Lys Ser Arg
                420                 425                 430
```

Trp Gln Glu Gly Asn Val Phe Ser Cys Ser Val Met His Glu Ala Leu
            435                 440                 445

His Asn His Tyr Thr Gln Lys Ser Leu Ser Leu Ser Leu Gly Lys Ala
    450                 455                 460

Ser
465

<210> SEQ ID NO 111
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Ser Tyr Gly Ile Ser Phe Met His Trp Tyr Gln Gln Lys Pro
    50                  55                  60

Gly Gln Pro Pro Lys Leu Leu Ile Tyr Arg Ala Ser Asn Gln Glu Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Ala Asp Asp Val Ala Thr Tyr Tyr Cys
            100                 105                 110

Gln Gln Ser Asn Glu Asp Pro Leu Thr Phe Gly Ala Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 112
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asn Arg Leu Thr Ser Ser Leu Leu Leu Leu Ile Val Pro Ala Tyr Val
1               5                   10                  15

-continued

Leu Ser Gln Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
            35                  40                  45

Ser Thr Ser Gly Met Gly Val Ser Trp Ile Arg Gln Pro Ser Gly Lys
 50                  55                  60

Gly Leu Glu Trp Leu Ala His Ile Tyr Trp Asp Asp Lys Arg Tyr
 65                  70                  75                  80

Asn Pro Ser Leu Lys Ser Arg Leu Thr Ile Phe Lys Asp Pro Ser Ser
                85                  90                  95

Asn Gln Val Phe Leu Arg Ile Thr Ser Val Asp Thr Ala Asp Thr Ala
            100                 105                 110

Thr Tyr Tyr Cys Ala Arg Asn Ser His Tyr Tyr Gly Ser Thr Tyr Gly
            115                 120                 125

Gly Tyr Phe Asp Val Trp Gly Ala Gly Thr Thr Val Thr Val Ser Ser
 130                 135                 140

Ala Lys Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Ser Leu Gly Thr Lys Thr
 210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Cys Pro Pro Cys Pro Ala Pro
                245                 250                 255

Glu Phe Glu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser Gln Glu Asp Pro Glu Val Gln Phe Asn Trp Tyr Val Asp
 290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
            355                 360                 365

Glu Pro Gln Val Tyr Thr Leu Pro Pro Ser Gln Glu Met Thr Lys
 370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

```
Arg Leu Thr Val Asp Lys Ser Arg Trp Gln Glu Gly Asn Val Phe Ser
            435                 440                 445

Cys Ser Val Met His Glu Ala Leu His Asn His Tyr Thr Gln Lys Ser
        450                 455                 460

Leu Ser Leu Ser Leu Gly Lys Ala Ser
465                 470

<210> SEQ ID NO 113
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Glu Thr Asp Thr Leu Leu Leu Trp Val Leu Leu Leu Gly Val Pro
1               5                   10                  15

Gly Ser Thr Gly Asn Ile Val Leu Thr Gln Ser Pro Thr Ser Phe Thr
            20                  25                  30

Val Ser Leu Gly Gln Arg Ala Thr Ile Ser Cys Arg Ala Ser Glu Ser
        35                  40                  45

Val His Ser Tyr Gly Asn Ser Phe Met His Trp Tyr Gln Gln Lys Pro
    50                  55                  60

Gly Gln Pro Pro Lys Leu Leu Ile Tyr Leu Ala Ser Asn Val Glu Ser
65                  70                  75                  80

Gly Val Pro Ala Arg Phe Ser Gly Ser Gly Ser Arg Thr Asp Phe Thr
                85                  90                  95

Leu Thr Ile Asp Pro Val Glu Ala Asp Ala Ala Thr Tyr Tyr Cys
            100                 105                 110

Gln Gln Asn Ser Glu Asp Pro Trp Thr Phe Gly Gly Gly Thr Lys Leu
            115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 114
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Met Glu Trp Thr Trp Val Phe Leu Phe Leu Leu Ser Val Thr Ala Gly
1               5                   10                  15
```

```
Val His Ser Gln Val Gln Leu Gln Gln Ser Gly Thr Glu Leu Met Lys
            20                  25                  30

Pro Gly Ala Ser Val Lys Ile Ser Cys Lys Ala Thr Gly Tyr Thr Phe
        35                  40                  45

Ser Thr Tyr Trp Ile Glu Trp Val Lys Gln Arg Pro Gly His Gly Leu
    50                  55                  60

Glu Trp Ile Gly Glu Ile Leu Pro Gly Ser Gly Arg Thr Asn Asp Asn
65                  70                  75                  80

Glu Lys Phe Lys Gly Lys Ala Thr Ile Thr Ala Asp Thr Ser Ser Lys
                85                  90                  95

Lys Ala Tyr Met Gln Leu Ser Ser Leu Thr Ser Glu Asp Ser Ala Val
            100                 105                 110

Tyr Tyr Cys Ala Arg Arg Gly Gly Tyr Ser Phe Ala Phe Trp Gly Gln
        115                 120                 125

Gly Thr Leu Val Ser Val Ser Ala Ala Lys Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Glu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Gln Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
```

```
                    435                 440                 445

His Asn His Tyr Thr Gln Lys Ser Leu Ser Leu Ser Leu Gly Lys Ala
    450                 455                 460

Ser
465

<210> SEQ ID NO 115
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Met Thr Met Phe Ser Leu Ala Leu Leu Ser Leu Leu Leu Leu Cys
1               5                  10                  15

Val Ser Asp Ser Arg Ala Glu Thr Thr Val Thr Gln Ser Pro Ala Ser
                20                  25                  30

Leu Ser Met Ala Ile Gly Glu Lys Val Thr Ile Arg Cys Val Thr Ser
            35                  40                  45

Thr Asp Ile Asp Asp Asp Val Asn Trp Tyr Gln Gln Lys Pro Gly Glu
    50                  55                  60

Pro Pro Lys Leu Leu Ile Ser Glu Gly Asn Thr Leu Arg Ala Gly Val
65                  70                  75                  80

Pro Ser Arg Phe Ser Ser Gly Tyr Gly Thr Asp Phe Val Phe Thr
                85                  90                  95

Ile Glu Asn Met Leu Ser Glu Asp Val Ala Asp Tyr Tyr Cys Leu Gln
                100                 105                 110

Ser Gly Asn Leu Pro Tyr Thr Phe Gly Gly Gly Thr Lys Leu Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 116
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Asn Arg Leu Thr Ser Ser Leu Leu Leu Leu Ile Val Pro Ala Tyr
1               5                   10                  15

Val Leu Ser Gln Val Thr Leu Lys Glu Ser Gly Pro Gly Ile Leu Gln
```

```
                20                  25                  30
Pro Ser Gln Thr Leu Ser Leu Thr Cys Ser Phe Ser Gly Phe Ser Leu
            35                  40                  45
Ser Thr Ser Gly Met Gly Leu Ser Trp Ile Arg Gln Pro Ser Gly Lys
        50                  55                  60
Gly Leu Glu Trp Leu Ala His Ile Tyr Trp Asp Asp Lys Arg Tyr
65                  70                  75                  80
Asn Pro Ser Leu Lys Ser Arg Leu Thr Ile Ser Lys Asp Thr Ser Ser
                85                  90                  95
Asn Gln Val Phe Leu Lys Ile Thr Ile Val Asp Thr Ala Asp Ala Ala
            100                 105                 110
Thr Tyr Tyr Cys Ala Arg Ser Ser His Tyr Gly Tyr Gly Tyr Gly
        115                 120                 125
Gly Tyr Phe Asp Val Trp Gly Ala Gly Thr Thr Val Thr Val Ser Ser
        130                 135                 140
Ala Lys Thr Lys Gly Pro Ser Val Phe Pro Leu Ala Pro Cys Ser Arg
145                 150                 155                 160
Ser Thr Ser Glu Ser Thr Ala Ala Leu Gly Cys Leu Val Lys Asp Tyr
                165                 170                 175
Phe Pro Glu Pro Val Thr Val Ser Trp Asn Ser Gly Ala Leu Thr Ser
            180                 185                 190
Gly Val His Thr Phe Pro Ala Val Leu Gln Ser Ser Gly Leu Tyr Ser
        195                 200                 205
Leu Ser Ser Val Val Thr Val Pro Ser Ser Ser Leu Gly Thr Lys Thr
    210                 215                 220
Tyr Thr Cys Asn Val Asp His Lys Pro Ser Asn Thr Lys Val Asp Lys
225                 230                 235                 240
Arg Val Glu Ser Lys Tyr Gly Pro Pro Cys Pro Pro Cys Pro Ala Pro
                245                 250                 255
Glu Phe Glu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
        275                 280                 285
Asp Val Ser Gln Glu Asp Pro Glu Val Gln Phe Asn Trp Tyr Val Asp
    290                 295                 300
Gly Val Glu Val His Asn Ala Lys Thr Lys Pro Arg Glu Glu Gln Phe
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Gly Leu
            340                 345                 350
Pro Ser Ser Ile Glu Lys Thr Ile Ser Lys Ala Lys Gly Gln Pro Arg
        355                 360                 365
Glu Pro Gln Val Tyr Thr Leu Pro Pro Ser Gln Glu Glu Met Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Arg Leu Thr Val Asp Lys Ser Arg Trp Gln Glu Gly Asn Val Phe Ser
        435                 440                 445
```

Cys Ser Val Met His Glu Ala Leu His Asn His Tyr Thr Gln Lys Ser
        450                 455                 460

Leu Ser Leu Ser Leu Gly Lys Ala Ser
465                 470

<210> SEQ ID NO 117
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Met Glu Thr Asp Thr Leu Leu Leu Trp Val Leu Leu Leu Trp Val Pro
1               5                   10                  15

Gly Ser Thr Gly Asn Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Ile His Ser Tyr Gly Asn Ser Phe Leu His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Arg Thr Asp Phe Thr
                85                  90                  95

Leu Thr Ile Asp Pro Val Glu Ala Asp Asp Ala Ala Thr Tyr Tyr Cys
            100                 105                 110

Gln Gln Asn Asn Glu Asp Pro Trp Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 118
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (309)..(309)
<223> OTHER INFORMATION: Any amino acid

<400> SEQUENCE: 118

Met Lys Cys Ser Trp Val Ile Phe Phe Leu Met Ala Val Val Thr Gly

-continued

```
1               5                   10                  15
Val Asn Ser Glu Val Gln Leu Gln Gln Ser Gly Ala Glu Leu Val Arg
             20                  25                  30
Pro Gly Ala Leu Val Lys Leu Ser Cys Lys Ala Ser Gly Phe Asn Ile
             35                  40                  45
Asn Asp Tyr Tyr Ile His Trp Val Lys Gln Arg Pro Glu Gln Gly Leu
         50                  55                  60
Glu Arg Ile Gly Trp Ile Asp Pro Asp Asn Gly Asn Thr Ile Tyr Asp
65                  70                  75                  80
Pro Lys Phe Gln Gly Lys Ala Ser Ile Thr Ala Asp Thr Ser Pro Asn
                 85                  90                  95
Thr Ala Tyr Leu Gln Leu Ser Ser Leu Thr Ser Glu Asp Thr Ala Val
             100                 105                 110
Tyr Tyr Cys Ala Arg Thr Arg Ser Pro Met Val Thr Gly Phe Val
             115                 120                 125
Tyr Trp Gly Gln Gly Thr Val Val Thr Val Ser Ala Ala Lys Thr Lys
         130                 135                 140
Gly Pro Ser Val Phe Pro Leu Ala Pro Cys Ser Arg Ser Thr Ser Glu
145                 150                 155                 160
Ser Thr Ala Ala Leu Gly Cys Leu Val Lys Asp Tyr Phe Pro Glu Pro
                 165                 170                 175
Val Thr Val Ser Trp Asn Ser Gly Ala Leu Thr Ser Gly Val His Thr
             180                 185                 190
Phe Pro Ala Val Leu Gln Ser Ser Gly Leu Tyr Ser Leu Ser Ser Val
             195                 200                 205
Val Thr Val Pro Ser Ser Ser Leu Gly Thr Lys Thr Tyr Thr Cys Asn
         210                 215                 220
Val Asp His Lys Pro Ser Asn Thr Lys Val Asp Lys Arg Val Glu Ser
225                 230                 235                 240
Lys Tyr Gly Pro Pro Cys Pro Pro Cys Pro Ala Pro Glu Phe Glu Gly
                 245                 250                 255
Gly Pro Ser Val Phe Leu Phe Pro Pro Lys Pro Lys Asp Thr Leu Met
             260                 265                 270
Ile Ser Arg Thr Pro Glu Val Thr Cys Val Val Val Asp Val Ser Gln
             275                 280                 285
Glu Asp Pro Glu Val Gln Phe Asn Trp Tyr Val Asp Gly Val Glu Val
         290                 295                 300
His Asn Ala Lys Xaa Lys Pro Arg Glu Glu Gln Phe Asn Ser Thr Tyr
305                 310                 315                 320
Arg Val Val Ser Val Leu Thr Val Leu His Gln Asp Trp Leu Asn Gly
                 325                 330                 335
Lys Glu Tyr Lys Cys Lys Val Ser Asn Lys Gly Leu Pro Ser Ser Ile
             340                 345                 350
Glu Lys Thr Ile Ser Lys Ala Lys Gly Gln Pro Arg Glu Pro Gln Val
             355                 360                 365
Tyr Thr Leu Pro Pro Ser Gln Glu Glu Met Thr Lys Asn Gln Val Ser
         370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                 405                 410                 415
Val Leu Asp Ser Asp Gly Ser Phe Phe Leu Tyr Ser Arg Leu Thr Val
             420                 425                 430
```

-continued

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys
465

<210> SEQ ID NO 119
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Glu Arg His Trp Ile Phe Leu Phe Leu Phe Ser Val Thr Ala Gly
1               5                   10                  15

Val His Ser Gln Val Gln Leu Gln Gln Ser Gly Ala Glu Leu Ala Lys
            20                  25                  30

Pro Gly Ala Ser Val Lys Met Ser Cys Lys Ala Ser Gly Tyr Thr Phe
        35                  40                  45

Thr Thr Tyr Trp Met His Trp Val Lys Gln Arg Pro Gly Gln Gly Leu
    50                  55                  60

Glu Trp Ile Gly Tyr Ile Asn Pro Ile Thr Gly Tyr Thr Glu Tyr Asn
65                  70                  75                  80

Gln Lys Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Glu Gly Leu Ser Ala Met Asp Tyr Trp Gly Gln
        115                 120                 125

Gly Thr Ser Val Thr Val Thr Ser Ala Lys Thr Thr Ala Pro Ser Val
    130                 135                 140

Tyr Pro Leu Ala Pro Val Cys Gly Asp Thr Thr Gly Ser Ser Val Thr
145                 150                 155                 160

Leu Gly Cys Leu Val Lys Gly Tyr Phe Pro Glu Pro Val Thr Leu Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Thr Ser
        195                 200                 205

Ser Thr Trp Pro Ser Gln Thr Val Thr Cys Ser Val Ala His Pro Ala
    210                 215                 220

Ser Ser Thr Thr Val Asp Lys Lys Leu Glu Pro Ser Gly Pro Ile Ser
225                 230                 235                 240

Thr Ile Asn Pro Cys Pro Pro Cys Lys Glu Cys His Lys Cys Pro Ala
                245                 250                 255

Pro Asn Leu Glu Gly Gly Pro Ser Val Phe Ile Phe Pro Pro Asn Ile
            260                 265                 270

Lys Asp Val Leu Met Ile Ser Leu Thr Pro Lys Val Thr Cys Val Val
        275                 280                 285

Val Asp Val Ser Glu Asp Asp Pro Asp Val Gln Ile Ser Trp Phe Val
    290                 295                 300

Asn Asn Val Glu Val His Thr Ala Gln Thr Gln Thr His Arg Glu Asp

```
            305                 310                 315                 320
Tyr Asn Ser Thr Ile Arg Val Val Ser Thr Leu Pro Ile Gln His Gln
                325                 330                 335

Asp Trp Met Ser Gly Lys Glu Phe Lys Cys Lys Val Asn Asn Lys Asp
                340                 345                 350

Leu Pro Ser Pro Ile Glu Arg Thr Ile Ser Lys Ile Lys Gly Leu Val
                355                 360                 365

Arg Ala Pro Gln Val Tyr Ile Leu Pro Pro Ala Glu Gln Leu Ser
370                 375                 380

Arg Lys Asp Val Ser Leu Thr Cys Leu Val Val Gly Phe Asn Pro Gly
385                 390                 395                 400

Asp Ile Ser Val Glu Trp Thr Ser Asn Gly His Thr Glu Glu Asn Tyr
                405                 410                 415

Lys Asp Thr Ala Pro Val Leu Asp Ser Asp Gly Ser Tyr Phe Ile Tyr
                420                 425                 430

Ser Lys Leu Asn Met Lys Thr Ser Lys Trp Glu Lys Thr Asp Ser Phe
                435                 440                 445

Ser Cys Asn Val Arg His Glu Gly Leu Lys Asn Tyr Tyr Leu Lys Lys
                450                 455                 460

Thr Ile Ser Arg Ser Pro Gly Lys Ala Ser
465                 470

<210> SEQ ID NO 120
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Glu Ser Arg Ile Gln Ala Phe Val Phe Val Phe Leu Trp Leu Ser
1               5                   10                  15

Gly Val Gly Gly Asp Ile Val Met Thr Gln Ser His Lys Phe Met Ser
                20                  25                  30

Thr Ser Val Gly Asp Arg Val Ser Val Thr Cys Lys Ala Ser Gln Asp
                35                  40                  45

Val Thr Ser Ala Val Ala Trp Tyr Gln Gln Lys Pro Gly Gln Ser Pro
                50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Tyr Thr Leu Thr Ile Ser
                85                  90                  95

Ser Gly Gln Ala Glu Asp Leu Ala Leu Tyr Tyr Cys His Gln Tyr Tyr
                100                 105                 110

Ser Ala Pro Arg Thr Phe Gly Gly Gly Thr Lys Leu Glu Val Lys Arg
                115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
                180                 185                 190
```

```
Tyr Ser Met Ser Ser Thr Leu Thr Leu Thr Lys Asp Glu Tyr Glu Arg
            195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 121
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Met Glu Arg His Trp Ile Phe Leu Phe Leu Phe Ser Val Thr Ala Gly
1               5                   10                  15

Val His Ser Gln Val Gln Leu Gln Gln Ser Gly Ala Glu Leu Ala Lys
            20                  25                  30

Pro Gly Ala Ser Val Lys Met Ser Cys Lys Ala Ser Gly Tyr Thr Phe
        35                  40                  45

Thr Thr Tyr Trp Met His Trp Val Lys Gln Arg Pro Gly Gln Gly Leu
    50                  55                  60

Glu Trp Ile Gly Tyr Ile Asn Pro Ile Thr Gly Tyr Thr Glu Tyr Asn
65                  70                  75                  80

Gln Lys Phe Lys Asp Lys Ala Thr Leu Thr Ala Asp Lys Ser Ser Ser
            85                  90                  95

Thr Ala Tyr Met Gln Leu Ser Ser Leu Thr Ser Glu Asp Ser Ala Val
            100                 105                 110

Tyr Tyr Cys Ala Arg Glu Gly Leu Ser Ala Met Asp Tyr Trp Gly Gln
        115                 120                 125

Gly Thr Ser Val Thr Val Thr Ser Ala Lys Thr Thr Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Glu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320
```

Val Leu Thr Val Leu His Gln Asp Trp Leu Asn Gly Lys Glu Tyr Lys
            325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
            355                 360                 365

Pro Ser Gln Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
            405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
            435                 440                 445

His Asn His Tyr Thr Gln Lys Ser Leu Ser Leu Ser Leu Gly Lys Ala
            450                 455                 460

Ser
465

<210> SEQ ID NO 122
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Met Glu Ser Gln Ile Gln Ala Phe Val Phe Val Leu Trp Leu Ser
1               5                   10                  15

Gly Val Gly Gly Asp Ile Val Met Thr Gln Ser His Lys Phe Met Ser
            20                  25                  30

Thr Ser Val Gly Asp Arg Val Ser Val Thr Cys Lys Ala Ser Gln Asp
            35                  40                  45

Val Thr Ser Ala Val Ala Trp Tyr Gln Gln Lys Pro Gly Gln Ser Pro
        50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Tyr Thr Leu Thr Ile Ser
            85                  90                  95

Ser Gly Gln Ala Glu Asp Leu Ala Leu Tyr Tyr Cys His Gln Tyr Tyr
            100                 105                 110

Ser Ala Pro Arg Thr Phe Gly Gly Gly Thr Lys Leu Glu Ile Lys Arg
            115                 120                 125

Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
            165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys

```
                195                 200                 205
His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 123
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Met Ala Val Leu Ala Leu Leu Cys Leu Val Ala Phe Pro Thr Cys
1               5                   10                  15

Thr Leu Ser Gln Val Gln Leu Lys Glu Ser Gly Pro Gly Leu Val Ala
            20                  25                  30

Pro Ser Gln Ser Leu Ser Ile Thr Cys Ser Val Ser Gly Phe Ser Leu
        35                  40                  45

Ser Asn Tyr Asp Ile Ser Trp Ile Arg Gln Pro Pro Gly Lys Gly Leu
50                  55                  60

Glu Trp Leu Gly Val Met Trp Thr Gly Gly Ala Asn Tyr Asn Ser
65                  70                  75                  80

Ala Phe Met Ser Arg Leu Ser Ile Asn Lys Asp Asn Ser Lys Ser Gln
                85                  90                  95

Val Phe Leu Lys Met Asn Asn Leu Gln Thr Asp Asp Thr Ala Ile Tyr
            100                 105                 110

Tyr Cys Val Arg Asp Ala Val Arg Tyr Trp Asn Phe Asp Val Trp Gly
        115                 120                 125

Ala Gly Thr Thr Val Thr Val Ser Ser Ala Lys Thr Lys Gly Pro Ser
130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Glu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320
```

```
Ser Val Leu Thr Val Leu His Gln Asp Trp Leu Asn Gly Lys Glu Tyr
            325                 330                 335

Lys Cys Lys Val Ser Asn Lys Gly Leu Pro Ser Ser Ile Glu Lys Thr
        340                 345                 350

Ile Ser Lys Ala Lys Gly Gln Pro Arg Glu Pro Gln Val Tyr Thr Leu
    355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
    450                 455                 460

Ala Ser
465

<210> SEQ ID NO 124
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Asp Phe Gln Ala Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Ile His Trp Tyr Gln Gln Lys Pro Gly Ser Ser
    50                  55                  60

Pro Lys Pro Trp Ile Tyr Ala Thr Ser His Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Thr Ala Thr Tyr Tyr Cys Gln Gln Trp
            100                 105                 110

Ser Ser Asn Pro Phe Thr Phe Gly Ser Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205
```

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 125
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Glu Arg His Trp Ile Phe Leu Leu Leu Ser Val Thr Ala Gly
1               5                   10                  15

Val His Ser Gln Val Gln Leu Gln Gln Ser Gly Ala Glu Leu Ala Arg
                20                  25                  30

Pro Gly Ala Ser Val Lys Met Ser Cys Lys Ala Ser Gly Tyr Thr Phe
                35                  40                  45

Thr Thr Tyr Thr Met His Trp Val Lys Gln Arg Pro Gly Gln Gly Leu
50                  55                  60

Glu Trp Ile Gly Tyr Ile Asn Pro Ser Ser Gly Tyr Thr Asn Tyr Asn
65                  70                  75                  80

Gln Lys Phe Lys Asp Lys Ala Thr Leu Thr Ala Asp Lys Ser Ser Ser
                85                  90                  95

Thr Ala Ser Met Gln Leu Ser Ser Leu Thr Ser Glu Asp Ser Ala Val
                100                 105                 110

Tyr Tyr Cys Ala Arg Glu Arg Ala Val Leu Val Pro Tyr Ala Met Asp
                115                 120                 125

Tyr Trp Gly Gln Gly Thr Ser Val Thr Val Ser Ser Ala Lys Thr Lys
                130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Lys Thr Tyr Thr Cys Asn
                210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Glu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser Gln
                275                 280                 285

Glu Asp Pro Glu Val Gln Phe Asn Trp Tyr Val Asp Gly Val Glu Val
                290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly

```
                         325                 330                 335
Lys Glu Tyr Lys Cys Lys Val Ser Asn Lys Gly Leu Pro Ser Ser Ile
                340                 345                 350
Glu Lys Thr Ile Ser Lys Ala Lys Gly Gln Pro Arg Glu Pro Gln Val
            355                 360                 365
Tyr Thr Leu Pro Pro Ser Gln Glu Glu Met Thr Lys Asn Gln Val Ser
        370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Arg Leu Thr Val
                420                 425                 430
Asp Lys Ser Arg Trp Gln Glu Gly Asn Val Phe Ser Cys Ser Val Met
            435                 440                 445
His Glu Ala Leu His Asn His Tyr Thr Gln Lys Ser Leu Ser Leu Ser
        450                 455                 460
Leu Gly Lys Ala Ser
465

<210> SEQ ID NO 126
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Met His Phe Gln Val Gln Ile Phe Ser Phe Leu Leu Ile Ser Ala Ser
1               5                   10                  15
Val Ile Met Ser Arg Gly Gln Ile Val Leu Thr Gln Ser Pro Ala Val
                20                  25                  30
Met Ser Ala Ser Pro Gly Glu Lys Val Thr Ile Thr Cys Thr Ala Ser
            35                  40                  45
Ser Ser Leu Ser Tyr Met His Trp Phe Gln Gln Lys Pro Gly Thr Ser
        50                  55                  60
Pro Lys Leu Trp Leu Tyr Ser Thr Ser Ile Leu Ala Ser Gly Val Pro
65                  70                  75                  80
Thr Arg Phe Ser Gly Ser Gly Ser Gly Thr Ser Tyr Ser Leu Thr Ile
                85                  90                  95
Ser Arg Met Glu Ala Glu Asp Ala Ala Thr Tyr Tyr Cys Gln Gln Arg
            100                 105                 110
Ser Ser Ser Pro Phe Thr Phe Gly Ser Gly Thr Lys Leu Glu Ile Lys
        115                 120                 125
Arg Thr Val Ala Ala Pro Ser Val Phe Ile Phe Pro Pro Ser Asp Glu
130                 135                 140
Gln Leu Lys Ser Gly Thr Ala Ser Val Val Cys Leu Leu Asn Asn Phe
145                 150                 155                 160
Tyr Pro Arg Glu Ala Lys Val Gln Trp Lys Val Asp Asn Ala Leu Gln
                165                 170                 175
Ser Gly Asn Ser Gln Glu Ser Val Thr Glu Gln Asp Ser Lys Asp Ser
            180                 185                 190
Thr Tyr Ser Leu Ser Ser Thr Leu Thr Leu Ser Lys Ala Asp Tyr Glu
        195                 200                 205
```

```
Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 127
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Gly Trp Thr Trp Ile Phe Ile Leu Ile Leu Ser Val Thr Thr Gly
1               5                   10                  15

Val His Ser Glu Val Gln Leu Gln Gln Ser Gly Pro Glu Leu Glu Lys
            20                  25                  30

Pro Gly Ala Ser Val Lys Ile Ser Cys Lys Ala Ser Gly Tyr Ser Phe
        35                  40                  45

Thr Gly Tyr Asn Met Asn Trp Val Lys Gln Ser Asn Gly Lys Ser Leu
    50                  55                  60

Glu Trp Ile Gly Asn Ile Asp Pro Tyr Tyr Gly Asp Thr Asn Tyr Asn
65                  70                  75                  80

Gln Lys Phe Lys Gly Lys Ala Thr Leu Thr Val Asp Lys Ser Ser Ser
                85                  90                  95

Thr Ala Tyr Met His Leu Lys Ser Leu Thr Ser Glu Asp Ser Ala Val
            100                 105                 110

Tyr Tyr Cys Ala Arg Pro Tyr Gly Ser Glu Ala Tyr Phe Ala Tyr Trp
        115                 120                 125

Gly Gln Gly Thr Leu Val Thr Val Ser Ala Ala Lys Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Glu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335
```

```
Tyr Lys Cys Lys Val Ser Asn Lys Gly Leu Pro Ser Ser Ile Glu Lys
                340                 345                 350

Thr Ile Ser Lys Ala Lys Gly Gln Pro Arg Glu Pro Gln Val Tyr Thr
            355                 360                 365

Leu Pro Pro Ser Gln Glu Glu Met Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys Ala Ser
465

<210> SEQ ID NO 128
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ala Gln Ser Ile Ser Gly Ile Pro Ser Arg Phe Ser Gly
    50                  55                  60

Ser Gly Ser Gly Ser Asp Phe Thr Leu Ser Ile Asn Gly Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

<210> SEQ ID NO 129
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 129

Gln Val Gln Leu Arg Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Asp Ile Tyr Pro Gly Ser Gly Tyr Ser Phe Tyr Asn Glu Asn Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Thr Tyr Tyr Asn Tyr Pro Phe Ala Tyr Trp Gly Gln Gly Thr Leu
            100                 105                 110

Val Thr Val Ser Ala Ala Lys Thr Thr Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

```
Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys Ala Ser
            435                 440                 445

<210> SEQ ID NO 130
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asn Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 131
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 131

```
Met Thr Leu Asn Met Leu Leu Gly Leu Arg Trp Val Phe Phe Val Val
1               5                   10                  15

Phe Tyr Gln Gly Val His Cys Glu Val Gln Leu Val Glu Ser Gly Gly
            20                  25                  30

Gly Leu Val Gln Pro Lys Gly Ser Leu Lys Leu Ser Cys Ala Ala Ser
        35                  40                  45

Gly Leu Thr Phe Asn Ile Tyr Ala Met Asn Trp Val Arg Gln Ala Pro
    50                  55                  60

Gly Lys Gly Leu Glu Trp Val Ala Arg Ile Arg Asn Lys Ser Asn Asn
65                  70                  75                  80

Tyr Ala Thr Tyr Tyr Ala Asp Ser Val Lys Asp Arg Phe Thr Ile Ser
                85                  90                  95

Arg Asp Asp Ser Gln Ser Leu Leu Tyr Leu Gln Met Asn Asn Leu Lys
            100                 105                 110

Thr Glu Asp Thr Ala Met Tyr Tyr Cys Val Gly Arg Asp Trp Phe Asp
        115                 120                 125

Tyr Trp Gly Gln Gly Thr Leu Val Thr Val Ser Ala Ala Lys Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Glu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
```

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys Ala Ser
465

<210> SEQ ID NO 132
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Ala Trp Ile Ser Leu Ile Leu Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Val Ser Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn His Trp Val Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 133
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 133

Met Glu Trp Thr Trp Val Phe Leu Phe Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Ile Ser Cys Lys Ala Thr Gly Tyr Thr Phe
        35                  40                  45

Gly Ser Tyr Trp Ile Glu Trp Val Lys Gln Arg Pro Gly His Gly Leu
    50                  55                  60

Glu Trp Ile Gly Glu Ile Leu Pro Gly Ser Gly Asn Thr Asn Tyr Asn
65                  70                  75                  80

Glu Asn Phe Lys Gly Lys Ala Thr Phe Thr Ala Asp Thr Ser Ser Asn
                85                  90                  95

Thr Ala Tyr Met Gln Leu Thr Ser Leu Thr Ser Glu Asp Ser Ala Val
            100                 105                 110

Tyr Tyr Cys Ala Arg Ala Gly Ile Tyr Trp Gly Gln Gly Thr Leu Val
        115                 120                 125

Thr Val Ser Ala Ala Lys Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
210                 215                 220

Lys Val Asp Lys Arg Val Glu Ser Lys Tyr Gly Pro Pro Cys Pro Pro
225                 230                 235                 240

Cys Pro Ala Pro Glu Phe Glu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415
```

```
Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
            435                 440                 445

Thr Gln Lys Ser Leu Ser Leu Ser Leu Gly Lys Ala Ser
            450                 455                 460

<210> SEQ ID NO 134
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Glu Lys Asp Thr Leu Leu Leu Trp Val Leu Leu Leu Trp Val Pro
1               5                   10                  15

Gly Ser Thr Gly Asp Ile Val Leu Thr Gln Ser Pro Ala Phe Leu Ala
            20                  25                  30

Val Ser Leu Gly Gln Arg Ala Thr Ile Ser Cys Arg Ala Ser Glu Ser
        35                  40                  45

Val Asp Asn Tyr Gly Ile Ser Phe Met Asn Trp Phe Gln Gln Lys Pro
    50                  55                  60

Gly Gln Pro Pro Lys Leu Leu Ile Tyr Val Ala Ser Lys Gln Gly Ser
65                  70                  75                  80

Gly Val Pro Ala Arg Phe Ser Gly Ser Gly Ser Gly Thr Asp Phe Ser
                85                  90                  95

Leu Asn Ile His Pro Met Glu Glu Asp Asp Thr Ala Met Tyr Phe Cys
            100                 105                 110

Gln Gln Ser Lys Glu Val Pro Arg Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 135
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Met Glu Cys Asn Trp Ile Leu Pro Phe Ile Leu Ser Val Thr Ser Gly
1               5                   10                  15
```

```
Val Tyr Ser Glu Val Gln Leu Gln Gln Ser Gly Thr Val Leu Ala Arg
            20                  25                  30

Pro Gly Ala Ser Val Lys Met Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Ala Ile Tyr Pro Gly Asn Ser Asp Thr Thr Tyr Asn
65                  70                  75                  80

Gln Lys Phe Lys Gly Lys Ala Lys Leu Thr Ala Val Thr Ser Thr Ser
                85                  90                  95

Thr Ala Tyr Met Glu Leu Ser Ser Leu Thr Asn Glu Asp Ser Ala Val
            100                 105                 110

Tyr Tyr Cys Thr Pro Thr Tyr Tyr Phe Asp Tyr Trp Gly Gln Gly Thr
        115                 120                 125

Ser Leu Thr Val Ser Ser Ala Lys Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Glu Ser Lys Tyr Gly Pro Pro Cys
225                 230                 235                 240

Pro Pro Cys Pro Ala Pro Glu Phe Glu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Gln Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Arg Leu Thr Val Asp Lys Ser Arg Trp Gln
            420                 425                 430
```

Glu Gly Asn Val Phe Ser Cys Ser Val Met His Glu Ala Leu His Asn
            435                 440                 445

His Tyr Thr Gln Lys Ser Leu Ser Leu Ser Leu Gly Lys Ala Ser
    450                 455                 460

<210> SEQ ID NO 136
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Met Ser Pro Ala Gln Phe Leu Phe Leu Leu Val Leu Trp Ile Arg Glu
1               5                   10                  15

Thr Asn Gly Asp Val Val Met Thr Gln Thr Pro Leu Thr Leu Ser Val
            20                  25                  30

Thr Ile Gly Gln Pro Ala Ser Ile Ser Cys Lys Ser Ser Gln Ser Leu
        35                  40                  45

Leu Asp Ser Asp Gly Lys Thr Tyr Leu Asn Trp Phe Leu Gln Arg Pro
    50                  55                  60

Gly Gln Ser Pro Lys Arg Leu Ile Tyr Leu Val Ser Lys Leu Asp Ser
65                  70                  75                  80

Gly Val Pro Asp Arg Phe Thr Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Trp Gln Gly Thr His Phe Pro Trp Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 137
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Met Gly Gly Ile Trp Ile Phe Leu Phe Leu Leu Ser Gly Thr Ala Gly
1               5                   10                  15

Ala His Ser Glu Ile Gln Leu Gln Gln Thr Gly Pro Gly Leu Val Lys
            20                  25                  30

-continued

```
Pro Gly Ala Ser Val Lys Ile Ser Cys Lys Ala Ser Gly Tyr Pro Phe
             35                  40                  45
Thr Asp Tyr Ile Met Val Trp Val Lys Gln Ser His Gly Lys Ser Leu
 50                  55                  60
Glu Trp Ile Gly Asn Ile Ser Pro Tyr Tyr Gly Thr Thr Asn Tyr Asn
 65                  70                  75                  80
Leu Lys Phe Lys Gly Lys Ala Thr Leu Thr Val Asp Lys Ser Ser Ser
                 85                  90                  95
Thr Ala Tyr Met Gln Leu Asn Ser Leu Thr Ser Glu Asp Ser Ala Val
                100                 105                 110
Tyr Tyr Cys Ala Arg Ser Pro Asn Trp Asp Gly Ala Trp Phe Ala His
            115                 120                 125
Trp Gly Gln Gly Ala Leu Val Thr Val Ser Ala Ala Lys Thr Lys Gly
130                 135                 140
Pro Ser Val Phe Pro Leu Ala Pro Cys Ser Arg Ser Thr Ser Glu Ser
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
        195                 200                 205
Thr Val Pro Ser Ser Ser Leu Gly Thr Lys Thr Tyr Thr Cys Asn Val
210                 215                 220
Asp His Lys Pro Ser Asn Thr Lys Val Asp Lys Arg Val Glu Ser Lys
225                 230                 235                 240
Tyr Gly Pro Pro Cys Pro Pro Cys Pro Ala Pro Glu Phe Glu Gly Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser Gln Glu
        275                 280                 285
Asp Pro Glu Val Gln Phe Asn Trp Tyr Val Asp Gly Val Glu Val His
290                 295                 300
Asn Ala Lys Thr Lys Pro Arg Glu Glu Gln Phe Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Gly Leu Pro Ser Ser Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Gln Glu Glu Met Thr Lys Asn Gln Val Ser Leu
370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Arg Leu Thr Val Asp
            420                 425                 430
Lys Ser Arg Trp Gln Glu Gly Asn Val Phe Ser Cys Ser Val Met His
        435                 440                 445
Glu Ala Leu His Asn His Tyr Thr Gln Lys Ser Leu Ser Leu Ser Leu
```

Gly Lys Ala Ser
465

<210> SEQ ID NO 138
<211> LENGTH: 238
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 138

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Ser Tyr Met Asn Trp Phe Gln Gln Lys Pro
    50                  55                  60

Gly Gln Pro Pro Lys Leu Leu Ile Tyr Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

Gln Gln Ser Asn Glu Asp Pro Phe Thr Phe Gly Ser Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 139
<211> LENGTH: 467
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 139

Met Ala Val Leu Gly Leu Leu Leu Cys Leu Val Thr Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu

```
            35                  40                  45
Ser Arg Tyr Ser Val Phe Trp Val Arg Gln Pro Pro Gly Lys Gly Leu
 50                  55                  60
Glu Trp Leu Gly Leu Ile Trp Gly Gly Gly Ser Thr Asp Tyr Asn Ser
 65                  70                  75                  80
Ala Leu Lys Ser Arg Leu Ser Ile Ser Lys Asp Asn Ser Lys Ser Gln
                 85                  90                  95
Val Phe Leu Lys Met Asn Ser Leu Gln Thr Asp Asp Thr Ala Met Tyr
            100                 105                 110
Tyr Cys Ala Arg Ile Tyr Phe Asp Tyr Asp Gly Ala Met Asp Tyr Trp
            115                 120                 125
Gly Gln Gly Thr Ser Val Thr Val Ser Ser Ala Lys Thr Thr Gly Pro
130                 135                 140
Ser Val Phe Pro Leu Ala Pro Cys Ser Arg Ser Thr Ser Glu Ser Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Ser Val Val Thr
            195                 200                 205
Val Pro Ser Ser Ser Leu Gly Thr Lys Thr Tyr Thr Cys Asn Val Asp
210                 215                 220
His Lys Pro Ser Asn Thr Lys Val Asp Lys Arg Val Glu Ser Lys Tyr
225                 230                 235                 240
Gly Pro Pro Cys Pro Pro Cys Pro Ala Pro Glu Phe Glu Gly Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser Gln Glu Asp
            275                 280                 285
Pro Glu Val Gln Phe Asn Trp Tyr Val Asp Gly Val Glu Val His Asn
290                 295                 300
Ala Lys Thr Lys Pro Arg Glu Glu Gln Phe Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Gly Leu Pro Ser Ser Ile Glu Lys
            340                 345                 350
Thr Ile Ser Lys Ala Lys Gly Gln Pro Arg Glu Pro Gln Val Tyr Thr
            355                 360                 365
Leu Pro Pro Ser Gln Glu Glu Met Thr Lys Asn Gln Val Ser Leu Thr
370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Arg Leu Thr Val Asp Lys
            420                 425                 430
Ser Arg Trp Gln Glu Gly Asn Val Phe Ser Cys Ser Val Met His Glu
            435                 440                 445
Ala Leu His Asn His Tyr Thr Gln Lys Ser Leu Ser Leu Ser Leu Gly
450                 455                 460
```

Lys Ala Ser
465

<210> SEQ ID NO 140
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met His Arg Thr Ser Met Gly Ile Lys Met Glu Ser Arg Ile Gln Ala
1               5                   10                  15

Phe Val Phe Val Phe Leu Trp Leu Ser Gly Val Gly Gly Asp Ile Val
                20                  25                  30

Met Thr Gln Ser His Lys Phe Met Ser Thr Ser Val Gly Asp Arg Val
            35                  40                  45

Ser Val Thr Cys Lys Ala Ser Gln Asp Val Thr Ser Ala Val Ala Trp
        50                  55                  60

Tyr Gln Gln Lys Pro Gly Gln Ser Pro Lys Leu Leu Ile Tyr Trp Ala
65                  70                  75                  80

Ser Thr Arg His Thr Gly Val Pro Asp Arg Phe Thr Gly Ser Gly Ser
                85                  90                  95

Gly Thr Asp Tyr Thr Leu Thr Ile Ser Ser Gly Gln Ala Glu Asp Leu
            100                 105                 110

Ala Leu Tyr Tyr Cys His Gln Tyr Tyr Ser Ala Pro Arg Thr Phe Gly
        115                 120                 125

Gly Gly Thr Lys Leu Glu Ile Lys Arg Thr Val Ala Ala Pro Ser Val
    130                 135                 140

Phe Ile Phe Pro Pro Ser Asp Glu Gln Leu Lys Ser Gly Thr Ala Ser
145                 150                 155                 160

Val Val Cys Leu Leu Asn Asn Phe Tyr Pro Arg Glu Ala Lys Val Gln
                165                 170                 175

Trp Lys Val Asp Asn Ala Leu Gln Ser Gly Asn Ser Gln Glu Ser Val
            180                 185                 190

Thr Glu Gln Asp Ser Lys Asp Ser Thr Tyr Ser Leu Ser Ser Thr Leu
        195                 200                 205

Thr Leu Ser Lys Ala Asp Tyr Glu Lys His Lys Val Tyr Ala Cys Glu
    210                 215                 220

Val Thr His Gln Gly Leu Ser Ser Pro Val Thr Lys Ser Phe Asn Arg
225                 230                 235                 240

Gly Glu Cys

<210> SEQ ID NO 141
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Met Glu Trp Asn Trp Val Val Leu Phe Leu Leu Ser Leu Thr Ala Gly
1               5                   10                  15

Val Tyr Ala Gln Gly Gln Met Gln Ser Gly Ala Glu Leu Val Lys
                20                  25                  30

-continued

```
Pro Gly Ala Ser Val Lys Leu Ser Cys Lys Thr Ser Gly Phe Thr Phe
            35                  40                  45

Ser Ser Asn Tyr Ile Ser Trp Leu Lys Gln Lys Pro Gly Gln Ser Leu
    50                  55                  60

Glu Trp Ile Ala Trp Ile Tyr Ala Gly Thr Gly Ile Thr Tyr Asn
65                  70                  75                  80

Gln Lys Phe Arg Gly Arg Ala Gln Leu Thr Val Asp Thr Ser Ser
                85                  90                  95

Thr Ala Tyr Met Gln Phe Ser Ser Leu Thr Thr Asp Asp Ser Ala Ile
                100                 105                 110

Tyr Tyr Cys Ala Arg His Val Arg Gly Tyr His Pro Met Asp Tyr Trp
            115                 120                 125

Gly Gln Gly Thr Ser Val Thr Val Ser Ser Ala Lys Thr Lys Gly Pro
130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Ser Leu Gly Thr Lys Thr Tyr Thr Cys Asn Val Asp
                210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Glu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser Gln Glu Asp
                275                 280                 285

Pro Glu Val Gln Phe Asn Trp Tyr Val Asp Gly Val Glu Val His Asn
                290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
                340                 345                 350

Thr Ile Ser Lys Ala Lys Gly Gln Pro Arg Glu Pro Gln Val Tyr Thr
                355                 360                 365

Leu Pro Pro Ser Gln Glu Glu Met Thr Lys Asn Gln Val Ser Leu Thr
                370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
                420                 425                 430

Ser Arg Trp Gln Glu Gly Asn Val Phe Ser Cys Ser Val Met His Glu
                435                 440                 445

Ala Leu His Asn His Tyr Thr Gln Lys Ser Leu Ser Leu Ser Leu Gly
```

Lys Ala Ser
465

<210> SEQ ID NO 142
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Met Glu Ser Gln Thr Gln Val Phe Val Tyr Met Leu Leu Trp Leu Ser
1               5                   10                  15

Gly Val Asp Gly Asp Ile Val Met Thr Gln Ser Gln Lys Phe Met Ser
            20                  25                  30

Ala Ser Val Gly Asp Arg Val Ser Val Thr Cys Arg Ala Ser Gln Asn
        35                  40                  45

Val Val Thr Asn Val Gly Trp Tyr Gln Gln Lys Pro Gly Gln Ser Pro
    50                  55                  60

Lys Val Leu Ile Tyr Ser Ala Ser Phe Arg Tyr Ser Gly Val Pro Asp
65                  70                  75                  80

Arg Phe Thr Gly Ser Gly Ser Gly Thr Asp Phe Thr Leu Thr Ile Thr
                85                  90                  95

Asn Val Gln Ser Glu Asp Leu Ala Glu Tyr Phe Cys Gln Gln Tyr Asn
            100                 105                 110

Asn Tyr Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 143
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Met Gly Trp Ser Tyr Ile Ile Leu Phe Leu Val Ala Thr Ala Thr Asp
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe

-continued

```
                35                  40                  45
Thr Ser Tyr Trp Met His Trp Val Lys Gln Arg Pro Gly Glu Gly Leu
 50                  55                  60
Glu Trp Ile Gly Glu Ile Asn Pro Ser Tyr Gly Arg Thr Asp Tyr Asn
 65                  70                  75                  80
Gly Lys Phe Lys Asn Lys Ala Thr Leu Thr Val Ala Lys Ser Ser Ser
                 85                  90                  95
Thr Ala Tyr Met Gln Leu Ser Ser Leu Thr Ser Glu Asp Ser Ala Val
                100                 105                 110
Tyr Tyr Cys Ala Arg Gly Asp Tyr Tyr Gly Ser Ser Phe Ala Tyr
                115                 120                 125
Trp Gly Gln Gly Thr Leu Val Thr Val Ser Ala Ala Lys Thr Lys Gly
130                 135                 140
Pro Ser Val Phe Pro Leu Ala Pro Cys Ser Arg Ser Thr Ser Glu Ser
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
                180                 185                 190
Pro Ala Val Leu Gln Ser Ser Gly Leu Tyr Ser Leu Ser Ser Val Val
                195                 200                 205
Thr Val Pro Ser Ser Ser Leu Gly Thr Lys Thr Tyr Thr Cys Asn Val
210                 215                 220
Asp His Lys Pro Ser Asn Thr Lys Val Asp Lys Arg Val Glu Ser Lys
225                 230                 235                 240
Tyr Gly Pro Pro Cys Pro Cys Pro Ala Pro Glu Phe Glu Gly Gly
                245                 250                 255
Pro Ser Val Phe Leu Phe Pro Pro Lys Pro Lys Asp Thr Leu Met Ile
                260                 265                 270
Ser Arg Thr Pro Glu Val Thr Cys Val Val Val Asp Val Ser Gln Glu
                275                 280                 285
Asp Pro Glu Val Gln Phe Asn Trp Tyr Val Asp Gly Val Glu Val His
290                 295                 300
Asn Ala Lys Thr Lys Pro Arg Glu Glu Gln Phe Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Gly Leu Pro Ser Ser Ile Glu
                340                 345                 350
Lys Thr Ile Ser Lys Ala Lys Gly Gln Pro Arg Glu Pro Gln Val Tyr
                355                 360                 365
Thr Leu Pro Pro Ser Gln Glu Met Thr Lys Asn Gln Val Ser Leu
370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Pro Pro Val
                405                 410                 415
Leu Asp Ser Asp Gly Ser Phe Phe Leu Tyr Ser Arg Leu Thr Val Asp
                420                 425                 430
Lys Ser Arg Trp Gln Glu Gly Asn Val Phe Ser Cys Ser Val Met His
                435                 440                 445
Glu Ala Leu His Asn His Tyr Thr Gln Lys Ser Leu Ser Leu Ser Leu
450                 455                 460
```

Gly Lys Ala Ser
465

<210> SEQ ID NO 144
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Met Glu Ser Gln Thr Gln Val Phe Val Tyr Met Leu Leu Trp Leu Ser
1               5                   10                  15

Gly Val Asp Gly Asp Ile Val Met Thr Gln Ser Gln Lys Phe Met Ser
            20                  25                  30

Thr Ser Leu Gly Asp Arg Val Ser Val Thr Cys Lys Ala Ser Gln Asn
        35                  40                  45

Val Gly Thr Asn Val Ala Trp Tyr Gln Gln Lys Pro Gly His Ser Pro
    50                  55                  60

Lys Ala Leu Ile Tyr Ser Ala Ser Tyr Arg Tyr Ser Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Glu Phe Phe Cys Gln Gln Tyr Asn
            100                 105                 110

Asn Tyr Pro Tyr Thr Phe Gly Gly Gly Thr Thr Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 145
<211> LENGTH: 335
<212> TYPE: DNA
<213> ORGANISM: Hepatitis C virus

<400> SEQUENCE: 145
actagtactc cttgtacctg cggctcatcc gacctgtacc tggtcacccg gcacgcagac      60
gtcattcctg tacgccgacg cggggatagt aggggagcc tgctctctcc aagacccata     120
tcctacctca agggcagcag cggtggacca ctgctgtgtc ccgctggtca tgctgtggga     180
atatttaggg ccgcagtgtg taccagaggc gtggccaaag ctgttgattt tattcccgtc     240
gaaaatcttg aaacaaccat gagaagccca gtgttcacag acaactcatc tcccccagca     300
gtgccgcaga gtgctagctg agaattcgcg gccgc                                335

<210> SEQ ID NO 146
<211> LENGTH: 488
<212> TYPE: DNA
<213> ORGANISM: Hepatitis C virus

<400> SEQUENCE: 146

```
actagtgtga ctgtgcccca ccccaatatc gaagaggtgg cccttagtac taccggggaa      60
attcctttct acgggaaggc catccctctc gaggttatta aaggagggcg acatctgatt     120
ttttgccact ccaagaagaa gtgtgacgag ctggccgcga aactggttgc cttgggcatc     180
aacgctgtcg catactatcg gggactggat gtatcagtga tacccaccag cggagtggta     240
gttgtcgtcg ctacagacgc attgatgacc ggctttacag gagatttcga ctccgtcatc     300
gactgtaaca catgcgtgac tcagacagtg gatttcagcc ttgacccgac gtttacgatt     360
gagaccacca ctctccctca ggatgctgtg tctaggaccc aaagacgcgg tcgcacaggc     420
cggggcaaac caggcatcta taggttcgtg gcaccagggg aaagagctag ctgagaattc     480
gcggccgc                                                              488
```

<210> SEQ ID NO 147
<211> LENGTH: 629
<212> TYPE: DNA
<213> ORGANISM: Hepatitis C virus

<400> SEQUENCE: 147

```
actagtgtgc tggactctca ctaccaggat gtcctgaagg aagtaaaagc agccgcttct      60
aaagtcaaag cgaacgctct gtacgatgtc gtttccaaac tgccgctggc tgtcatgggc     120
tcttcctacg gctttcagta ttccccgggt cagcgcgttg agttcctggt ccaggcgtgg     180
aaatccaaaa agactccgat gggttttttcc tatgacactc gctgcttcga cagcaccgtt     240
accgaaagcg acattcgcac cgaggaagca atctaccagt gctgcgacct ggacccacag     300
gcccgcgtgg cgatcaaatc tctgaccgaa cgcctgtacg ttggccgctg tcgcgcttcc     360
ggtgttctga cgacctcctg cggtaatacg ctgacctgct acatcaaagc acgcgctgcc     420
tgtcgcgcag ccggtctgca ggactgcacc atgctggtgt gtggcgatga cctggtggtg     480
atctgcgaaa gcgctggcgt gcaggaagac gcagcaagcc tgcgcgcttt caccgaagct     540
atgactcgct actctgcgcc gccgggtgac ccgccgcagc cagaatacga tctggagctg     600
atcaccgcta gctaagaatt cgcggccgc                                       629
```

<210> SEQ ID NO 148
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148

```
gagctcggat ccactagtac tccttgtacc tgcggctcat cc                          42
```

<210> SEQ ID NO 149
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
gcccgcggcc gcgaattctc agctagcact ctgcggcact gctggggg                48

<210> SEQ ID NO 150
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
tctaaagtca aagcgaacgc tctgtacgat gtcgtttcc                           39

<210> SEQ ID NO 151
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
accggaagcg cgacagcggc caacgtacag gcgttcggt                           39

<210> SEQ ID NO 152
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
accgaacgcc tgtacgttgg ccgctgtcgc gcttccggt                           39

<210> SEQ ID NO 153
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
gcggccgcga attcttagct agcggtgatc agctccag                            38

<210> SEQ ID NO 154
<211> LENGTH: 100
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
caagcccaac cccactagtg tgctggactc tcactaccag gatgtcctga aggaagtaaa    60
agcagccgct tctaaagtca aagcgaacgc tctgtacgat                          100

<210> SEQ ID NO 155
<211> LENGTH: 100
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155

```
atcgtacaga gcgttcgctt tgactttaga agcggctgct tttacttcct tcaggacatc    60
ctggtagtga gagtccagca cactagtggg gttgggcttg                         100
```

<210> SEQ ID NO 156
<211> LENGTH: 13
<212> TYPE: DNA
<213> ORGANISM: Artificial Sequence
<220> FEATURE:
<223> OTHER INFORMATION: Description of Artificial Sequence: Synthetic primer

<400> SEQUENCE: 156

```
caagcccaac ccc                                                       13
```

<210> SEQ ID NO 157
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 157

```
gcggccgcga attcttagct agcggtgatc agctccag                            38
```

<210> SEQ ID NO 158
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 158

```
Asp Ile Gln Met Thr Gln Ser Pro Ser Ser Leu Ser Ala Ser Val Gly
  1               5                  10                  15

Asp Arg Val Thr Ile Thr Cys Ser Ala Ser Gln Gly Ile Ser Asn Tyr
                 20                  25                  30

Leu Asn Trp Tyr Gln Gln Lys Pro Gly Lys Ala Val Lys Leu Leu Ile
             35                  40                  45

Tyr Tyr Thr Ser Ile Leu His Ser Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Phe Asn Lys Leu Pro Pro
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 159
<211> LENGTH: 992
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Pro Phe His Ala Met Asp Tyr Trp Gly Gln Gly
            100                 105                 110

Thr Leu Val Thr Val Ser Ser Ala Lys Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
```

```
              325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
            405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys Ala Ser
            435                 440                 445
Gln Thr Pro Thr Asn Thr Ile Ser Val Thr Pro Thr Asn Asn Ser Thr
            450                 455                 460
Pro Thr Asn Asn Ser Asn Pro Lys Pro Asn Pro Ala Ser Val Thr Val
465                 470                 475                 480
Pro His Pro Asn Ile Glu Glu Val Ala Leu Ser Thr Thr Gly Glu Ile
                  485                 490                 495
Pro Phe Tyr Gly Lys Ala Ile Pro Leu Glu Val Ile Lys Gly Gly Arg
            500                 505                 510
His Leu Ile Phe Cys His Ser Lys Lys Lys Cys Asp Glu Leu Ala Ala
            515                 520                 525
Lys Leu Val Ala Leu Gly Ile Asn Ala Val Ala Tyr Tyr Arg Gly Leu
            530                 535                 540
Asp Val Ser Val Ile Pro Thr Ser Gly Val Val Val Val Ala Thr
545                 550                 555                 560
Asp Ala Leu Met Thr Gly Phe Thr Gly Asp Phe Asp Ser Val Ile Asp
                  565                 570                 575
Cys Asn Thr Cys Val Thr Gln Thr Val Asp Phe Ser Leu Asp Pro Thr
            580                 585                 590
Phe Thr Ile Glu Thr Thr Thr Leu Pro Gln Asp Ala Val Ser Arg Thr
            595                 600                 605
Gln Arg Arg Gly Arg Thr Gly Arg Gly Lys Pro Gly Ile Tyr Arg Phe
            610                 615                 620
Val Ala Pro Gly Glu Arg Ala Ser Ser Val Ser Pro Thr Thr Ser
625                 630                 635                 640
Val His Pro Thr Pro Thr Ser Val Pro Pro Thr Pro Lys Ser Ser
                  645                 650                 655
Pro Ala Ser Thr Pro Cys Thr Cys Gly Ser Ser Asp Leu Tyr Leu Val
            660                 665                 670
Thr Arg His Ala Asp Val Ile Pro Val Arg Arg Arg Gly Asp Ser Arg
            675                 680                 685
Gly Ser Leu Leu Ser Pro Arg Pro Ile Ser Tyr Leu Lys Gly Ser Ser
            690                 695                 700
Gly Gly Pro Leu Leu Cys Pro Ala Gly His Ala Val Gly Ile Phe Arg
705                 710                 715                 720
Ala Ala Val Cys Thr Arg Gly Val Ala Lys Ala Val Asp Phe Ile Pro
                  725                 730                 735
Val Glu Asn Leu Glu Thr Thr Met Arg Ser Pro Val Phe Thr Asp Asn
            740                 745                 750
```

```
Ser Ser Pro Pro Ala Val Pro Gln Ser Ala Ser Pro Thr Ser Thr Pro
        755                 760                 765

Ala Asp Ser Ser Thr Ile Thr Pro Thr Ala Thr Pro Thr Ala Thr Pro
770                 775                 780

Thr Ile Lys Gly Ala Ser Val Leu Asp Ser His Tyr Gln Asp Val Leu
785                 790                 795                 800

Lys Glu Val Lys Ala Ala Ser Lys Val Lys Ala Asn Ala Leu Tyr
            805                 810                 815

Asp Val Val Ser Lys Leu Pro Leu Ala Val Met Gly Ser Ser Tyr Gly
            820                 825                 830

Phe Gln Tyr Ser Pro Gly Gln Arg Val Glu Phe Leu Val Gln Ala Trp
            835                 840                 845

Lys Ser Lys Lys Thr Pro Met Gly Phe Ser Tyr Asp Thr Arg Cys Phe
            850                 855                 860

Asp Ser Thr Val Thr Glu Ser Asp Ile Arg Thr Glu Glu Ala Ile Tyr
865                 870                 875                 880

Gln Cys Cys Asp Leu Asp Pro Gln Ala Arg Val Ala Ile Lys Ser Leu
                885                 890                 895

Thr Glu Arg Leu Tyr Val Gly Arg Cys Arg Ala Ser Gly Val Leu Thr
            900                 905                 910

Thr Ser Cys Gly Asn Thr Leu Thr Cys Tyr Ile Lys Ala Arg Ala Ala
            915                 920                 925

Cys Arg Ala Ala Gly Leu Gln Asp Cys Thr Met Leu Val Cys Gly Asp
            930                 935                 940

Asp Leu Val Val Ile Cys Glu Ser Ala Gly Val Gln Glu Asp Ala Ala
945                 950                 955                 960

Ser Leu Arg Ala Phe Thr Glu Ala Met Thr Arg Tyr Ser Ala Pro Pro
            965                 970                 975

Gly Asp Pro Pro Gln Pro Glu Tyr Asp Leu Glu Leu Ile Thr Ala Ser
            980                 985                 990

<210> SEQ ID NO 160
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Ile His Ser Tyr
            20                  25                  30

Gly Asn Ser Phe Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
```

```
              115                 120                 125
Leu Lys Ser Gly Thr Ala Ser Val Cys Leu Leu Asn Asn Phe Tyr
        130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                    165                 170                 175
Tyr Ser Leu Ser Ser Thr Leu Thr Leu Ser Lys Ala Asp Tyr Glu Lys
                180                 185                 190
His Lys Val Tyr Ala Cys Glu Val Thr His Gln Gly Leu Ser Ser Pro
            195                 200                 205
Val Thr Lys Ser Phe Asn Arg Gly Glu Cys
        210                 215
```

<210> SEQ ID NO 161
<211> LENGTH: 998
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 161

```
Gln Val Thr Leu Lys Glu Ser Gly Pro Ala Ile Val Lys Pro Thr Gln
1               5                   10                  15
Thr Leu Thr Leu Thr Cys Ser Phe Ser Gly Phe Ser Leu Ser Thr Ser
                20                  25                  30
Gly Met Gly Leu Ser Trp Ile Arg Gln Pro Ser Gly Lys Ala Leu Glu
            35                  40                  45
Trp Leu Ala His Ile Tyr Trp Asp Asp Asp Lys Arg Tyr Asn Pro Ser
        50                  55                  60
Leu Lys Ser Arg Leu Thr Ile Ser Lys Asp Thr Ser Lys Asn Gln Val
65                  70                  75                  80
Val Leu Thr Met Thr Ile Val Asp Thr Val Asp Ala Ala Thr Tyr Tyr
                85                  90                  95
Cys Ala Arg Ser Ser His Tyr Tyr Gly Tyr Gly Tyr Gly Gly Tyr Phe
                100                 105                 110
Asp Val Trp Gly Gln Gly Thr Thr Val Thr Val Ser Ser Ala Lys Thr
            115                 120                 125
Lys Gly Pro Ser Val Phe Pro Leu Ala Pro Cys Ser Arg Ser Thr Ser
        130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Lys Thr Tyr Thr Cys
        195                 200                 205
Asn Val Asp His Lys Pro Ser Asn Thr Lys Val Asp Lys Arg Val Glu
210                 215                 220
Ser Lys Tyr Gly Pro Pro Cys Pro Pro Cys Pro Ala Pro Glu Phe Glu
225                 230                 235                 240
Gly Gly Pro Ser Val Phe Leu Phe Pro Pro Lys Pro Lys Asp Thr Leu
                245                 250                 255
```

```
Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys Ala Ser Gln Thr Pro Thr Asn Thr Ile Ser Val Thr
    450                 455                 460

Pro Thr Asn Asn Ser Thr Pro Thr Asn Asn Ser Asn Pro Lys Pro Asn
465                 470                 475                 480

Pro Ala Ser Val Thr Val Pro His Pro Asn Ile Glu Glu Val Ala Leu
                485                 490                 495

Ser Thr Thr Gly Glu Ile Pro Phe Tyr Gly Lys Ala Ile Pro Leu Glu
            500                 505                 510

Val Ile Lys Gly Gly Arg His Leu Ile Phe Cys His Ser Lys Lys Lys
        515                 520                 525

Cys Asp Glu Leu Ala Ala Lys Leu Val Ala Leu Gly Ile Asn Ala Val
    530                 535                 540

Ala Tyr Tyr Arg Gly Leu Asp Val Ser Val Ile Pro Thr Ser Gly Val
545                 550                 555                 560

Val Val Val Val Ala Thr Asp Ala Leu Met Thr Gly Phe Thr Gly Asp
                565                 570                 575

Phe Asp Ser Val Ile Asp Cys Asn Thr Cys Val Thr Gln Thr Val Asp
            580                 585                 590

Phe Ser Leu Asp Pro Thr Phe Thr Ile Glu Thr Thr Leu Pro Gln
        595                 600                 605

Asp Ala Val Ser Arg Thr Gln Arg Arg Gly Arg Thr Gly Arg Gly Lys
    610                 615                 620

Pro Gly Ile Tyr Arg Phe Val Ala Pro Gly Glu Arg Ala Ser Ser Ser
625                 630                 635                 640

Val Ser Pro Thr Thr Ser Val His Pro Thr Pro Thr Ser Val Pro Pro
                645                 650                 655

Thr Pro Thr Lys Ser Ser Pro Ala Ser Thr Pro Cys Thr Cys Gly Ser
            660                 665                 670

Ser Asp Leu Tyr Leu Val Thr Arg His Ala Asp Val Ile Pro Val Arg
```

```
                675                 680                 685
Arg Arg Gly Asp Ser Arg Gly Ser Leu Leu Ser Pro Arg Pro Ile Ser
690                 695                 700

Tyr Leu Lys Gly Ser Ser Gly Pro Leu Leu Cys Pro Ala Gly His
705                 710                 715                 720

Ala Val Gly Ile Phe Arg Ala Val Cys Thr Arg Gly Val Ala Lys
                725                 730                 735

Ala Val Asp Phe Ile Pro Val Glu Asn Leu Glu Thr Thr Met Arg Ser
                740                 745                 750

Pro Val Phe Thr Asp Asn Ser Ser Pro Pro Ala Val Pro Gln Ser Ala
                755                 760                 765

Ser Pro Thr Ser Thr Pro Ala Asp Ser Ser Thr Ile Thr Pro Thr Ala
770                 775                 780

Thr Pro Thr Ala Thr Pro Thr Ile Lys Gly Ala Ser Val Leu Asp Ser
785                 790                 795                 800

His Tyr Gln Asp Val Leu Lys Glu Val Lys Ala Ala Ser Lys Val
                805                 810                 815

Lys Ala Asn Ala Leu Tyr Asp Val Val Ser Lys Leu Pro Leu Ala Val
                820                 825                 830

Met Gly Ser Ser Tyr Gly Phe Gln Tyr Ser Pro Gly Gln Arg Val Glu
                835                 840                 845

Phe Leu Val Gln Ala Trp Lys Ser Lys Lys Thr Pro Met Gly Phe Ser
850                 855                 860

Tyr Asp Thr Arg Cys Phe Asp Ser Thr Val Thr Glu Ser Asp Ile Arg
865                 870                 875                 880

Thr Glu Glu Ala Ile Tyr Gln Cys Cys Asp Leu Asp Pro Gln Ala Arg
                885                 890                 895

Val Ala Ile Lys Ser Leu Thr Glu Arg Leu Tyr Val Gly Arg Cys Arg
                900                 905                 910

Ala Ser Gly Val Leu Thr Thr Ser Cys Gly Asn Thr Leu Thr Cys Tyr
                915                 920                 925

Ile Lys Ala Arg Ala Ala Cys Arg Ala Ala Gly Leu Gln Asp Cys Thr
930                 935                 940

Met Leu Val Cys Gly Asp Asp Leu Val Val Ile Cys Glu Ser Ala Gly
945                 950                 955                 960

Val Gln Glu Asp Ala Ala Ser Leu Arg Ala Phe Thr Glu Ala Met Thr
                965                 970                 975

Arg Tyr Ser Ala Pro Pro Gly Asp Pro Pro Gln Pro Gly Tyr Asp Leu
                980                 985                 990

Glu Leu Ile Thr Ala Ser
            995

<210> SEQ ID NO 162
<211> LENGTH: 371
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30
```

Leu Asn Trp Tyr Gln Gln Lys Pro Gly Lys Ala Val Lys Leu Leu Ile
            35                  40                  45

Tyr Tyr Thr Ser Ile Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Phe Asn Lys Leu Pro Pro
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Ala Ser Val Thr Val Pro His Pro Asn Ile
210                 215                 220

Glu Glu Val Ala Leu Ser Thr Thr Gly Glu Ile Pro Phe Tyr Gly Lys
225                 230                 235                 240

Ala Ile Pro Leu Glu Val Ile Lys Gly Arg His Leu Ile Phe Cys
                245                 250                 255

His Ser Lys Lys Lys Cys Asp Glu Leu Ala Ala Lys Leu Val Ala Leu
            260                 265                 270

Gly Ile Asn Ala Val Ala Tyr Tyr Arg Gly Leu Asp Val Ser Val Ile
            275                 280                 285

Pro Thr Ser Gly Val Val Val Val Ala Thr Asp Ala Leu Met Thr
290                 295                 300

Gly Phe Thr Gly Asp Phe Asp Ser Val Ile Asp Cys Asn Thr Cys Val
305                 310                 315                 320

Thr Gln Thr Val Asp Phe Ser Leu Asp Pro Thr Phe Thr Ile Glu Thr
                325                 330                 335

Thr Thr Leu Pro Gln Asp Ala Val Ser Arg Thr Gln Arg Arg Gly Arg
            340                 345                 350

Thr Gly Arg Gly Lys Pro Gly Ile Tyr Arg Phe Val Ala Pro Gly Glu
            355                 360                 365

Arg Ala Ser
370

<210> SEQ ID NO 163
<211> LENGTH: 810
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Tyr Ile Asn Ser Gly Gly Ser Thr Tyr Tyr Pro Asp Thr Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Pro Phe His Ala Met Asp Tyr Trp Gly Gln Gly
            100                 105                 110

Thr Leu Val Thr Val Ser Ser Ala Lys Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys Ala Ser
            435                 440                 445

Gln Thr Pro Thr Asn Thr Ile Ser Val Thr Pro Thr Asn Asn Ser Thr
        450                 455                 460

Pro Thr Asn Asn Ser Asn Pro Lys Pro Asn Pro Ala Ser Thr Pro Cys
465                 470                 475                 480

Thr Cys Gly Ser Ser Asp Leu Tyr Leu Val Thr Arg His Ala Asp Val
                485                 490                 495

Ile Pro Val Arg Arg Arg Gly Asp Ser Arg Gly Ser Leu Leu Ser Pro
            500                 505                 510

Arg Pro Ile Ser Tyr Leu Lys Gly Ser Ser Gly Gly Pro Leu Leu Cys
        515                 520                 525

Pro Ala Gly His Ala Val Gly Ile Phe Arg Ala Ala Val Cys Thr Arg
530                 535                 540

Gly Val Ala Lys Ala Val Asp Phe Ile Pro Val Glu Asn Leu Glu Thr
545                 550                 555                 560

Thr Met Arg Ser Pro Val Phe Thr Asp Asn Ser Ser Pro Pro Ala Val
                565                 570                 575

Pro Gln Ser Ala Ser Ser Val Ser Pro Thr Thr Ser Val His Pro
            580                 585                 590

Thr Pro Thr Ser Val Pro Pro Thr Pro Thr Lys Ser Ser Pro Ala Ser
        595                 600                 605

Val Leu Asp Ser His Tyr Gln Asp Val Leu Lys Glu Val Lys Ala Ala
610                 615                 620

Ala Ser Lys Val Lys Ala Asn Ala Leu Tyr Asp Val Val Ser Lys Leu
625                 630                 635                 640

Pro Leu Ala Val Met Gly Ser Ser Tyr Gly Phe Gln Tyr Ser Pro Gly
                645                 650                 655

Gln Arg Val Glu Phe Leu Val Gln Ala Trp Lys Ser Lys Lys Thr Pro
            660                 665                 670

Met Gly Phe Ser Tyr Asp Thr Arg Cys Phe Asp Ser Thr Val Thr Glu
        675                 680                 685

Ser Asp Ile Arg Thr Glu Glu Ala Ile Tyr Gln Cys Cys Asp Leu Asp
690                 695                 700

Pro Gln Ala Arg Val Ala Ile Lys Ser Leu Thr Glu Arg Leu Tyr Val
705                 710                 715                 720

Gly Arg Cys Arg Ala Ser Gly Val Leu Thr Thr Ser Cys Gly Asn Thr
                725                 730                 735

Leu Thr Cys Tyr Ile Lys Ala Arg Ala Ala Cys Arg Ala Ala Gly Leu
            740                 745                 750

Gln Asp Cys Thr Met Leu Val Cys Gly Asp Asp Leu Val Val Ile Cys
        755                 760                 765

Glu Ser Ala Gly Val Gln Glu Asp Ala Ala Ser Leu Arg Ala Phe Thr
770                 775                 780

Glu Ala Met Thr Arg Tyr Ser Ala Pro Pro Gly Asp Pro Pro Gln Pro
785                 790                 795                 800

Glu Tyr Asp Leu Glu Leu Ile Thr Ala Ser
                805                 810

<210> SEQ ID NO 164
<211> LENGTH: 375
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 164

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Ile His Ser Tyr
            20                  25                  30

Gly Asn Ser Phe Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Ala Ser Val Thr Val Pro
    210                 215                 220

His Pro Asn Ile Glu Glu Val Ala Leu Ser Thr Thr Gly Glu Ile Pro
225                 230                 235                 240

Phe Tyr Gly Lys Ala Ile Pro Leu Glu Val Ile Lys Gly Gly Arg His
                245                 250                 255

Leu Ile Phe Cys His Ser Lys Lys Lys Cys Asp Glu Leu Ala Ala Lys
            260                 265                 270

Leu Val Ala Leu Gly Ile Asn Ala Val Ala Tyr Tyr Arg Gly Leu Asp
        275                 280                 285

Val Ser Val Ile Pro Thr Ser Gly Val Val Val Val Ala Thr Asp
    290                 295                 300

Ala Leu Met Thr Gly Phe Thr Gly Asp Phe Asp Ser Val Ile Asp Cys
305                 310                 315                 320

Asn Thr Cys Val Thr Gln Thr Val Asp Phe Ser Leu Asp Pro Thr Phe
                325                 330                 335

Thr Ile Glu Thr Thr Thr Leu Pro Gln Asp Ala Val Ser Arg Thr Gln
            340                 345                 350

Arg Arg Gly Arg Thr Gly Arg Gly Lys Pro Gly Ile Tyr Arg Phe Val
        355                 360                 365

Ala Pro Gly Glu Arg Ala Ser
    370                 375
```

<210> SEQ ID NO 165
<211> LENGTH: 816

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gln Val Thr Leu Lys Glu Ser Gly Pro Ala Ile Val Lys Pro Thr Gln
1               5                   10                  15

Thr Leu Thr Leu Thr Cys Ser Phe Ser Gly Phe Ser Leu Ser Thr Ser
            20                  25                  30

Gly Met Gly Leu Ser Trp Ile Arg Gln Pro Ser Gly Lys Ala Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Ile Val Asp Thr Val Asp Ala Ala Thr Tyr Tyr
                85                  90                  95

Cys Ala Arg Ser Ser His Tyr Tyr Gly Tyr Gly Tyr Gly Gly Tyr Phe
            100                 105                 110

Asp Val Trp Gly Gln Gly Thr Thr Val Thr Val Ser Ser Ala Lys Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
        420                 425                 430

Met His Glu Ala Leu His Asn His Tyr Thr Gln Lys Ser Leu Ser Leu
    435                 440                 445

Ser Leu Gly Lys Ala Ser Gln Thr Pro Thr Asn Thr Ile Ser Val Thr
450                 455                 460

Pro Thr Asn Asn Ser Thr Pro Thr Asn Asn Ser Asn Pro Lys Pro Asn
465                 470                 475                 480

Pro Ala Ser Thr Pro Cys Thr Cys Gly Ser Ser Asp Leu Tyr Leu Val
            485                 490                 495

Thr Arg His Ala Asp Val Ile Pro Val Arg Arg Gly Asp Ser Arg
        500                 505                 510

Gly Ser Leu Leu Ser Pro Arg Pro Ile Ser Tyr Leu Lys Gly Ser Ser
        515                 520                 525

Gly Gly Pro Leu Leu Cys Pro Ala Gly His Ala Val Gly Ile Phe Arg
530                 535                 540

Ala Ala Val Cys Thr Arg Gly Val Ala Lys Ala Val Asp Phe Ile Pro
545                 550                 555                 560

Val Glu Asn Leu Glu Thr Thr Met Arg Ser Pro Val Phe Thr Asp Asn
            565                 570                 575

Ser Ser Pro Pro Ala Val Pro Gln Ala Ser Ser Ser Val Ser Pro
            580                 585                 590

Thr Thr Ser Val His Pro Thr Pro Thr Ser Val Pro Pro Thr Pro Thr
        595                 600                 605

Lys Ser Ser Pro Ala Ser Val Leu Asp Ser His Tyr Gln Asp Val Leu
        610                 615                 620

Lys Glu Val Lys Ala Ala Ser Lys Val Lys Ala Asn Ala Leu Tyr
625                 630                 635                 640

Asp Val Val Ser Lys Leu Pro Leu Ala Val Met Gly Ser Ser Tyr Gly
                645                 650                 655

Phe Gln Tyr Ser Pro Gly Gln Arg Val Glu Phe Leu Val Gln Ala Trp
            660                 665                 670

Lys Ser Lys Lys Thr Pro Met Gly Phe Ser Tyr Asp Thr Arg Cys Phe
    675                 680                 685

Asp Ser Thr Val Thr Glu Ser Asp Ile Arg Thr Glu Glu Ala Ile Tyr
    690                 695                 700

Gln Cys Cys Asp Leu Asp Pro Gln Ala Arg Val Ala Ile Lys Ser Leu
705                 710                 715                 720

Thr Glu Arg Leu Tyr Val Gly Arg Cys Arg Ala Ser Gly Val Leu Thr
            725                 730                 735

Thr Ser Cys Gly Asn Thr Leu Thr Cys Tyr Ile Lys Ala Arg Ala Ala
            740                 745                 750

Cys Arg Ala Ala Gly Leu Gln Asp Cys Thr Met Leu Val Cys Gly Asp
        755                 760                 765

Asp Leu Val Val Ile Cys Glu Ser Ala Gly Val Gln Glu Asp Ala Ala
        770                 775                 780

Ser Leu Arg Ala Phe Thr Glu Ala Met Thr Arg Tyr Ser Ala Pro Pro
785                 790                 795                 800
```

```
Gly Asp Pro Pro Gln Pro Glu Tyr Asp Leu Glu Leu Ile Thr Ala Ser
                805                 810                 815

<210> SEQ ID NO 166
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ser Ser Val Ser Pro Thr Thr Ser Val His Pro Thr Pro Thr Ser Val
1               5                   10                  15

Pro Pro Thr Pro Thr Lys Ser Ser Pro
            20                  25

<210> SEQ ID NO 167
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Pro Thr Ser Thr Pro Ala Asp Ser Ser Thr Ile Thr Pro Thr Ala Thr
1               5                   10                  15

Pro Thr Ala Thr Pro Thr Ile Lys Gly
            20                  25

<210> SEQ ID NO 168
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Thr Val Thr Pro Thr Ala Thr Ala Thr Pro Ser Ala Ile Val Thr Thr
1               5                   10                  15

Ile Thr Pro Thr Ala Thr Thr Lys Pro
            20                  25

<210> SEQ ID NO 169
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Thr Asn Gly Ser Ile Thr Val Ala Ala Thr Ala Pro Thr Val Thr Pro
1               5                   10                  15

Thr Val Asn Ala Thr Pro Ser Ala Ala
            20                  25

<210> SEQ ID NO 170
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 170

Gln Thr Pro Thr Asn Thr Ile Ser Val Thr Pro Thr Asn Asn Ser Thr
1               5                   10                  15

Pro Thr Asn Asn Ser Asn Pro Lys Pro Asn Pro
            20                  25
```